US012600780B2

(12) United States Patent
Smith et al.

(10) Patent No.: US 12,600,780 B2
(45) **Date of Patent: *Apr. 14, 2026**

(54) ANTI-CD3 ANTIBODIES, BISPECIFIC ANTIGEN-BINDING MOLECULES THAT BIND CD3 AND CD20, AND USES THEREOF

(71) Applicant: Regeneron Pharmaceuticals, Inc., Tarrytown, NY (US)

(72) Inventors: Eric Smith, New York, NY (US); Nicholas J. Papadopoulos, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/512,432

(22) Filed: Nov. 17, 2023

(65) Prior Publication Data

US 2024/0352124 A1 Oct. 24, 2024

Related U.S. Application Data

(60) Continuation of application No. 17/355,532, filed on Jun. 23, 2021, now abandoned, which is a division of application No. 15/489,666, filed on Apr. 17, 2017, now Pat. No. 11,072,656, which is a continuation of application No. 14/031,075, filed on Sep. 19, 2013, now Pat. No. 9,657,102.

(60) Provisional application No. 61/827,098, filed on May 24, 2013, provisional application No. 61/763,110, filed on Feb. 11, 2013, provisional application No. 61/753,461, filed on Jan. 17, 2013, provisional application No. 61/704,029, filed on Sep. 21, 2012.

(51) Int. Cl.
*C07K 16/28* (2006.01)
*A61K 39/00* (2006.01)

(52) U.S. Cl.
CPC ...... *C07K 16/2809* (2013.01); *C07K 16/2887* (2013.01); *A61K 2039/505* (2013.01); *C07K 2317/21* (2013.01); *C07K 2317/31* (2013.01); *C07K 2317/33* (2013.01); *C07K 2317/35* (2013.01); *C07K 2317/734* (2013.01); *C07K 2317/74* (2013.01); *C07K 2317/92* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,500,362 | A | 3/1996 | Robinson et al. |
| 5,658,570 | A | 8/1997 | Newman et al. |
| 5,677,180 | A | 10/1997 | Robinson et al. |
| 5,721,108 | A | 2/1998 | Robinson et al. |
| 5,736,137 | A | 4/1998 | Anderson et al. |
| 5,776,456 | A | 7/1998 | Anderson et al. |
| 5,843,439 | A | 12/1998 | Anderson et al. |
| 6,120,767 | A | 9/2000 | Robinson et al. |
| 6,224,866 | B1 | 5/2001 | Barbera-Guillem |
| 6,399,061 | B1 | 6/2002 | Anderson et al. |
| 6,455,043 | B1 | 9/2002 | Grillo-Lopez |
| 6,528,624 | B1 | 3/2003 | Idusogie et al. |
| 6,551,592 | B2 | 4/2003 | Lindhofer et al. |
| 6,652,852 | B1 | 11/2003 | Robinson et al. |
| 6,682,734 | B1 | 1/2004 | Anderson et al. |
| 6,893,625 | B1 | 5/2005 | Robinson et al. |
| 7,151,164 | B2 | 12/2006 | Hansen et al. |
| 7,214,775 | B2 | 5/2007 | Hanai et al. |
| 7,728,114 | B2 | 6/2010 | Mach et al. |
| 7,879,984 | B2 | 2/2011 | Martin et al. |
| 8,076,459 | B2 | 12/2011 | Hofmeister et al. |

(Continued)

FOREIGN PATENT DOCUMENTS

| | | | |
|---|---|---|---|
| EP | 1400534 | A1 | 3/2004 |
| EP | 1176981 | B1 | 11/2005 |

(Continued)

OTHER PUBLICATIONS

Advani et al., "New immune strategies for the treatment of acute pymphoblastic leukemia: antibodies and chimeric antigen receptors," Hematology, vol. 2013 (No. 1): (Dec. 1, 2013).

(Continued)

*Primary Examiner* — Amy E Juedes

(74) *Attorney, Agent, or Firm* — Schwabe, Williamson & Wyatt PC; Aparna Patankar

(57) ABSTRACT

The present invention provides antibodies that bind to CD3 and methods of using the same. According to certain embodiments, the antibodies of the invention bind human CD3 with high affinity and induce human T cell proliferation. The invention includes antibodies that bind CD3 and induce T cell-mediated killing of tumor cells. According to certain embodiments, the present invention provides bispecific antigen-binding molecules comprising a first antigen-binding domain that specifically binds human CD3, and a second antigen-binding molecule that specifically binds human CD20. In certain embodiments, the bispecific antigen-binding molecules of the present invention are capable of inhibiting the growth of B-cell tumors expressing CD20. The antibodies and bispecific antigen-binding molecules of the invention are useful for the treatment of diseases and disorders in which an upregulated or induced targeted immune response is desired and/or therapeutically beneficial. For example, the antibodies of the invention are useful for the treatment of various cancers as well as other CD20-related diseases and disorders.

20 Claims, 10 Drawing Sheets

Specification includes a Sequence Listing.

(56) References Cited

U.S. PATENT DOCUMENTS

| | | | |
|---|---|---|---|
| 8,097,713 | B2 | 1/2012 | Martin et al. |
| 8,329,181 | B2 | 12/2012 | Martin et al. |
| 8,597,648 | B2 | 12/2013 | Guo et al. |
| 9,657,102 | B2 | 5/2017 | Smith et al. |
| 10,550,193 | B2 | 2/2020 | Smith et al. |
| 10,662,244 | B2 | 5/2020 | Smith et al. |
| 11,072,656 | B2 | 7/2021 | Smith et al. |
| 11,155,621 | B2 | 10/2021 | Smith et al. |
| 11,590,223 | B2 | 2/2023 | Brownstein et al. |
| 12,054,557 | B2 | 8/2024 | Varghese et al. |
| 2003/0026804 | A1 | 2/2003 | Grillo-Lopez |
| 2004/0093621 | A1 | 5/2004 | Shitara et al. |
| 2004/0167319 | A1 | 8/2004 | Teeling et al. |
| 2005/0025764 | A1 | 2/2005 | Watkins et al. |
| 2005/0053602 | A1 | 3/2005 | Brunetta |
| 2005/0191297 | A1 | 9/2005 | Brunetta |
| 2005/0271658 | A1 | 12/2005 | Brunetta et al. |
| 2006/0024295 | A1 | 2/2006 | Brunetta |
| 2006/0110387 | A1 | 5/2006 | Brunetta |
| 2006/0121032 | A1 | 6/2006 | Dahiyat et al. |
| 2006/0193852 | A1 | 8/2006 | Dorken et al. |
| 2006/0233797 | A1 | 10/2006 | Gujrathi |
| 2006/0240007 | A1 | 10/2006 | Sanders |
| 2006/0263355 | A1 | 11/2006 | Quan et al. |
| 2007/0014720 | A1 | 1/2007 | Gazit-Bornstein et al. |
| 2007/0020259 | A1 | 1/2007 | Hansen et al. |
| 2007/0081993 | A1 | 4/2007 | Kufer et al. |
| 2009/0022738 | A1 | 1/2009 | Hofmeister et al. |
| 2009/0035322 | A1 | 2/2009 | Martin et al. |
| 2010/0178298 | A1 | 7/2010 | Lindhofer |
| 2010/0183554 | A1 | 7/2010 | Mach et al. |
| 2010/0183615 | A1 | 7/2010 | Kufer et al. |
| 2010/0331527 | A1 | 12/2010 | Davis et al. |
| 2014/0112914 | A1 | 4/2014 | Nezu et al. |
| 2015/0166661 | A1 | 6/2015 | Chen et al. |
| 2015/0203579 | A1 | 7/2015 | Papadopoulos et al. |
| 2015/0266966 | A1 | 9/2015 | Smith et al. |
| 2016/0168247 | A1 | 6/2016 | Van Den Brink et al. |

FOREIGN PATENT DOCUMENTS

| | | | |
|---|---|---|---|
| EP | 1185299 | B1 | 1/2007 |
| EP | 2500353 | A2 | 9/2012 |
| EP | 2918604 | A1 | 9/2015 |
| WO | 04/106380 | A2 | 9/2004 |
| WO | 04/106383 | A1 | 12/2004 |
| WO | 05/000901 | A2 | 1/2005 |
| WO | 05/040220 | A1 | 5/2005 |
| WO | 05/118635 | A3 | 12/2005 |
| WO | 06/130458 | A2 | 12/2006 |
| WO | 07/024715 | A2 | 3/2007 |
| WO | 07/042261 | A2 | 4/2007 |
| WO | 07/093630 | A1 | 8/2007 |
| WO | 08/076379 | A3 | 6/2008 |
| WO | 08/119567 | A2 | 10/2008 |
| WO | 09/018411 | A1 | 2/2009 |
| WO | 09/023540 | A1 | 2/2009 |
| WO | 09/030368 | A1 | 3/2009 |
| WO | 09/106096 | A1 | 9/2009 |
| WO | 10/151792 | A1 | 12/2010 |
| WO | 11/090762 | A1 | 7/2011 |
| WO | 11/163566 | A1 | 12/2011 |
| WO | 12/073985 | A1 | 6/2012 |
| WO | 12/0109285 | A2 | 8/2012 |
| WO | 12/162067 | A2 | 11/2012 |
| WO | 13/072406 | A1 | 5/2013 |
| WO | 13/072415 | A1 | 5/2013 |
| WO | 14/012085 | A2 | 1/2014 |
| WO | 14/022540 | A1 | 2/2014 |
| WO | 14/047231 | A1 | 3/2014 |
| WO | 14/121087 | A1 | 8/2014 |
| WO | 15/006749 | A2 | 1/2015 |
| WO | 15/143079 | A1 | 9/2015 |

OTHER PUBLICATIONS

Aklilu et al., "Depletion of normal B cells with rituximab as an adjunct to IL-2 therapy for renal cell carcinoma and melanoma," Annals of Oncology 15: 1109-1114; Chicago, IL (2004).

Anonymous, "Clinical Trails Register: A Phase I Study to Assess Safety and Tolerability of REGN1979, an anti-CD20 x anti-CD3 bispecific monoclonal antibody, and REGN2810, and anti-programmed death-1 (PD-1) monoclonal antibody, in Patients with B-cell Malignancies," p. 1, section A.3; p. 3, section E.1 [Retrieved from the Internet Mar. 14, 2017: <URL: https://www.clinicaltrailsregister.eu/ctr-search/trial/2015-001697-17/ES>1.

Anonymous, "Study of REGN2810 and REGN1979 in Patients with Lymphoma or Acute Lymphoblastic Leukemia." [Retrieved from the Internet Mar. 15, 2017: <URL: https://www.api.liveclinicaltrials.com/trialpage?dcn=10963&city=Baltimore&country=UnitedStates&start=20&state=Maryland&conditions=lymphoma&id=207048402254>].

Bannerji et al., "Phase 1 Study of REGN1979, an Anti-CD20 x Anti-CD3 Bispecific Monoclonal Antibody, in Patients with CD20+ B-Cell Malignancies Previously Treated with CD20-Directed Antibody Therapy," Blood, vol. 128 (22): 621 (2016). [http://doi.org/10.1182/blood.V128.22.621.621].

Bargou et al., "Tumor egression in Cancer Patients by Very Low Doses of a T Cell-Engaging Antibody," Science Magazine, vol. 321: 974-977, (2008).

Boehrer et al., "Cytotoxic effects of the trifunctional bispecific antibody FBTACI5 in ex-vivo cells of chronic lymphocytic leukaemia depend on immune-mediated mechanisms," Anti-Cancer Drugs, 22:519-530, (2011).

Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplantation, 43:383-397, (2009).

Carter, "Potent Antibody Therapeutics by Design," Journal of Immunology, Nature Pub. Group, 6:343-357, (2006).

Chatenoud et al., "CD3-specific antibodies: a portal to the treatment of autoimmunity," Nature, vol. (7):622-632, (Aug. 2007). [doi:10.1038/nri2134: <URL: www.nature.com/reviews/immunol>].

Chen et al., "Strategies for Generating Diverse Antibody Reportoires Using Transgenic Animals Expressing Human Antibodies," Front. Immunol. Vol. 9, Article 460; Mar. 2018; 7 pages. doi: 10.3389/fimmu.2018.00460.

Conrad et al., "TCR and CD3 Antibody Cross-Reactivity in 44 Species," Cytometry Part A, 71A:925-933, (2007).

Damschroder et al., "Analysis of human and primate CD2 molecules by protein sequence and epitope mapping with anti-human CD2 antibodies," Molecular Immunology, vol. 41:985-1000, (2004).

Frey et al., "Cytokine release syndrome: Who is at risk and how to treat," Best Practice & Research Clinical Haematology, vol. 30 (No. 4): 336-340, (Dec. 2017). [Retrieved from the Internet Sep. 11, 2023: <URL: https://www.sciencedirect.com/journal/best-practice-and-research-clinical-haematology>1.

Gall et al., "T cells armed with anti-CD3 x anti-CD20 bispecific antibody enhance killing of CD20+ malignant B cells and bypass complement-mediated rituximab resistance in vitro", Experimental Hematology, 33(4):452-459, (2005).

Grubb, "Human Immunoglobulin Allotypes and Mendelian Polymorphisms of the Human Immunoglobulin Genes," in Oss CJ, Regenmortel MHV (eds); Immunochemistry, New York, Dekker (1994); pp. 47-68.

Harlow et al., Antibodies, A Laboratory Manual, Cold Spring Harbor Laboratory; (1998) pp. 37-47.

Haso et al., "Anti-CD22-chimeric antigen receptors targeting B-cell precursor acute lymophoblastic leukemia," Blood, vol. 121(No. 7):1165-1174, (2013).

Imabori Kazutomo, Biochemical Encyclopedia, 1998, 3rd Edition; pp. 265-266; including English translation.

Kapur et al., "IgG-effector functions: The Good, The Bad and The Ugly," El Sevier, vol. 160:139-144, (2014).

(56) References Cited

OTHER PUBLICATIONS

Klein et al., "Progress in overcoming the chain association issue in bispecific heterodimeric IgG antibodies," mAbs, Landes Bioscience, 4(6):1-11, (2012).
Klinger et al., "Immunopharmacologic response of patients with B-lineage acute lymphoblastic leukemia to continuous infusion of T cell-engaging CD19/CD3-bispecific BiTE antibody blinatumomab," Blood, 119:6226-6233, (2012).
Kontermann, "Dual targeting strategies with bispecific antibodies," mAbs, Landes Bioscience, 4(2):182-197, (2012).
Köhnke et al., "Increase of PD-L1 expressing B-precursor ALL cells in a patient resistant to the CD19/CD3-bispecific T cell engager antibody blinatumomab," Journal of Hematoloty & Oncology, vol. 8 (No. 111):5 pages, (2015).
Kumar et al., "Expression of CD20 in B Cell Precursor Acute Lymphoblastic Leukemia," Indian J. Hematol Blood Transfus, vol. 30 (No. 1):16-18, (2014).
Kung et al., "Monoclonal Antibodies Defining Distinctive Human T Cell Surface Antigens," Science, 206:347-349, (1979).
Leonard et al., "Targeted Treatment and New Agents in Diffuse Large B-Cell Lymphoma," Semin Hematol, 45(suppl 2):S11-S16, (2008).
Liu et al., "Improvement in soluble expression levels of a diabody by exchanging expression vectors", Protein Expression and Purification, 62:15-20, (2008).
Lum et al., "CD20-Targeted T Cells after Stem Cell Transplantation for High Risk and Refractory Non-Hodgkin's Lymphoma," Pbiol Blood Marrow Transplant, 19(6):925-933, (2013).
Lum et al., "Multiple infusions of CD20-targeted T cells and low-dose IL-2 after SCT for high-risk non-Hodgkin's lymphoma: A pilot study," Bone Marrow Transplantation, 49:73-79, (2014). [Published online Sep. 23, 2013].
Nagorsen et al., "Blinatumomab: A historical perspective," Pharmacology & Therapeutics, 136:334-342 (2012).
NCBI MedGen 44126 definition for "Pre-B Acute Lymphoblastic Leukemia" retrieved from the Internet on Dec. 11, 2018; pp. 1-4, available at <https://www.ncbi.nlm.nih.gov/medgen/44126> (2018).
Ontology Lookup Serviec, EFO 0000220, "acute lumphoblastic leukemia" retrieved from the Internet on Dec. 11, 2018, pp. 1-6; available at <http://www.ebi.ac.uk/ols/ontologies/efo/terms?short_form=EFO_0000220> (2018).
Patel et al., "IGG subclass variation of a monoclonal antibody binding to human Fc-gamma receptors", American Journal of Biochemistry and Biotechnology, 9(3):206-218, (2013).
Pessano et al., "The T3/T cell receptor complex: antigenic distinction between the two 20-kd T3 (T3-0 and T3-δ) subunits," The EMBO Journal, 4(2):337-344, (1985).
Ruf et al., "Induction of a long-lasting antitumor immunity by a trifunctional bispecific antibody," Blood Journal, vol. 98, No. 9: 2526-2534, (2001).
Schuster et al., "Immunotherapy with the trifunctional anti-CD20 x anti-CD3 antibody FBTA05 Lymphomun) in paediatric high-risk patients with recurrent CD20-positive B cell malignancies," British Journal of Haematolgy, vol. 169 (No. 1): (Apr. 11, 2015); pp. 90-102.
Scott et al., "Antibody Therapy of Cancer," Nature, vol. 12:278-287, (Apr. 2012).
Segal et al., "Bispecific antibodies in cancer therapy," Current Opinion in Immunology, 11:558-562, (1999).
Siiman et al., "Cell Surface Receptor-Antibody Association Constants and Enumeration of Receptor Sites for Monoclonal Antibodies," Cytometry, 40:316-326, (2000).
Smith et al., "A novel, native-format bispecific antibody triggering T-cell killing of B-cell is robustly active in mouse tumor models and cynomolgus monkeys," Scientific Reports, vol. 5(No. 11):(Dec. 11, 2015); p. 17943.
Stanglmaier et al., "Bi20 (FBTA05), a novel trifunctional bispecific antibody (anti-CD20 x anti-CD3), mediates efficient killing of B-cell lymphoma cells even with very low CD20 expression levels", Int. J. Cancer, 123(5):1181-1189, (2008).
Stel et al., "The role of B cell-mediated T cell costimulation in the efficacy of the T cell retargeting bispecific antibody BIS20x3," J Immunol, 173(10):6009-6016, (2004).
Strop et al., "Generating Bispecific Human IgG1 and IgG2 Antibodies from Any Antibody Pair", J. Mol. Biol., 420(3):204-219, (2012).
Stubenrauch et al., "Impact of Molecular Processing in the Hinge Region of Therapeutic lgG4 Antibodies on Disposition Profiles in Cynomolgus Monkeys," Drug Metabolism and Disposition, vol. 38(No. 1):84-91, (2010).
Sun et al., "Anti-CD20/CD3 T cell-dependent bispecific antibody for the treatment of B cell malignancies," Science Translational Medicine, 7(287):287ra70, 10 pages, (2015).
Teeling et al., "Characterization of new human CD20 monoclonal antibodies with potent cytolytic activity against non-Hodgkin lymphomas," Blood, 104:1793-1800, (2004).
Thakur et al., "Activated T cells from umbilical cord blood armed with anti-CD3 x anti-CD20 bispecific antibody mediate specific cytotoxicity against CD20+ targets with minimal allogeneic reactivity: a strategy for providing antitumor effects after cord blood transplants", Transfusion, 52:63-75, (2012).
Thakur et al., "Cancer therapy with bispecific antibodies: Clinical experience," NIH Public Access, Curr Opin Mol Ther., vol. 12(3): 340-349, (2010).
Thomas et al., "Chemiommunotherapy with a modified hyper-CVAD and Rituximab Regiment improves outcome in De Novo Philadelphia Chromosome-Negative Precursor B-Lineage Acute Lymphoblastic Leukemia," Journal of Clinical Oncology, vol. 28 (No. 24):3880-3889, (2010).
Topp et al., "Safety and activity of blinatumomab for adult patients with relapsed or refractory B-precursor acute lymphoblastic leu, aemia: a multiventre, single-arm, phase 2 study," The Lancet, vol. 16:57-66, (2015).
Tsai et al., "Regulation of CD20 in Rituximab-Resistant Cell Lines and B-cell Non-Hodgkin Lymphoma," Clinical Cancer Research, vol. 18(No. 4):1039-1050, (2012).
U.S. Appl. No. 14/031,075, Final Office Action mailed Sep. 14, 2016.
U.S. Appl. No. 14/031,075, Non-Final Office Action mailed Apr. 15, 2016.
U.S. Appl. No. 14/031,075, Notice of Allowance mailed Jan. 18, 2017.
U.S. Appl. No. 14/031,075, Requirement for Restriction/Election mailed Nov. 19, 2015.
U.S. Appl. No. 15/489,666, Non-Final Office Action mailed Feb. 11, 2020.
U.S. Appl. No. 15/489,666, Requirement for Restriction/Election mailed Jun. 18, 2019.
U.S. Appl. No. 15/934,447, Requirement for Restriction/Election mailed Oct. 17, 2019.
U.S. Appl. No. 15/934,447, Non-Final Office Action mailed May 8, 2020.
U.S. Appl. No. 15/489,666, Final Office Action mailed Sep. 10, 2020.
U.S. Appl. No. 15/934,447, Final Office Action mailed Dec. 4, 2020.
U.S. Appl. No. 15/489,666, Notice of Allowance mailed Mar. 24, 2021.
U.S. Appl. No. 15/934,447, Notice of Allowance mailed Jun. 24, 2021.
U.S. Appl. No. 16/556,885, Non-Final Office Action mailed Mar. 29, 2022.
U.S. Appl. No. 17/355,532, Non-Final Office Action mailed May 19, 2023.
Van Meerten et al., "CD20-Targeted Therapy: The Next Generation of Antibodies," Semin Hematol, 47:199-210, (2010).
Varghese et al., "A Novel CD20-CD3 Bispecific Fully Human Antibody Induces Potent Anti-Tumor Effects Against B Cell Lymphoma in Mice," Blood, vol. 124 (21) 4501 (2014). [http://doi.org/10.1182/blood.V124.21.4501.4501].
Wark et al., "Latest technologies for the enhancement of antibody affinity", Advanced Drug Delivery Reviews, 58(5-6):657-670, (2006).

(56) References Cited

OTHER PUBLICATIONS

Winkler et al., "Changing the Antigen Binding Specificity by Single Point Mutations of an Anti-p24 (HIV-1) Antibody," J. Immunol., 165:4505-4514, (2000).
WIPO Application No. PCT/US2013/060511, PCT International Search Report and Written Opinion of the International Searching Authority mailed Feb. 20, 2014.
WIPO Application No. PCT/US2015/021322, PCT International Search Report and Written Opinion of the International Searching Authority mailed Jul. 2, 2015.
Wolach et al., "Blinatumomab for the Treatment of Philadelphia Chromosome-Negative, Precursor B-cell Acute Lymphoblastic Leukemia," Clinical Cancer Research, vol. 21 (No. 19):4262-4269, (2015).
Xiong et al., "Efficient inhibition of human B-cell lymphoma xenografts with an anti-CD20 X anti-CD3 bispecific diabody", Cancer Letters, 177:29-39, (2002).
Yuen et al., "B lymphocytes and cancer: a love-hate relationship," Trends Cancer Dec. 2016; 2(12): 747-757.
U.S. Appl. No. 61/704,029, filed Sep. 21, 2012, Expired.
U.S. Appl. No. 61/753,461, filed Jan. 17, 2013, Expired.
U.S. Appl. No. 61/763,110, filed Feb. 11, 2013, Expired.
U.S. Appl. No. 61/827,098, filed May 24, 2013, Expired.
U.S. Appl. No. 14/031,075, filed Sep. 19, 2013, U.S. Pat. No. 9,657,102, Issued.
U.S. Appl. No. 15/489,666, filed Apr. 17, 2017, U.S. Pat. No. 11,072,656, Issued.
PCT/US2013/060511, Sep. 19, 2013, WO 2014/047231, Expired.
U.S. Appl. No. 15/934,447, filed Mar. 23, 2018., U.S. Pat. No. 11,155,621, Issued.
U.S. Appl. No. 17/355,532, filed Jun. 23, 2021, US-2022-0144947, Abandoned.
U.S. Appl. No. 61/955,663, filed Mar. 19, 2014, Expired.
U.S. Appl. No. 61/981,641, filed Apr. 18, 2014, Expired.
U.S. Appl. No. 62/007,385, filed Jun. 3, 2014, Expired.
U.S. Appl. No. 62/033,460, filed Aug. 5, 2014, Expired.
U.S. Appl. No. 14/661,334, filed Mar. 18, 2015, U.S. Pat. No. 10,550,193, Issued.
PCT/US2015/021322, Mar. 18, 2015, WO 2015/143079, Expired.
U.S. Appl. No. 16/716,980, filed Dec. 17, 2019, U.S. Pat. No. 11,434,300, Issued.
U.S. Appl. No. 17/875,295, filed Jul. 27, 2022, US-2023-0220101, Published.
U.S. Appl. No. 62/080,716, filed Nov. 17, 2014, Expired.
U.S. Appl. No. 62/160,788, filed May 13, 2015, Expired.
PCT/US2015/061139, Nov. 17, 2015, WO 2016/081490, Expired.
U.S. Appl. No. 15/527,002, filed Nov. 17, 2015, U.S. Pat. No. 10,662,244, Issued.
U.S. Appl. No. 62/306,031, filed Mar. 9, 2016, Expired.
U.S. Appl. No. 15/386,443, filed Dec. 21, 2016, US 2017-0174781, Abandon.
PCT/US2016/068003, Dec. 21, 2016, WO 2017/112762, Expired.
U.S. Appl. No. 16/556,885, filed Aug. 30, 2019, U.S. Pat. No. 11,590,223, Issued.
U.S. Appl. No. 62/726,137, filed Aug. 31, 2018, Expired.
U.S. Appl. No. 62/774,019, filed Nov. 30, 2018, Expired.
U.S. Appl. No. 62/861,100, filed Jun. 13, 2019, Expired.
PCT/US2019/049027, Aug. 30, 2019, WO 2020/047389, Expired.
U.S. Appl. No. 18/101,310, filed Jan. 25, 2023, US-2023-0165959, Published.
U.S. Appl. No. 63/313,932, filed Feb. 25, 2022, Expired.
U.S. Appl. No. 63/393,212, filed Jul. 28, 2022, Expired.
U.S. Appl. No. 63/420,782, filed Oct. 31, 2022, Expired.
U.S. Appl. No. 63/424,210, filed Nov. 10, 2022, Expired.
U.S. Appl. No. 63/440,304, filed Jan. 20, 2023, Expired.
U.S. Appl. No. 18/114,057, filed Feb. 24, 2023, US-2023-0272118.
PCT/US2023/013836, Feb. 24, 2023, WO2023/164143, Published.
U.S. Appl. No. 17/875,295, Non-Final Office Action mailed Mar. 13, 2025.
Chao et al. (Cancer Management and Research 2013:5 251-269). (Year: 2013).
Wong et al. (Haematologica. Dec. 2013 98(12):1930-1938, supplemental pages included, document has been renumbered as pp. 1-27). (Year: 2013).
P01834 (GenPept, Ig kappa chain C region, pp. 1-4, Feb. 19, 2014). (Year: 2014).

ANTI-CD3 ANTIBODIES, BISPECIFIC ANTIGEN-BINDING MOLECULES THAT BIND CD3 AND CD20, AND USES THEREOF

CROSS-REFERENCE TO RELATED APPLICATIONS

This application is a continuation of U.S. application Ser. No. 17/355,532, filed Jun. 23, 2021, which is a division of U.S. application Ser. No. 15/489,666, filed Apr. 17, 2017, now U.S. Pat. No. 11,072,656, which is a continuation of U.S. application Ser. No. 14/031,075, filed Sep. 19, 2013, now U.S. Pat. No. 9,657,102, which claims the benefit under 35 USC § 119(e) of U.S. Provisional Application No. 61/704,029, filed on Sep. 21, 2012; 61/753,461, filed on Jan. 17, 2013; 61/763,110, filed on Feb. 11, 2013; and 61/827,098, filed on May 24, 2013, the disclosures of which are herein incorporated by reference in their entireties.

REFERENCE TO A SEQUENCE LISTING

This application incorporates by reference a computer readable Sequence Listing in ST.26 XML format, titled 9250US05_Sequence, created on Nov. 17, 2023, and containing 1,643,963 bytes.

FIELD OF THE INVENTION

The present invention relates to antibodies, and antigen-binding fragments thereof, which are specific for CD3, and methods of use thereof. The present invention also relates to bispecific antigen-binding molecules that bind CD3 and a target molecule such as CD20, and methods of use thereof.

BACKGROUND

CD3 is a homodimeric or heterodimeric antigen expressed on T cells in association with the T cell receptor complex (TCR) and is required for T cell activation. Functional CD3 is formed from the dimeric association of two of four different chains: epsilon, zeta, delta and gamma. The CD3 dimeric arrangements include gamma/epsilon, delta/epsilon and zeta/zeta. Antibodies against CD3 have been shown to cluster CD3 on T cells, thereby causing T cell activation in a manner similar to the engagement of the TCR by peptide-loaded MHC molecules. Thus, anti-CD3 antibodies have been proposed for therapeutic purposes involving the activation of T cells. In addition, bispecific antibodies that are capable of binding CD3 and a target antigen have been proposed for therapeutic uses involving targeting T cell immune responses to tissues and cells expressing the target antigen.

CD20 is a non-glycosylated phosphoprotein expressed on the cell membranes of mature B cells. CD20 is considered a B cell tumor-associated antigen because it is expressed by more than 95% of B-cell non-Hodgkin lymphomas (NHLs) and other B-cell malignancies, but it is absent on precursor B-cells, dendritic cells and plasma cells. Methods for treating cancer by targeting CD20 are known in the art. For example, the chimeric anti-CD20 monoclonal antibody rituximab has been used or suggested for use in treating cancers such as NHL, chronic lymphocytic leukemia (CLL) and small lymphocytic lymphoma (SLL). CD20 is believed to kill CD20-expressing tumor cells by complement dependent cytotoxicity (CDC), antibody-dependent cell mediated cytotoxicity (ADCC) and/or induction of apoptosis and sensitization to chemotherapy. Although anti-CD20 tumor targeting strategies have shown great promise in clinical settings, not all patients respond to anti-CD20 therapy, and some patients have been shown to develop resistance to or exhibit incomplete responses to anti-CD20 therapy (e.g., resistance to rituximab).

Bispecific antigen-binding molecules that bind both CD3 and a target antigen (such as CD20) would be useful in therapeutic settings in which specific targeting and T cell-mediated killing of cells that express the target antigen is desired.

BRIEF SUMMARY OF THE INVENTION

In a first aspect, the present invention provides antibodies and antigen-binding fragments thereof that bind human CD3. The antibodies according to this aspect of the invention are useful, inter alia, for targeting T cells expressing CD3, and for stimulating T cell activation, e.g., under circumstances where T cell-mediated killing is beneficial or desirable. The anti-CD3 antibodies of the invention, or antigen-binding portions thereof, may be included as part of a bispecific antibody that directs CD3-mediated T cell activation to specific cell types such as tumor cells or infectious agents.

Exemplary anti-CD3 antibodies of the present invention are listed in Tables 1 and 2 herein. Table 1 sets forth the amino acid sequence identifiers of the heavy chain variable regions (HCVRs) and light chain variable regions (LCVRs), as well as heavy chain complementarity determining regions (HCDR1, HCDR2 and HCDR3), and light chain complementarity determining regions (LCDR1, LCDR2 and LCDR3) of the exemplary anti-CD3 antibodies. Table 2 sets forth the sequence identifiers of the nucleic acid molecules encoding the HCVRs, LCVRs, HCDR1, HCDR2 HCDR3, LCDR1, LCDR2 and LCDR3 of the exemplary anti-CD3 antibodies.

The present invention provides antibodies, or antigen-binding fragments thereof, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-CD3 antibodies listed in Table 1. In certain embodiments, the HCVR/LCVR amino acid sequence pair is selected from the group consisting of SEQ ID NOs: 2/10 (e.g., H1H2712N); 114/122 (e.g., H2M2609N); 514/522 (e.g., H2M3563N); 770/778 (e.g., H1H5778P); 1050/1234 (e.g., H1H7195B); and 1090/1234 (e.g., H1H7208B).

The present invention also provides antibodies, or antigen-binding fragments thereof, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-CD3 antibodies listed in Table 1. In certain embodiments, the HCDR3/LCDR3 amino acid sequence pair is selected from the group consisting of SEQ ID NOs: 8/16 (e.g., H1H2712N); 120/128 (e.g., H2M2609N); 520/528 (e.g., H2M3563N); 776/784 (e.g., H1H5778P); 1056/1240 (e.g., H1H7195B); and 1096/1240 (e.g., H1H7208B).

The present invention also provides antibodies, or antigen-binding fragments thereof, comprising a set of six CDRs (i.e., HCDR1-HCDR2-HCDR3-LCDR1-LCDR2-LCDR3) contained within any of the exemplary anti-CD3 antibodies listed in Table 1. In certain embodiments, the HCDR1-HCDR2-HCDR3-LCDR1-LCDR2-LCDR3 amino acid sequences set is selected from the group consisting of SEQ ID NOs: 4-6-8-12-GAS-16 (e.g., H1H2712N); 116-118-120-124-GAS-128 (e.g., H2M2609N); 516-518-520-524-AAS-528 (e.g., H2M3563N); 772-774-776-780-GAS-784 (e.g., H1H5778P); 1052-1054-1056-1236-AAS-1240 (e.g., H1H7195B); and 1092-1094-1096-1236-AAS-1240 (e.g., H1H7208B).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined by any of the exemplary anti-CD3 antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NOs: 2/10 (e.g., H1H2712N); 114/122 (e.g., H2M2609N); 514/522 (e.g., H2M3563N); 770/778 (e.g., H1H5778P); 1050/1234 (e.g., H1H7195B); and 1090/1234 (e.g., H1H7208B). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-CD3 antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-CD3 antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-CD3 antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-CD3 antibody listed in Table 1.

The present invention also provides recombinant expression vectors capable of expressing a polypeptide comprising a heavy or light chain variable region of an anti-CD3 antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present invention includes anti-CD3 antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds CD3 and a pharmaceutically acceptable carrier. In a related aspect, the invention features a composition which is a combination of an anti-CD3 antibody and a second therapeutic agent. In one embodiment, the second therapeutic agent is any agent that is advantageously combined with an anti-CD3 antibody. Exemplary agents that may be advantageously combined with an anti-CD3 antibody include, without limitation, other agents that bind and/or activate CD3 signaling (including other antibodies or antigen-binding fragments thereof, etc.) and/or agents which do not directly bind CD3 but nonetheless activate or stimulate immune cell activation. Additional combination therapies and co-formulations involving the anti-CD3 antibodies of the present invention are disclosed elsewhere herein.

In yet another aspect, the invention provides therapeutic methods for stimulating T cell activation using an anti-CD3 antibody or antigen-binding portion of an antibody of the invention, wherein the therapeutic methods comprise administering a therapeutically effective amount of a pharmaceutical composition comprising an antibody or antigen-binding fragment of an antibody of the invention to a subject in need thereof. The disorder treated is any disease or condition which is improved, ameliorated, inhibited or prevented by stimulation of CD3 activity or signaling.

According to another aspect, the present invention provides bispecific antigen-binding molecules that bind CD3 and a target antigen. According to certain exemplary embodiments, the bispecific antigen-binding molecules bind CD3 and CD20; such bispecific antigen-binding molecules are also referred to herein as "anti-CD3/anti-CD20 bispecific molecules." The anti-CD20 portion of the anti-CD3/anti-CD20 bispecific molecule is useful for targeting tumor cells that express CD20 (e.g., B-cell tumors), and the anti-CD3 portion of the bispecific molecule is useful for activating T-cells. The simultaneous binding of CD20 on a tumor cell and CD3 on a T-cell facilitates directed killing (cell lysis) of the targeted tumor cell by the activated T-cell. The anti-CD3/anti-CD20 bispecific molecules of the invention are therefore useful, inter alia, for treating diseases and disorders related to or caused by CD20-expressing tumors (e.g., lymphomas).

The bispecific antigen-binding molecules according to this aspect of the present invention comprise a first antigen-binding domain that specifically binds human CD3, and a second antigen-binding domain that specifically binds CD20. The present invention includes anti-CD3/anti-CD20 bispecific molecules (e.g., bispecific antibodies) wherein each antigen-binding domain comprises a heavy chain variable region (HCVR) paired with a light chain variable region (LCVR). In certain exemplary embodiments of the invention, the anti-CD3 antigen-binding domain and the anti-CD20 antigen binding domain each comprise different, distinct HCVRs paired with a common LCVR. For example, as illustrated in Example 7 herein, bispecific antibodies were constructed comprising a first antigen-binding domain that specifically binds CD3, wherein the first antigen-binding domain comprises an HCVR/LCVR pair derived from an anti-CD3 antibody; and a second antigen-binding domain that specifically binds CD20, wherein the second antigen-binding domain comprises an HCVR derived from an anti-CD20 antibody paired with an LCVR derived from an anti-CD3 antibody (e.g., the same LCVR that is included in the anti-CD3 antigen-binding domain). In other words, in the exemplary molecules disclosed herein, the pairing of an HCVR from an anti-CD20 antibody with an LCVR from an anti-CD3 antibody creates an antigen-binding domain that specifically binds CD20 (but does not bind CD3). In such embodiments, the first and second antigen-binding domains comprise distinct anti-CD3 and anti-CD20 HCVRs but share a common anti-CD3 LCVR.

The present invention provides anti-CD3/anti-CD20 bispecific molecules, wherein the first antigen-binding domain that specifically binds CD3 comprises any of the HCVR amino acid sequences as set forth in Table 1 or Table 18. The first antigen-binding domain that specifically binds CD3 may also comprise any of the LCVR amino acid sequences as set forth in Table 1 or Table 19. According to certain embodiments, the first antigen-binding domain that specifically binds CD3 comprises any of the HCVR/LCVR amino acid sequence pairs as set forth in Table 1 or Table 17. The present invention also provides anti-CD3/anti-CD20 bispecific molecules, wherein the first antigen-binding domain that specifically binds CD3 comprises any of the heavy chain CDR1-CDR2-CDR3 amino acid sequences as set forth in Table 1 or Table 18, and/or any of the light chain CDR1-CDR2-CDR3 amino acid sequences as set forth in Table 1 or Table 19.

According to certain embodiments, the present invention provides anti-CD3/anti-CD20 bispecific molecules, wherein the first antigen-binding domain that specifically binds CD3 comprises a heavy chain variable region (HCVR) having an amino acid sequence selected from the group consisting of SEQ ID NOs:1250, 1266, 1282, 1298, 1314 and 1329 or a substantially similar sequence thereof having at least 90%, at least 95%, at least 98% or at least 99% sequence identity.

The present invention also provides anti-CD3/anti-CD20 bispecific molecules, wherein the first antigen-binding domain that specifically binds CD3 comprises a light chain variable region (LCVR) having an amino acid sequence selected from the group consisting of SEQ ID NOs:1258, 1274, 1290, 1306, 1322 and 1333, or a substantially similar sequence thereof having at least 90%, at least 95%, at least 98% or at least 99% sequence identity.

The present invention also provides anti-CD3/anti-CD20 bispecific molecules, wherein the first antigen-binding domain that specifically binds CD3 comprises a HCVR and LCVR (HCVR/LCVR) amino acid sequence pair selected from the group consisting of SEQ ID NOs:1250/1258, 1266/1274, 1282/1290, 1298/1306, 1314/1322, and 1329/1333.

The present invention also provides anti-CD3/anti-CD20 bispecific molecules, wherein the first antigen-binding domain that specifically binds CD3 comprises a heavy chain CDR3 (HCDR3) domain having an amino acid sequence selected from the group consisting of SEQ ID NOs:1256, 1272, 1288, 1304, 1320 and 1332, or a substantially similar sequence thereto having at least 90%, at least 95%, at least 98% or at least 99% sequence identity; and a light chain CDR3 (LCDR3) domain having an amino acid sequence selected from the group consisting of SEQ ID NOs:1264, 1280, 1296, 1312, 1328 and 1336, or a substantially similar sequence thereof having at least 90%, at least 95%, at least 98% or at least 99% sequence identity.

In certain embodiments, the first antigen-binding domain that specifically binds CD3 comprises a HCDR3/LCDR3 amino acid sequence pair selected from the group consisting of SEQ ID NOs: 1256/1264, 1272/1280, 1288/1296, 1304/1312, 1320/1328 and 1332/1336.

The present invention also provides anti-CD3/anti-CD20 bispecific antigen-binding molecules, wherein the first antigen-binding domain that specifically binds CD3 comprises a heavy chain CDR1 (HCDR1) domain having an amino acid sequence selected from the group consisting of SEQ ID NOs: 1252, 1268, 1284, 1300, 1316 and 1330, or a substantially similar sequence thereof having at least 90%, at least 95%, at least 98% or at least 99% sequence identity; a heavy chain CDR2 (HCDR2) domain having an amino acid sequence selected from the group consisting of SEQ ID NOs: 1254, 1270, 1286, 1302, 1318 and 1331, or a substantially similar sequence thereof having at least 90%, at least 95%, at least 98% or at least 99% sequence identity; a light chain CDR1 (LCDR1) domain having an amino acid sequence selected from the group consisting of SEQ ID NOs: 1260, 1276, 1292, 1308, 1324 and 1334, or a substantially similar sequence thereof having at least 90%, at least 95%, at least 98% or at least 99% sequence identity; and a light chain CDR2 (LCDR2) domain having an amino acid sequence selected from the group consisting of GAS and DTS, or a substantially similar sequence thereof having at least 90%, at least 95%, at least 98% or at least 99% sequence identity.

Certain non-limiting, exemplary anti-CD3/anti-CD20 bispecific antigen-binding molecules of the invention include a first antigen-binding domain that specifically binds CD3 comprising HCDR1-HCDR2-HCDR3-LCDR1-LCDR2-LCDR3 domains, respectively, having the amino acid sequences selected from the group consisting of: SEQ ID NOs: 1252-1254-1256-1260-GAS-1264 (e.g. BS3/20-001); 1268-1270-1272-1276-GAS-1280 (e.g. BS3/20-002); 1284-1286-1288-1292-GAS-1296 (e.g. BS3/20-003); 1300-1302-1304-1308-GAS-1312 (e.g. BS3/20-004); 1316-1318-1320-1324-GAS-1328 (e.g. BS3-20-005); and 1330-1331-1332-1334-DTS-1336 (e.g. BS3/20-007).

The present invention also provides anti-CD3/anti-CD20 bispecific molecules, wherein the second antigen-binding domain that specifically binds CD20 comprises a heavy chain variable region (HCVR) having the amino acid sequence of SEQ ID NO:1242, or a substantially similar sequence thereof having at least 90%, at least 95%, at least 98% or at least 99% sequence identity.

The present invention also provides anti-CD3/anti-CD20 bispecific molecules, wherein the second antigen-binding domain that specifically binds CD20 comprises a light chain variable region (LCVR) having the amino acid sequence selected from the group consisting of SEQ ID NOs:1258, 1274, 1290, 1306, 1322 and 1333, or a substantially similar sequence thereof having at least 90%, at least 95%, at least 98% or at least 99% sequence identity.

The present invention also provides anti-CD3/anti-CD20 bispecific molecules, wherein the second antigen-binding domain that specifically binds CD20 comprises a HCVR and LCVR (HCVR/LCVR) amino acid sequence pair selected from the group consisting of SEQ ID NOs: 1242/1258, 1242/1274, 1242/1290, 1242/1306, 1242/1322 and 1242/1333.

The present invention also provides anti-CD3/anti-CD20 bispecific molecules, wherein the second antigen-binding domain that specifically binds CD20 comprises a heavy chain CDR3 (HCDR3) domain having the amino acid sequence of SEQ ID NO:1248, or a substantially similar sequence thereto having at least 90%, at least 95%, at least 98% or at least 99% sequence identity; and a light chain CDR3 (LCDR3) domain having an amino acid sequence selected from the group consisting of SEQ ID NOs: 1264, 1280, 1296, 1312, 1328 and 1336, or a substantially similar sequence thereof having at least 90%, at least 95%, at least 98% or at least 99% sequence identity.

In certain embodiments, the second antigen-binding domain that specifically binds CD20 comprises a HCDR3/LCDR3 amino acid sequence pair selected from the group consisting of SEQ ID NOs: 1248/1264, 1248/1280, 1248/1296, 1248/1312, 1248/1328 and 1248/1336.

The present invention also provides anti-CD3/anti-CD20 bispecific antigen-binding molecules, wherein the second antigen-binding domain that specifically binds CD20 comprises a heavy chain CDR1 (HCDR1) domain having the amino acid sequence of SEQ ID NO:1244, or a substantially similar sequence thereof having at least 90%, at least 95%, at least 98% or at least 99% sequence identity; a heavy chain CDR2 (HCDR2) domain having the amino acid sequence of SEQ ID NO:1246, or a substantially similar sequence thereof having at least 90%, at least 95%, at least 98% or at least 99% sequence identity; a light chain CDR1 (LCDR1) domain having an amino acid sequence selected from the group consisting of SEQ ID NOS: 1260, 1276, 1292, 1308, 1324 and 1334, or a substantially similar sequence thereof having at least 90%, at least 95%, at least 98% or at least 99% sequence identity; and a light chain CDR2 (LCDR2) domain having an amino acid sequence selected from the group consisting of GAS and DTS, or a substantially similar sequence thereof having at least 90%, at least 95%, at least 98% or at least 99% sequence identity.

Certain non-limiting, exemplary anti-CD3/anti-CD20 bispecific antigen-binding molecules of the invention include a second antigen-binding domain that specifically binds CD20 comprising HCDR1-HCDR2-HCDR3-LCDR1-LCDR2-LCDR3 domains, respectively, having the amino acid sequences selected from the group consisting of: SEQ ID NOs: 1244-1246-1248-1260-GAS-1264 (e.g. BS3/20-001); 1244-1246-1248-1276-GAS-1280 (e.g. BS3/20-002); 1244-1246-1248-1292-GAS-1296 (e.g. BS3/20-003); 1244-1246-1248-1308-GAS-1312 (e.g. BS3/20-004); 1244-1246-1248-1324-GAS-1328 (e.g. BS3-20-005); and 1244-1246-1248-1334-DTS-1336 (e.g. BS3/20-007).

In a related embodiment, the invention includes anti-CD3/anti-CD20 bispecific antigen-binding molecules wherein the second antigen-binding domain that specifically binds CD20 comprises the heavy and light chain CDR domains contained within heavy and light chain variable region (HCVR/LCVR) sequences selected from the group consisting of SEQ ID NOs: 1242/1258, 1242/1274, 1242/1290, 1242/1306, 1242/1322 and 1242/1333.

In another aspect, the present invention provides nucleic acid molecules encoding any of the HCVR, LCVR or CDR sequences of the anti-CD3/anti-CD20 bispecific antigen-binding molecules disclosed herein, including nucleic acid molecules comprising the polynucleotide sequences as set forth in Tables 20 and 21 herein, as well as nucleic acid molecules comprising two or more of the polynucleotide sequences as set forth in Tables 20 and 21 in any functional combination or arrangement thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

The present invention includes anti-CD3/anti-CD20 bispecific antigen-binding molecules wherein any of the aforementioned antigen-binding domains that specifically bind CD3 is combined, connected or otherwise associated with any of the aforementioned antigen-binding domains that specifically bind CD20 to form a bispecific antigen-binding molecule that binds CD3 and CD20.

The present invention includes anti-CD3/anti-CD20 bispecific antigen-binding molecules having a modified glycosylation pattern. In some applications, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising an anti-CD3/anti-CD20 bispecific antigen-binding molecule as disclosed herein and a pharmaceutically acceptable carrier. In a related aspect, the invention features a composition which is a combination of an anti-CD3/anti-CD20 bispecific antigen-binding molecule and a second therapeutic agent. In one embodiment, the second therapeutic agent is any agent that is advantageously combined with an anti-CD3/anti-CD20 bispecific antigen-binding molecule. Exemplary agents that may be advantageously combined with an anti-CD3/anti-CD20 bispecific antigen-binding molecule are discussed in detail elsewhere herein.

In yet another aspect, the invention provides therapeutic methods for targeting/killing tumor cells expressing CD20 using an anti-CD3/anti-CD20 bispecific antigen-binding molecule of the invention, wherein the therapeutic methods comprise administering a therapeutically effective amount of a pharmaceutical composition comprising an anti-CD3/anti-CD20 bispecific antigen-binding molecule of the invention to a subject in need thereof.

The present invention also includes the use of an anti-CD3/anti-CD20 bispecific antigen-binding molecule of the invention in the manufacture of a medicament for the treatment of a disease or disorder related to or caused by CD20 expression.

Other embodiments will become apparent from a review of the ensuing detailed description.

DETAILED DESCRIPTION

Figure 1:
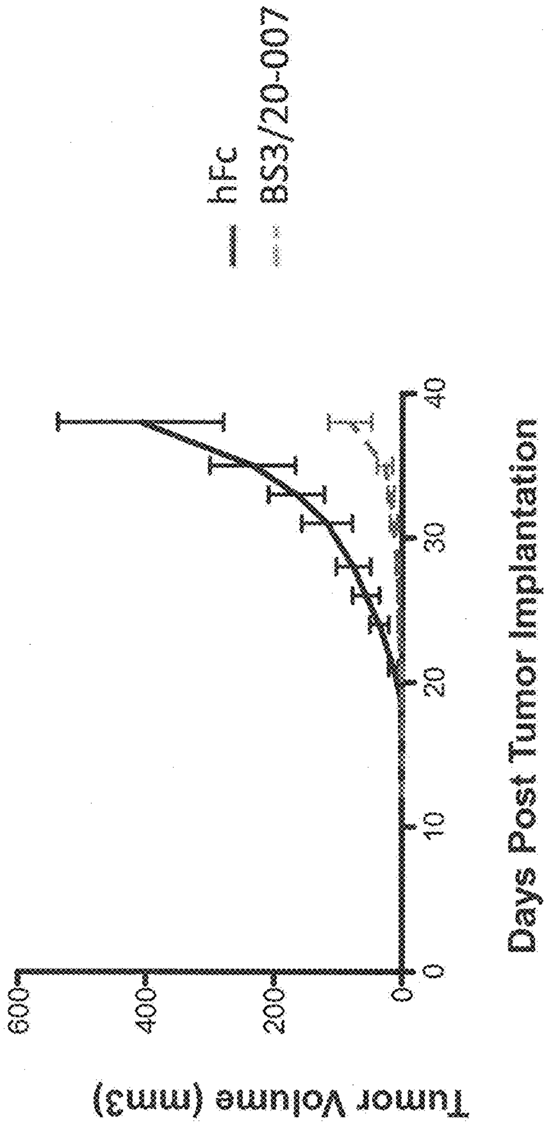
FIG. 1 shows the tumor volume (in $mm^3$) over time in NOD/SCID mice implanted subcutaneously with a mixture of Raji tumor cells and PBMCs following tumor implantation and treatment, starting the day of tumor implantation, with either human Fc (hFc, solid line) or CD3×CD20 bispecific antibody (BS3/20-007, dashed line).

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The expression "CD3," as used herein, refers to an antigen which is expressed on T cells as part of the multimolecular T cell receptor (TCR) and which consists of a homodimer or heterodimer formed from the association of two of four receptor chains: CD3-epsilon, CD3-delta, CD3-zeta, and CD3-gamma. Human CD3-epsilon comprises the amino acid sequence as set forth in SEQ ID NO:1370; human CD3-delta comprises the amino acid sequence as set forth in SEQ ID NO:1371. All references to proteins, polypeptides and protein fragments herein are intended to refer to the human version of the respective protein, polypeptide or protein fragment unless explicitly specified as being from a non-human species. Thus, the expression "CD3" means human CD3 unless specified as being from a non-human species, e.g., "mouse CD3," "monkey CD3," etc.

As used herein, "an antibody that binds CD3" or an "anti-CD3 antibody" includes antibodies and antigen-binding fragments thereof that specifically recognize a single CD3 subunit (e.g., epsilon, delta, gamma or zeta), as well as antibodies and antigen-binding fragments thereof that specifically recognize a dimeric complex of two CD3 subunits (e.g., gamma/epsilon, delta/epsilon, and zeta/zeta CD3 dimers). The antibodies and antigen-binding fragments of the present invention may bind soluble CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane.

As used herein, the expression "cell surface-expressed CD3" means one or more CD3 protein(s) that is/are expressed on the surface of a cell in vitro or in vivo, such that at least a portion of a CD3 protein is exposed to the extracellular side of the cell membrane and is accessible to an antigen-binding portion of an antibody. "Cell surface-expressed CD3" includes CD3 proteins contained within the context of a functional T cell receptor in the membrane of a cell. The expression "cell surface-expressed CD3" includes CD3 protein expressed as part of a homodimer or heterodimer on the surface of a cell (e.g., gamma/epsilon, delta/epsilon, and zeta/zeta CD3 dimers). The expression, "cell surface-expressed CD3" also includes a CD3 chain (e.g., CD3-epsilon, CD3-delta or CD3-gamma) that is expressed by itself, without other CD3 chain types, on the surface of a cell. A "cell surface-expressed CD3" can comprise or consist of a CD3 protein expressed on the surface of a cell which normally expresses CD3 protein. Alternatively, "cell surface-expressed CD3" can comprise or consist of CD3 protein expressed on the surface of a cell that normally does not express human CD3 on its surface but has been artificially engineered to express CD3 on its surface.

As used herein, the expression "anti-CD3 antibody" includes both monovalent antibodies with a single specificity, as well as bispecific antibodies comprising a first arm that binds CD3 and a second arm that binds a second (target) antigen, wherein the anti-CD3 arm comprises any of the HCVR/LCVR or CDR sequences as set forth in Table 1 or Tables 18/19 herein. Examples of anti-CD3 bispecific antibodies are described elsewhere herein. The term "antigen-binding molecule" includes antibodies and antigen-binding fragments of antibodies, including, e.g., bispecific antibodies.

The term "antibody", as used herein, means any antigen-binding molecule or molecular complex comprising at least one complementarity determining region (CDR) that specifically binds to or interacts with a particular antigen (e.g., CD3). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-CD3 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-CL; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H^2$—$C_{H3}$; (xiii) $V_L$-$C_H2$-$C_{H3}$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-CD3 antibodies of the invention (monospecific or bispecific) are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention also includes one-arm antibodies that bind CD3. As used herein, a "one-arm antibody" means an antigen-binding molecule comprising a single antibody heavy chain and a single antibody light chain. The one-arm antibodies of the present invention may comprise any of the HCVR/LCVR or CDR amino acid sequences as set forth in Table 1 or Tables 18/19 herein.

The anti-CD3 antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-CD3 antibodies comprising variants of any of the HCVR, LCVR, and/or CDR amino acid sequences disclosed herein having one or more conservative substitutions. For example, the present invention includes anti-CD3 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

Bispecific Antigen-Binding Molecules

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-CD3 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

Use of the expression "anti-CD3 antibody" herein is intended to include both monospecific anti-CD3 antibodies as well as bispecific antibodies comprising a CD3-binding arm and a second arm that binds a target antigen. Thus, the present invention includes bispecific antibodies wherein one arm of an immunoglobulin binds human CD3, and the other arm of the immunoglobulin is specific for a target antigen. The target antigen that the other arm of the CD3 bispecific antibody binds can be any antigen expressed on or in the vicinity of a cell, tissue, organ, microorganism or virus, against which a targeted immune response is desired. The CD3-binding arm can comprise any of the HCVR/LCVR or CDR amino acid sequences as set forth in Table 1 or Tables 18/19 herein. In certain embodiments, the CD3-binding arm binds human CD3 and induces human T cell proliferation.

In the context of bispecific antibodies of the present invention wherein one arm of the antibody binds CD3 and the other arm binds a target antigen, the target antigen can be a tumor-associated antigen. Non-limiting examples of specific tumor-associated antigens include, e.g., AFP, ALK, BAGE proteins, β-catenin, brc-abl, BRCA1, BORIS, CA9, carbonic anhydrase IX, caspase-8, CCR5, CD19, CD20, CD30, CD40, CDK4, CEA, CTLA4, cyclin-B1, CYP1B1, EGFR, EGFRvIII, ErbB2/Her2, ErbB3, ErbB4, ETV6-AML, EpCAM, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1, -2, -3, -4, -6, and -12), MART-1, mesothelin, ML-IAP, Muc1, Muc2, Muc3, Muc4, Muc5, Muc16 (CA-125), MUM1, NA17, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE proteins, Ras, RGS5, Rho, SART-1, SART-3, Steap-1, Steap-2, survivin, TAG-72, TGF-β, TMPRSS2, Tn, TRP-1, TRP-2, tyrosinase, and uroplakin-3.

In the context of bispecific antibodies of the present invention wherein one arm of the antibody binds CD3 and the other arm binds a target antigen, the target antigen can be an infectious disease-associated antigen. Non-limiting examples of infectious disease-associated antigens include, e.g., an antigen that is expressed on the surface of a virus particle, or preferentially expressed on a cell that is infected with a virus, wherein the virus is selected from the group consisting of HIV, hepatitis (A, B or C), herpes virus (e.g., HSV-1, HSV-2, CMV, HAV-6, VZV, Epstein Barr virus), adenovirus, influenza virus, flavivirus, echovirus, rhinovirus, coxsackie virus, coronavirus, respiratory syncytial virus, mumps virus, rotavirus, measles virus, rubella virus, parvovirus, vaccinia virus, HTLV, dengue virus, papillomavirus, molluscum virus, poliovirus, rabies virus, JC virus, and arboviral encephalitis virus. Alternatively, the target antigen can be an antigen that is expressed on the surface of a bacterium, or preferentially expressed on a cell that is infected with a bacterium, wherein the bacterium is selected from the group consisting of chlamydia, rickettsia, mycobacteria, staphylococci, streptococci, pneumonococci, meningococci, gonococci, klebsiella, proteus, serratia, pseudomonas, legionella, diphtheria, salmonella, bacilli, cholera, tetanus, botulism, anthrax, plague, leptospira, and Lyme disease bacteria. In certain embodiments, the target antigen is an antigen that is expressed on the surface of a fungus, or preferentially expressed on a cell that is infected with a fungus, wherein the fungus is selected from the group consisting of *Candida* (*albicans, krusei, glabrata, tropicalis*, etc.), *Crytococcus neoformans, Aspergillus* (*fumigatus, niger*, etc.), Mucorales (*mucor, absidia, rhizopus*, etc.), *Sporothrix schenkii, Blastomyces dermatitidis, Paracoccidioides brasiliensis, Coccidioides immitis*, and *Histoplasma capsulatum*. In certain embodiments, the target antigen is an antigen that is expressed on the surface of a parasite, or preferentially expressed on a cell that is infected with a parasite, wherein the parasite is selected from the group consisting of *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis, Taenia crassiceps*, and *Brugia malayi*. Non-limiting examples of specific pathogen-associated antigens include, e.g., HIV gp120, HIV CD4, hepatitis B glucoprotein L, hepatitis B glucoprotein M, hepatitis B glucoprotein S, hepatitis C E1, hepatitis C E2, hepatocyte-specific protein, herpes simplex virus gB, cytomegalovirus gB, and HTLV envelope protein.

According to certain exemplary embodiments, the present invention includes bispecific antigen-binding molecules that specifically bind CD3 and CD20. Such molecules may be referred to herein as, e.g., "anti-CD3/anti-CD20," or "anti-CD3×CD20" or "CD3×CD20" bispecific molecules, or other similar terminology.

The term "CD20," as used herein, refers to the human CD20 protein unless specified as being from a non-human species (e.g., "mouse CD20," "monkey CD20," etc.). The human CD20 protein has the amino acid sequence shown in SEQ ID NO:1369.

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., CD3), and the second antigen-binding domain specifically binds a second, distinct antigen (e.g., CD20).

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen-binding domain (e.g., a bispecific antibody), the CDRs of the first antigen-binding domain may be designated with the prefix "A1" and the CDRs of the second antigen-binding domain may be designated with the prefix "A2". Thus, the CDRs of the first antigen-binding domain may be referred to herein as A1-HCDR1, A1-HCDR2, and A1-HCDR3; and the CDRs of the second antigen-binding domain may be referred to herein as A2-HCDR1, A2-HCDR2, and A2-HCDR3.

The first antigen-binding domain and the second antigen-binding domain may be directly or indirectly connected to one another to form a bispecific antigen-binding molecule of the present invention. Alternatively, the first antigen-binding domain and the second antigen-binding domain may each be connected to a separate multimerizing domain. The association of one multimerizing domain with another multimerizing domain facilitates the association between the two antigen-binding domains, thereby forming a bispecific antigen-binding molecule. As used herein, a "multimerizing domain" is any macromolecule, protein, polypeptide, peptide, or amino acid that has the ability to associate with a second multimerizing domain of the same or similar structure or constitution. For example, a multimerizing domain may be a polypeptide comprising an immunoglobulin $C_H3$ domain. A non-limiting example of a multimerizing component is an Fc portion of an immunoglobulin (comprising a $C_H2$-$C_H3$ domain), e.g., an Fc domain of an IgG selected from the isotypes IgG1, IgG2, IgG3, and IgG4, as well as any allotype within each isotype group.

Bispecific antigen-binding molecules of the present invention will typically comprise two multimerizing domains, e.g., two Fc domains that are each individually part of a separate antibody heavy chain. The first and second multimerizing domains may be of the same IgG isotype such as, e.g., IgG1/IgG1, IgG2/IgG2, IgG4/IgG4. Alternatively, the first and second multimerizing domains may be of different IgG isotypes such as, e.g., IgG1/IgG2, IgG1/IgG4, IgG2/IgG4, etc.

In certain embodiments, the multimerizing domain is an Fc fragment or an amino acid sequence of 1 to about 200 amino acids in length containing at least one cysteine residues. In other embodiments, the multimerizing domain is a cysteine residue, or a short cysteine-containing peptide. Other multimerizing domains include peptides or polypeptides comprising or consisting of a leucine zipper, a helix-loop motif, or a coiled-coil motif.

Any bispecific antibody format or technology may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and $Mab^2$ bispecific formats (see, e.g., Klein et al. 2012, mAbs 4:6, 1-11, and references cited therein, for a review of the foregoing formats).

In the context of bispecific antigen-binding molecules of the present invention, the multimerizing domains, e.g., Fc domains, may comprise one or more amino acid changes (e.g., insertions, deletions or substitutions) as compared to the wild-type, naturally occurring version of the Fc domain. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

The present invention also includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies.

In certain embodiments, the Fc domain may be chimeric, combining Fc sequences derived from more than one immunoglobulin isotype. For example, a chimeric Fc domain can comprise part or all of a $C_H2$ sequence derived from a human IgG1, human IgG2 or human IgG4 $C_H2$ region, and part or all of a $C_H3$ sequence derived from a human IgG1, human IgG2 or human IgG4. A chimeric Fc domain can also contain a chimeric hinge region. For example, a chimeric hinge may comprise an "upper hinge" sequence, derived from a human IgG1, a human IgG2 or a human IgG4 hinge region, combined with a "lower hinge" sequence, derived from a human IgG1, a human IgG2 or a human IgG4 hinge region. A particular example of a chimeric Fc domain that can be included in any of the antigen-binding molecules set forth herein comprises, from N- to C-terminus: [IgG4 $C_H1$]-[IgG4 upper hinge]-[IgG2 lower hinge]-[IgG4 CH2]-[IgG4 CH3]. Another example of a chimeric Fc domain that can be included in any of the antigen-binding molecules set forth herein comprises, from N- to C-terminus: [IgG1 $C_H1$]-[IgG1 upper hinge]-[IgG2 lower hinge]-[IgG4 CH2]-[IgG1 CH3]. These and other examples of chimeric Fc domains that can be included in any of the antigen-binding molecules of the present invention are described in U.S. Provisional Application No. 61/759,578, filed Feb. 1, 2013, which is herein incorporated in its entirety. Chimeric Fc domains having these general structural arrangements, and variants thereof, can have altered Fc receptor binding, which in turn affects Fc effector function.

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germline sequences available from, for example, public antibody sequence databases. The antigen-binding molecules of the present invention may comprise antigen-binding domains which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

The present invention also includes antigen-binding molecules wherein one or both antigen-binding domains comprise variants of any of the HCVR, LCVR, and/or CDR amino acid sequences disclosed herein having one or more conservative substitutions. For example, the present invention includes antigen-binding molecules comprising an antigen-binding domain having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

The present invention also includes antigen-binding molecules comprising an antigen-binding domain with an HCVR, LCVR, and/or CDR amino acid sequence that is substantially identical to any of the HCVR, LCVR, and/or CDR amino acid sequences disclosed herein. The term "substantial identity" or "substantially identical," when referring to an amino acid sequence means that two amino acid sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

pH-Dependent Binding

The present invention includes anti-CD3 antibodies, and anti-CD3/anti-CD20 bispecific antigen-binding molecules, with pH-dependent binding characteristics. For example, an anti-CD3 antibody of the present invention may exhibit reduced binding to CD3 at acidic pH as compared to neutral pH. Alternatively, anti-CD3 antibodies of the invention may exhibit enhanced binding to CD3 at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to CD3 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Antibodies Comprising Fc Variants

According to certain embodiments of the present invention, anti-CD3 antibodies, and anti-CD3/anti-CD20 bispecific antigen-binding molecules, are provided comprising an Fc domain comprising one or more mutations which enhance or diminish antibody binding to the FcRn receptor, e.g., at acidic pH as compared to neutral pH. For example, the present invention includes antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 2591 (e.g., V2591), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, the present invention includes anti-CD3 antibodies, and anti-CD3/anti-CD20 bispecific antigen-binding molecules, comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present invention.

Biological Characteristics of the Antibodies and Bispecific Antigen-Binding Molecules The present invention includes antibodies and antigen-binding fragments thereof that bind human CD3 and induce T cell proliferation. For example, the present invention includes anti-CD3 antibodies that induce human T cell proliferation with an $EC_{50}$ value of less than about 0.33 pM, as measured by an in vitro T cell proliferation assay, e.g., using the assay format as defined in Example 4 herein (e.g., assessing the proliferation of Jurkat cells or human PBMCs in the presence of anti-CD3 antibodies), or a substantially similar assay. In certain embodiments, the antibodies or antigen-binding fragments of the present invention induce human T cell proliferation (e.g., Jurkat cell proliferation and/or PBMC proliferation) with an $EC_{50}$ value of less than about 0.32 pM, less than about 0.31 pM, less than about 0.30 pM, less than about 0.28 pM, less than about 0.26 pM, less than about 0.24 pM, less than about 0.22 pM, or less than about 0.20 pM, as measured by an in vitro T cell proliferation assay, e.g., using the assay format as defined in Example 4 herein, or a substantially similar assay.

The present invention also includes antibodies and antigen-binding fragments thereof that bind human CD3 and induce T cell-mediated killing of tumor cells. For example, the present invention includes anti-CD3 antibodies that induce T cell-mediated killing of tumor cells with an $EC_{50}$ of less than about 2.3 pM, as measured in an in vitro T cell-mediated tumor cell killing assay, e.g., using the assay format as defined in Example 6 herein (e.g., assessing the extent of U937 tumor cell killing by human PBMCs in the presence of anti-CD3 antibodies), or a substantially similar assay. In certain embodiments, the antibodies or antigen-binding fragments of the present invention induce T cell-mediated tumor cell killing (e.g., PBMC-mediated killing of U937 cells) with an $EC_{50}$ value of less than about 2.3 pM, less than about 2.2 pM, less than about 2.1 pM, less than about 2.0 pM, less than about 1.8 pM, less than about 1.6 pM, less than about 1.4 pM, less than about 1.2 pM, less than about 1.0 pM, less than about 0.8 pM, less than about 0.6 pM, or less than about 0.5 pM, as measured by an in vitro T cell-mediated tumor cell killing assay, e.g., using the assay format as defined in Example 6 herein, or a substantially similar assay.

The present invention includes antibodies and antigen-binding fragments thereof that bind human CD3 with high affinity. The present invention also includes antibodies and antigen-binding fragments thereof that bind human CD3 with medium or low affinity, depending on the therapeutic context and particular targeting properties that are desired. For example, in the context of a bispecific antigen-binding molecule, wherein one arm binds CD3 and another arm binds a target antigen (e.g., CD20), it may be desirable for the target antigen-binding arm to bind the target antigen with high affinity while the anti-CD3 arm binds CD3 with only moderate or low affinity. In this manner, preferential targeting of the antigen-binding molecule to cells expressing the target antigen may be achieved while avoiding general/untargeted CD3 binding and the consequent adverse side effects associated therewith.

According to certain embodiments, the present invention includes antibodies and antigen-binding fragments of antibodies that bind human CD3 (e.g., at 25° C.) with a $K_D$ of less than about 15 nM as measured by surface plasmon resonance, e.g., using an assay format as defined in Example 3 herein. In certain embodiments, the antibodies or antigen-binding fragments of the present invention bind CD3 with a $K_D$ of less than about 5 nM, less than about 2 nM, less than about 1 nM, less than about 800 pM, less than about 600 pM, less than about 500 pM, less than about 400 pM, less than about 300 pM, less than about 200 pM, less than about 180 pM, less than about 160 pM, less than about 140 pM, less than about 120 pM, less than about 100 pM, less than about 80 pM, less than about 60 pM, less than about 40 pM, less than about 20 pM, or less than about 10 pM, as measured by surface plasmon resonance, e.g., using an assay format as defined in Example 3 herein (e.g., mAb-capture or antigen-capture format), or a substantially similar assay.

The present invention also includes antibodies and antigen-binding fragments thereof that bind CD3 with a dissociative half-life (t½) of greater than about 10 minutes as measured by surface plasmon resonance at 25° C. or 37° C., e.g., using an assay format as defined in Example 3 herein, or a substantially similar assay. In certain embodiments, the antibodies or antigen-binding fragments of the present invention bind CD3 with a t/2 of greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 100 minutes, greater than about 200 minutes, greater than about 300 minutes, greater than about 400 minutes, greater than about 500 minutes, greater than about 600 minutes, greater than about 700 minutes, greater than about 800 minutes, greater than about 900 minutes, greater than about 1000 minutes, or greater than about 1200 minutes, as measured by surface plasmon resonance at 25° C. or 37° C., e.g., using an assay format as defined in Example 3 herein (e.g., mAb-capture or antigen-capture format), or a substantially similar assay.

The present invention includes bispecific antigen-binding molecules (e.g., bispecific antibodies) which are capable of simultaneously binding to human CD3 and human CD20. According to certain embodiments, the bispecific antigen-binding molecules of the invention specifically interact with cells that express CD3 and/or CD20. The extent to which a bispecific antigen-binding molecule binds cells that express CD3 and/or CD20 can be assessed by fluorescence activated cell sorting (FACS), as illustrated in Example 8 herein. For example, the present invention includes bispecific antigen-binding molecules which specifically bind human T-cell lines which express CD3 but not CD20 (e.g., Jurkat), human B-cell lines which express CD20 but not CD3 (e.g., Raji), and/or primate T-cells (e.g., cynomolgus peripheral blood mononuclear cells [PBMCs]). The present invention includes bispecific antigen-binding molecules which bind any of the aforementioned cells and cell lines with an $EC_{50}$ value of from about $9.0\times10^{-6}$ to about $2.0\times10^{-9}$, or less, as determined using a FACS assay as set forth in Example 8 or a substantially similar assay.

The present invention also includes anti-CD3/anti-CD20 bispecific antigen-binding molecules which bind to CD3-expressing human T-cells (e.g., Jurkat) with an $EC_{50}$ value of between 1.0 pM and 1000 nM. In certain embodiments, the anti-CD3/anti-CD20 bispecific antigen-binding molecules bind to CD3-expressing human T-cells with an EC50 value of between 1 nM and 60 nM. For example, the present invention includes anti-CD3/anti-CD20 bispecific antigen-binding molecules which bind to CD3-expressing human T-cells (e.g., Jurkat) with an $EC_{50}$ value of about 1 pM. about 10 pM, about 100 pM, about 500 pM, about 1 nM, about 2 nM, about 5 nM, about 10 nM, about 20 nM, about 30 nM, about 40 nM, about 50 nM about 60 nM, about 70 nM, about 80 nM, about 90 nM, about 100 nM, about 200 nM, about 300 nM, about 500 nM, about 800 nM, about 1000 nM, or more.

The present invention also includes anti-CD3/anti-CD20 bispecific antigen-binding molecules which exhibit one or more characteristics selected from the group consisting of: (a) inducing PBMC proliferation in vitro (see, e.g., Example 9 herein); (b) activating T-cells, inducing IFN-gamma release and CD25 up-regulation in human whole blood (see, e.g., Example 10 herein); (c) inducing T-cell mediated cytotoxicity on anti-CD20-resistant cell lines (see, e.g., Example 11 herein); (d) inducing cytotoxicity to human B-cells (e.g., Raji; see, e.g., Example 13 herein); (e) depleting B-cells (e.g., CD19+ B-cells) in mice reconstituted with human immune cells (see, e.g., Example 14 herein); and (f) decreasing B-cell tumor volume (e.g., Raji tumor volume) in mouse xenografts (see, e.g., Example 15).

The present invention includes anti-CD3/anti-CD20 bispecific antigen-binding molecules which are capable of depleting B cells in a subject (see, e.g., Example 16). For example, according to certain embodiments, anti-CD3/anti-CD20 bispecific antigen-binding molecules are provided, wherein a single administration of the bispecific antigen-binding molecule to a subject (e.g., at a dose of about 0.1 mg/kg, about 0.08 mg/kg, about 0.06 mg/kg about 0.04 mg/kg, about 0.04 mg/kg, about 0.02 mg/kg, about 0.01 mg/kg, or less) causes a reduction in the number of B cells in the subject (e.g., in a blood sample taken from the subject) below detectable levels. In certain embodiments, a single administration of the anti-CD3/anti-CD20 bispecific antigen-binding molecule at a dose of about 0.1 mg/kg causes a reduction in the number of B cells in the subject below detectable levels by about day 7, about day 6, about day 5, about day 4, about day 3, about day 2, or about day 1 after administration of the bispecific antigen-binding molecule to the subject. According to certain embodiments, a single administration of an anti-CD3/anti-CD20 bispecific antigen-binding molecule of the invention, at a dose of about 0.01 mg/kg, causes the number of B-cells to remain below detectable levels until at least about 7 days, 8 days, 9 days, 10 days, 11 days, 12 days, 13 days, 14 days, 15 days, 16 days, 17 days or more, following the administration. As used herein, the expression "below detectable levels" means that no B cells can be directly or indirectly detected in a blood sample drawn from a subject using standard B-cell detection assays, e.g., a FACS assay for B-cell markers, as set forth in Example 16, herein.

In related embodiments, an anti-CD3/anti-CD20 bispecific antigen-binding molecule is provided, wherein the number of B-cells per microliter of blood drawn from a subject at about day 1 through about day 28 after administration of a single dose of about 0.01 mg/kg of the antigen-binding molecule to the subject is less than 25% the number of B-cells per microliter of blood drawn from the subject prior to the administration. In certain other embodiments, an anti-CD3/anti-CD20 bispecific antigen-binding molecule is provided, wherein the number of B-cells per microliter of blood drawn from a subject at about day 1 through about day 56 after administration of a single dose of about 0.01 mg/kg of the antigen-binding molecule to the subject is less than 50% the number of B-cells per microliter of blood drawn from the subject prior to the administration.

The present invention also provides anti-CD3/anti-CD20 bispecific antigen-binding molecules that, when administered to a subject, cause no more than a transient decrease in T cells. For example, anti-CD3/anti-CD20 bispecific antigen-binding molecules are provided that, when administered to a subject at a dose of about 0.01 mg/kg cause the number of T cells to decline at day 1 following administration, but wherein the number of T cells per microliter of blood rebounds at timepoints thereafter (e.g., by about day 2, day 7, day 14, day 28, day 42, day 56 or later following the administration). For example the present invention provides an anti-CD3/anti-CD20 bispecific antigen-binding molecule, wherein the number of T cells per microliter of blood drawn from the subject at about day 14 through about day 56 after administration of the antigen binding molecule to the subject at a dose of about 0.01 mg/kg is equal to or greater than the number of T cells per microliter of blood drawn from the subject prior to administration of the bispecific antigen-binding molecule.

Epitope Mapping and Related Technologies

The epitope on CD3 to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a CD3 protein. Alternatively, the epitope may consist of a plurality of non-contiguous amino acids (or amino acid sequences) of CD3. The antibodies of the invention may interact with amino acids contained within a single CD3 chain (e.g., CD3-epsilon, CD3-delta or CD3-gamma), or may interact with amino acids on two or more different CD3 chains. The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., NY), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography of the antigen/antibody complex may also be used for epitope mapping purposes.

The present invention further includes anti-CD3 antibodies that bind to the same epitope as any of the specific exemplary antibodies described herein (e.g. antibodies comprising any of the amino acid sequences as set forth in Table 1 herein). Likewise, the present invention also includes anti-CD3 antibodies that compete for binding to CD3 with any of the specific exemplary antibodies described herein (e.g. antibodies comprising any of the amino acid sequences as set forth in Table 1 herein).

The present invention also includes bispecific antigen-binding molecules comprising a first antigen-binding domain that specifically binds human CD3, and a second antigen binding domain that specifically binds human CD20, wherein the first antigen-binding domain binds to the same epitope on CD3 as any of the specific exemplary CD3-specific antigen-binding domains described herein, and/or wherein the second antigen-binding domain binds to the same epitope on CD20 as any of the specific exemplary CD20-specific antigen-binding domains described herein.

Likewise, the present invention also includes bispecific antigen-binding molecules comprising a first antigen-binding domain that specifically binds human CD3, and a second antigen binding domain that specifically binds human CD20, wherein the first antigen-binding domain competes for binding to CD3 with any of the specific exemplary CD3-specific antigen-binding domains described herein, and/or wherein the second antigen-binding domain competes for binding to CD20 with any of the specific exemplary CD20-specific antigen-binding domains described herein.

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on CD3 (or CD20) as a reference bispecific antigen-binding molecule of the present invention, the reference bispecific molecule is first allowed to bind to a CD3 protein (or CD20 protein). Next, the ability of a test antibody to bind to the CD3 (or CD20) molecule is assessed. If the test antibody is able to bind to CD3 (or CD20) following saturation binding with the reference bispecific antigen-binding molecule, it can be concluded that the test antibody binds to a different epitope of CD3 (or CD20) than the reference bispecific antigen-binding molecule. On the other hand, if the test antibody is not able to bind to the CD3 (or CD20) molecule following saturation binding with the reference bispecific antigen-binding molecule, then the test antibody may bind to the same epitope of CD3 (or CD20) as the epitope bound by the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., Cancer Res. 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a CD3 protein (or CD20 protein) under saturating conditions followed by assessment of binding of the test antibody to the CD3 (or CD20) molecule. In a second orientation, the test antibody is allowed to bind to a CD3 (or CD20) molecule under saturating conditions followed by assessment of binding of the reference antigen-binding molecule to the CD3 (or CD20) molecule. If, in both orientations, only the first (saturating) antigen-binding molecule is capable of binding to the CD3 (or CD20) molecule, then it is concluded that the test antibody and the reference antigen-binding molecule compete for binding to CD3 (or CD20). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD3 and CD20), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD3 or CD20) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454 for a detailed discussion of such engineered mice and the use thereof to produce bispecific antigen-binding molecules).

Bioequivalents

The present invention encompasses antigen-binding molecules having amino acid sequences that vary from those of the exemplary molecules disclosed herein but that retain the ability to bind CD3 and/or CD20. Such variant molecules may comprise one or more additions, deletions, or substitutions of amino acids when compared to parent sequence, but exhibit biological activity that is essentially equivalent to that of the described bispecific antigen-binding molecules.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary bispecific antigen-binding molecules set forth herein comprising amino acid changes which modify the glycosylation characteristics of the molecules, e.g., mutations which eliminate or remove glycosylation.

Species Selectivity and Species Cross-Reactivity

According to certain embodiments of the invention, antigen-binding molecules are provided which bind to human CD3 but not to CD3 from other species. Also provided are antigen-binding molecules which bind to human CD20 but not to CD20 from other species. The present invention also includes antigen-binding molecules that bind to human CD3 and to CD3 from one or more non-human species; and/or antigen-binding molecules that bind to human CD20 and to CD20 from one or more non-human species.

According to certain exemplary embodiments of the invention, antigen-binding molecules are provided which bind to human CD3 and/or human CD20 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee CD3 and/or CD20. For example, in a particular exemplary embodiment of the present invention bispecific antigen-binding molecules are provided comprising a first antigen-binding domain that binds human CD3 and cynomolgous CD3, and a second antigen-binding domain that specifically binds human CD20.

Immunoconjugates

The present invention encompasses antigen-binding molecules conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Therapeutic Formulation and Administration

The present invention provides pharmaceutical compositions comprising the antigen-binding molecules of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™, Life Technologies, Carlsbad, CA), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antigen-binding molecule administered to a patient may vary depending upon the age and the size of the patient, target disease, conditions, route of administration, and the like. The preferred dose is typically calculated according to body weight or body surface area. When a bispecific antigen-binding molecule of the present invention is used for therapeutic purposes in an adult patient, it may be advantageous to intravenously administer the bispecific antigen-binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ 1, || and Ill (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park IL), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antigen-Binding Molecules

The present invention includes methods comprising administering to a subject in need thereof a therapeutic composition comprising an anti-CD3 antibody or a bispecific antigen-binding molecule that specifically binds CD3 and a target antigen (e.g., CD20). The therapeutic composition can comprise any of the antibodies or bispecific antigen-binding molecules as disclosed herein and a pharmaceutically acceptable carrier or diluent. As used herein, the expression "a subject in need thereof" means a human or non-human animal that exhibits one or more symptoms or indicia of cancer (e.g., a subject expressing a tumor or suffering from any of the cancers mentioned herein below), or who otherwise would benefit from an inhibition or reduction in CD20 activity or a depletion of CD20+ B cells.

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the anti-CD3/anti-CD20 bispecific antigen-binding molecules of the present invention may be used for the treatment, prevention and/or amelioration of any disease or disorder associated with or mediated by CD20 expression or activity or the proliferation of CD20+ B cells. The mechanism of action by which the therapeutic methods of the invention are achieved include killing of the cells expressing CD20 in the presence of effector cells, for example, by CDC, apoptosis, ADCC, phagocytosis, or by a combination of two or more of these mechanisms. Cells expressing CD20 which can be inhibited or killed using the bispecific antigen-binding molecules of the invention include, for example, tumorigenic B cells.

The antigen-binding molecules of the present invention may be used to treat, e.g., primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the bispecific antigen-binding molecules of the invention are used to treat one or more of the following cancers: renal cell carcinoma, pancreatic carcinoma, breast cancer, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer, synovial sarcoma, thyroid cancer, or melanoma. According to certain exemplary embodiments, the bispecific antigen-binding molecules of the present invention are used to treat a B cell cancer (e.g., Hodgkin's lymphoma, non-Hodgkin's lymphoma [NHL], precursor B cell lymphoblastic leukemia/lymphoma, mature B cell neoplasms, B cell chronic lymphocytic leukemia/small lymphocytic lymphoma, B cell prolymphocytic leukemia, lymphoplasmacytic lymphoma, mantle cell lymphoma, follicular lymphoma, cutaneous follicle center lymphoma, marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma).

According to certain embodiments of the present invention, the antigen-binding molecules are useful for treating a patient afflicted with a B-cell lymphoma (e.g., NHL) that is resistant to, or incompletely responsive to anti-CD20 therapy alone (e.g., resistant to rituximab therapy). According to other related embodiments of the invention, methods are provided comprising administering an anti-CD3/anti-CD20 bispecific antigen-binding molecule as disclosed herein to a patient who is afflicted with a B-cell lymphoma (e.g., NHL) that is refractory to anti-CD20 therapy (e.g., a patient with a rituximab-refractory tumor or with relapsed or refractory B-cell lymphoma). Analytic/diagnostic methods known in the art, such as tumor scanning, etc., may be used to ascertain whether a patient harbors as tumor that is resistant to, incompletely responsive to, or refractory to anti-CD20 therapy alone.

The present invention also includes methods for treating residual cancer in a subject. As used herein, the term "residual cancer" means the existence or persistence of one or more cancerous cells in a subject following treatment with an anti-cancer therapy.

According to certain aspects, the present invention provides methods for treating a disease or disorder associated with CD20 expression (e.g., B cell lymphoma) comprising administering one or more of the bispecific antigen-binding molecules described elsewhere herein to a subject after the subject has received anti-CD20 mono-therapy (e.g., after administration of a pharmaceutical composition comprising an anti-CD20 antibody such as rituximab). For example, the present invention includes methods for treating B cell lymphoma comprising administering an anti-CD3/anti-CD20 bispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received anti-CD20 mono-therapy (e.g., rituximab treatment or an equivalent treatment thereof). In other aspects, a bispecific antigen-binding molecule of the invention (an anti-CD3/anti-CD20 bispecific antigen-binding molecule) comprising an IgG4 Fc domain is initially administered to a subject at one or more time points (e.g., to provide robust initial depletion of B cells), followed by administration of an equivalent bispecific antigen-binding molecule comprising a different IgG domain, such as an IgG1 Fc domain, at subsequent time points.

Combination Therapies and Formulations

The present invention provides methods which comprise administering a pharmaceutical composition comprising any of the exemplary antibodies and bispecific antigen-binding molecules described herein in combination with one or more additional therapeutic agents. Exemplary additional therapeutic agents that may be combined with or administered in combination with an antigen-binding molecule of the present invention include, e.g., an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody), a VEGF antagonist (e.g., a VEGF-Trap, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 antagonist (e.g., an anti-FOLH1 antibody), a PRLR antagonist (e.g., an anti-PRLR antibody), a STEAP1 or STEAP2 antagonist (e.g., an anti-STEAPi antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin antibody), a monovalent CD20 antagonist (e.g., a monovalent anti-CD20 antibody such as rituximab), etc. Other agents that may be beneficially administered in combination with the antigen-binding molecules of the invention include cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present invention (e.g., pharmaceutical compositions comprising an anti-CD3/anti-CD20 bispecific antigen-binding molecule as disclosed herein) may also be administered as part of a therapeutic regimen comprising one or more therapeutic combinations selected from "ICE": ifosfamide (e.g., Ifex®), carboplatin (e.g., Paraplatin®), etoposide (e.g., Etopophos®, Toposar®, VePesid®, VP-16); "DHAP": dexamethasone (e.g., Decadron®), cytarabine (e.g., Cytosar-U®, cytosine arabinoside, ara-C), cisplatin (e.g., Platinol®-AQ); and "ESHAP": etoposide (e.g., Etopophos®, Toposar®, VePesid®, VP-16), methylprednisolone (e.g., Medrol®), high-dose cytarabine, cisplatin (e.g., Platinol®-AQ).

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvIII, cMet, IGF1R, B-raf, PDGFR-α, PDGFR-β, FOLH1, PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; $F(ab')_2$ fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, corticosteroids and/or NSAIDs. The antigen-binding molecules of the invention may also be administered as part of a treatment regimen that also includes radiation treatment and/or conventional chemotherapy.

The additional therapeutically active component(s) may be administered just prior to, concurrent with, or shortly after the administration of an antigen-binding molecule of the present invention; (for purposes of the present disclosure, such administration regimens are considered the administration of an antigen-binding molecule "in combination with" an additional therapeutically active component).

The present invention includes pharmaceutical compositions in which an antigen-binding molecule of the present invention is co-formulated with one or more of the additional therapeutically active component(s) as described elsewhere herein.

Administration Regimens

According to certain embodiments of the present invention, multiple doses of an antigen-binding molecule (e.g., an anti-CD3 antibody or a bispecific antigen-binding molecule that specifically binds CD20 and CD3) may be administered to a subject over a defined time course. The methods according to this aspect of the invention comprise sequentially administering to a subject multiple doses of an antigen-binding molecule of the invention. As used herein, "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule (e.g., an anti-CD3 antibody or a bispecific antigen-binding molecule that specifically binds CD20 and CD3). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-CD3 antibodies of the present invention may also be used to detect and/or measure CD3, or CD3-expressing cells in a sample, e.g., for diagnostic purposes. For example, an anti-CD3 antibody, or fragment thereof, may be used to diagnose a condition or disease characterized by aberrant expression (e.g., over-expression, under-expression, lack of expression, etc.) of CD3. Exemplary diagnostic assays for CD3 may comprise, e.g., contacting a sample, obtained from a patient, with an anti-CD3 antibody of the invention, wherein the anti-CD3 antibody is labeled with a detectable label or reporter molecule. Alternatively, an unlabeled anti-CD3 antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure CD3 in a sample include enzyme-linked immunosorbent assay (ELISA), radioimmunoassay (RIA), and fluorescence-activated cell sorting (FACS). Samples that can be used in CD3 diagnostic assays according to the present invention include any tissue or fluid sample obtainable from a patient which contains detectable quantities of CD3 protein, or fragments thereof, under normal or pathological conditions. Generally, levels of CD3 in a particular sample obtained from a healthy patient (e.g., a patient not afflicted with a disease or condition associated with abnormal CD3 levels or activity) will be measured to initially establish a baseline, or standard, level of CD3. This baseline level of CD3 can then be compared against the levels of CD3 measured in samples obtained from individuals suspected of having a CD3 related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Anti-CD3 Antibodies

Anti-CD3 antibodies were obtained by immunizing a VELOCIMMUNE® mouse (i.e., an engineered mouse comprising DNA encoding human Immunoglobulin heavy and kappa light chain variable regions) with cells expressing CD3 or with DNA encoding CD3. The antibody immune response was monitored by a CD3-specific immunoassay. When a desired immune response was achieved splenocytes were harvested and fused with mouse myeloma cells to preserve their viability and form hybridoma cell lines. The hybridoma cell lines were screened and selected to identify cell lines that produce CD3-specific antibodies. Using this technique several anti-CD3 chimeric antibodies (i.e., antibodies possessing human variable domains and mouse constant domains) were obtained. In addition, several fully human anti-CD3 antibodies were isolated directly from antigen-positive B cells without fusion to myeloma cells, as described in US 2007/0280945A1.

Certain biological properties of the exemplary anti-CD3 antibodies generated in accordance with the methods of this Example are described in detail in the Examples set forth below.

Example 2. Heavy and Light Chain Variable Region Amino Acid and Nucleic Acid Sequences Table 1 sets forth the amino acid sequence identifiers of the heavy and light chain variable regions and CDRs of selected anti-CD3 antibodies of the invention. The corresponding nucleic acid sequence identifiers are set forth in Table 2.

TABLE 1

| Amino Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1H2712N | 2 | 4 | 6 | 8 | 10 | 12 | 14 | 16 |
| H1M2692N | 18 | 20 | 22 | 24 | 26 | 28 | 30 | 32 |
| H1M3542N | 34 | 36 | 38 | 40 | 42 | 44 | 46 | 48 |
| H1M3544N | 50 | 52 | 54 | 56 | 58 | 60 | 62 | 64 |
| H1M3549N | 66 | 68 | 70 | 72 | 74 | 76 | 78 | 80 |
| H1M3613N | 82 | 84 | 86 | 88 | 90 | 92 | 94 | 96 |
| H2M2689N | 98 | 100 | 102 | 104 | 106 | 108 | 110 | 112 |
| H2M2690N | 114 | 116 | 118 | 120 | 122 | 124 | 126 | 128 |
| H2M2691N | 130 | 132 | 134 | 136 | 138 | 140 | 142 | 144 |
| H2M2704N | 146 | 148 | 150 | 152 | 154 | 156 | 158 | 160 |
| H2M2705N | 162 | 164 | 166 | 168 | 170 | 172 | 174 | 176 |
| H2M2706N | 178 | 180 | 182 | 184 | 186 | 188 | 190 | 192 |
| H2M2707N | 194 | 196 | 198 | 200 | 202 | 204 | 206 | 208 |
| H2M2708N | 210 | 212 | 214 | 216 | 218 | 220 | 222 | 224 |
| H2M2709N | 226 | 228 | 230 | 232 | 234 | 236 | 238 | 240 |
| H2M2710N | 242 | 244 | 246 | 248 | 250 | 252 | 254 | 256 |
| H2M2711N | 258 | 260 | 262 | 264 | 266 | 268 | 270 | 272 |
| H2M2774N | 274 | 276 | 278 | 280 | 282 | 284 | 286 | 288 |
| H2M2775N | 290 | 292 | 294 | 296 | 298 | 300 | 302 | 304 |
| H2M2776N | 306 | 308 | 310 | 312 | 314 | 316 | 318 | 320 |
| H2M2777N | 322 | 324 | 326 | 328 | 330 | 332 | 334 | 336 |
| H2M2778N | 338 | 340 | 342 | 344 | 346 | 348 | 350 | 352 |
| H2M2779N | 354 | 356 | 358 | 360 | 362 | 364 | 366 | 368 |
| H2M2789N | 370 | 372 | 374 | 376 | 378 | 380 | 382 | 384 |
| H2M2862N | 386 | 388 | 390 | 392 | 394 | 396 | 398 | 400 |
| H2M2885N | 402 | 404 | 406 | 408 | 410 | 412 | 414 | 416 |
| H2M2886N | 418 | 420 | 422 | 424 | 426 | 428 | 430 | 432 |
| H2M3540N | 434 | 436 | 438 | 440 | 442 | 444 | 446 | 448 |
| H2M3541N | 450 | 452 | 454 | 456 | 458 | 460 | 462 | 464 |
| H2M3543N | 466 | 468 | 470 | 472 | 474 | 476 | 478 | 480 |
| H2M3547N | 482 | 484 | 486 | 488 | 490 | 492 | 494 | 496 |
| H2M3548N | 498 | 500 | 502 | 504 | 506 | 508 | 510 | 512 |
| H2M3563N | 514 | 516 | 518 | 520 | 522 | 524 | 526 | 528 |
| H1H5751P | 530 | 532 | 534 | 536 | 538 | 540 | 542 | 544 |
| H1H5752P | 546 | 548 | 550 | 552 | 554 | 556 | 558 | 560 |
| H1H5753B | 562 | 564 | 566 | 568 | 570 | 572 | 574 | 576 |
| H1H5754B | 578 | 580 | 582 | 584 | 586 | 588 | 590 | 592 |
| H1H5755B | 594 | 596 | 598 | 600 | 602 | 604 | 606 | 608 |
| H1H5756B | 610 | 612 | 614 | 616 | 618 | 620 | 622 | 624 |
| H1H5757B | 626 | 628 | 630 | 632 | 634 | 636 | 638 | 640 |
| H1H5758B | 642 | 644 | 646 | 648 | 650 | 652 | 654 | 656 |
| H1H5761P | 658 | 660 | 662 | 664 | 666 | 668 | 670 | 672 |
| H1H5763P | 674 | 676 | 678 | 680 | 682 | 684 | 686 | 688 |
| H1H5764P | 690 | 692 | 694 | 696 | 698 | 700 | 702 | 704 |
| H1H5769P | 706 | 708 | 710 | 712 | 714 | 716 | 718 | 720 |
| H1H5771P | 722 | 724 | 726 | 728 | 730 | 732 | 734 | 736 |
| H1H5772P | 738 | 740 | 742 | 744 | 746 | 748 | 750 | 752 |
| H1H5777P | 754 | 756 | 758 | 460 | 762 | 764 | 766 | 768 |
| H1H5778P | 770 | 772 | 774 | 776 | 778 | 780 | 782 | 784 |
| H1H5780P | 786 | 788 | 790 | 792 | 794 | 796 | 798 | 800 |
| H1H5781P | 802 | 804 | 806 | 808 | 810 | 812 | 814 | 816 |
| H1H5782P | 818 | 820 | 822 | 824 | 826 | 828 | 830 | 832 |
| H1H5785B | 834 | 836 | 838 | 840 | 842 | 844 | 846 | 848 |
| H1H5786B | 850 | 852 | 854 | 856 | 858 | 860 | 862 | 864 |
| H1H5788P | 866 | 868 | 870 | 872 | 874 | 876 | 878 | 880 |
| H1H5790B | 882 | 884 | 886 | 888 | 890 | 892 | 894 | 896 |
| H1H5791B | 898 | 900 | 902 | 904 | 906 | 908 | 910 | 912 |
| H1H5792B | 914 | 916 | 918 | 920 | 922 | 924 | 926 | 928 |
| H1H5793B | 930 | 932 | 934 | 936 | 938 | 940 | 942 | 944 |
| H1H5795B | 946 | 948 | 950 | 952 | 954 | 956 | 958 | 960 |
| H1H5796B | 962 | 964 | 966 | 968 | 970 | 972 | 974 | 976 |
| H1H5797B | 978 | 980 | 982 | 984 | 986 | 988 | 990 | 992 |
| H1H5798B | 994 | 996 | 998 | 1000 | 1002 | 1004 | 1006 | 1008 |
| H1H5799P | 1010 | 1012 | 1014 | 1016 | 1018 | 1020 | 1022 | 1024 |
| H1H5801B | 1026 | 1028 | 1030 | 1032 | 1034 | 1036 | 1038 | 1040 |
| H1H7194B | 1042 | 1044 | 1046 | 1048 | 1234 | 1236 | 1238 | 1240 |
| H1H7195B | 1050 | 1052 | 1054 | 1056 | 1234 | 1236 | 1238 | 1240 |
| H1H7196B | 1058 | 1060 | 1062 | 1064 | 1234 | 1236 | 1238 | 1240 |
| H1H7198B | 1066 | 1068 | 1070 | 1072 | 1234 | 1236 | 1238 | 1240 |
| H1H7203B | 1074 | 1076 | 1078 | 1080 | 1234 | 1236 | 1238 | 1240 |
| H1H7204B | 1082 | 1084 | 1086 | 1088 | 1234 | 1236 | 1238 | 1240 |
| H1H7208B | 1090 | 1092 | 1094 | 1096 | 1234 | 1236 | 1238 | 1240 |
| H1H7211B | 1098 | 1100 | 1102 | 1104 | 1234 | 1236 | 1238 | 1240 |
| H1H7221B | 1106 | 1108 | 1110 | 1112 | 1234 | 1236 | 1238 | 1240 |

TABLE 1-continued

| Amino Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1H7223B | 1114 | 1116 | 1118 | 1120 | 1234 | 1236 | 1238 | 1240 |
| H1H7226B | 1122 | 1124 | 1126 | 1128 | 1234 | 1236 | 1238 | 1240 |
| H1H7232B | 1130 | 1132 | 1134 | 1136 | 1234 | 1236 | 1238 | 1240 |
| H1H7233B | 1138 | 1140 | 1142 | 1144 | 1234 | 1236 | 1238 | 1240 |
| H1H7241B | 1146 | 1148 | 1150 | 1152 | 1234 | 1236 | 1238 | 1240 |
| H1H7242B | 1154 | 1156 | 1158 | 1160 | 1234 | 1236 | 1238 | 1240 |
| H1H7250B | 1162 | 1164 | 1166 | 1168 | 1234 | 1236 | 1238 | 1240 |
| H1H7251B | 1170 | 1172 | 1174 | 1176 | 1234 | 1236 | 1238 | 1240 |
| H1H7254B | 1178 | 1180 | 1182 | 1184 | 1234 | 1236 | 1238 | 1240 |
| H1H7258B | 1186 | 1188 | 1190 | 1192 | 1234 | 1236 | 1238 | 1240 |
| H1H7269B | 1194 | 1196 | 1198 | 1200 | 1234 | 1236 | 1238 | 1240 |
| H1H7279B | 1202 | 1204 | 1206 | 1208 | 1234 | 1236 | 1238 | 1240 |
| H1xH7221G | 1210 | 1212 | 1214 | 1216 | 1234 | 1236 | 1238 | 1240 |
| H1xH7221G3 | 1218 | 1220 | 1222 | 1224 | 1234 | 1236 | 1238 | 1240 |
| H1xH7221G5 | 1226 | 1228 | 1230 | 1232 | 1234 | 1236 | 1238 | 1240 |

Antibodies are typically referred to herein according to the following nomenclature: Fc prefix (e.g. "H1H," "H1M," "H2M," etc.), followed by a numerical identifier (e.g. "2712," "2692," etc., as shown in Table 1), followed by a "P," "N," or "B" suffix. Thus, according to this nomenclature, an antibody may be referred to herein as, e.g., "H1H2712N," "H1M2692N," "H2M2689N," etc. The H1H, H1M and H2M prefixes on the antibody designations used herein indicate the particular Fc region isotype of the antibody. For example, an "H1H" antibody has a human IgG1 Fc, an "H1M" antibody has a mouse IgG1 Fc, and an "H2M" antibody has a mouse IgG2 Fc, (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Table 1—will remain the same, and the binding properties are expected to be identical or substantially similar regardless of the nature of the Fc domain.

Control Constructs Used in the Following Examples

Various control constructs (anti-CD3 antibodies) were included in the following experiments for comparative purposes: "OKT-3," a mouse monoclonal antibody against human T-cell surface antigens available from the American Type Culture Collection (ATCC) under catalog no. CRL-8001; and "SP34," a commercially available mouse monoclonal antibody obtained from Biolegend, San Diego, CA (Cat. No. 302914), reactive against the epsilon chain of the T3 complex on human T lymphocyte cells.

Example 3. Surface Plasmon Resonance Derived Binding Affinities and Kinetic Constants of Human Monoclonal Anti-CD3 Antibodies Binding affinities and kinetic constants of human monoclonal anti-CD3 antibodies were determined by surface plasmon resonance at 25° C. using either an antibody-capture format (Tables 3, 5 and 7) or an antigen-capture format (Tables 4, 6 and 8). Measurements were conducted on a T200 Biacore instrument.

In the antibody-capture format, the Biacore sensor surface was derivatized with a rabbit anti-mouse Fc for hybridoma capture (antibody prefix H1M or H2M) or a mouse anti-human Fc surface for human IgG formatted antibodies (antibody prefix H1H). Soluble heterodimeric CD3 protein (hCD3-epsilon/hCD3-delta; SEQ ID NOs:1370/1371) with either a human Fc tag (hFcΔΔdp/hFc; SEQ ID NOs:1372/1373) or a mouse Fc tag (mFcΔΔdp/mFc; SEQ ID NOs: 1374/1375) was injected over the antibody captured surface and the binding response was recorded. Heterodimeric CD3 protein was purified using the method described in Davis et al. (US2010/0331527).

In the antigen-capture format, heterodimeric CD3 protein was captured using a rabbit anti-mouse Fc or mouse anti-human Fc and the respective antibodies were injected over the captured antigen.

Antibodies were analyzed in their conventional divalent format (Tables 3 to 6) or in a monovalent 1-arm configuration (Tables 7 and 8) in which the second Fab from the antibody was removed and only the Fc portion (CH2-CH3) was expressed.

Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D$ (M)=$k_d/k_a$; and $t_{1/2}$ (min)=(ln2/(60*$k_d$)). NT=not tested; NB=no binding observed.

TABLE 3

| Biacore Binding Affinities of Hybridoma mAbs (H1M and H2M) Binding at 25° C./Antibody-Capture Format | | | | |
|---|---|---|---|---|
| Antibody | ka ($Ms^{-1}$) | kd ($s^{-1}$) | $K_D$ (Molar) | T½ (min) |
| H2M2689N | 7.73E+05 | 3.23E−03 | 4.18E−09 | 4 |
| H2M2690N | 9.70E+03 | 2.02E−04 | 2.09E−08 | 57 |
| H2M2691N | 1.03E+04 | 2.07E−04 | 2.01E−08 | 56 |
| H1M2692N | 8.05E+03 | 4.34E−04 | 5.39E−08 | 27 |
| H2M2704N | 3.46E+04 | 6.92E−04 | 2.00E−08 | 17 |
| H2M2705N | 6.62E+04 | 9.10E−04 | 1.37E−08 | 13 |
| H2M2706N | 3.29E+04 | 4.44E−03 | 1.35E−07 | 3 |
| H2M2707N | 2.95E+04 | 1.87E−03 | 6.35E−08 | 6 |
| H2M2708N | 6.94E+04 | 6.12E−04 | 8.82E−09 | 19 |
| H2M2709N | NT | NT | NT | NT |
| H2M2710N | 6.72E+04 | 7.53E−04 | 1.12E−08 | 15 |
| H2M2711N | 6.72E+04 | 7.67E−04 | 1.14E−08 | 15 |
| H1M2712N | 9.32E+03 | 2.19E−04 | 2.35E−08 | 53 |
| H2M2774N | 7.79E+04 | 9.18E−04 | 1.18E−08 | 13 |
| H2M2775N | 6.97E+04 | 6.26E−04 | 8.98E−09 | 18 |

TABLE 3-continued

Biacore Binding Affinities of Hybridoma mAbs (H1M and H2M) Binding at 25° C./Antibody-Capture Format

| Antibody | ka ($Ms^{-1}$) | kd ($s^{-1}$) | $K_D$ (Molar) | T½ (min) |
|---|---|---|---|---|
| H2M2776N | 6.29E+04 | 6.39E−04 | 1.02E−08 | 18 |
| H2M2777N | 3.70E+04 | 1.63E−03 | 4.39E−08 | 7 |
| H2M2778N | 2.13E+04 | 1.89E−04 | 8.90E−09 | 61 |
| H2M2779N | 2.18E+04 | 2.28E−04 | 1.05E−08 | 51 |
| H2M2789N | NT | NT | NT | NT |
| H2M2862N | 3.72E+04 | 3.00E−03 | 8.07E−08 | 4 |
| H2M2885N | 6.82E+04 | 6.51E−04 | 9.54E−09 | 18 |
| H2M2886N | 7.29E+04 | 6.53E−04 | 8.96E−09 | 18 |
| H2M3540N | 3.77E+04 | 6.11E−04 | 1.62E−08 | 19 |
| H2M3541N | 7.10E+03 | 1.35E−03 | 1.89E−07 | 9 |
| H1M3542N | 2.37E+04 | 5.08E−04 | 2.14E−08 | 23 |
| H2M3543N | 7.53E+03 | 2.26E−04 | 3.00E−08 | 51 |
| H1M3544N | 9.69E+03 | 1.42E−04 | 1.46E−08 | 82 |
| H2M3547N | 2.18E+04 | 3.47E−04 | 1.59E−08 | 33 |
| H2M3548N | 3.87E+04 | 5.04E−03 | 1.30E−07 | 2 |
| H1M3549N | 1.18E+04 | 9.19E−04 | 7.76E−08 | 13 |
| H2M3563N | 3.24E+04 | 1.19E−04 | 3.66E−09 | 97 |
| H1M3613N | 1.93E+04 | 3.04E−04 | 1.57E−08 | 38 |

TABLE 4

Biacore Binding Affinities of Hybridoma mAbs (H1M and H2M) Binding at 25° C./Antigen-Capture Format

| Antibody | ka ($Ms^{-1}$) | kd ($s^{-1}$) | $K_D$ (Molar) | T½ (min) |
|---|---|---|---|---|
| H2M2689N | 1.71E+06 | 9.97E−05 | 5.83E−11 | 116 |
| H2M2690N | 7.51E+04 | 6.35E−06 | 7.99E−11 | 1820 |
| H2M2691N | 3.94E+04 | 9.98E−06 | 2.54E−10 | 1158 |
| H1M2692N | 4.19E+04 | 9.90E−06 | 2.38E−10 | 1167 |
| H2M2704N | 1.32E+06 | 2.48E−04 | 1.87E−10 | 47 |
| H2M2705N | 2.43E+06 | 3.41E−04 | 1.40E−10 | 34 |
| H2M2706N | 5.63E+05 | 3.06E−04 | 5.44E−10 | 38 |
| H2M2707N | 3.99E+05 | 2.85E−04 | 7.15E−10 | 41 |
| H2M2708N | 1.73E+06 | 2.27E−04 | 1.31E−10 | 51 |
| H2M2709N | NT | NT | NT | NT |
| H2M2710N | 1.59E+06 | 2.43E−04 | 1.53E−10 | 48 |
| H2M2711N | 1.59E+06 | 2.40E−04 | 1.51E−10 | 48 |
| H1M2712N | 4.75E+04 | 1.37E−05 | 2.95E−10 | 846 |
| H2M2774N | 2.49E+06 | 3.36E−04 | 1.35E−10 | 34 |
| H2M2775N | 1.56E+06 | 2.16E−04 | 1.38E−10 | 53 |
| H2M2776N | 1.58E+06 | 2.22E−04 | 1.40E−10 | 52 |
| H2M2777N | 5.80E+05 | 3.21E−04 | 5.54E−10 | 36 |
| H2M2778N | 1.50E+05 | 6.57E−06 | 4.68E−11 | 1758 |
| H2M2779N | 1.28E+05 | 1.23E−05 | 9.38E−11 | 941 |
| H2M2789N | NT | NT | NT | NT |
| H2M2862N | 5.91E+05 | 3.21E−04 | 5.41E−10 | 36 |
| H2M2885N | 1.37E+06 | 1.52E−04 | 1.11E−10 | 76 |
| H2M2886N | 1.42E+06 | 1.36E−04 | 9.56E−11 | 85 |
| H2M3540N | 2.55E+06 | 5.87E−04 | 2.31E−10 | 20 |
| H2M3541N | 8.40E+04 | 1.16E−03 | 1.38E−08 | 10 |
| H1M3542N | 4.37E+05 | 2.00E−04 | 4.57E−10 | 58 |
| H2M3543N | 1.22E+05 | 7.96E−05 | 6.53E−10 | 145 |
| H1M3544N | 5.74E+04 | 5.98E−05 | 1.04E−09 | 193 |
| H2M3547N | 4.70E−05 | 1.00E−05 | 2.15E−11 | 1155 |
| H2M3548N | NT | NT | NT | NT |
| H1M3549N | 2.81E+05 | 2.89E−04 | 1.03E−09 | 40 |
| H2M3563N | 6.16E+05 | 4.77E−05 | 7.73E−11 | 242 |
| H1M3613N | 2.20E+05 | 9.60E−05 | 4.35E−10 | 120 |

TABLE 5

Biacore Binding Affinities of Human Fc mAbs (H1H) Binding at 25° C./Antibody-Capture Format

| Antibody | ka ($Ms^{-1}$) | kd ($s^{-1}$) | $K_D$ (Molar) | T½ (min) |
|---|---|---|---|---|
| H1H2690N | NT | NT | NT | NT |
| H1H2712N | 3.06E+03 | 2.70E−04 | 8.82E−08 | 43 |
| H1H5751P | 4.01E+03 | 5.18E−04 | 1.29E−07 | 22 |

TABLE 5-continued

Biacore Binding Affinities of Human Fc mAbs (H1H) Binding at 25° C./Antibody-Capture Format

| Antibody | ka ($Ms^{-1}$) | kd ($s^{-1}$) | $K_D$ (Molar) | T½ (min) |
|---|---|---|---|---|
| H1H5752P | NB | NB | NB | NB |
| H1H5753B | NT | NT | NT | NT |
| H1H5755B | 8.21E+03 | 4.72E−04 | 5.75E−08 | 24 |
| H1H5756B | 8.15E+03 | 2.66E−04 | 3.26E−08 | 43 |
| H1H5757B | 6.63E+03 | 7.85E−04 | 1.18E−07 | 15 |
| H1H5758B | 5.02E+03 | 1.17E−03 | 2.33E−07 | 10 |
| H1H5761P | 4.72E+03 | 2.44E−02 | 5.16E−06 | 0 |
| H1H5763P | 1.85E+04 | 5.40E−02 | 2.92E−06 | 0 |
| H1H5764P | 4.16E+03 | 1.59E−02 | 3.82E−06 | 1 |
| H1H5769P | 7.80E+03 | 9.41E−04 | 1.21E−07 | 12 |
| H1H5771P | 3.00E+04 | 6.26E−04 | 2.09E−08 | 18 |
| H1H5772S | 1.56E+04 | 1.55E−03 | 9.96E−08 | 7 |
| H1H5777P | 1.35E+04 | 3.02E−03 | 2.24E−07 | 4 |
| H1H5778P | 5.52E+03 | 1.54E−04 | 2.78E−08 | 75 |
| H1H5780P | 1.31E+04 | 3.99E−04 | 3.04E−08 | 29 |
| H1H5781P | 8.61E+03 | 4.97E−04 | 5.77E−08 | 23 |
| H1H5782P | NB | NB | NB | NB |
| H1H5785B | NT | NT | NT | NT |
| H1H5786B | 1.26E+04 | 1.08E−03 | 8.54E−08 | 11 |
| H1H5788P | 2.88E+03 | 2.91E−04 | 1.01E−07 | 40 |
| H1H5790B | 1.82E+04 | 5.17E−04 | 2.83E−08 | 22 |
| H1H5791B | 1.09E+04 | 7.90E−04 | 7.25E−08 | 15 |
| H1H5792B | NT | NT | NT | NT |
| H1H5793B | 8.54E+03 | 3.82E−04 | 4.47E−08 | 30 |
| H1H5795B | 1.73E+04 | 5.76E−04 | 3.33E−08 | 20 |
| H1H5796B | 1.47E+04 | 8.91E−04 | 6.05E−08 | 13 |
| H1H5797B | NT | NT | NT | NT |
| H1H5798B | NT | NT | NT | NT |
| H1H5799P | 1.36E+04 | 7.88E−03 | 5.79E−07 | 1 |
| H1H5801B | 6.57E+03 | 1.62E−03 | 2.46E−07 | 7 |
| OKT3 | 2.10E+06 | 2.00E+00 | 1.00E−06 | 0.35 sec |

TABLE 6

Biacore Binding Affinities of Human Fc mAbs (H1H) Binding at 25° C./Antigen-Capture Format

| Antibody | ka ($Ms^{-1}$) | kd ($s^{-1}$) | $K_D$ (Molar) | T½ (min) |
|---|---|---|---|---|
| H1H2690N | NT | NT | NT | NT |
| H1H2712N | 8.93E+04 | 8.68E−05 | 9.71E−10 | 133 |
| H1H5751P | 7.24E+04 | 2.47E−04 | 3.42E−09 | 47 |
| H1H5752P | NB | NB | NB | NB |
| H1H5753B | NT | NT | NT | NT |
| H1H5755B | 2.15E+05 | 2.01E−04 | 9.36E−10 | 57 |
| H1H5756B | 1.44E+05 | 1.11E−04 | 7.67E−10 | 105 |
| H1H5757B | 1.80E+05 | 2.95E−04 | 1.64E−09 | 39 |
| H1H5758B | 1.42E+05 | 5.62E−04 | 3.97E−09 | 21 |
| H1H5761P | 2.11E+05 | 1.13E−02 | 5.34E−08 | 1 |
| H1H5763P | 1.84E+05 | 1.70E−02 | 9.24E−08 | 1 |
| H1H5764P | 3.50E+05 | 7.36E−03 | 2.10E−08 | 2 |
| H1H5769P | 1.19E+05 | 5.23E−04 | 4.41E−09 | 22 |
| H1H5771P | 9.23E+05 | 3.42E−04 | 3.71E−10 | 34 |
| H1H5772S | 5.19E+05 | 8.69E−04 | 1.67E−09 | 13 |
| H1H5777P | 4.83E+05 | 1.70E−03 | 3.52E−09 | 7 |
| H1H5778P | 3.99E+05 | 3.42E−05 | 8.56E−11 | 338 |
| H1H5780P | 4.78E+05 | 1.71E−04 | 3.58E−10 | 68 |
| H1H5781P | 1.40E+05 | 2.68E−04 | 1.92E−09 | 43 |
| H1H5782P | NB | NB | NB | NB |
| H1H5785B | NT | NT | NT | NT |
| H1H5786B | 3.00E+06 | 4.24E−04 | 1.41E−10 | 27 |
| H1H5788P | 7.06E+04 | 1.64E−04 | 2.33E−09 | 70 |
| H1H5790B | 9.25E+05 | 2.36E−04 | 2.54E−10 | 49 |
| H1H5791B | 7.86E+05 | 3.40E−04 | 4.33E−10 | 34 |
| H1H5792B | NT | NT | NT | NT |
| H1H5793B | 4.78E+05 | 1.59E−04 | 3.33E−10 | 73 |
| H1H5795B | 1.58E+06 | 2.29E−04 | 1.45E−10 | 50 |
| H1H5796B | 1.05E+05 | 2.44E−04 | 2.32E−09 | 47 |
| H1H5797B | NT | NT | NT | NT |
| H1H5798B | NT | NT | NT | NT |

TABLE 6-continued

| Biacore Binding Affinities of Human Fc mAbs (H1H) Binding at 25° C./Antigen-Capture Format | | | | |
|---|---|---|---|---|
| Antibody | ka ($Ms^{-1}$) | kd ($s^{-1}$) | $K_D$ (Molar) | T½ (min) |
| H1H5799P | 7.18E+05 | 5.64E−03 | 7.85E−09 | 2 |
| H1H5801B | 3.31E+05 | 1.12E−03 | 3.38E−09 | 10 |
| OKT3 | 3.94E+06 | 2.18E−02 | 5.53E−09 | 0.5 |

TABLE 7

| Biacore Binding Affinities of monovalent 1-arm mAbs Binding at 25° C./Antibody-Capture Format | | | | |
|---|---|---|---|---|
| Antibody | ka ($Ms^{-1}$) | kd ($s^{-1}$) | $K_D$ (Molar) | T½ (min) |
| H1H7194P | 1.16E+04 | 1.51E−04 | 1.30E−08 | 76 |
| H1H7195P | 3.13E+04 | 9.89E−05 | 3.16E−09 | 117 |
| H1H7196P | 1.07E+04 | 4.43E−04 | 4.13E−08 | 26 |
| H1H7198P | 2.63E+04 | 1.58E−04 | 6.02E−09 | 73 |
| H1H7203P | 1.46E+04 | 2.67E−04 | 1.83E−08 | 43 |
| H1H7204P | 1.43E+04 | 3.62E−04 | 2.53E−08 | 32 |
| H1H7208P | NT | NT | NT | NT |
| H1H7211P | 1.41E+04 | 1.59E−04 | 1.13E−08 | 73 |
| H1H7221P | 1.07E+04 | 2.92E−04 | 2.75E−08 | 40 |
| H1H7223P | 1.60E+04 | 3.07E−04 | 1.92E−08 | 38 |
| H1H7226P | 1.30E+04 | 3.55E−04 | 2.72E−08 | 33 |
| H1H7232P | 8.03E+03 | 1.77E−03 | 2.20E−07 | 7 |
| H1H7233P | 1.11E+04 | 2.69E−04 | 2.42E−08 | 43 |
| H1H7241P | 1.34E+04 | 2.95E−04 | 2.20E−08 | 39 |
| H1H7242P | 2.15E+04 | 6.64E−04 | 3.09E−08 | 17 |
| H1H7250P | 2.34E+04 | 2.47E−04 | 1.05E−08 | 47 |
| H1H7251P | 2.56E+04 | 1.07E−03 | 4.17E−08 | 11 |
| H1H7254P | 2.60E+04 | 3.88E−04 | 1.49E−08 | 30 |
| H1H7258P | 1.26E+04 | 3.02E−04 | 2.40E−08 | 38 |
| H1H7269P | 2.57E+04 | 6.24E−03 | 2.43E−07 | 2 |
| H1H7279P | NB | NB | NB | NB |
| H1xH7221G | NT | NT | NT | NT |
| H1xH7221G3 | NB | NB | NB | NB |
| H1xH7221G5 | NB | NB | NB | NB |

TABLE 8

| Biacore Binding Affinities of monovalent 1-arm mAbs Binding at 25° C./Antigen-Capture Format | | | | |
|---|---|---|---|---|
| Antibody | ka ($Ms^{-1}$) | kd ($s^{-1}$) | $K_D$ (Molar) | T½ (min) |
| H1H7194P | 3.50E+05 | 8.43E−05 | 2.41E−10 | 137 |
| H1H7195P | 5.66E+05 | 7.14E−05 | 1.26E−10 | 162 |
| H1H7196P | 1.85E+05 | 4.61E−04 | 2.49E−09 | 25 |
| H1H7198P | 6.28E+05 | 7.07E−05 | 1.12E−10 | 163 |
| H1H7203P | 4.79E+05 | 2.38E−04 | 4.98E−10 | 48 |
| H1H7204P | 1.73E+05 | 3.65E−04 | 2.12E−09 | 32 |
| H1H7208P | NT | NT | NT | NT |
| H1H7211P | 3.45E+05 | 9.61E−05 | 2.79E−10 | 120 |
| H1H7221P | 1.36E+05 | 2.39E−04 | 1.75E−09 | 48 |
| H1H7223P | 1.87E+05 | 2.86E−04 | 1.53E−09 | 40 |
| H1H7226P | 4.18E+05 | 2.36E−04 | 5.65E−10 | 49 |
| H1H7232P | 1.49E+05 | 1.49E−03 | 1.00E−08 | 8 |
| H1H7233P | 1.61E+05 | 2.04E−04 | 1.27E−09 | 57 |
| H1H7241P | 1.87E+05 | 2.36E−04 | 1.26E−09 | 49 |
| H1H7242P | 3.83E+05 | 1.01E−03 | 2.63E−09 | 11 |
| H1H7250P | 2.31E+05 | 1.89E−04 | 8.20E−10 | 61 |
| H1H7251P | 4.47E+05 | 1.19E−03 | 2.67E−09 | 10 |
| H1H7254P | 4.33E+05 | 3.30E−04 | 7.62E−10 | 35 |
| H1H7258P | 1.33E+05 | 2.90E−04 | 2.18E−09 | 40 |
| H1H7269P | 2.77E+05 | 6.89E−03 | 2.49E−08 | 2 |
| H1H7279P | NB | NB | NB | NB |
| H1xH7221G | NT | NT | NT | NT |
| H1xH7221G3 | NB | NB | NB | NB |
| H1xH7221G5 | NB | NB | NB | NB |

As shown in Tables 3-8, Several anti-CD3 antibodies of the present invention bind CD3, in either antibody-capture or antigen-capture formats, with high affinity.

Example 4. Anti-CD3 Antibodies Bind and Proliferate Human T-Cells

Anti-CD3 antibodies of the present invention were tested for their ability to bind to human T-cells and induce their proliferation. Binding was assessed using Jurkat cells (a CD3+ human T-cell line), while proliferation of Peripheral Blood Mononuclear Cells (PBMC) was assessed using ATP catalyzed quantification (CellTiter Glo®). Anti-CD3 antibody OKT3 acted as a positive control and irrelevant isotype matched antibodies served as negative controls.

FACS data was acquired using the following protocol: Cells at $2\times10^5$ per well were incubated with serially diluted antibodies for 30 min on ice. Post incubation, cells were washed and secondary antibody was added and incubated for an additional 30 minutes. After incubation, cells were washed, re-suspended in cold PBS containing 1% BSA and analyzed by flow cytometry with viable Jurkat cells gated by side and forward scatters. The $EC_{50}S$ for cell binding titration were determined using Prism software with values calculated using a 4-parameter non-linear regression analysis.

Proliferation data was acquired using the following protocol: Human PBMC ($5\times10^4$/well) were incubated with a 3-fold serial dilution of anti-CD3 and a fixed concentration of a commercial anti-CD28 antibody (200 ng/ml) in 96 well plates for 72 h at 3700. Following incubation, CellTiter Glo® was added and luminescence was measured using a VICTOR X5 multi-label plate reader (PerkinElmer). The $EC_{50}$ of cell viability (ATP catalyzed quantification) was calculated using a 4-parameter non-linear regression analysis in GraphPad Prism.

Results of the binding and proliferation experiments are summarized in Tables 9-11.

TABLE 9

| Hybridoma Anti-CD3 mAbs Bind & Proliferate Human T-Cells | | |
|---|---|---|
| Antibody | EC50 [M] FACS JURKAT | EC50 [M] hPBMC Proliferation |
| H2M2689N | NB | 0.00E+00 |
| H2M2690N | 4.37E−09 | 5.37E−12 |
| H2M2691N | 6.77E−09 | 3.43E−11 |
| H1M2692N | 5.99E−09 | 1.42E−10 |
| H2M2704N | 8.45E−10 | 2.93E−12 |
| H2M2705N | 2.96E−10 | 1.76E−11 |
| H2M2706N | 2.37E−09 | 3.86E−12 |
| H2M2707N | 1.24E−07 | 1.92E−12 |
| H2M2708N | 6.58E−10 | 2.69E−08 |
| H2M2709N | 7.11E−10 | 2.48E−11 |
| H2M2710N | 7.10E−10 | 2.11E−10 |
| H2M2711N | 1.16E−09 | 6.48E−10 |
| H1M2712N | 2.19E−08 | 1.28E−10 |
| H2M2774N | 3.52E−10 | 4.92E−10 |
| H2M2775N | 1.32E−09 | 1.09E−09 |
| H2M2776N | 4.91E−10 | 2.84E−11 |
| H2M2777N | 2.16E−09 | 2.51E−11 |
| H2M2778N | 3.62E−09 | 0.00E+00 |
| H2M2779N | NT | 0.00E+00 |
| H2M2789N | NT | 2.85E−08 |
| H2M2862N | 7.68E−09 | 6.72E−13 |
| H2M2885N | 2.09E−09 | 2.49E−12 |
| H2M2886N | 3.97E−09 | 2.69E−12 |
| H2M3540N | 3.99E−09 | 3.16E−12 |
| H2M3541N | 3.70E−09 | 6.40E−12 |

TABLE 9-continued

| Hybridoma Anti-CD3 mAbs Bind & Proliferate Human T-Cells | | |
|---|---|---|
| Antibody | EC50 [M] FACS JURKAT | EC50 [M] hPBMC Proliferation |
| H1M3542N | 2.01E−09 | 0.00E+00 |
| H2M3543N | 5.63E−09 | 6.12E−12 |
| H1M3544N | 2.32E−08 | 0.00E+00 |
| H2M3547N | 2.71E−09 | 5.02E−12 |
| H2M3548N | 1.10E−09 | 1.89E−12 |
| H1M3549N | 2.30E−09 | 0.00E+00 |
| H2M3563N | 1.07E−09 | 7.74E−12 |
| H1M3613N | 1.03E−08 | 0.00E+00 |
| Isotype Ctrl | NB | 0.00E+00 |

NB: No Binding;
NT: Not Tested

TABLE 10

| Human Fc Anti-CD3 mAbs Bind & Proliferate Human T-Cells | | |
|---|---|---|
| Antibody | EC50 [M] FACS JURKAT | EC50 [M] hPBMC Proliferation |
| H1H5751P | 2.12E−09 | 9.29E−12 |
| H1H5752P | 3.43E−10 | 1.09E−12 |
| H1H5753B | NB | 9.14E−11 |
| H1H5755B | 1.23E−09 | 4.24E−12 |
| H1H5756B | NB | 0.00E+00 |
| H1H5757B | 3.38E−09 | 4.86E−12 |
| H1H5758B | 1.90E−09 | 2.13E−12 |
| H1H5761P | 2.10E−09 | 3.62E−13 |
| H1H5763P | 2.76E−09 | 3.11E−13 |
| H1H5764P | 8.80E−10 | 3.27E−13 |
| H1H5769P | 4.10E−09 | 6.17E−12 |
| H1H5771P | NT | 6.35E−12 |
| H1H5772S | 6.64E−10 | 4.42E−12 |
| H1H5777P | 5.71E−10 | 3.04E−12 |
| H1H5778P | 6.85E−10 | 5.04E−12 |
| H1H5780P | 7.62E−10 | 3.44E−12 |
| H1H5781P | 1.23E−09 | 6.08E−12 |
| H1H5782P | NB | 5.17E−12 |
| H1H5785B | NB | 0.00E+00 |
| H1H5786B | 1.10E−09 | 1.79E−12 |
| H1H5788P | 3.53E−09 | 4.62E−12 |
| H1H5790B | 3.55E−09 | 2.71E−12 |
| H1H5791B | 3.77E−09 | 1.75E−12 |
| H1H5792B | 5.87E−09 | 6.47E−12 |
| H1H5793B | 4.62E−09 | 3.28E−12 |
| H1H5795B | 2.04E−09 | 3.09E−12 |
| H1H5796B | 9.82E−09 | 4.37E−12 |
| H1H5797B | 3.96E−08 | 1.07E−11 |
| H1H5798B | 5.57E−09 | 2.59E−12 |
| H1H5799P | NT | 1.63E−13 |
| H1H5801B | 1.55E−08 | 1.09E−12 |
| OKT3 | 1.96E−10 | 3.30E−13 |
| Isotype Ctrl | NB | 0.00E+00 |

NB: No Binding;
NT: Not Tested

TABLE 11

| Monovalent 1-arm Anti-CD3 mAbs Bind & Proliferate Human T-Cells | | |
|---|---|---|
| Antibody | EC50 [M] FACS JURKAT | EC50 [M] hPBMC Proliferation |
| H1H7194P | 1.50E−09 | 2.37E−12 |
| H1H7195P | 3.42E−10 | 2.42E−12 |
| H1H7196P | 3.44E−08 | 1.27E−12 |
| H1H7198P | 7.26E−10 | 2.55E−12 |
| H1H7203P | 3.24E−09 | 1.64E−12 |
| H1H7204P | 2.29E−09 | 1.51E−12 |
| H1H7208P | 5.19E−08 | 1.46E−12 |
| H1H7211P | 7.01E−10 | 2.75E−12 |
| H1H7221P | 1.40E−09 | 2.60E−12 |
| H1H7223P | 9.37E−10 | 1.07E−12 |
| H1H7226P | 7.95E−10 | 9.52E−13 |
| H1H7232P | 1.50E−09 | 1.03E−12 |
| H1H7233P | 7.15E−10 | 7.34E−13 |
| H1H7241P | 1.01E−09 | 1.05E−12 |
| H1H7242P | 1.83E−09 | 2.13E−12 |
| H1H7250P | 1.37E−09 | 2.43E−12 |
| H1H7251P | 1.45E−09 | 1.30E−12 |
| H1H7254P | 1.09E−09 | 2.80E−12 |
| H1H7258P | 1.07E−09 | 2.17E−12 |
| H1H7269P | 1.95E−09 | 1.15E−12 |
| H1H7279P | NB | 0.00E+00 |
| Isotype Ctrl | NB | 0.00E+00 |

NB: No Binding;
NT: Not Tested

As shown in Tables 7-9, the vast majority of anti-CD3 antibodies of the invention bound human T-cells and induced T-cell proliferation.

Example 5. Anti-CD3 Antibodies Bind and Proliferate Monkey T-Cells

A subset of antd-CD3 antibodies of the invention was tested for the ability to bind to and induce proliferation of monkey T-cells.

FACS data was acquired using the following protocol: Cells at $2\times10^5$ per well were incubated with serially diluted antibodies for 30 min on ice. Post incubation, cells were washed and secondary antibodies were added and incubated for an additional 30 minutes. After incubation, cells were washed, re-suspended in cold PBS containing 1% BSA and analyzed by flow cytometry. CD4+ monkey T cells were gated by side and forward scatters, and on the CD2+CD4+ CD20− population. The $EC_{50}$S for cell binding titration were calculated using a 4-parameter non-linear regression analysis in GraphPad Prism.

Proliferation data was acquired using the following protocol: Freshly isolated cynomolgus monkey derived PBMC ($5\times10^4$/well) were incubated with a 3-fold serial dilution of anti-CD3 antibody and a fixed concentration of a commercial anti-CD28 antibody (500 ng/ml) antibody in 96 well plates for 72 h at 3700. Following incubation, CellTiter Glo® was added and luminescence was measured using a VICTOR X5 multi-label plate reader (PerkinElmer). The $EC_{50}$ of cell viability (ATP catalyzed quantification) was calculated using a 4-parameter non-linear regression analysis in GraphPad Prism.

Results of the binding and proliferation experiments are summarized in Tables 12 and 13.

TABLE 12

| Anti-CD3 mAbs Bind & Proliferate monkey PBMCs | | |
|---|---|---|
| Antibody | EC50 [M] FACS PBMCs | EC50 [M] mfPBMC Proliferation |
| H1H2690N | 5.66E−09 | 2.71E−12 |
| H1H2712N | 2.29E−09 | 2.72E−12 |

TABLE 12-continued

| Anti-CD3 mAbs Bind & Proliferate monkey PBMCs | | |
|---|---|---|
| Antibody | EC50 [M] FACS PBMCs | EC50 [M] mfPBMC Proliferation |
| H2M3547N | 1.12E−10 | NT |
| H2M3563N | 1.65E−10 | NT |
| H1H5761P | NT | 2.81E−09 |
| H1H5763P | NT | 0.00E+00 |
| H1H5764P | NT | 4.06E−10 |
| H1H5769P | NT | 8.33E−13 |
| H1H5771P | NT | 2.74E−12 |
| H1H5772S | NT | 1.47E−12 |
| H1H5778P | NT | 5.93E−13 |
| H1H5780P | NT | 3.13E−13 |
| H1H5781P | NT | 7.92E−13 |
| H1H5788P | NT | 2.01E−12 |
| OKT3 | NB | NT |
| SP34 | 7.03E−11 | 1.71E−12 |

NB: No Binding;
NT: not tested

TABLE 13

| Monovalent 1-arm Anti-CD3 mAbs Bind & Proliferate Monkey PBMCs | | |
|---|---|---|
| Antibody | EC50 [M] FACS PBMCs | EC50 [M] mfPBMC Proliferation |
| H1H7194P | NT | 4.84E−12 |
| H1H7195P | NT | 1.36E−12 |
| H1H7196P | NT | 1.40E−08 |
| H1H7198P | NT | 2.29E−12 |
| H1H7203P | NT | 4.97E−13 |
| H1H7204P | NT | 1.26E−11 |
| H1H7208P | NT | 7.02E−12 |
| H1H7211P | NT | 2.81E−13 |
| H1H7221P | NT | 1.72E−12 |
| H1H7223P | NT | 6.75E−11 |
| H1H7226P | NT | 2.26E−11 |
| H1H7232P | NT | 4.90E−11 |
| H1H7233P | NT | 4.35E−12 |
| H1H7241P | NT | 2.05E−11 |
| H1H7242P | NT | 1.38E−11 |
| H1H7250P | NT | 7.27E−11 |
| H1H7251P | NT | 1.83E−11 |
| H1H7254P | NT | 8.88E−11 |
| H1H7258P | NT | 1.11E−11 |

NB: No Binding;
NT: not tested

As shown in Tables 12 and 13, several anti-CD3 antibodies of the invention bound CD2+CD4+ monkey T-cells and induced their proliferation. OKT3 did not drive monkey PBMC proliferation, while SP34 was active against monkey PBMCs.

Example 6. Anti-CD3 mAbs Support T-Cell-Mediated Killing of Tumor Cells

The ability of anti-CD3 antibodies to redirect T-cell mediated killing via Fc/FcR interactions was studied using a calcein based U937 killing assay. Briefly, human PBMC were isolated over Ficoll-Paque and activated over a course of several days with media containing human IL-2 (30 U/ml) and T-cell activation beads (anti-CD3/CD28). U937 cells were labeled with calcein, and then incubated with activated T-cells at a 10:1 effector:target ratio using 3-fold serial dilutions of antibodies over a course of 3 hours at 37° C. Following incubation, the plates were centrifuged and supernatants were transferred to a translucent black clear bottom plate for fluorescence analysis. $EC_{50}$ values, defined as the molar concentration of CD3 antibody that induces 50% cytotoxicity, were calculated using a 4-parameter non-linear regression analysis in GraphPad Prism. Results using hybridoma antibodies, human Fc antibodies, and monovalent one-arm antibodies are shown in Tables 14, 15 and 16, respectively.

TABLE 14

| Hybridoma Anti-CD3 mAbs Redirect T-Cell Killing to U937 Cells | |
|---|---|
| Antibody | U937 Cytotoxicity Human T-cells [M] |
| H2M2689N | 0.00E+00 |
| H2M2690N | 2.79E−11 |
| H2M2691N | 2.34E−11 |
| H1M2692N | 3.59E−10 |
| H2M2704N | 2.49E−12 |
| H2M2705N | 1.73E−12 |
| H2M2706N | 7.91E−12 |
| H2M2707N | 7.21E−12 |
| H2M2708N | 3.27E−12 |
| H2M2709N | 3.47E−12 |
| H2M2710N | 3.97E−12 |
| H2M2711N | 3.66E−12 |
| H1M2712N | 3.14E−10 |
| H2M2774N | 2.46E−12 |
| H2M2775N | 3.38E−12 |
| H2M2776N | 4.06E−12 |
| H2M2777N | 4.86E−12 |
| H2M2778N | 0.00E+00 |
| H2M2779N | 6.75E−10 |
| H2M2789N | NT |
| H2M2862N | 7.66E−12 |
| H2M2885N | 3.71E−12 |
| H2M2886N | 8.06E−12 |
| H2M3540N | 1.25E−11 |
| H2M3541N | 5.39E−11 |
| H1M3542N | 2.92E−11 |
| H2M3543N | 1.31E−11 |
| H1M3544N | 1.72E−10 |
| H2M3547N | 3.17E−11 |
| H2M3548N | 5.50E−12 |
| H1M3549N | 1.07E−10 |
| H2M3563N | 4.05E−11 |
| H1M3613N | 8.66E−10 |
| Isotype Ctrl | 0.00E+00 |

NT: Not Tested

TABLE 15

| Human Fc formatted Anti-CD3 mAbs Redirect T-Cell Killing to U937 Cells | |
|---|---|
| Antibody | U937 Cytotoxicity Human T-cells [M] |
| H1H5751P | 1.30E−10 |
| H1H5752P | 1.85E−11 |
| H1H5753B | 3.79E−10 |
| H1H5755B | 5.16E−11 |
| H1H5756B | 7.69E−11 |
| H1H5757B | 9.65E−11 |
| H1H5758B | 8.86E−08 |
| H1H5761P | 2.00E−12 |
| H1H5763P | NT |
| H1H5764P | NT |
| H1H5769P | 5.65E−11 |
| H1H5771P | NT |
| H1H5772S | 6.89E−13 |
| H1H5777P | 4.87E−13 |
| H1H5778P | 3.41E−13 |
| H1H5780P | 4.03E−12 |
| H1H5781P | 1.83E−12 |
| H1H5782P | 5.18E−12 |
| H1H5785B | 4.43E−11 |

TABLE 15-continued

Human Fc formatted Anti-CD3 mAbs Redirect T-Cell Killing to U937 Cells

| Antibody | U937 Cytotoxicity Human T-cells [M] |
|---|---|
| H1H5786B | 6.10E−11 |
| H1H5788P | 1.54E−11 |
| H1H5790B | 8.71E−11 |
| H1H5791B | 8.01E−11 |
| H1H5792B | 1.40E−10 |
| H1H5793B | 8.85E−11 |
| H1H5795B | 6.74E−11 |
| H1H5796B | 5.03E−10 |
| H1H5797B | 5.76E−10 |
| H1H5798B | 1.81E−10 |
| H1H5799P | NT |
| H1H5801B | 9.23E−11 |
| OKT3 | 2.35E−12 |
| Isotype Ctrl | 0.00E+00 |

NT: Not Tested

TABLE 16

Monovalent 1-arm Anti-CD3 mAbs Redirect T-Cell Killing to U937 Cells

| Antibody | U937 Cytotoxicity Human T-cells [M] |
|---|---|
| H1H7194P | 4.71E−12 |
| H1H7195P | 6.10E−12 |
| H1H7196P | 1.96E−11 |
| H1H7198P | 5.21E−12 |
| H1H7203P | 5.47E−12 |
| H1H7204P | 1.08E−11 |
| H1H7208P | 4.59E−11 |
| H1H7211P | 7.89E−12 |
| H1H7221P | 9.21E−12 |
| H1H7223P | 5.30E−12 |
| H1H7226P | 1.04E−11 |
| H1H7232P | 9.96E−12 |
| H1H7233P | 1.19E−11 |
| H1H7241P | 1.23E−11 |
| H1H7242P | 7.50E−12 |
| H1H7250P | 5.91E−12 |
| H1H7251P | 1.81E−12 |
| H1H7254P | 4.18E−12 |
| H1H7258P | 1.53E−11 |
| H1H7269P | 1.08E−11 |
| H1H7279P | 0.00E+00 |
| Isotype Ctrl | 0.00E+00 |

NT: Not Tested

As shown in Tables 14-16, most anti-CD3 antibodies, as well as OKT3, supported redirected T-cell mediated killing in this assay system. The observed killing, believed to be dependent on the antibody's Fc engagement with the Fc Receptor on U937 cells leading to clustering of CD3 on adjacent T-cells, was squelched by addition of non-specific human IgG (data not shown).

Example 7. Generation of Bispecific Antibodies that Bind CD3 and CD20

Bispecific antibodies comprising an anti-CD3-specific binding domain and an anti-CD20-specific binding domain were constructed using standard methodologies wherein a heavy chain and a light chain from an anti-CD3 antibody were combined with a heavy chain from an anti-CD20 antibody. The anti-CD3 antibodies used to construct the bispecific antibodies of this example were obtained by immunizing a VelocImmune® mouse with cells expressing CD3 or with DNA encoding CD3, or in the case of BS3/20-007 and -009, from a known anti-CD3 antibody (i.e., the anti-CD3 antibody "12K" as set forth in WO2004/106380). The anti-CD20 antibodies used to construct the bispecific antibodies of this example are as set forth in U.S. Pat. No. 7,879,984.

The bispecific antibodies created in accordance with the present Example comprise two separate antigen-binding domains (i.e., binding arms). The first antigen-binding domain comprises a heavy chain variable region derived from an anti-CD20 antibody ("CD20-VH"), paired with a light chain variable region derived from an anti-CD3 antibody ("CD3-VL"). The CD20-VH/CD3-VL pairing creates an antigen-binding domain that specifically recognizes CD20. The second antigen-binding domain comprises a heavy chain variable region derived from an anti-CD3 antibody ("CD3-VH"), paired with a light chain variable region derived from an anti-CD3 antibody ("CD3-VL"). The CD3-VH/CD3-VL pairing creates an antigen-binding domain that specifically recognizes CD3. The same CD20-VH was used in all bispecific antibodies created in this example and is designated "CD20-VH-A" (except for BS3/20-009, which used a different CD20-VH called "CD20-VH-B"). However, several different CD3-VH and CD3-VL components (designated "CD3-VH-A, CD3-VH-B, etc. and CD3-VL-A, CD3-VL-B, etc., derived from different anti-CD3 antibodies) were used in the different bispecific antibodies of the following Examples.

A summary of the component parts of the antigen-binding domains of the various bispecific antibodies made in accordance with this Example is set forth in Table 17.

TABLE 17

| | Anti-CD20 Antigen-Binding Domain | | Anti-CD3 Antigen-Binding Domain | |
|---|---|---|---|---|
| Bispecific Antibody Identifier | Heavy Chain Variable Region | Light Chain Variable Region | Heavy Chain Variable Region | Light Chain Variable Region |
| BS3/20-001 | CD20-VH-A | CD3-VL-A | CD3-VH-A | CD3-VL-A |
| BS3/20-002 | CD20-VH-A | CD3-VL-B | CD3-VH-B | CD3-VL-B |
| BS3/20-003 | CD20-VH-A | CD3-VL-C | CD3-VH-C | CD3-VL-C |
| BS3/20-004 | CD20-VH-A | CD3-VL-D | CD3-VH-D | CD3-VL-D |
| BS3/20-005 | CD20-VH-A | CD3-VL-E | CD3-VH-E | CD3-VL-E |
| BS3/20-007 | CD20-VH-A | CD3-VL-F# | CD3-VH-F# | CD3-VL-F# |
| BS3/20-009* | CD20-VH-B | CD3-VL-F# | CD3-VH-F# | CD3-VL-F# |

#The heavy and light chain variable regions of CD3-VH-F and CD3-VL-F were derived from the anti-CD3 antibody designated "L2K" as set forth in WO2004/106380.
*The anti-CD20 arm of BS3/20-009, comprising the CD20-VH-B/CD3-VL-F pairing, is non-functional; i.e., it does not bind CD20. However, the anti-CD3 arm (comprising the CD3-VH-F/CD3-VL-F pairing) specifically binds CD3. Thus, BS3/20-009 retains the same general "bispecific" structure of the other bispecific molecules generated in this example, but it only binds CD3.

Tables 18 and 19 set out the amino acid sequence identifiers for the various heavy chain variable regions (Table 18) and light chain variable regions (Table 19), and their corresponding CDRs, of the bispecific antibodies of this Example.

TABLE 18

(Heavy Chain Variable Region Amino Acid Sequences)

| | SEQ ID NOs | | | |
|---|---|---|---|---|
| Heavy Chain Identifier | HCVR | HCDR1 | HCDR2 | HCDR3 |
| CD20-VH-A | 1242 | 1244 | 1246 | 1248 |
| CD20-VH-B | 1338 | 1340 | 1342 | 1344 |
| CD3-VH-A | 1250 | 1252 | 1254 | 1256 |

TABLE 18-continued

| (Heavy Chain Variable Region Amino Acid Sequences) | | | | |
|---|---|---|---|---|
| | SEQ ID NOs | | | |
| Heavy Chain Identifier | HCVR | HCDR1 | HCDR2 | HCDR3 |
| CD3-VH-B | 1266 | 1268 | 1270 | 1272 |
| CD3-VH-C | 1282 | 1284 | 1286 | 1288 |
| CD3-VH-D | 1298 | 1300 | 1302 | 1304 |
| CD3-VH-E | 1314 | 1316 | 1318 | 1320 |
| CD3-VH-F | 1329 | 1330 | 1331 | 1332 |

TABLE 19

| (Light Chain Variable Region Amino Acid Sequences) | | | | |
|---|---|---|---|---|
| | SEQ ID NOs | | | |
| Light Chain Identifier | LCVR | LCDR1 | LCDR2 | LCDR3 |
| CD3-VL-A | 1258 | 1260 | 1262 | 1264 |
| CD3-VL-B | 1274 | 1276 | 1278 | 1280 |
| CD3-VL-C | 1290 | 1292 | 1294 | 1296 |
| CD3-VL-D | 1306 | 1308 | 1310 | 1312 |
| CD3-VL-E | 1322 | 1324 | 1326 | 1328 |
| CD3-VL-F | 1333 | 1334 | 1335 | 1336 |

In addition, Tables 20 and 21 set out the sequence identifiers for the nucleotide sequences encoding the heavy chain variable regions (Table 20) and light chain variable regions (Table 21), and their corresponding CDRs, of the bispecific antibodies of this Example.

TABLE 20

| (Nucleotide Sequences Encoding Heavy Chain Variable Region Sequences) | | | | |
|---|---|---|---|---|
| Heavy Chain | SEQ ID NOs | | | |
| Identifier | HCVR | HCDR1 | HCDR2 | HCDR3 |
| CD20-VH-A | 1241 | 1243 | 1245 | 1247 |
| CD20-VH-B | 1337 | 1339 | 1341 | 1343 |
| CD3-VH-A | 1249 | 1251 | 1253 | 1255 |
| CD3-VH-B | 1265 | 1267 | 1269 | 1271 |
| CD3-VH-C | 1281 | 1283 | 1285 | 1287 |
| CD3-VH-D | 1297 | 1299 | 1301 | 1303 |
| CD3-VH-E | 1313 | 1315 | 1317 | 1319 |

TABLE 21

| (Nucleotide Sequences Encoding Light Chain Variable Region Sequences) | | | | |
|---|---|---|---|---|
| Light Chain | SEQ ID NOs | | | |
| Identifier | LCVR | LCDR1 | LCDR2 | LCDR3 |
| CD3-VL-A | 1257 | 1259 | 1261 | 1263 |
| CD3-VL-B | 1273 | 1275 | 1277 | 1279 |
| CD3-VL-C | 1289 | 1291 | 1293 | 1295 |
| CD3-VL-D | 1305 | 1307 | 1309 | 1311 |
| CD3-VL-E | 1321 | 1323 | 1325 | 1327 |

In addition to the bispecific antibodies described above, the following control antibodies were also used in certain of the experiments set out in the Examples that follow:

Control I: Monoclonal antibody "OKT-3" against human T-cell surface antigens as set forth in U.S. Pat. No. 4,361,549 and available from hybridoma CRL-8001 (American Type Culture Collection, Manassas, VA).

Control II: Antibody "SP34" reactive against the epsilon chain of the T3 complex on human T lymphocyte cells, available from BD Pharmagen, Cat #55052.

Control III: anti-CD20 therapeutic antibody, with heavy and light chain sequences of Rituxan (Rituximab) as disclosed in U.S. Pat. No. 5,736,137.

Control IV: Monoclonal anti-CD20 antibody designated "3B9-10" as disclosed in U.S. Pat. No. 7,879,984, and set forth herein as an antibody comprising the HCVR/LCVR amino acid sequence pair of SEQ ID NOs: 1242/1346 and HCDR1-HCDR2-HCDR3-LCDR1-LCDR2-LCDR3 amino acid sequences of SEQ ID NOs: 1244-1246-1248-1348-GTS-1352.

Control V: Monoclonal anti-CD20 antibody designated "10F2-13" as disclosed in U.S. Pat. No. 7,879,984, and set forth herein as an antibody comprising the HCVR/LCVR amino acid sequence pair of SEQ ID NOs: 1354/1362 and HCDR1-HCDR2-HCDR3-LCDR1-LCDR2-LCDR3 amino acid sequences of SEQ ID NOs: 1356-1358-1360-1364-EAS-1368.

Example 8. CD20×CD3 Bispecific Antibodies Selectively Bind Jurkat, Raji and Monkey T-Cells CD20×CD3 bispecific antibodies and Control constructs, as set forth in Example 1, were tested via FACS for their ability to bind to Jurkat (CD3+, CD20− human T-cell line), Raji (CD3−, CD20+ Human B-cell line), or cynomolgus PBMCs ("mkT cells").

FACS data was acquired using the following protocol: Cells at $2\times10^5$ per well were incubated with serially diluted antibodies for 30 min on ice. Post incubation, cells were washed and appropriate secondary (Jurkat, RAJI cells) or cocktail of secondary antibodies (for cyno PBMC) was added and incubated for an additional 30 minutes. After incubation, cells were washed, re-suspended in cold PBS containing 1% BSA and analyzed by flow cytometry on a BD FACS Canto II. Jurkat and Raji cells were gated by side and forward scatters, while cynomolgus T cells were also gated in a CD2+CD4+ population. The $EC_{50}$s for cell binding titration were determined using Prism software with values calculated using a 4-parameter non-linear regression analysis. Results are shown in Table 22.

TABLE 22

| EC50 Binding Values (Molar) for CD3 × CD20 Bispecific Antibodies | | | |
|---|---|---|---|
| Antibody | FACS—Jurkat | FACS—RAJI | FACS—mkT cells |
| Control I (anti-CD3) | 1.96E−10 | NB | NB |
| Control II (anti-CD3) | (+) | NB | 7.03E−11 |
| Control IV (anti-CD20) | No Binding | (+) | NB |
| BS3/20-001 | 3.85E−08 | 5.99E−08 | 8.74E−06 |
| BS3/20-002 | 5.62E−08 | 1.15E−08 | NT |
| BS3/20-003 | 5.67E−08 | 9.24E−08 | 2.48E−08 |
| BS3/20-004 | 4.89E−08 | 1.02E−08 | NT |
| BS3/20-005 | 1.95E−09 | 8.17E−08 | NT |

(+) $EC_{50}$ values not determined, but binding observed;
NB no binding;
NT not tested As shown in Table 22, the panel of tested antibodies showed a range of binding affinities on the various cell lines, depending on their specificities. Bispecific antibodies (BS3/20-001, -002, -003, -004 and -005) showed the ability to bind both human target lines. A subset of antibodies also showed the ability to bind to cynomolgus cells (Control II, BS3/20-001 and BS3/20-003). Anti-CD3 Control I (OKT3), anti-CD3 Control II (SP34), and anti-CD20 Control IV bound to Jurkat, cynomolgus T cells, and RAJI, respectively.

Example 9. CD20×CD3 Bispecific Antibodies Induce PBMC Proliferation In Vitro

The ability of selected CD20×CD3 bispecific antibodies and Control constructs to stimulate Peripheral Blood Mononuclear Cells (PBMC) and induce proliferation was assessed using ATP catalyzed quantification (CellTiter Glo®). The activation of PBMCs results in the release of cytokines, which drive cellular proliferation.

Proliferation data was acquired using the following protocol: Human or cynomolgus monkey derived PBMC ($5\times10^5$/well) were incubated with a 3-fold serial dilution of anti-CD3×CD20 or Control antibody in 96 well plates for 72 h at 37° C. Following incubation, CellTiter Glo® was added and luminescence was measured using a VICTOR X5 multilabel plate reader (PerkinElmer). The $EC_{50}$ of cell viability (ATP catalyzed quantification) was determined using Prism software. Values were calculated using a 4-parameter nonlinear regression analysis and are shown in Table 23.

TABLE 23

$EC_{50}$s for human and cynomolgus PBMC proliferation induced by anti-CD20 × CD3 bispecific antibodies

| Antibody | Human PBMC Proliferation $EC_{50}$ [M] | Cyno PBMC Proliferation $EC_{50}$ [M] |
|---|---|---|
| Control I | 3.30E−13 | NA |
| Control II | 8.93E−12 | 1.71E−12 |
| BS3/20-001 | 1.08E−11* | 4.02E−11* |
| BS3/20-002 | 8.59E−12* | 2.60E−11* |
| BS3/20-003 | 9.55E−12* | 2.78E−11* |
| BS3/20-004 | 1.45E−12* | NT |
| BS3/20-005 | 1.05E−12* | NT |

*Data are median values of 3 or more independent assays.
Data without a (*) are representative/average values of 1 or 2 independent assays.
NA = no activity; NT = not tested.

As shown in Table 23, all CD20×CD3 bispecific antibodies of the invention were activators of human or cynomolgus PBMCs. In general, anti-CD3 mono specific bivalent parental antibodies (Contros I and II) were 2-10 fold more potent than the bispecific counterparts. Control I (OKT3) did not drive monkey PBMC proliferation, while Control II (SP34) was active against both human and monkey PBMCs.

Example 10. CD20×CD3 Bispecific Antibodies Activate T-Cells and Induce IFN-Gamma Release and CD25 Upregulation in Human Whole Blood Selected CD20×CD3 bispecific antibodies were tested for their ability to activate T-cells in human whole blood. The extent of T-cell activation was determined by measuring interferon-gamma (IFNγ) secretion as well as the upregulation of CD25 on CD8+ T cells.

Interferon-gamma (IFNγ) secretion was quantified by combining heparinized whole blood with 5-fold serial dilutions of bispecific antibodies in 96-well plates. After 20 hours, the plates were centrifuged for 5 minutes and plasma was removed for ELISA analysis to determine IFNγ levels. Extrapolated IFNγ concentrations were plotted versus antibody concentration, and $EC_{50}$ values were calculated using a 4-parameter non-linear regression analysis using Prism software.

For analysis of CD25 expression on CD8+ T-cells, following incubation with antibodies and removal of plasma, 150 μl of blood was transferred to a deep well plate and lysed for 15 minutes with 1.5 mL RBC lysis buffer. Cells were washed twice, blocked for 10 minutes at room temperature with hFcR blocking reagent, and then incubated for 30 min at 4° C. with antibodies conjugated directly to CD2, CD19, CD4, CD8, and CD25. Next, cells were washed twice before analysis with a FACSCanto cytometer and FlowJo software.

The percentage of CD2+CD8+ T cells expressing the activation marker CD25 was plotted versus antibody concentration, and $EC_{50}$ values were calculated using a 4-parameter non-linear regression analysis using Prism software. Results are shown in Table 24.

TABLE 24

$EC_{50}$ values of Bispecific antibody mediated upregulation of CD25 and IFNγ production in whole blood

| Bispecific Antibody | $EC_{50}$ of CD25 Upregulation [M] | $EC_{50}$ of IFNγ Production [M] | Max IFNγ (pg/mL) |
|---|---|---|---|
| BS3/20-001 | 1.3E−10 | 3.9E−10 | 1815 |
| BS3/20-003 | 1.7E−10 | 5.7E−10 | 1693 |
| BS3/20-004 | 2.9E−10 | 2.3E−09 | 5810 |

Median values of at least 3 independent experiments (except IFN-gamma expression of BS3/20-003, which is n = 2)

As shown in Table 24, the CD20×CD3 bispecific antibodies mediated the upregulation of CD25 on CD8+ T cells in whole blood with $EC_{50}$ values ranging from 130-290 pM with corresponding $EC_{50}$ values for IFNγ that were slightly higher ranging from 390 pM to 2 nM. BS3/20-004 was less slightly less potent then BS3/20-001 and BS3/20-003 in mediating CD25 upregulation and IFNγ production as determined by $EC_{50}$, however BS3/20-004 could induce greater levels of IFNγ in whole blood cultures.

Example 11. CD20×CD3 Bispecific Antibodies Induce T-Cell Mediated Cytotoxicity on Rituximab Resistant Cell Lines The ability of selected CD20×CD3 bispecific antibodies and Control constructs to mediate complement-dependent cytotoxicity (CDC) and T-cell mediated cytotoxicity was evaluated using parental Raji cells and Raji SCID lines. The later (Raji SCID lines) were derived from individual anti-CD20 resistant tumors isolated from immunodeficient mice injected subcutaneously with Raji cells following treatment with the anti-CD20 mAb Rituximab. Four lines (Raji SCID 1-4) were used in this Example.

The expression of CD20 and the complement inhibitory molecules CD55 and CD59 on Raji cell lines was determined by FACS. Briefly, $1\times10^6$ cells were incubated in individual tubes for 30 minutes with antibodies directly conjugated to CD20, CD55 and CD59. Cells were washed twice before FACS acquisition by a FACSCanto cytometer and analysis with FlowJo software.

To determine the ability of anti-CD20 and anti-CD3×CD20 antibodies to mediate T-cell directed killing of Raji cell lines, calcein labeled Raji cells were incubated for 2 hours at 37° C. with pre-activated T cells (ficoll-isolated human PBMC activated with rhIL-2 (30 U/mL) and anti-CD3/CD28 activation beads) and 3-fold serial dilutions of antibodies starting at 2 nM. Following incubation, plates were centrifuged and supernatants were transferred to a translucent black clear bottom plate for 530 nm fluorescence detection at 485 nm emission. Percent cytotoxicity was determined based on spontaneous (target cells alone) and maximum release (target cells lysed with detergent) values. $EC_{50}$ values were calculated using a 4-parameter non-linear regression analysis using Prism software.

To determine the activity of the antibodies to mediate CDC, Raji cell lines were incubated with 5% normal human serum complement and 3-fold serial dilutions of antibodies starting at 100 nM. After incubation for 4.5 hours at 37 C, cell death was determined using CellTiter Glo®. Percent cytotoxicity was determined based on spontaneous (target cells alone) and maximum release (target cells lysed with detergent) values. $EC_{50}$ values were calculated using a 4-parameter non-linear regression analysis using Prism software.

Results are shown in Table 25.

TABLE 25

EC50 values for antibody mediated CDC and T-cell mediated cytotoxicity

| Cell Line | CD20 MFI | % CD55/ | CDC BS3/ 20-007 | CDC Control IV (anti-CD20) | CDC Control III (anti-CD20) | T-Cell Mediated Cytotoxicity BS3/ 20-007 | T-Cell Mediated Cytotoxicity Control IV (anti-CD20) |
|---|---|---|---|---|---|---|---|
| Raji | 1709 | 8.81 | 2.62E−09 | 2.47E−10 | 9.66E−11 | 1.66E−12 | No Activity |
| Raji SCID1 | 570 | 80.7 | 1.01E−07 | 5.19E−08 | 8.56E−08 | 1.11E−12 | No Activity |
| Raji SCID2 | 1373 | 9.1 | 8.83E−09 | 2.29E−10 | 5.87E−11 | 6.52E−13 | No Activity |
| Raji SCID3 | 1151 | 97.3 | 3.77E−08 | 5.71E−09 | 2.55E−08 | 2.93E−13 | No Activity |
| Raji SCID4 | 1717 | 64.6 | 1.40E−07 | 1.14E−09 | 5.29E−09 | 1.53E−12 | No Activity |

Compared to parental Raji cells, 2 of 4 Raji SCID lines showed reduced expression of CD20 (Table 25; lines Raji SCID 1 and 3), with significantly higher percentage of cells expressing the complement inhibitory molecules CD55 and CD59. The sensitivity of the Raji SCID cells to CDC mediated by either anti-CD20 or anti-CD20×CD3 antibodies was dependent on the percentage of CD55/CD59 expressing cells, but not on the levels of CD20, such that increased expression of CD55/CD59 on target cells inhibited CDC.

The anti-CD20 antibodies (Control IV & Control Ill [Rituximab]) were more potent than the anti-CD20×CD3 (BS3/20-007) in mediating CDC, as the bispecific is monovalent for CD20. However, in contrast to CDC, T-cell mediated cytotoxicity was not dependent on CD20 or CD55/CD59 levels, as all cell lines were equally susceptible to cell death by activated T-cells in the presence of anti-CD20×CD3 bispecific antibody. Additionally, the bispecific antibody was 100-1000 fold more potent in mediating T-cell dependent killing of Raji cells than the anti-CD20 antibody in the CDC assay.

Example 12. CD25 Upregulation on CD8+ T-Cells is Dependent on CD20 Concentration when in the Presence of CD20×CD3 Bispecific Antibodies To evaluate if higher concentrations of target cell (CD20+ lymphomas) would lead to an increased potency of CD20×CD3 bispecific antibodies, human peripheral blood mononuclear cells (PBMCs) were co-cultured in the presence of a Burkitt's lymphoma-derived cell line, i.e., Raji.

CD25 upregulation on CD8+ T-cells was determined using the following protocol: Human PBMCs ($5 \times 10^5$/mL), isolated via centrifugation of mononuclear-cell enriched leukapharesis-derived blood over Ficoll, were incubated in the presence ($1 \times 10^5$/mL) or absence of Raji cells, at 37° C. in 96-well flat bottom plates with 5-fold serial dilutions of the bispecific antibodies. After 48 hours, cells were washed 2×, blocked for 10 minutes at room temperature with hFcR blocking reagent, and then incubated for 30 minutes at 4° C. with directly conjugated antibodies to CD2, CD19, CD4, CD8, and CD25. After staining, cells were washed twice before FACS acquisition by a FACSCanto cytometer and analysis with FlowJo software. The percentage of activated CD2+CD8+ T cells expressing CD25 was plotted versus antibody concentration, and $EC_{50}$ values were calculated using a 4-parameter non-linear regression analysis using Prism software. Results are shown in Table 26.

TABLE 26

CD25 upregulation on CD8+ T-cells following incubation of human PBMC with CD20 × CD3 bispecific antibodies plus or minus Raji cells

| Antibody | PBMC $EC_{50}$ (M) | PBMC Max % CD25+ | PBMC + Raji $EC_50$ (M) | PBMC + Raji Max % CD25+ |
|---|---|---|---|---|
| BS3/20-001 | 1.12E−10 | 14.2 | 1.35E−12 | 92.2 |
| BS3/20-003 | 3.65E−10 | 21.1 | 3.38E−13 | 94.4 |

As shown in Table 26, activated T-cells when cultured in the presence of Raji (target) cells showed an upregulation of CD25, and a subsequent 100-fold decrease in their $EC_{50}$ values.

Example 13. CD20×CD3 Bispecific Antibodies Induce Cytotoxicity to Raji Cells in the Presence of Activated T-Cells The ability of CD20×CD3 bispecific antibodies to redirect T-cell mediated killing to CD20-expressing Raji cells was tested in an in vitro cytotoxicity assay. In addition, the ability of both bispecific and parental anti-CD3 antibodies to kill U937 cells via Fc/FcR interactions was also studied.

Calcein killing assays were carried out using the following protocol: Human and cynomolgus PBMC were isolated over ficoll-Plaque or via Lympholyte Mammal cell separation media, respectively. The isolated PBMCs were activated over a course of several days with media containing recombinant human IL-2 (30 U/ml) and T-cell activation beads (anti-CD3/CD28 for human PBMC, anti-CD2/CD3/CD28 for cynomolgus PBMC).

Target cells (Raji for CD20 mediated killing and U937 for FcR mediated killing) were labeled with calcein, and incubated with activated T-cells at a 10:1 effector: target ratio using 3-fold serial dilutions of antibodies over a course of 3 hours at 37° C. Following incubation, the plates were centrifuged and supernatants were transferred to a translucent black clear bottom plate for fluorescence analysis. $EC_{50}$s defined as the molar concentration of bispecific antibody that induces 50% cytotoxicity was determined using Prism. Values were calculated using a 4-parameter non-linear regression analysis. Results are summarized in Table 27.

TABLE 27

$EC_{50}$ values for CD20 × CD3-Induced Cytotoxicity to Raji and U937 cells

| Antibody | Raji Cytotoxicity Human T-cells [M] | U937 Cytotoxicity Human T-cells [M] | Raji Cytotoxicity Monkey T-cells [M] |
|---|---|---|---|
| Control I (anti-CD3) | NA | 3.04E−12 | NA |
| BS3/20-001 | 5.63E−11* | 8.86E−11* | 1.27E−12* |
| BS3/20-002 | 7.71E−11* | 8.24E−10 | NT |
| BS3/20-003 | 7.38E−11* | 8.10E−11* | 4.36E−14 |
| BS3/20-004 | 1.29E−11* | 6.07E−11 | NT |
| BS3/20-005 | 1.95E−11 | 1.48E−10 | NT |

*Data are median values of 3 or more independent assays.
Data without a (*) are representative/average values of 1 or 2 independent assays.
NA = No Activity; NT = Not Tested.

As shown in Table 27, bispecific CD20×CD3 antibodies containing human-specific or human/cynomolgus cross reactive anti-CD3 arms were able to specifically redirect cytotoxicity to Raji cells in the presence of human activated T cells. In the presence of cynomolgus activated T cells, Raji were killed when they were incubated with BS3/20-001 or BS3/20-003, bispecific antibodies that have anti-CD3 arms that activate monkey T-cells. All bispecific antibodies as well as Control I, an anti-CD3 mAb, showed activity in the U937 Fc/FcR dependent killing assay. This activity could be blocked by the addition of blocking non-specific human IgG to the reaction (Data not shown).

Example 14. CD3×CD20 Bispecific Antibodies can Deplete CD19+ B-Cells in Mice Reconstituted with Human Immune Cells To determine the in vivo potency of CD3×CD20 bispecific antibody administration, changes in CD19+ B-cell and CD2+ T-cell levels were examined via FACS after administration of 10 μg or 0.1 pg of anti-CD3×CD20 bispecific antibody into mice, which were reconstituted with human immune cells.

Briefly, newborn BALB/Rag2$^{null}$/$\gamma_c^{null}$ mice were irradiated with 2×150 Rads and reconstituted with 4×$10^5$ human $CD34^+$ hematopoietic progenitor cells via intrahepatic injection. After 12 weeks, the composition of reconstituted human immune system in peripheral blood was determined by flow cytometry. Typically by three months post reconstitution, between 10%-60% percent of peripheral white blood cells are human CD45+ of which 40%-70% are B cells, 15%-40% are T-cells and the remaining are small populations of natural killer and dendritic cells.

Five months post-reconstitution, mice were injected intraperitoneally with 10 μg or 0.1 μg of anti-CD3×CD20 bispecific antibody BS3/20-007, 10 μg of a monovalent 1-arm CD3 antibody (BS3/20-009, see Table 1) or 10 μg of an irrelevant hIgG isotype control. One, eight, and twenty-five days post injection, mice were bled retro-orbitally and immune cell populations in the peripheral blood were determined by flow cytometry (FACS).

For FACS analysis, 100 μl of blood was incubated with 1.5 ml RBC lysis buffer in Eppendorf tubes for three minutes. Cells were centrifuged for five minutes at 0.4×g, washed 2× with FACS wash (PBS+3% FBS), and blocked for 10 minutes at room temperature with mouse Fc blocking reagent. Cells were then incubated for 30 minutes at 4° C. with directly conjugated antibodies to CD2, CD3, CD19, CD4, CD8, hCD45, hHLA-DR, and mCD45. After staining, cells were washed two times before FACS acquisition by a FACSCanto cytometer and analysis with FlowJo software. Results are shown in Table 28.

TABLE 28

Percentage of circulating CD45, CD19 and CD2 positive cells in mice reconstituted with human immune cells

| | | Isotype Ctrl (10 μg) | | BS3/20-007 (10 μg) | | BS3/20-007 (0.1 μg) | | | BS3/20-009 [one-arm CD3] (10 μg) | |
|---|---|---|---|---|---|---|---|---|---|---|
| | | Mouse ID | | | | | | | | |
| | Day | 1 | 2 | 3 | 4 | 5 | 6 | 7 | 8 | 9 |
| % huCD45+ | Pre | 13.7 | 14.8 | 16.1 | 30.9 | 37.2 | 22.5 | 25.5 | 26.6 | 33.3 |
| | 1 d | 7.7 | 10.8 | 0.01 | 0.13 | 1.7 | 1.2 | 0.8 | 2.7 | 8.9 |
| | 8 d | 14.1 | 12.7 | 0.12 | 0.16 | 3.3 | 7.7 | 3.9 | 3.2 | 4.5 |
| | 25 d | 13.0 | 7.3 | 0.15 | 0.12 | 9.0 | 1.2 | 1.0 | 2.8 | 5.1 |
| % CD19+ | 1 d | 58.7 | 66.8 | 0.00 | 7.69 | 20.2 | 7.0 | 5.2 | 75.3 | 87.1 |
| (of | 8 d | 66.2 | 56.2 | 0.00 | 0.00 | 21.3 | 0.4 | 0.0 | 70.4 | 76.6 |
| huCD45+) | 25 d | 37.3 | 62.8 | 9.7 | 2.6 | 58.3 | 0.7 | 0.6 | 38.9 | 51.3 |
| % CD2+ | 1 d | 58.7 | 66.8 | 0.00 | 7.69 | 20.2 | 7.0 | 5.2 | 75.3 | 87.1 |
| (of | 8 d | 66.2 | 56.2 | 0.00 | 0.00 | 21.3 | 0.4 | 0.0 | 70.4 | 76.6 |
| huCD45+) | 25 d | 37.3 | 62.8 | 9.7 | 2.6 | 58.3 | 0.7 | 0.6 | 38.9 | 51.3 |

As shown in Table 28, a single 10 pg dose of anti-CD3×CD20 bispecific antibody BS3/20-007 resulted in a disappearance of circulating hCD45+ cells in 2 of 2 treated mice which did not recover over the length of the experiment. A single 0.1 μg dose of BS3/20-007 reduced circulating hCD45+ cells, including CD19+ B-cells and CD2+ T-cells 24 hours post injection in 2 of 3 treated mice. Once depleted, the percentage of hCD45+ cells did not recover significantly in the responding mice treated with 0.1 μg BS3/20-007. However, what cells remained in these mice were predominantly hCD2+ T-cells, and CD19+ B cells were not present in the responding mice even at 25 days post treatment. A single 10 μg dose of a monovalent 1-arm CD3 antibody (BS3/20-009) also resulted in a persistent but modest reduction in CD45+ cells, notably CD2+ T-cells, in 2 of 2 treated mice. A single 10 μg dose of an irrelevant hIgG1 control had no significant effect on the percentage of circulating hCD45+, hCD19+, or hCD2+ cells.

Example 15. Treatment with CD20×CD3 Bispecific Antibody Decreases Raji Tumor Volume in NOD/SCID Mice To assess the efficacy of selected anti-CD3×CD20 bispecific antibodies in reducing Raji tumor growth, NOD/SCID mice (Taconic) were implanted subcutaneously with a mixture of $2\times10^6$ Raji tumor cells and $8\times10^6$ human PBMC. Mice were treated three times per week, starting on the day of tumor implantation, with either human Fc (hFc) or CD3×CD20 bispecific antibody (BS3/20-007) at a dose of 1 μg per mouse (N=20 mice per treatment group). Reagents were delivered by intraperitoneal (i.p.) injection. Tumor size was measured three times per week using calipers, and tumor volume calculated as Volume=(length×width$^2$)/2. Results are shown in FIG. 1.

Figure 2:
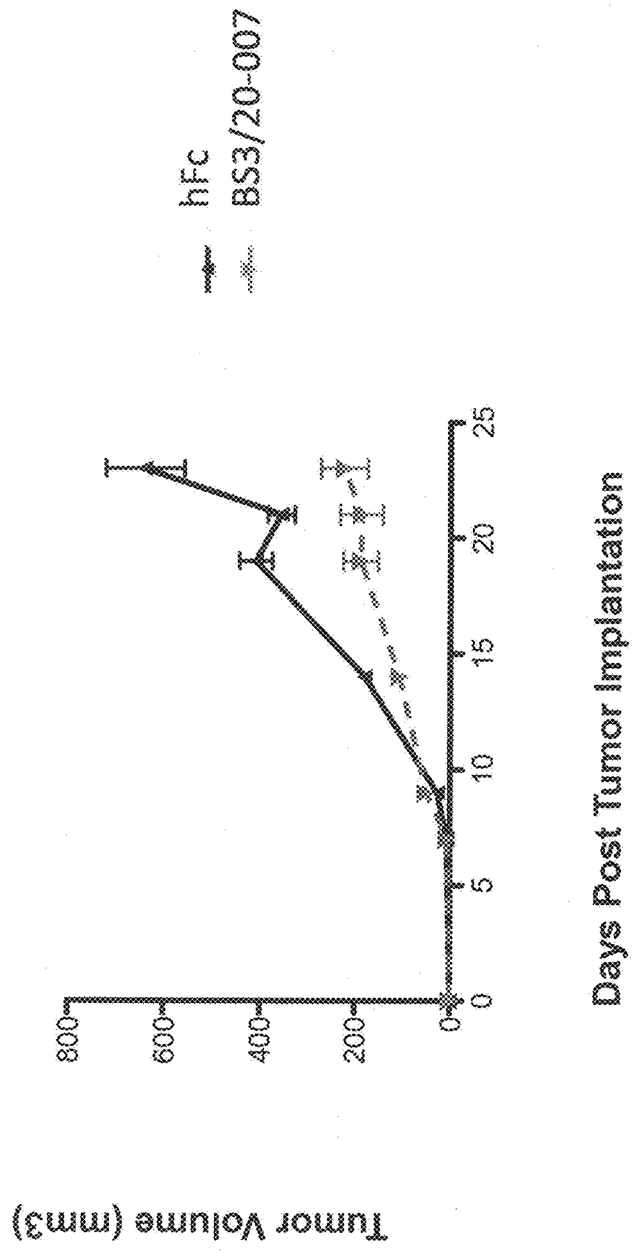
FIG. 2 shows the tumor volume (in $mm^3$) over time in NOD/SCID mice implanted subcutaneously with a mixture of Raji tumor cells and PBMCs following tumor implantation and treatment, starting 7 days after tumor implantation, with either human Fc (hFc, solid line) or CD3×CD20 bispecific antibody (BS3/20-007, dashed line).

In a second experiment, NOD/SCID mice were implanted subcutaneously with a mixture of $2\times10^6$ Raji tumor cells and $4\times10^6$ human PBMC. Treatment with CD3×CD20 bispecific antibody (BS3/20-007) or control reagent (hFc) began 7 days post tumor implantation to allow tumors to become palpable. Mice were treated two times per week at a dose of 1 μg per mouse (N=6 mice per treatment group). Reagents were injected subcutaneously, away from the site of tumor implantation. Tumor size was measured two times per week using calipers, and tumor volume calculated as Volume=(length×width$^2$)/2. Results are shown in FIG. 2.

This Example demonstrates that treatment with CD3×CD20 bispecific antibody BS3/20-007 was effective in inhibiting tumor growth both at the time of tumor implantation and once tumors were established. Tumor volume in mice was decreased 25 days post implantation in both studies, relative to control.

Figure 3:
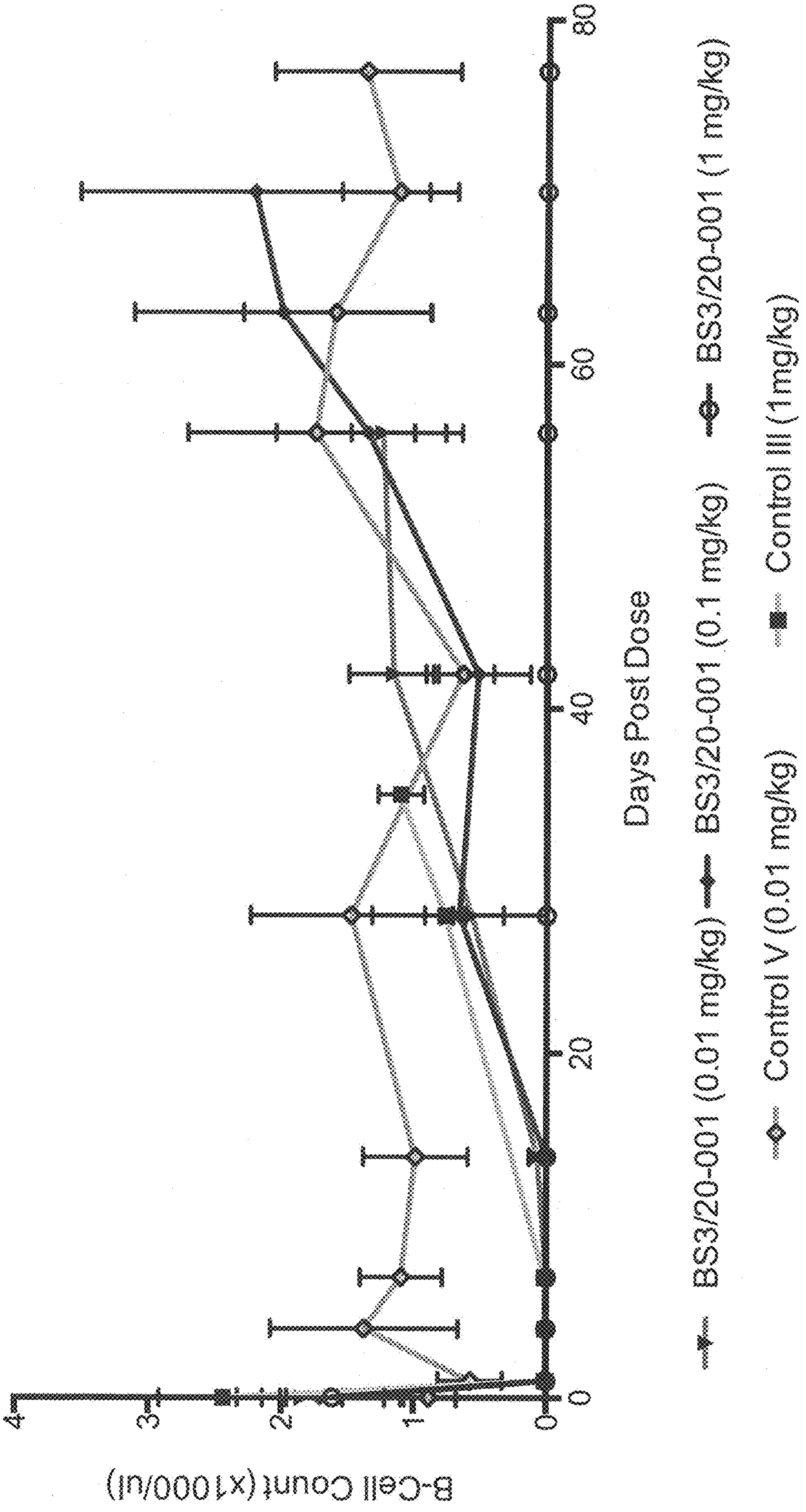
FIG. 3 shows a plot of B-cell numbers (×1000/μL) over time in blood samples from cynomolgus monkeys treated with three different doses of bispecific antibody BS3/20-001 (0.01, 0.1 or 1.0 mg/kg); low-dose anti-CD20 control antibody (Control V, 0.01 mg/kg); or high-dose anti-CD20 control antibody (Control III (1.0 mg/kg).
Figure 4:
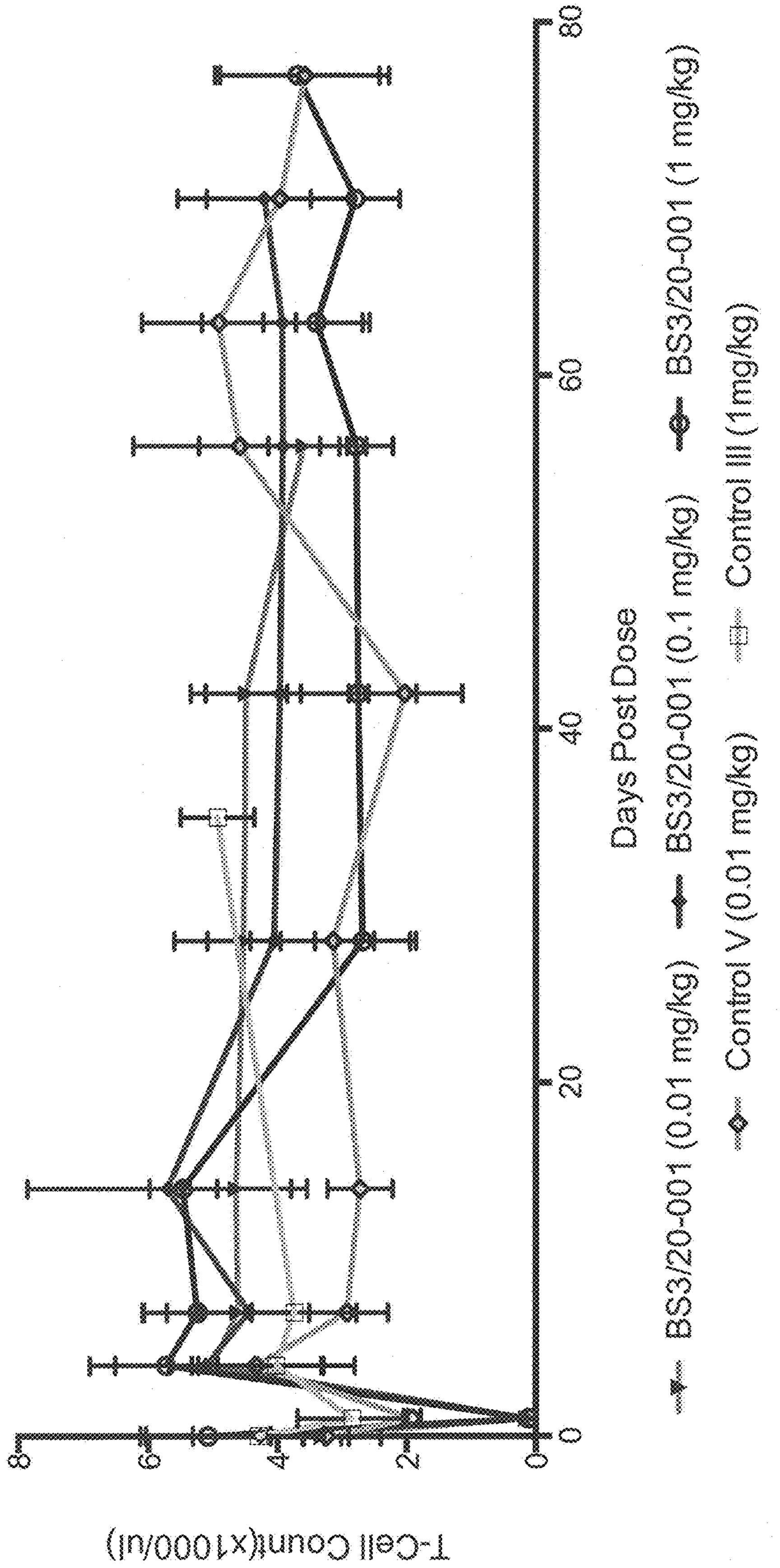
FIG. 4 shows a plot of T-cell numbers (×1000/μL) over time in blood samples from cynomolgus monkeys treated with three different doses of bispecific antibody BS3/20-001 (0.01, 0.1 or 1.0 mg/kg); low-dose anti-CD20 control antibody (Control V, 0.01 mg/kg); or high-dose anti-CD20 control antibody (Control III (1.0 mg/kg).
Figure 5A:
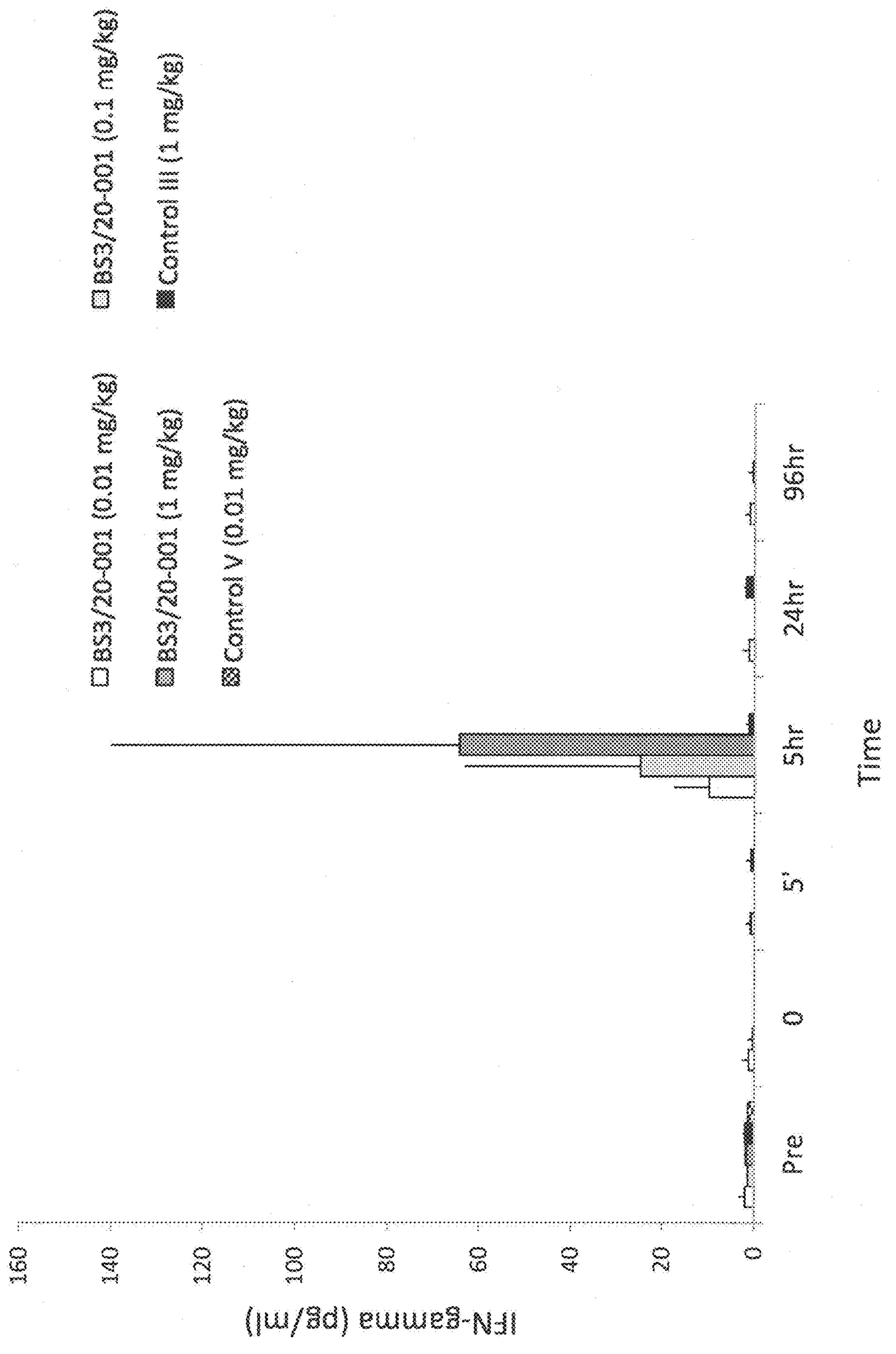
FIGS. 5A, 5B, 5C and 5D show the pre-dose and post-dose levels (pg/mL) of IFN-gamma, IL-2, IL-6, and TNF-alpha, respectively, for cynomolgous monkeys treated with a single dose of BS3/20-001 (0.01, 0.1 or 1.0 mg/kg), low dose anti-CD20 control antibody (0.01 mg/kg Control V), or high-dose anti-CD20 control antibody (1.0 mg/kg Control III).
Figure 5B:
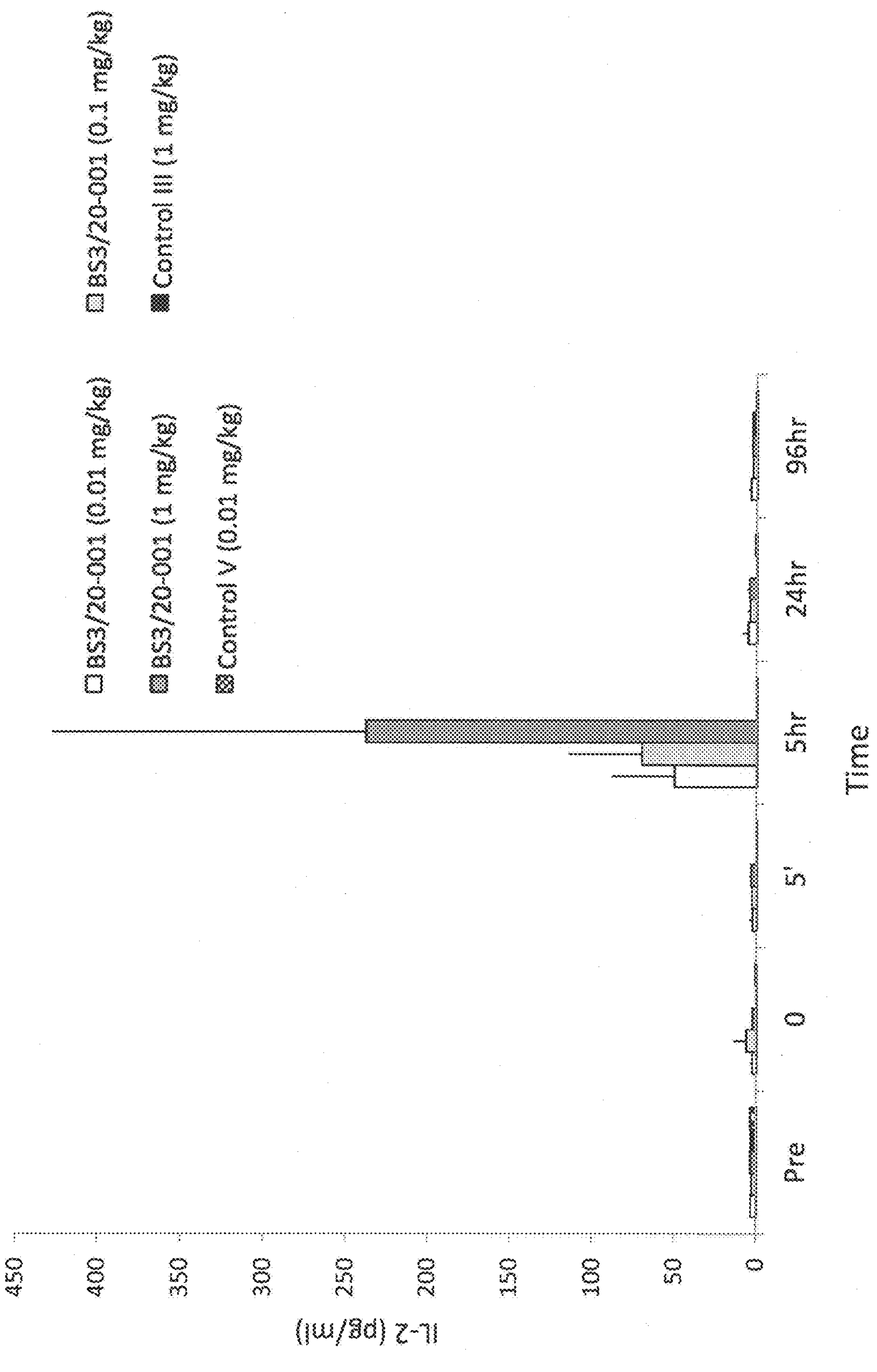
Figure 5C:
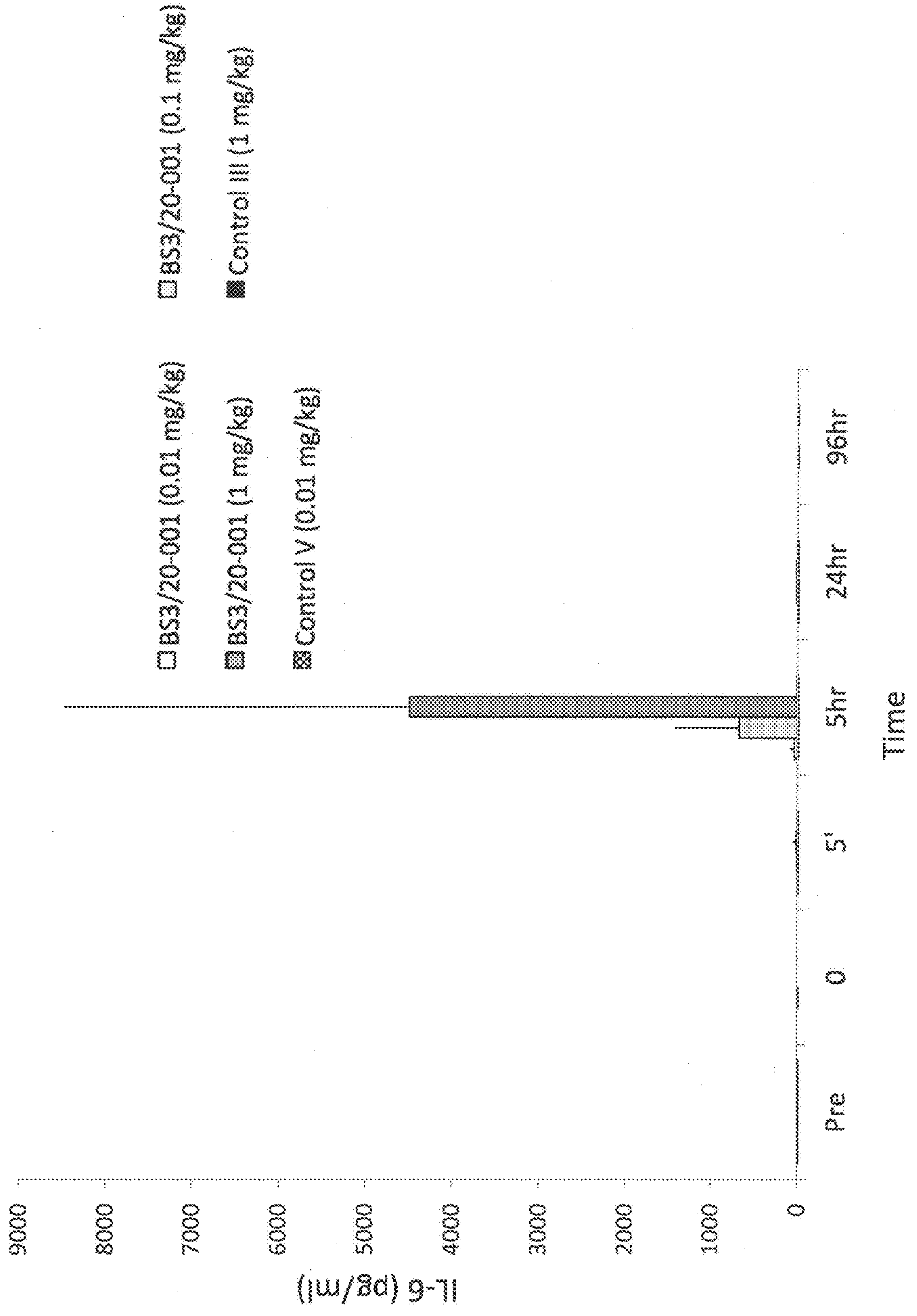
Figure 5D:
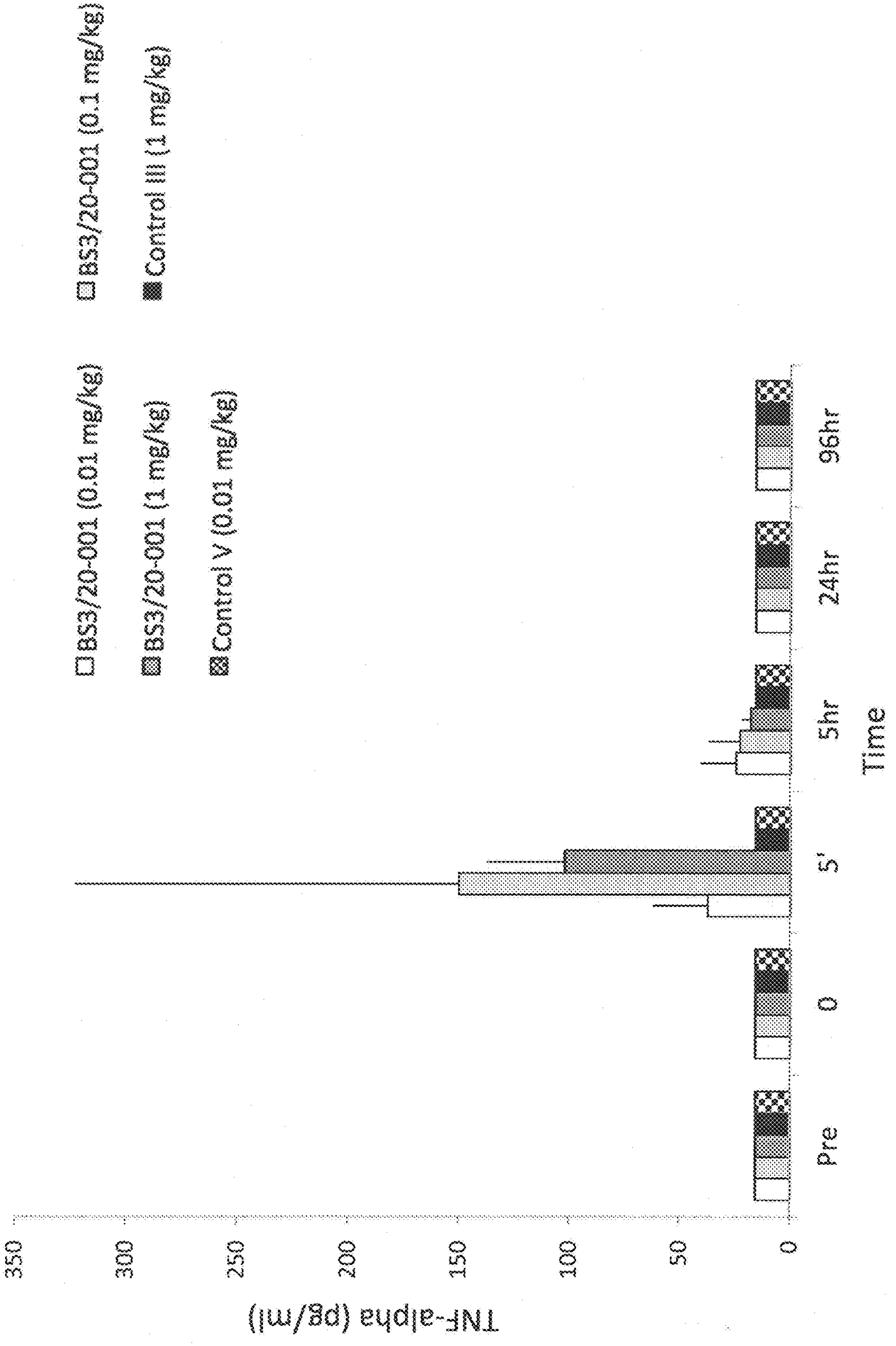

Example 16. CD20×CD3 Bispecific Antibodies Deplete B-Cell Populations in Cynomolgus Monkeys and have a Pharmacokinetic Profile Typical of Monoclonal Antibodies A pilot non-GLP toxicology and pharmacology study was performed in cynomolgus monkeys (*Macaca fascicularis*) to determine the ability of the CD3×CD20 bispecific antibodies to deplete B-cell populations in these animals. Male animals were organized into three cohorts. Cohort 1 received bispecific antibody BS3/20-001 and included three different dosing groups (0.01, 0.10 and 1.00 mg/kg) with 3-4 animals per dosing group. Cohort 2 was a two-animal cohort that received a low dose of anti-CD20 control antibody (Control V; 0.01 mg/kg). Cohort 3 was a four-animal cohort that received a high dose of anti-CD20 control antibody (Control III; 1.0 mg/kg). Blood was drawn at day −7 and immediately prior to dosing in order to establish baseline levels for B and T cells in these animals. Doses of drug at 0.01, 0.10, or 1.00 mg/kg were administered by i.v. infusion and blood was drawn at 5 minutes, 5 hours, and 1, 4, 7, and 14 days post dosing. Following day 14 post-dose, blood was drawn every two weeks until the conclusion of the study. Blood samples were analyzed by FACS for B and T cell markers and the absolute number of these cell types was determined. Serum samples were also analyzed for cytokine levels (IFNγ, IL-2, IL-6 and TNFα) using standard analytic methods. Results are shown in FIG. 3 (B-cells), FIG. 4 (T-cells), and FIGS. 5A-5D (cytokines).

As shown in this Example, administration of the CD3×CD20 bispecific antibody resulted in depletion of circulating B-cells to baseline levels by the first time point measured (day 1). This depletion was not seen in the control animal cohort. B-cell depletion in the bispecific cohort was maintained until two weeks after dosing and in the 0.01 and 0.10 mg/kg dose cohorts was followed by a gradual recovery of B-cell levels until the experiment was concluded at around 11 weeks post dosing. In the 1.0 mg/kg cohort, however, no recovery of B-cell levels was seen for the duration of the experiment (11 weeks). T-cell levels were also monitored in this experiment. A transient loss of circulating T-cells was observed at day 1 post-dose in the bispecific cohorts. T-cell levels returned to baseline levels in these cohorts by the day 4 time-point and maintained at those baseline levels until the end of the experiment. In addition, serum cytokine levels for BS3/20-001 at 5 hours exhibited a dose- and time-dependent response that is consistent with T-cell activation (see FIGS. 5A-5D).

Figure 6:
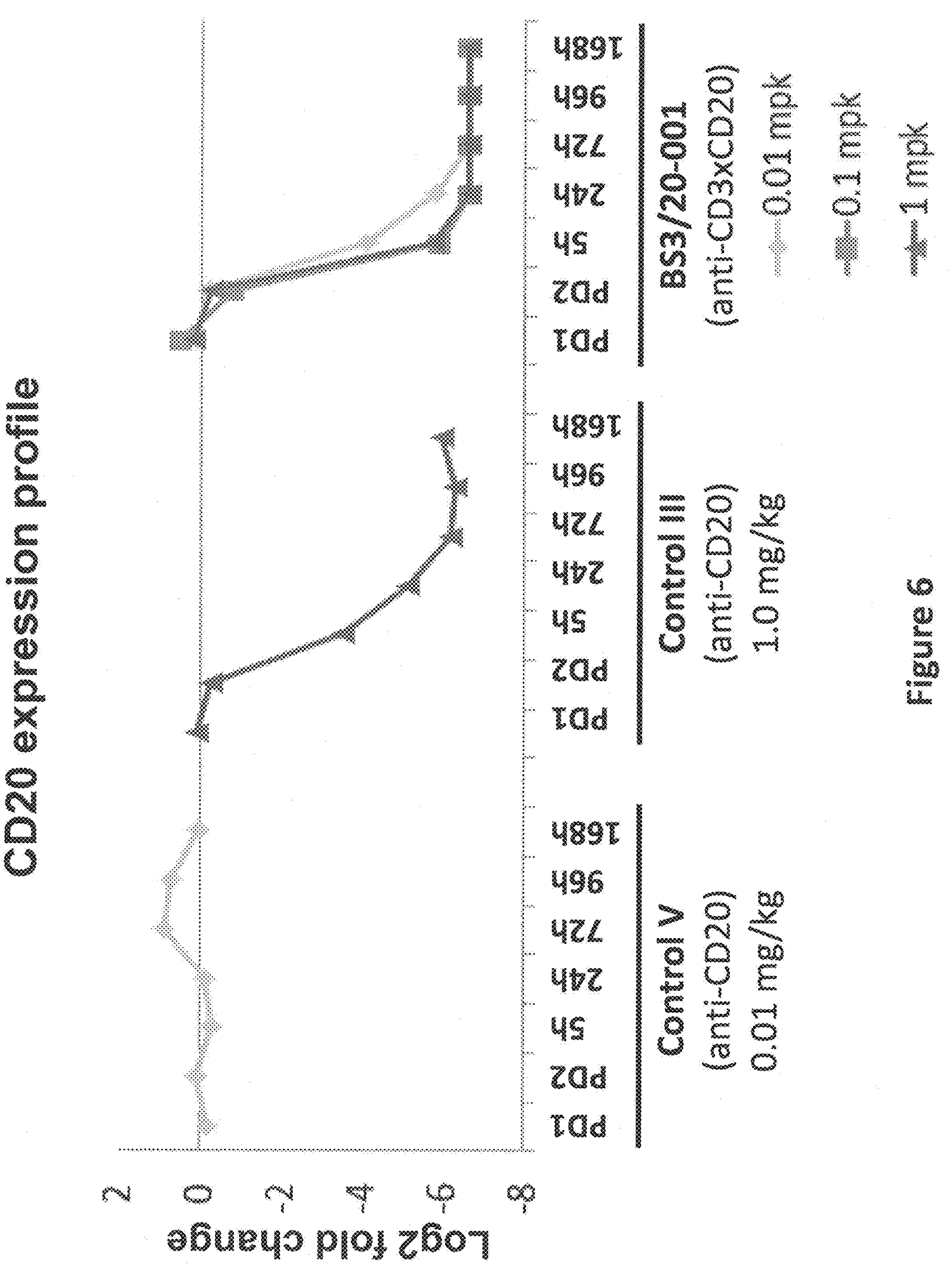
FIG. 6 shows the CD20 expression profile (expressed in terms of Log 2 fold change in expression) determined from blood samples taken at various time points from cynomolgus monkeys treated with 0.01 mg/kg Control V (anti-CD20 antibody); 1.0 mg/kg Control III (anti-CD20 antibody); and 0.01 mg/kg, 0.1 mg/kg and 1.0 mg/kg BS3/20-001 (anti-CD3×CD20 bispecific antibody).

Gene expression levels in the peripheral blood were also analyzed during this experiment. Blood samples were obtained from animals at two pre-dose time points (Day 7 pre-dose and immediately pre-dose) and at 5, 24, 72, 96, and 168 hours post-dosing. RNA was isolated from these samples and analyzed by microarray. When compared to pre-dose levels and gene expression levels from the control group, a notable decrease in the gene expression of B-cell markers in animals treated with the bispecific antibody was observed; this effect was similar to the effect observed in samples obtained from animals treated with 1.0 mg/kg Control III (anti-CD20 antibody corresponding to Rituximab). The observed change in B-cell marker expression corresponds to the loss of B-cells detected in the blood of treated animals. The expression of T-cell marker genes in samples from animals treated with the CD3×CD20 bispecific antibody showed an initial decrease followed by a return to normal levels by the 24 hour time point. In addition, genes associated with an inflammatory response showed an initial upregulation in animals in the bispecific cohort but returned to normal or below normal levels after 24 hours. Finally, examination of the raw intensity of the CD20 gene expression signal suggests that a greater depletion of B-cells arises from treatment of animals with the CD3×CD20 bispecific antibody than with the control anti-CD20 antibodies. (See FIG. 6 and Table 29).

TABLE 29

CD20 Gene Expression Levels at Day 7

| Antibody | Dose mg/kg | CD20 Expression (Raw Intensity) |
|---|---|---|
| Control V | 0.01 | 26485.44 |
| (anti-CD20) | 0.01 | 24335.17 |
| Control III | 1.0 | 1813.46 |
| (anti-CD20) | 1.0 | 47.09 |
| | 1.0 | 98.88 |
| | 1.0 | 70.52 |

TABLE 29-continued

| CD20 Gene Expression Levels at Day 7 | | |
|---|---|---|
| Antibody | Dose mg/kg | CD20 Expression (Raw Intensity) |
| BS3/20-001 | 0.01 | 24.93 |
| | 0.01 | 226.45 |
| | 0.01 | 4.78 |
| | 0.01 | 8.12 |
| | 0.1 | 8.26 |
| | 0.1 | 5.62 |
| | 0.1 | 4.82 |
| | 0.1 | 23.61 |
| | 1.0 | 9.38 |
| | 1.0 | 9.19 |
| | 1.0 | 8.22 |

As shown in Table 29, at seven days post-dosing the raw intensity of CD20 signal remained at background levels in all but one of the CD3×CD20 animals while 3 of 4 animals treated with 1 mg/kg of Control Ill showed either marginal or detectable CD20 signal levels.

Figure 7:
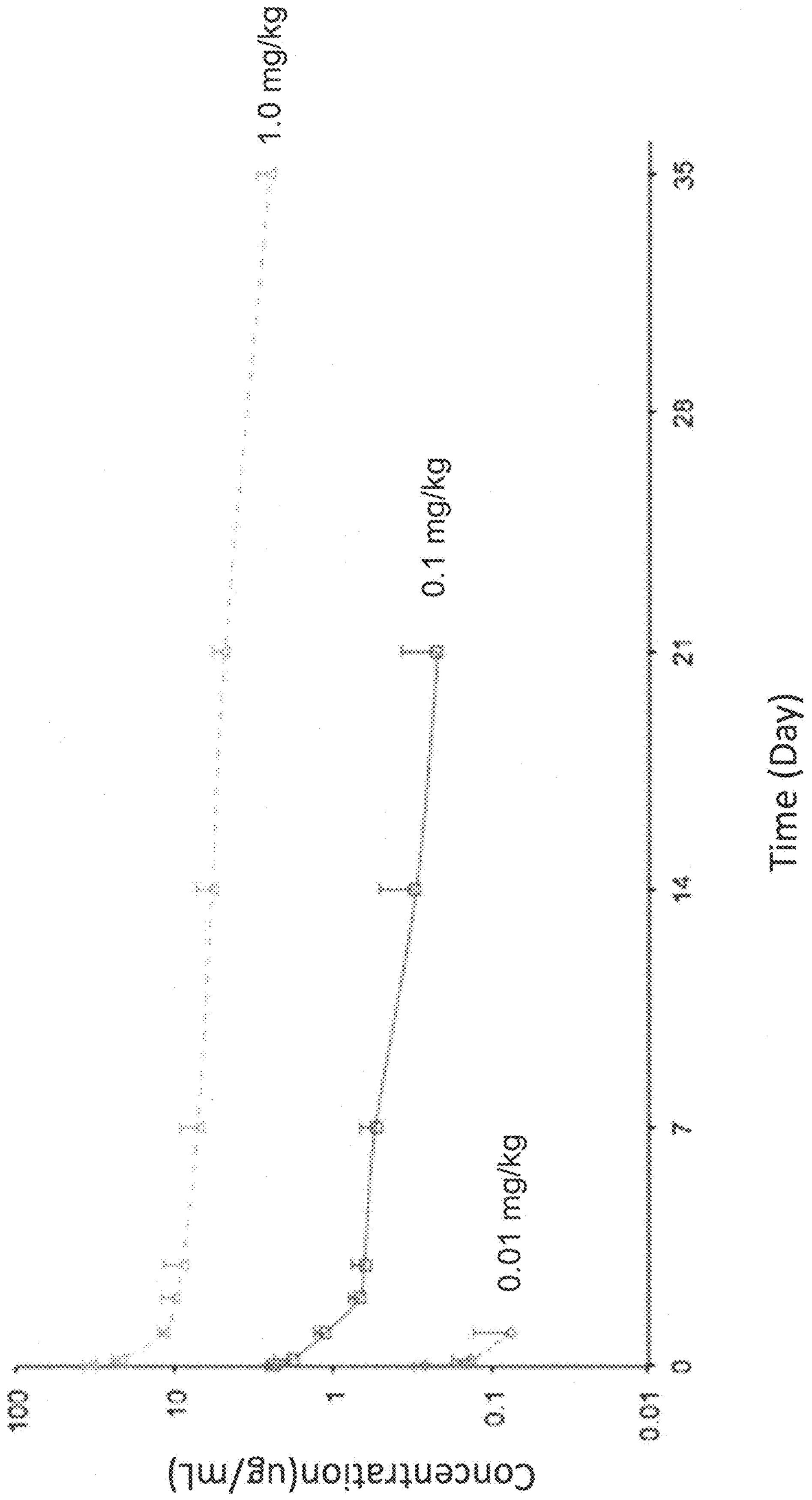
FIG. 7 shows the total serum concentration (pg/mL) of CD3×CD20 bispecific antibody (BS3/20-001) over time in blood samples from cynomolgus monkeys treated with 1.0 mg/kg (open triangles), 0.1 mg/kg (open squares) or 0.01 mg/kg (open diamonds) of CD3×CD20 bispecific antibody.

In the same experiment the pharmacokinetic profile of the bispecific antibody (FIG. 7) was evaluated by obtaining blood samples at pre-dose and at 0.083, 5, 24, 48, 72, 168, 336, 504 and 840 hours. The resultant serum samples were analyzed by a direct enzyme linked immunosorbent assay (ELISA) to determine the concentration of total bispecific antibody. Serum total bispecific (BS3/20-001) concentration data were analyzed by non-compartmental analysis (Phoenix WinNonLin) to determine pharmacokinetic parameters Results are shown in Table 30 (AUC=area under the curve vs. time; $C_{max}$=maximum concentration of compound observed in matrix of interest).

TABLE 30

| Pharmacokinetic Parameters of BS3/20-001 in Cynomolgus Monkey | | | | | | |
|---|---|---|---|---|---|---|
| | | 0.01 mg/kg | | 0.10 mg/kg | | 1.0 mg/kg |
| Parameter | Units | Mean | SD | Mean | SD | Mean | SD |
| $C_{max}$ | μg/mL | 0.261 | 0.0413 | 2.32 | 0.274 | 33.4 | 4.20 |
| $C_{max}$/Dose | kg * μg/mL/mg | 26.1 | 4.13 | 23.2 | 2.74 | 33.4 | 4.20 |
| $t_{max}$ | hr | 0.083 | 0.00 | 0.083 | 0.00 | 0.083 | 0.00 |
| $AUC_{all}$ | μg * hr/mL | 4.42 | 2.37 | 289 | 87.2 | 4940 | 1080 |
| $AUC_{all}$/Dose | hr * kg * μg/mL/mg | 442 | 237 | 2890 | 872 | 4940 | 1080 |

Following a single intravenous dose of 0.01, 0.10 or 1.0 mg/kg of BS3/20-001 in cynomolgus monkeys, mean peak concentrations ($C_{max}$) of 0.261, 2.32 and 33.4 ug/mL, respectively, were observed at the first sampling time point (0.083 hr). Mean $AUC_{all}$ values of 4.42, 289 and 4940 μg*hr/mL were observed at doses of 0.01, 0.1 and 1.0 mg/kg. Dose-normalized AUC values ($AUC_{all}$/Dose) of 442, 2890 and 4940 μg*hr/mL per mg/kg indicate that plasma exposure ($AUC_{all}$) increases with increasing dose in a non-linear fashion. Greater than proportional increase in plasma drug exposure was observed with increased antibody dose, suggesting that BS3/20-001 may be undergoing some target-mediated clearance. The overall pharmacokinetic profile of BS3/20-001 is typical of monoclonal antibodies dosed in cynomolgus monkey.

TABLE 31

| Sequences Excluded from ST.26-Formatted Sequence Listing | |
|---|---|
| Sequence No. | Sequence |
| 13 | ggtgcatcc |
| 14 | GAS |
| 29 | ggtgcatcc |
| 30 | GAS |
| 45 | gctgcatcc |
| 46 | AAS |
| 61 | ggtgcatcc |
| 62 | GAS |
| 77 | gctgcatcc |
| 78 | AAS |
| 93 | gctgcatcc |
| 94 | AAS |
| 109 | gatgcatcc |
| 110 | DAS |
| 125 | ggtgcatcc |
| 126 | GAS |

TABLE 31-continued

| Sequences Excluded from ST.26-Formatted Sequence Listing | |
|---|---|
| Sequence No. | Sequence |
| 141 | ggtgcatcc |
| 142 | GAS |
| 157 | ggtgcatcc |
| 158 | GAS |
| 173 | ggtgcatcc |
| 174 | GAS |
| 189 | ggtgcatcc |
| 190 | GAS |

TABLE 31-continued

| Sequences Excluded from ST.26-Formatted Sequence Listing | |
|---|---|
| Sequence No. | Sequence |
| 205 | ggtgcatcc |
| 206 | GAS |
| 221 | ggtgcatcc |
| 222 | GAS |
| 237 | ggtgcatcc |
| 238 | GAS |
| 253 | ggtgcatcc |
| 254 | GAS |
| 269 | ggtgcatcc |
| 270 | GAS |
| 285 | ggtgcatcc |
| 286 | GAS |
| 301 | ggtgcaacc |
| 302 | GAT |
| 317 | ggtgcaacc |
| 318 | GAT |
| 333 | ggtgcatcc |
| 334 | GAS |
| 349 | ggtgcatcc |
| 350 | GAS |
| 365 | tgggcatct |
| 366 | WAS |
| 381 | gctgcatcc |
| 382 | AAS |
| 397 | ggtgcatcc |
| 398 | GAS |
| 413 | ggtgcaacc |
| 414 | GAT |
| 429 | ggtgcaacc |
| 430 | GAT |
| 445 | gctgcatcc |
| 446 | AAS |
| 461 | gctgcatcc |
| 462 | AAS |
| 477 | gctgcatcc |
| 478 | AAS |
| 493 | gctgcatcc |
| 494 | AAS |

TABLE 31-continued

| Sequences Excluded from ST.26-Formatted Sequence Listing | |
|---|---|
| Sequence No. | Sequence |
| 509 | gctgcatcc |
| 510 | AAS |
| 525 | gctgcatcc |
| 526 | AAS |
| 541 | gctgcttcc |
| 542 | AAS |
| 557 | gaagcttct |
| 558 | EAS |
| 573 | gctgtatcc |
| 574 | AVS |
| 589 | gatgcatcc |
| 590 | DAS |
| 605 | gctgcatcc |
| 606 | AAS |
| 621 | gctgcatcc |
| 622 | AAS |
| 637 | gctgcatcc |
| 638 | AAS |
| 653 | gctgcatcc |
| 654 | AAS |
| 669 | gctgcatcc |
| 670 | AAS |
| 685 | gctgcgtcc |
| 686 | AAS |
| 701 | gctgcatcc |
| 702 | AAS |
| 717 | ggtgcgtcc |
| 718 | GAS |
| 733 | ggtgcgtcc |
| 734 | GAS |
| 749 | ggtgcgtcc |
| 750 | GAS |
| 765 | ggtgcgtcc |
| 766 | GAS |
| 781 | ggtgcatcc |
| 782 | GAS |
| 797 | ggtgcgtcc |

TABLE 31-continued

| Sequences Excluded from ST.26-Formatted Sequence Listing | |
|---|---|
| Sequence No. | Sequence |
| 798 | GAS |
| 813 | ggtgcgtcc |
| 814 | GAS |
| 829 | aaggcgtct |
| 830 | KAS |
| 845 | tgggcatct |
| 846 | WAS |
| 861 | actgcatcc |
| 862 | TAS |
| 877 | ggtgcatcc |
| 878 | GAS |
| 893 | actgcatcc |
| 894 | TAS |
| 909 | actgcatcc |
| 910 | TAS |
| 925 | actgcatcc |
| 926 | TAS |
| 941 | gttgcatcc |
| 942 | VAS |
| 957 | actgcatcc |
| 958 | TAS |
| 973 | gctgcatcc |
| 974 | AAS |
| 989 | gttgcatcc |
| 990 | VAS |
| 1005 | actgcatcc |
| 1006 | TAS |
| 1021 | actgcatcc |
| 1022 | TAS |
| 1037 | gttgcatcc |
| 1038 | VAS |
| 1237 | gctgcatcc |
| 1238 | AAS |
| 1261 | ggtgcatcc |
| 1262 | GAS |
| 1277 | ggtgcatcc |
| 1278 | GAS |
| 1293 | ggtgcatcc |
| 1294 | GAS |
| 1309 | ggtgcatcc |
| 1310 | GAS |
| 1325 | ggtgcatcc |
| 1326 | GAS |
| 1335 | DTS |
| 1349 | ggtacatcc |
| 1350 | GTS |
| 1365 | gaagcatct |
| 1366 | EAS |

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

TABLE 2

| Nucleic Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1H2712N | 1 | 3 | 5 | 7 | 9 | 11 | 13 | 15 |
| H1M2692N | 17 | 19 | 21 | 23 | 25 | 27 | 29 | 31 |
| H1M3542N | 33 | 35 | 37 | 39 | 41 | 43 | 45 | 47 |
| H1M3544N | 49 | 51 | 53 | 55 | 57 | 59 | 61 | 63 |
| H1M3549N | 65 | 67 | 69 | 71 | 73 | 75 | 77 | 79 |
| H1M3613N | 81 | 83 | 85 | 87 | 89 | 91 | 93 | 95 |
| H2M2689N | 97 | 99 | 101 | 103 | 105 | 107 | 109 | 111 |
| H2M2690N | 113 | 115 | 117 | 119 | 121 | 123 | 125 | 127 |
| H2M2691N | 129 | 131 | 133 | 135 | 137 | 139 | 141 | 143 |
| H2M2704N | 145 | 147 | 149 | 151 | 153 | 155 | 157 | 159 |
| H2M2705N | 161 | 163 | 165 | 167 | 169 | 171 | 173 | 175 |
| H2M2706N | 177 | 179 | 181 | 183 | 185 | 187 | 189 | 191 |

TABLE 2-continued

| Nucleic Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H2M2707N | 193 | 195 | 197 | 199 | 201 | 203 | 205 | 207 |
| H2M2708N | 209 | 211 | 213 | 215 | 217 | 219 | 221 | 223 |
| H2M2709N | 225 | 227 | 229 | 231 | 233 | 235 | 237 | 239 |
| H2M2710N | 241 | 243 | 245 | 247 | 249 | 251 | 253 | 255 |
| H2M2711N | 257 | 259 | 261 | 263 | 265 | 267 | 269 | 271 |
| H2M2774N | 273 | 275 | 277 | 279 | 281 | 283 | 285 | 287 |
| H2M2775N | 289 | 291 | 293 | 295 | 297 | 299 | 301 | 303 |
| H2M2776N | 305 | 307 | 309 | 311 | 313 | 315 | 317 | 319 |
| H2M2777N | 321 | 323 | 325 | 327 | 329 | 331 | 333 | 335 |
| H2M2778N | 337 | 339 | 341 | 343 | 345 | 347 | 349 | 351 |
| H2M2779N | 353 | 355 | 357 | 359 | 361 | 363 | 365 | 367 |
| H2M2789N | 369 | 371 | 373 | 375 | 377 | 379 | 381 | 383 |
| H2M2862N | 385 | 387 | 389 | 391 | 393 | 395 | 397 | 399 |
| H2M2885N | 401 | 403 | 405 | 407 | 409 | 411 | 413 | 415 |
| H2M2886N | 417 | 419 | 421 | 423 | 425 | 427 | 429 | 431 |
| H2M3540N | 433 | 435 | 437 | 439 | 441 | 443 | 445 | 447 |
| H2M3541N | 449 | 451 | 453 | 455 | 457 | 459 | 461 | 463 |
| H2M3543N | 465 | 467 | 469 | 471 | 473 | 475 | 477 | 479 |
| H2M3547N | 481 | 483 | 485 | 487 | 489 | 491 | 493 | 495 |
| H2M3548N | 497 | 499 | 501 | 503 | 505 | 507 | 509 | 511 |
| H2M3563N | 513 | 515 | 517 | 519 | 521 | 523 | 525 | 527 |
| H1H5751P | 529 | 531 | 533 | 535 | 537 | 539 | 541 | 543 |
| H1H5752P | 545 | 547 | 549 | 551 | 553 | 555 | 557 | 559 |
| H1H5753B | 561 | 563 | 565 | 567 | 569 | 571 | 573 | 575 |
| H1H5754B | 577 | 579 | 581 | 583 | 585 | 587 | 589 | 591 |
| H1H5755B | 593 | 595 | 597 | 599 | 601 | 603 | 605 | 607 |
| H1H5756B | 609 | 611 | 613 | 615 | 617 | 619 | 621 | 623 |
| H1H5757B | 625 | 627 | 629 | 631 | 633 | 635 | 637 | 639 |
| H1H5758B | 641 | 643 | 645 | 647 | 649 | 651 | 653 | 655 |
| H1H5761P | 657 | 659 | 661 | 663 | 665 | 667 | 669 | 671 |
| H1H5763P | 673 | 675 | 677 | 679 | 681 | 683 | 685 | 687 |
| H1H5764P | 689 | 691 | 693 | 695 | 697 | 699 | 701 | 703 |
| H1H5769P | 705 | 707 | 709 | 711 | 713 | 715 | 717 | 719 |
| H1H5771P | 721 | 723 | 725 | 727 | 729 | 731 | 733 | 735 |
| H1H5772P | 737 | 739 | 741 | 743 | 745 | 747 | 749 | 751 |
| H1H5777P | 753 | 755 | 757 | 759 | 761 | 763 | 765 | 767 |
| H1H5778P | 769 | 771 | 773 | 775 | 777 | 779 | 781 | 783 |
| H1H5780P | 785 | 787 | 789 | 791 | 793 | 795 | 797 | 799 |
| H1H5781P | 801 | 803 | 805 | 807 | 809 | 811 | 813 | 815 |
| H1H5782P | 817 | 819 | 821 | 823 | 825 | 827 | 829 | 831 |
| H1H5785B | 833 | 835 | 837 | 839 | 841 | 843 | 845 | 847 |
| H1H5786B | 849 | 851 | 853 | 855 | 857 | 859 | 861 | 863 |
| H1H5788P | 865 | 867 | 869 | 871 | 873 | 875 | 877 | 879 |
| H1H5790B | 881 | 883 | 885 | 887 | 889 | 891 | 893 | 895 |
| H1H5791B | 897 | 899 | 901 | 903 | 905 | 907 | 909 | 911 |
| H1H5792B | 913 | 915 | 917 | 919 | 921 | 923 | 925 | 927 |
| H1H5793B | 929 | 931 | 933 | 935 | 937 | 939 | 941 | 943 |
| H1H5795B | 945 | 947 | 949 | 951 | 953 | 955 | 957 | 959 |
| H1H5796B | 961 | 963 | 965 | 967 | 969 | 971 | 973 | 975 |
| H1H5797B | 977 | 979 | 981 | 983 | 985 | 987 | 989 | 991 |
| H1H5798B | 993 | 995 | 997 | 999 | 1001 | 1003 | 1005 | 1007 |
| H1H5799P | 1009 | 1011 | 1013 | 1015 | 1017 | 1019 | 1021 | 1023 |
| H1H5801B | 1025 | 1027 | 1029 | 1031 | 1033 | 1035 | 1037 | 1039 |
| H1H7194B | 1041 | 1043 | 1045 | 1047 | 1233 | 1235 | 1237 | 1239 |
| H1H7195B | 1049 | 1051 | 1053 | 1055 | 1233 | 1235 | 1237 | 1239 |
| H1H7196B | 1057 | 1059 | 1061 | 1063 | 1233 | 1235 | 1237 | 1239 |
| H1H7198B | 1065 | 1067 | 1069 | 1071 | 1233 | 1235 | 1237 | 1239 |
| H1H7203B | 1073 | 1075 | 1077 | 1079 | 1233 | 1235 | 1237 | 1239 |
| H1H7204B | 1081 | 1083 | 1085 | 1087 | 1233 | 1235 | 1237 | 1239 |
| H1H7208B | 1089 | 1091 | 1093 | 1095 | 1233 | 1235 | 1237 | 1239 |
| H1H7211B | 1097 | 1099 | 1101 | 1103 | 1233 | 1235 | 1237 | 1239 |
| H1H7221B | 1105 | 1107 | 1109 | 1111 | 1233 | 1235 | 1237 | 1239 |
| H1H7223B | 1113 | 1115 | 1117 | 1119 | 1233 | 1235 | 1237 | 1239 |
| H1H7226B | 1121 | 1123 | 1125 | 1127 | 1233 | 1235 | 1237 | 1239 |
| H1H7232B | 1129 | 1131 | 1133 | 1135 | 1233 | 1235 | 1237 | 1239 |
| H1H7233B | 1137 | 1139 | 1141 | 1143 | 1233 | 1235 | 1237 | 1239 |
| H1H7241B | 1145 | 1147 | 1149 | 1151 | 1233 | 1235 | 1237 | 1239 |
| H1H7242B | 1153 | 1155 | 1157 | 1159 | 1233 | 1235 | 1237 | 1239 |
| H1H7250B | 1161 | 1163 | 1165 | 1167 | 1233 | 1235 | 1237 | 1239 |
| H1H7251B | 1169 | 1171 | 1173 | 1175 | 1233 | 1235 | 1237 | 1239 |
| H1H7254B | 1177 | 1179 | 1181 | 1183 | 1233 | 1235 | 1237 | 1239 |
| H1H7258B | 1185 | 1187 | 1189 | 1191 | 1233 | 1235 | 1237 | 1239 |
| H1H7269B | 1193 | 1195 | 1197 | 1199 | 1233 | 1235 | 1237 | 1239 |
| H1H7279B | 1201 | 1203 | 1205 | 1207 | 1233 | 1235 | 1237 | 1239 |

TABLE 2-continued

| Nucleic Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1xH7221G | 1209 | 1211 | 1213 | 1215 | 1233 | 1235 | 1237 | 1239 |
| H1xH7221G3 | 1217 | 1219 | 1221 | 1223 | 1233 | 1235 | 1237 | 1239 |
| H1xH7221G5 | 1225 | 1227 | 1229 | 1231 | 1233 | 1235 | 1237 | 1239 |

What is claimed is:

1. An antigen-binding molecule that binds human CD3, wherein the antigen-binding molecule comprises a heavy chain variable region (HCVR) comprising three heavy chain complementarity determining regions, HCDR1, HCDR2, and HCDR3, comprising the amino acid sequences of SEQ ID NOs: 1052, 1054 and 1056, respectively, and a light chain variable region (LCVR) comprising three light chain complementarity determining regions, LCDR1, LCDR2 and LCDR3, comprising the amino acid sequences of SEQ ID NO: 1236, AAS and SEQ ID NO: 1240, respectively.

2. The antigen-binding molecule of claim 1, wherein the HCVR comprises the amino acid sequence of SEQ ID NO: 1050.

3. The antigen-binding molecule of claim 2 that is an antibody or antigen-binding fragment thereof.

4. A pharmaceutical composition comprising the antigen-binding molecule of claim 2, and a pharmaceutically acceptable carrier or diluent.

5. The antigen-binding molecule of claim 1, wherein the LCVR comprises the amino acid sequence of SEQ ID NO: 1234.

6. The antigen-binding molecule of claim 5 that is an antibody or antigen-binding fragment thereof.

7. A pharmaceutical composition comprising the antigen-binding molecule of claim 5, and a pharmaceutically acceptable carrier or diluent.

8. The antigen-binding molecule of claim 1, wherein the HCVR comprises the amino acid sequence of SEQ ID NO: 1050, and the LCVR comprises the amino acid sequence of SEQ ID NO: 1234.

9. The antigen-binding molecule of claim 8 that is an antibody or antigen-binding fragment thereof.

10. A pharmaceutical composition comprising the antigen-binding molecule of claim 8, and a pharmaceutically acceptable carrier or diluent.

11. The antigen-binding molecule of claim 8, wherein the antigen-binding molecule comprises a scFv comprising the HCVR and the LCVR.

12. The antigen-binding molecule of claim 1 that is an antibody or antigen-binding fragment thereof.

13. A pharmaceutical composition comprising the antigen-binding molecule of claim 1, and a pharmaceutically acceptable carrier or diluent.

14. The antigen-binding molecule of claim 1, wherein the antigen-binding molecule comprises a single chain variable fragment (scFv) comprising the HCVR and the LCVR.

15. A pharmaceutical composition comprising the antigen-binding molecule of claim 14, and a pharmaceutically acceptable carrier or diluent.

16. A method of treating cancer in a subject in need thereof, the method comprising administering the antigen-binding molecule of claim 1 to the subject.

17. A pair of nucleic acid molecules comprising:

a first nucleic acid molecule encoding a heavy chain variable region (HCVR) comprising three heavy chain complementarity determining regions, HCDR1, HCDR2, and HCDR3, comprising the amino acid sequences of SEQ ID NOs: 1052, 1054 and 1056, respectively; and a second nucleic acid molecule encoding a light chain variable region (LCVR) comprising three light chain complementarity determining regions, LCDR1, LCDR2 and LCDR3, comprising the amino acid sequences of SEQ ID NO: 1236, AAS and SEQ ID NO: 1240, respectively.

18. The pair of nucleic acid molecules of claim 17, wherein the HCVR comprises the amino acid sequence of SEQ ID NO: 1050, and the LCVR comprises the amino acid sequence of SEQ ID NO: 1234.

19. An isolated host cell comprising the pair of nucleic acid molecules of claim 17.

20. A method of producing an antigen-binding molecule that binds human CD3, the method comprising:

(a) culturing a host cell comprising a first nucleic acid molecule encoding a heavy chain variable region (HCVR) comprising three heavy chain complementarity determining regions, HCDR1, HCDR2, and HCDR3, comprising the amino acid sequences of SEQ ID NOs: 1052, 1054 and 1056, respectively, and a second nucleic acid molecule encoding a light chain variable region (LCVR) comprising three light chain complementarity determining regions, LCDR1, LCDR2 and LCDR3, comprising the amino acid sequences of SEQ ID NO: 1236, AAS and SEQ ID NO: 1240, respectively, under conditions permitting production of the antigen-binding molecule; and (b) recovering the antigen-binding molecule so produced.

* * * * *

SEQUENCE LISTING

```
Sequence total quantity: 1375
SEQ ID NO: 1            moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 1
gaagtgcaac tggtggagtc tgggggaggc ttagtacagc ctggcgggtc cctgagactc  60
tcctgtgcag ccactggatt cacctttgat gattttacca tgcactgggt ccggcaagct  120
ccagggaagg gcctggagtg ggtctcaggt atcagttgga atagtggtag cataggctat  180
gtggactctg tgaagggccg attcaccatc tccagagaca acgccaagaa ctccctgtat  240
ctgcaaatga acagtctgag agctgaggac acggccttgt actactgtgc aaaagataat  300
agtggctacg gctattatta ctacggtatg gacgtctggg gccaagggac cacggtcacc  360
gtctcctca                                                          369

SEQ ID NO: 2            moltype = AA  length = 123
FEATURE                 Location/Qualifiers
REGION                  1..123
                        note = Synthetic
source                  1..123
                        mol_type = protein
                        organism = synthetic construct
SEQUENCE: 2
EVQLVESGGG LVQPGGSLRL SCAATGFTFD DFTMHWVRQA PGKGLEWVSG ISWNSGSIGY  60
VDSVKGRFTI SRDNAKNSLY LQMNSLRAED TALYYCAKDN SGYGYYYYGM DVWGQGTTVT  120
VSS                                                                123

SEQ ID NO: 3            moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 3
ggattcacct ttgatgattt tacc                                         24

SEQ ID NO: 4            moltype = AA  length = 8
FEATURE                 Location/Qualifiers
REGION                  1..8
                        note = Synthetic
source                  1..8
                        mol_type = protein
                        organism = synthetic construct
SEQUENCE: 4
GFTFDDFT                                                           8

SEQ ID NO: 5            moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 5
atcagttgga atagtggtag cata                                         24

SEQ ID NO: 6            moltype = AA  length = 8
FEATURE                 Location/Qualifiers
REGION                  1..8
                        note = Synthetic
```

-continued

```
source                  1..8
                        mol_type = protein
                        organism = synthetic construct
SEQUENCE: 6
ISWNSGSI                                                                8

SEQ ID NO: 7            moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 7
gcaaaagata atagtggcta cggctattat tactacggta tggacgtc                   48

SEQ ID NO: 8            moltype = AA  length = 16
FEATURE                 Location/Qualifiers
REGION                  1..16
                        note = Synthetic
source                  1..16
                        mol_type = protein
                        organism = synthetic construct
SEQUENCE: 8
AKDNSGYGYY YYGMDV                                                      16

SEQ ID NO: 9            moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 9
gaaatagtga tgacgcagtc tccagccacc ctgtctgtgt ctccagggga aagagccacc  60
ctctcctgca gggccagtca cagtgttagc aggaactcag cctggtacca gcagaaacct  120
ggccaggctc ccaggctcct catctatggt gcatccacca gggccactgg tatcccagcc  180
aggttcagtg gcagtgggtc tgggacagaa ttcactctca ccatcagcag cctgcagtct  240
gaagattttg caatttatta ctgtcagcag tataataatt ggcctctcac tttcggcgga  300
gggaccaagg tggagatcaa a                                                321

SEQ ID NO: 10           moltype = AA  length = 107
FEATURE                 Location/Qualifiers
REGION                  1..107
                        note = Synthetic
source                  1..107
                        mol_type = protein
                        organism = synthetic construct
SEQUENCE: 10
EIVMTQSPAT LSVSPGERAT LSCRASHSVS RNSAWYQQKP GQAPRLLIYG ASTRATGIPA  60
RFSGSGSGTE FTLTISSLQS EDFAIYYCQQ YNNWPLTFGG GTKVEIK                    107

SEQ ID NO: 11           moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 11
cacagtgtta gcaggaac                                                     18

SEQ ID NO: 12           moltype = AA  length = 6
FEATURE                 Location/Qualifiers
REGION                  1..6
                        note = Synthetic
source                  1..6
                        mol_type = protein
                        organism = synthetic construct
SEQUENCE: 12
HSVSRN                                                                  6

SEQ ID NO: 13           moltype =   length =
SEQUENCE: 13
000

SEQ ID NO: 14           moltype =   length =
SEQUENCE: 14
000
```

```
SEQ ID NO: 15          moltype = DNA  length = 27
FEATURE                Location/Qualifiers
misc_feature           1..27
                       note = Synthetic
source                 1..27
                       mol_type = other DNA
                       organism = synthetic construct
SEQUENCE: 15
cagcagtata ataattggcc tctcact                                        27

SEQ ID NO: 16          moltype = AA  length = 9
FEATURE                Location/Qualifiers
REGION                 1..9
                       note = Synthetic
source                 1..9
                       mol_type = protein
                       organism = synthetic construct
SEQUENCE: 16
QQYNNWPLT                                                            9

SEQ ID NO: 17          moltype = DNA  length = 372
FEATURE                Location/Qualifiers
misc_feature           1..372
                       note = Synthetic
source                 1..372
                       mol_type = other DNA
                       organism = synthetic construct
SEQUENCE: 17
gaagtgcaac tggtggaatc ggggggaggc ttggtacagc ctggcgggtc cctgagactc  60
tcctgtgcag cctctggatt ctcctttgat gattatacca tgcactgggt ccggcaacct  120
ccagggaagg gcctggagtg ggtctcaggt attagttgga atagtggtag cataggctat  180
gcggactctg tgaagggccg attcaccatc tccagagaca acgccaagaa ctccctgtat  240
ctgcaaatga acagtctgag agctggggac acggccttgt actactgtgc aaaagataat  300
agtggctacg gctattacta ctactacggt atggacgtct ggggccaagg gaccacggtc  360
accgtctcct ca                                                        372

SEQ ID NO: 18          moltype = AA  length = 124
FEATURE                Location/Qualifiers
REGION                 1..124
                       note = Synthetic
source                 1..124
                       mol_type = protein
                       organism = synthetic construct
SEQUENCE: 18
EVQLVESGGG LVQPGGSLRL SCAASGFSFD DYTMHWVRQP PGKGLEWVSG ISWNSGSIGY  60
ADSVKGRFTI SRDNAKNSLY LQMNSLRAGD TALYYCAKDN SGYGYYYYYG MDVWGQGTTV  120
TVSS                                                                 124

SEQ ID NO: 19          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 19
ggattctcct ttgatgatta tacc                                           24

SEQ ID NO: 20          moltype = AA  length = 8
FEATURE                Location/Qualifiers
REGION                 1..8
                       note = Synthetic
source                 1..8
                       mol_type = protein
                       organism = synthetic construct
SEQUENCE: 20
GFSFDDYT                                                             8

SEQ ID NO: 21          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 21
attagttgga atagtggtag cata                                           24
```

-continued

```
SEQ ID NO: 22          moltype = AA  length = 8
FEATURE                Location/Qualifiers
REGION                 1..8
                       note = Synthetic
source                 1..8
                       mol_type = protein
                       organism = synthetic construct
SEQUENCE: 22
ISWNSGSI                                                          8

SEQ ID NO: 23          moltype = DNA  length = 51
FEATURE                Location/Qualifiers
misc_feature           1..51
                       note = Synthetic
source                 1..51
                       mol_type = other DNA
                       organism = synthetic construct
SEQUENCE: 23
gcaaaagata atagtggcta cggctattac tactactacg gtatggacgt c          51

SEQ ID NO: 24          moltype = AA  length = 17
FEATURE                Location/Qualifiers
REGION                 1..17
                       note = Synthetic
source                 1..17
                       mol_type = protein
                       organism = synthetic construct
SEQUENCE: 24
AKDNSGYGYY YYYGMDV                                                17

SEQ ID NO: 25          moltype = DNA  length = 321
FEATURE                Location/Qualifiers
misc_feature           1..321
                       note = Synthetic
source                 1..321
                       mol_type = other DNA
                       organism = synthetic construct
SEQUENCE: 25
gaaatagtga tgacgcagtc tccagccacc ctgtctgtgt ctccagggga aagagccacc  60
ctctcctgca gggccagtca gagtgttagc agcaacttag cctggtacca gcagaaacct  120
ggccaggctc ccagactcct catctatggt gcatccacca gggccactgg tatcccagcc  180
aggttcagtg gcagtgggtc tgggacagaa ttcactctca ccatcagcag cctgcagtct  240
gaagattttg cagtttatta ctgtcagcag tattataact ggcctctcac tttcggcgga  300
gggaccaagg tggagatcaa a                                           321

SEQ ID NO: 26          moltype = AA  length = 107
FEATURE                Location/Qualifiers
REGION                 1..107
                       note = Synthetic
source                 1..107
                       mol_type = protein
                       organism = synthetic construct
SEQUENCE: 26
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YYNWPLTFGG GTKVEIK               107

SEQ ID NO: 27          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 27
cagagtgtta gcagcaac                                               18

SEQ ID NO: 28          moltype = AA  length = 6
FEATURE                Location/Qualifiers
REGION                 1..6
                       note = Synthetic
source                 1..6
                       mol_type = protein
                       organism = synthetic construct
SEQUENCE: 28
QSVSSN                                                            6

SEQ ID NO: 29          moltype =   length =
SEQUENCE: 29
000
```

```
SEQ ID NO: 30          moltype =   length =
SEQUENCE: 30
000

SEQ ID NO: 31          moltype = DNA  length = 27
FEATURE                Location/Qualifiers
misc_feature           1..27
                       note = Synthetic
source                 1..27
                       mol_type = other DNA
                       organism = synthetic construct
SEQUENCE: 31
cagcagtatt ataactggcc tctcact                                      27

SEQ ID NO: 32          moltype = AA  length = 9
FEATURE                Location/Qualifiers
REGION                 1..9
                       note = Synthetic
source                 1..9
                       mol_type = protein
                       organism = synthetic construct
SEQUENCE: 32
QQYYNWPLT                                                          9

SEQ ID NO: 33          moltype = DNA  length = 372
FEATURE                Location/Qualifiers
misc_feature           1..372
                       note = Synthetic
source                 1..372
                       mol_type = other DNA
                       organism = synthetic construct
SEQUENCE: 33
gaagtacagc tggtggagtc tgggggaggc ttggtacagc ctggcaggtc cctgagactc  60
tcctgtgtag cctctggatt cccctttgct gattatacca tgcactgggt ccggcaagct  120
ccagggaagg gcctggagtg ggtctcagat attagttgga atagtggtag caaaggctat  180
gcggactctg tgaagggccg attcaccatc tccagagaca atgccaagaa ctccctgtat  240
ctgcaaatga acagtctgag aactgaggac acggccttct attactgtgc aaaagatatg  300
agtggctacg cccactactt ctactacggt atggacgtct ggggccaagg gaccacggtc  360
accgtctcct ca                                                      372

SEQ ID NO: 34          moltype = AA  length = 124
FEATURE                Location/Qualifiers
REGION                 1..124
                       note = Synthetic
source                 1..124
                       mol_type = protein
                       organism = synthetic construct
SEQUENCE: 34
EVQLVESGGG LVQPGRSLRL SCVASGFPFA DYTMHWVRQA PGKGLEWVSD ISWNSGSKGY  60
ADSVKGRFTI SRDNAKNSLY LQMNSLRTED TAFYYCAKDM SGYAHYFYYG MDVWGQGTTV  120
TVSS                                                               124

SEQ ID NO: 35          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 35
ggattcccct ttgctgatta tacc                                         24

SEQ ID NO: 36          moltype = AA  length = 8
FEATURE                Location/Qualifiers
REGION                 1..8
                       note = Synthetic
source                 1..8
                       mol_type = protein
                       organism = synthetic construct
SEQUENCE: 36
GFPFADYT                                                           8

SEQ ID NO: 37          moltype = DNA  length = 24
FEATURE                Location/Qualifiers
misc_feature           1..24
                       note = Synthetic
source                 1..24
                       mol_type = other DNA
```

```
                        organism = synthetic construct
SEQUENCE: 37
attagttgga atagtggtag caaa                                        24

SEQ ID NO: 38           moltype = AA  length = 8
FEATURE                 Location/Qualifiers
REGION                  1..8
                        note = Synthetic
source                  1..8
                        mol_type = protein
                        organism = synthetic construct
SEQUENCE: 38
ISWNSGSK                                                          8

SEQ ID NO: 39           moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 39
gcaaaagata tgagtggcta cgcccactac ttctactacg gtatggacgt c          51

SEQ ID NO: 40           moltype = AA  length = 17
FEATURE                 Location/Qualifiers
REGION                  1..17
                        note = Synthetic
source                  1..17
                        mol_type = protein
                        organism = synthetic construct
SEQUENCE: 40
AKDMSGYAHY FYYGMDV                                                17

SEQ ID NO: 41           moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 41
gacatccaga tgacccagtc tccatcctcc ctgtctgcat ctgtaggaga cagagtcacc  60
atcacttgcc ggccaagtca gagcattagc agctatttaa attggtttca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                        324

SEQ ID NO: 42           moltype = AA  length = 108
FEATURE                 Location/Qualifiers
REGION                  1..108
                        note = Synthetic
source                  1..108
                        mol_type = protein
                        organism = synthetic construct
SEQUENCE: 42
DIQMTQSPSS LSASVGDRVT ITCRPSQSIS SYLNWFQQKP GKAPKLLIYA ASSLQSGVPS  60
RFSGSGSGTD FTLTISSLQP EDFATYYCQQ SYSTPPITFG QGTRLEIK              108

SEQ ID NO: 43           moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 43
cagagcatta gcagctat                                               18

SEQ ID NO: 44           moltype = AA  length = 6
FEATURE                 Location/Qualifiers
REGION                  1..6
                        note = Synthetic
source                  1..6
                        mol_type = protein
                        organism = synthetic construct
SEQUENCE: 44
QSISSY                                                            6
```

```
SEQ ID NO: 45          moltype =   length =
SEQUENCE: 45
000

SEQ ID NO: 46          moltype =   length =
SEQUENCE: 46
000

SEQ ID NO: 47          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 47
caacagagtt acagtacccc tccgatcacc                                      30

SEQ ID NO: 48          moltype = AA  length = 10
FEATURE                Location/Qualifiers
REGION                 1..10
                       note = Synthetic
source                 1..10
                       mol_type = protein
                       organism = synthetic construct
SEQUENCE: 48
QQSYSTPPIT                                                            10

SEQ ID NO: 49          moltype = DNA  length = 372
FEATURE                Location/Qualifiers
misc_feature           1..372
                       note = Synthetic
source                 1..372
                       mol_type = other DNA
                       organism = synthetic construct
SEQUENCE: 49
gaagtacaac tggtggagtc tgggggaggc ttggtacagc ctggcaggtc cctaagactc  60
tcctgtgcag cctctggatt cacctttgat gattatacca tgcactgggt ccggcaagtt  120
ccagggaagg gcctggagtg ggtctcaggt attagttgga atagtggcag cttggcctac  180
gcggactctg tgaagggccg attcaccatc tccagagaca acgccaagaa ttccctgtat  240
ctgcaaatga acagtcttca ccctgaggac acggccctct attactgtgt aaaagatggt  300
agtggctacg gccactactc ctactacggt ttggacgtct ggggccaggg gaccacggtc  360
accgtctcct ca                                                         372

SEQ ID NO: 50          moltype = AA  length = 124
FEATURE                Location/Qualifiers
REGION                 1..124
                       note = Synthetic
source                 1..124
                       mol_type = protein
                       organism = synthetic construct
SEQUENCE: 50
EVQLVESGGG LVQPGRSLRL SCAASGFTFD DYTMHWVRQV PGKGLEWVSG ISWNSGSLAY  60
ADSVKGRFTI SRDNAKNSLY LQMNSLHPED TALYYCVKDG SGYGHYSYYG LDVWGQGTTV  120
TVSS                                                                  124

SEQ ID NO: 51          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 51
ggattcacct ttgatgatta tacc                                            24

SEQ ID NO: 52          moltype = AA  length = 8
FEATURE                Location/Qualifiers
REGION                 1..8
                       note = Synthetic
source                 1..8
                       mol_type = protein
                       organism = synthetic construct
SEQUENCE: 52
GFTFDDYT                                                              8

SEQ ID NO: 53          moltype = DNA  length = 24
FEATURE                Location/Qualifiers
```

```
misc_feature          1..24
                      note = Synthetic
source                1..24
                      mol_type = other DNA
                      organism = synthetic construct
SEQUENCE: 53
attagttgga atagtggcag cttg                                  24

SEQ ID NO: 54         moltype = AA  length = 8
FEATURE               Location/Qualifiers
REGION                1..8
                      note = Synthetic
source                1..8
                      mol_type = protein
                      organism = synthetic construct
SEQUENCE: 54
ISWNSGSL                                                    8

SEQ ID NO: 55         moltype = DNA  length = 51
FEATURE               Location/Qualifiers
misc_feature          1..51
                      note = Synthetic
source                1..51
                      mol_type = other DNA
                      organism = synthetic construct
SEQUENCE: 55
gtaaaagatg gtagtggcta cggccactac tcctactacg gtttggacgt c    51

SEQ ID NO: 56         moltype = AA  length = 17
FEATURE               Location/Qualifiers
REGION                1..17
                      note = Synthetic
source                1..17
                      mol_type = protein
                      organism = synthetic construct
SEQUENCE: 56
VKDGSGYGHY SYYGLDV                                          17

SEQ ID NO: 57         moltype = DNA  length = 324
FEATURE               Location/Qualifiers
misc_feature          1..324
                      note = Synthetic
source                1..324
                      mol_type = other DNA
                      organism = synthetic construct
SEQUENCE: 57
gaaattgtgt tgacgcagtc tccaggcacc ctgtctttgt ctccagggga aagagccacc  60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gttcaccttg gacgttcggc  300
caagggacca aggtggaaat caaa                                  324

SEQ ID NO: 58         moltype = AA  length = 108
FEATURE               Location/Qualifiers
REGION                1..108
                      note = Synthetic
source                1..108
                      mol_type = protein
                      organism = synthetic construct
SEQUENCE: 58
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPWTFG QGTKVEIK        108

SEQ ID NO: 59         moltype = DNA  length = 21
FEATURE               Location/Qualifiers
misc_feature          1..21
                      note = Synthetic
source                1..21
                      mol_type = other DNA
                      organism = synthetic construct
SEQUENCE: 59
cagagtgtta gcagcagcta c                                     21

SEQ ID NO: 60         moltype = AA  length = 7
FEATURE               Location/Qualifiers
REGION                1..7
                      note = Synthetic
source                1..7
```

```
                        mol_type = protein
                        organism = synthetic construct
SEQUENCE: 60
QSVSSSY                                                                 7

SEQ ID NO: 61           moltype =   length =
SEQUENCE: 61
000

SEQ ID NO: 62           moltype =   length =
SEQUENCE: 62
000

SEQ ID NO: 63           moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 63
cagcagtatg gtagttcacc ttggacg                                           27

SEQ ID NO: 64           moltype = AA  length = 9
FEATURE                 Location/Qualifiers
REGION                  1..9
                        note = Synthetic
source                  1..9
                        mol_type = protein
                        organism = synthetic construct
SEQUENCE: 64
QQYGSSPWT                                                               9

SEQ ID NO: 65           moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 65
gaagtacagc tggtggagtc tgggggaggc ttggtacagc ctggcaggtc cctgagactc  60
tcctgtgtag cctctggatt cccctttgct gattatacca tgcactgggt ccggcaagct  120
ccagggaagg gcctggagtg ggtctcagat attagttgga atagtggtag cataggctat  180
gcggactctg tgaagggccg attcaccatc tccagagaca atgccaagaa ctccctgtat  240
ctgcaaatga acagtctgag aactgaggac acggccttgt attactgtgc aaaagatatg  300
agtggctacg cccactactt ctactacggt atggacgtct ggggccaagg gaccacggtc  360
accgtctcct ca                                                       372

SEQ ID NO: 66           moltype = AA  length = 124
FEATURE                 Location/Qualifiers
REGION                  1..124
                        note = Synthetic
source                  1..124
                        mol_type = protein
                        organism = synthetic construct
SEQUENCE: 66
EVQLVESGGG LVQPGRSLRL SCVASGFPFA DYTMHWVRQA PGKGLEWVSD ISWNSGSIGY  60
ADSVKGRFTI SRDNAKNSLY LQMNSLRTED TALYYCAKDM SGYAHYFYYG MDVWGQGTTV  120
TVSS                                                                124

SEQ ID NO: 67           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 67
ggattcccct ttgctgatta tacc                                              24

SEQ ID NO: 68           moltype = AA  length = 8
FEATURE                 Location/Qualifiers
REGION                  1..8
                        note = Synthetic
source                  1..8
                        mol_type = protein
                        organism = synthetic construct
SEQUENCE: 68
```

```
GFPFADYT                                                   8

SEQ ID NO: 69          moltype = DNA  length = 24
FEATURE                Location/Qualifiers
misc_feature           1..24
                       note = Synthetic
source                 1..24
                       mol_type = other DNA
                       organism = synthetic construct
SEQUENCE: 69
attagttgga atagtggtag cata                                 24

SEQ ID NO: 70          moltype = AA  length = 8
FEATURE                Location/Qualifiers
REGION                 1..8
                       note = Synthetic
source                 1..8
                       mol_type = protein
                       organism = synthetic construct
SEQUENCE: 70
ISWNSGSI                                                   8

SEQ ID NO: 71          moltype = DNA  length = 51
FEATURE                Location/Qualifiers
misc_feature           1..51
                       note = Synthetic
source                 1..51
                       mol_type = other DNA
                       organism = synthetic construct
SEQUENCE: 71
gcaaaagata tgagtggcta cgcccactac ttctactacg gtatggacgt c    51

SEQ ID NO: 72          moltype = AA  length = 17
FEATURE                Location/Qualifiers
REGION                 1..17
                       note = Synthetic
source                 1..17
                       mol_type = protein
                       organism = synthetic construct
SEQUENCE: 72
AKDMSGYAHY FYYGMDV                                         17

SEQ ID NO: 73          moltype = DNA  length = 324
FEATURE                Location/Qualifiers
misc_feature           1..324
                       note = Synthetic
source                 1..324
                       mol_type = other DNA
                       organism = synthetic construct
SEQUENCE: 73
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctttgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                 324

SEQ ID NO: 74          moltype = AA  length = 108
FEATURE                Location/Qualifiers
REGION                 1..108
                       note = Synthetic
source                 1..108
                       mol_type = protein
                       organism = synthetic construct
SEQUENCE: 74
DIQMTQSPSS LSASVGDRVT ITCRASQSIS SYLNWYQQKP GKAPKLLIFA ASSLQSGVPS  60
RFSGSGSGTD FTLTISSLQP EDFATYYCQQ SYSTPPITFG QGTRLEIK         108

SEQ ID NO: 75          moltype = DNA  length = 18
FEATURE                Location/Qualifiers
misc_feature           1..18
                       note = Synthetic
source                 1..18
                       mol_type = other DNA
                       organism = synthetic construct
SEQUENCE: 75
cagagcatta gcagctat                                        18

SEQ ID NO: 76          moltype = AA  length = 6
```

```
FEATURE                 Location/Qualifiers
REGION                  1..6
                        note = Synthetic
source                  1..6
                        mol_type = protein
                        organism = synthetic construct
SEQUENCE: 76
QSISSY                                                                   6

SEQ ID NO: 77           moltype =   length =
SEQUENCE: 77
000

SEQ ID NO: 78           moltype =   length =
SEQUENCE: 78
000

SEQ ID NO: 79           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 79
caacagagtt acagtacccc tccgatcacc                                         30

SEQ ID NO: 80           moltype = AA  length = 10
FEATURE                 Location/Qualifiers
REGION                  1..10
                        note = Synthetic
source                  1..10
                        mol_type = protein
                        organism = synthetic construct
SEQUENCE: 80
QQSYSTPPIT                                                               10

SEQ ID NO: 81           moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 81
gaagtgcagc tggtggagtc tgggggaggc ttggtacagc ctggcaggtc cctgaaactc  60
tcctgtacag cctctggatt cacctttgct gattatacca tgcactgggt ccgacaaggt  120
ccagggaagg gcctggagtg ggtctcagat attagttgga atagtggtag taaaggctat  180
gcggactctg tgaagggccg attcaccatc tccagagaca acgccaagaa ctccctgtat  240
ctgcaaatga acagtctgag aactgaggac acggccttgt attactgtgc aaaagatatg  300
agtggctacg cccactacta ctactacgct ttggacgtct ggggccaagg gaccacggtc  360
accgtctcct ca                                                      372

SEQ ID NO: 82           moltype = AA  length = 124
FEATURE                 Location/Qualifiers
REGION                  1..124
                        note = Synthetic
source                  1..124
                        mol_type = protein
                        organism = synthetic construct
SEQUENCE: 82
EVQLVESGGG LVQPGRSLKL SCTASGFTFA DYTMHWVRQG PGKGLEWVSD ISWNSGSKGY  60
ADSVKGRFTI SRDNAKNSLY LQMNSLRTED TALYYCAKDM SGYAHYYYYA LDVWGQGTTV  120
TVSS                                                               124

SEQ ID NO: 83           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 83
ggattcacct ttgctgatta tacc                                         24

SEQ ID NO: 84           moltype = AA  length = 8
FEATURE                 Location/Qualifiers
REGION                  1..8
                        note = Synthetic
```

```
source                  1..8
                        mol_type = protein
                        organism = synthetic construct
SEQUENCE: 84
GFTFADYT                                                                8

SEQ ID NO: 85           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 85
attagttgga atagtggtag taaa                                              24

SEQ ID NO: 86           moltype = AA  length = 8
FEATURE                 Location/Qualifiers
REGION                  1..8
                        note = Synthetic
source                  1..8
                        mol_type = protein
                        organism = synthetic construct
SEQUENCE: 86
ISWNSGSK                                                                8

SEQ ID NO: 87           moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 87
gcaaaagata tgagtggcta cgcccactac tactactacg ctttggacgt c                51

SEQ ID NO: 88           moltype = AA  length = 17
FEATURE                 Location/Qualifiers
REGION                  1..17
                        note = Synthetic
source                  1..17
                        mol_type = protein
                        organism = synthetic construct
SEQUENCE: 88
AKDMSGYAHY YYYALDV                                                      17

SEQ ID NO: 89           moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 89
gacatccaga tgacccagtc tccatcctcc ctgtctgcat ctgtaggaga cagagtcacc  60
atcacttgcc gggcaagtca gagcattagc aactatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta accccccgat caccttcggc  300
caagggacac gactggagat taaa                                         324

SEQ ID NO: 90           moltype = AA  length = 108
FEATURE                 Location/Qualifiers
REGION                  1..108
                        note = Synthetic
source                  1..108
                        mol_type = protein
                        organism = synthetic construct
SEQUENCE: 90
DIQMTQSPSS LSASVGDRVT ITCRASQSIS NYLNWYQQKP GKAPKLLIYA ASSLQSGVPS  60
RFSGSGSGTD FTLTISSLQP EDFATYYCQQ SYSNPPITFG QGTRLEIK               108

SEQ ID NO: 91           moltype = DNA  length = 18
FEATURE                 Location/Qualifiers
misc_feature            1..18
                        note = Synthetic
source                  1..18
                        mol_type = other DNA
                        organism = synthetic construct
```

```
SEQUENCE: 91
cagagcatta gcaactat                                              18

SEQ ID NO: 92           moltype = AA  length = 6
FEATURE                 Location/Qualifiers
REGION                  1..6
                        note = Synthetic
source                  1..6
                        mol_type = protein
                        organism = synthetic construct
SEQUENCE: 92
QSISNY                                                           6

SEQ ID NO: 93           moltype =   length =
SEQUENCE: 93
000

SEQ ID NO: 94           moltype =   length =
SEQUENCE: 94
000

SEQ ID NO: 95           moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 95
caacagagtt acagtaaccc cccgatcacc                                 30

SEQ ID NO: 96           moltype = AA  length = 10
FEATURE                 Location/Qualifiers
REGION                  1..10
                        note = Synthetic
source                  1..10
                        mol_type = protein
                        organism = synthetic construct
SEQUENCE: 96
QQSYSNPPIT                                                       10

SEQ ID NO: 97           moltype = DNA  length = 363
FEATURE                 Location/Qualifiers
misc_feature            1..363
                        note = Synthetic
source                  1..363
                        mol_type = other DNA
                        organism = synthetic construct
SEQUENCE: 97
caggtgcagc tggtggagtc tgggggaggc gtggtccagc ctgggaggtc cctgagactc  60
tcctgtgcag cctctggatt caccttcagt agaaaaggca tgcactgggt ccgccaggct  120
ccagtcaagg ggctggagtg ggtggcagtt atatcatatg atggaagtaa taaatactat  180
gcagactccg tgaagggccg attcaccatc tccagagaca attccaagaa cacgctgtat  240
ctgcaaatga acagcctgac agctgaggac acggctgtgt attactgtgc gaaagaaggg  300
gggcatgact atggtggtac ctttgactac tggggccagg gaaccctggt caccgtctcc  360
tca                                                              363

SEQ ID NO: 98           moltype = AA  length = 121
FEATURE                 Location/Qualifiers
REGION                  1..121
                        note = Synthetic
source                  1..121
                        mol_type = protein
                        organism = synthetic construct
SEQUENCE: 98
QVQLVESGGG VVQPGRSLRL SCAASGFTFS RKGMHWVRQA PVKGLEWVAV ISYDGSNKYY  60
ADSVKGRFTI SRDNSKNTLY LQMNSLTAED TAVYYCAKEG GHDYGGTFDY WGQGTLVTVS  120
S                                                                121

SEQ ID NO: 99           moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 99
ggattcacct tcagtagaaa aggc                                       24
```

-continued

```
SEQ ID NO: 100          moltype = AA  length = 8
FEATURE                 Location/Qualifiers
REGION                  1..8
                        note = Synthetic
source                  1..8
                        mol_type = protein
                        organism = synthetic construct
SEQUENCE: 100
GFTFSRKG                                                            8

SEQ ID NO: 101          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 101
atatcatatg atggaagtaa taaa                                          24

SEQ ID NO: 102          moltype = AA  length = 8
FEATURE                 Location/Qualifiers
REGION                  1..8
                        note = Synthetic
source                  1..8
                        mol_type = protein
                        organism = synthetic construct
SEQUENCE: 102
ISYDGSNK                                                            8

SEQ ID NO: 103          moltype = DNA  length = 42
FEATURE                 Location/Qualifiers
misc_feature            1..42
                        note = Synthetic
source                  1..42
                        mol_type = other DNA
                        organism = synthetic construct
SEQUENCE: 103
gcgaaagaag gggggcatga ctatggtggt acctttgact ac                      42

SEQ ID NO: 104          moltype = AA  length = 14
FEATURE                 Location/Qualifiers
REGION                  1..14
                        note = Synthetic
source                  1..14
                        mol_type = protein
                        organism = synthetic construct
SEQUENCE: 104
AKEGGHDYGG TFDY                                                     14

SEQ ID NO: 105          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 105
gacatccaga tgacccagtc tccatcctcc ctgtctgcat ctgtaggaga cagagtcacc  60
atcacttgcc aggcgagtca ggacattaac aactatttaa attggtatca gcagaaacca  120
gggaaagccc ctaagttcct gatctacgat gcatccaatt tggaaacagg ggtcccatca  180
aggttcagtg gaagtggatc tgggacagat tttactttca ccatcagcag cctgcagcct  240
gaagatattg caacatatta ctgtcaacag tatgatgatc tcccattcac tttcggccct  300
gggaccaaag tggatatcaa a                                             321

SEQ ID NO: 106          moltype = AA  length = 107
FEATURE                 Location/Qualifiers
REGION                  1..107
                        note = Synthetic
source                  1..107
                        mol_type = protein
                        organism = synthetic construct
SEQUENCE: 106
DIQMTQSPSS LSASVGDRVT ITCQASQDIN NYLNWYQQKP GKAPKFLIYD ASNLETGVPS  60
RFSGSGSGTD FTFTISSLQP EDIATYYCQQ YDDLPFTFGP GTKVDIK                107

SEQ ID NO: 107          moltype = DNA  length = 18
FEATURE                 Location/Qualifiers
misc_feature            1..18
```

```
                          note = Synthetic
source                    1..18
                          mol_type = other DNA
                          organism = synthetic construct
SEQUENCE: 107
caggacatta acaactat                                              18

SEQ ID NO: 108            moltype = AA  length = 6
FEATURE                   Location/Qualifiers
REGION                    1..6
                          note = Synthetic
source                    1..6
                          mol_type = protein
                          organism = synthetic construct
SEQUENCE: 108
QDINNY                                                           6

SEQ ID NO: 109            moltype =   length =
SEQUENCE: 109
000

SEQ ID NO: 110            moltype =   length =
SEQUENCE: 110
000

SEQ ID NO: 111            moltype = DNA  length = 27
FEATURE                   Location/Qualifiers
misc_feature              1..27
                          note = Synthetic
source                    1..27
                          mol_type = other DNA
                          organism = synthetic construct
SEQUENCE: 111
caacagtatg atgatctccc attcact                                    27

SEQ ID NO: 112            moltype = AA  length = 9
FEATURE                   Location/Qualifiers
REGION                    1..9
                          note = Synthetic
source                    1..9
                          mol_type = protein
                          organism = synthetic construct
SEQUENCE: 112
QQYDDLPFT                                                        9

SEQ ID NO: 113            moltype = DNA  length = 369
FEATURE                   Location/Qualifiers
misc_feature              1..369
                          note = Synthetic
source                    1..369
                          mol_type = other DNA
                          organism = synthetic construct
SEQUENCE: 113
gaagtgcagc tggtggagtc tgggggaggc ttggtacagc ctggcaggtc cctgagactc  60
tcctgtgcag cctctggatt cacctttgat gattatacca tgcactgggt ccggcaagct  120
ccagggaagg gcctggagtg ggtctcaggt attagttgga atagtggtag tataggctat  180
gcggactctg tgaagggccg attcaccatc tccagagaca acgccaagaa gtccctgtat  240
ctgcaaatga acagtctgag agctgaggac acggccttgt attactgtgc aaaagataat  300
agtggctacg gtcactacta ctacggaatg gacgtctggg gccaagggac cacggtcacc  360
gtcgcctca                                                        369

SEQ ID NO: 114            moltype = AA  length = 123
FEATURE                   Location/Qualifiers
REGION                    1..123
                          note = Synthetic
source                    1..123
                          mol_type = protein
                          organism = synthetic construct
SEQUENCE: 114
EVQLVESGGG LVQPGRSLRL SCAASGFTFD DYTMHWVRQA PGKGLEWVSG ISWNSGSIGY  60
ADSVKGRFTI SRDNAKKSLY LQMNSLRAED TALYYCAKDN SGYGHYYYGM DVWGQGTTVT  120
VAS                                                              123

SEQ ID NO: 115            moltype = DNA  length = 24
FEATURE                   Location/Qualifiers
misc_feature              1..24
                          note = Synthetic
source                    1..24
                          mol_type = other DNA
```

```
                       organism = synthetic construct
SEQUENCE: 115
ggattcacct ttgatgatta tacc                                      24

SEQ ID NO: 116         moltype = AA  length = 8
FEATURE                Location/Qualifiers
REGION                 1..8
                       note = Synthetic
source                 1..8
                       mol_type = protein
                       organism = synthetic construct
SEQUENCE: 116
GFTFDDYT                                                        8

SEQ ID NO: 117         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 117
attagttgga atagtggtag tata                                      24

SEQ ID NO: 118         moltype = AA  length = 8
FEATURE                Location/Qualifiers
REGION                 1..8
                       note = Synthetic
source                 1..8
                       mol_type = protein
                       organism = synthetic construct
SEQUENCE: 118
ISWNSGSI                                                        8

SEQ ID NO: 119         moltype = DNA  length = 48
FEATURE                Location/Qualifiers
misc_feature           1..48
                       note = Synthetic
source                 1..48
                       mol_type = other DNA
                       organism = synthetic construct
SEQUENCE: 119
gcaaaagata atagtggcta cggtcactac tactacggaa tggacgtc            48

SEQ ID NO: 120         moltype = AA  length = 16
FEATURE                Location/Qualifiers
REGION                 1..16
                       note = Synthetic
source                 1..16
                       mol_type = protein
                       organism = synthetic construct
SEQUENCE: 120
AKDNSGYGHY YYGMDV                                               16

SEQ ID NO: 121         moltype = DNA  length = 321
FEATURE                Location/Qualifiers
misc_feature           1..321
                       note = Synthetic
source                 1..321
                       mol_type = other DNA
                       organism = synthetic construct
SEQUENCE: 121
gaaatagtga tgacgcagtc tccagccacc ctgtctgtgt ctccagggga aagagccacc  60
ctctcctgca gggccagtca gagtgttagc agcaacttag cctggtacca gcaaaaacct  120
ggccaggctc ccaggctcct catctatggt gcatccacca gggccactgg tatcccagcc  180
aggttcagtg gcagtgggtc tgggacagag ttcactctca ccatcagcag cctgcagtct  240
gaagattttg cagtttatta ctgtcagcac tatattaact ggcctctcac tttcggcgga  300
gggaccaagg tggagatcaa a                                         321

SEQ ID NO: 122         moltype = AA  length = 107
FEATURE                Location/Qualifiers
REGION                 1..107
                       note = Synthetic
source                 1..107
                       mol_type = protein
                       organism = synthetic construct
SEQUENCE: 122
EIVMTQSPAT LSVSPGERAT LSCRASQSVS SNLAWYQQKP GQAPRLLIYG ASTRATGIPA  60
RFSGSGSGTE FTLTISSLQS EDFAVYYCQH YINWPLTFGG GTKVEIK             107
```

```
SEQ ID NO: 123          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 123
cagagtgtta gcagcaac                                             18

SEQ ID NO: 124          moltype = AA  length = 6
FEATURE                 Location/Qualifiers
REGION                  1..6
                        note = Synthetic
source                  1..6
                        mol_type = protein
                        organism = synthetic construct
SEQUENCE: 124
QSVSSN                                                          6

SEQ ID NO: 125          moltype =   length =
SEQUENCE: 125
000

SEQ ID NO: 126          moltype =   length =
SEQUENCE: 126
000

SEQ ID NO: 127          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 127
cagcactata ttaactggcc tctcact                                   27

SEQ ID NO: 128          moltype = AA  length = 9
FEATURE                 Location/Qualifiers
REGION                  1..9
                        note = Synthetic
source                  1..9
                        mol_type = protein
                        organism = synthetic construct
SEQUENCE: 128
QHYINWPLT                                                       9

SEQ ID NO: 129          moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 129
gaagtgcagc tggtggagtc tgggggaggc ttggtacagc ctggcaggtc cctgagactc  60
tcctgtgcag cctctggatt cacctttgat gattatacca tgcactgggt ccggcaagct  120
ccagggaagg gcctggagtg ggtctcaggt attagttgga atagtggtag tataggctat  180
gcggactctg tgaagggccg attcaccatc tccagagaca acgccaagaa gtccctgtat  240
ctgcaaatga acagtctgag agctgaggac acggccttgt attactgtgc aaaagataat  300
agtggctacg gtcactacta ctacggaatg gacgtctggg gccaagggac cacggtcacc  360
gtcgcctca                                                       369

SEQ ID NO: 130          moltype = AA  length = 123
FEATURE                 Location/Qualifiers
REGION                  1..123
                        note = Synthetic
source                  1..123
                        mol_type = protein
                        organism = synthetic construct
SEQUENCE: 130
EVQLVESGGG LVQPGRSLRL SCAASGFTFD DYTMHWVRQA PGKGLEWVSG ISWNSGSIGY  60
ADSVKGRFTI SRDNAKKSLY LQMNSLRAED TALYYCAKDN SGYGHYYYGM DVWGQGTTVT  120
VAS                                                             123

SEQ ID NO: 131          moltype = DNA  length = 24
FEATURE                 Location/Qualifiers
```

```
misc_feature          1..24
                      note = Synthetic
source                1..24
                      mol_type = other DNA
                      organism = synthetic construct
SEQUENCE: 131
ggattcacct ttgatgatta tacc                                          24

SEQ ID NO: 132        moltype = AA  length = 8
FEATURE               Location/Qualifiers
REGION                1..8
                      note = Synthetic
source                1..8
                      mol_type = protein
                      organism = synthetic construct
SEQUENCE: 132
GFTFDDYT                                                            8

SEQ ID NO: 133        moltype = DNA  length = 24
FEATURE               Location/Qualifiers
misc_feature          1..24
                      note = Synthetic
source                1..24
                      mol_type = other DNA
                      organism = synthetic construct
SEQUENCE: 133
attagttgga atagtggtag tata                                          24

SEQ ID NO: 134        moltype = AA  length = 8
FEATURE               Location/Qualifiers
REGION                1..8
                      note = Synthetic
source                1..8
                      mol_type = protein
                      organism = synthetic construct
SEQUENCE: 134
ISWNSGSI                                                            8

SEQ ID NO: 135        moltype = DNA  length = 48
FEATURE               Location/Qualifiers
misc_feature          1..48
                      note = Synthetic
source                1..48
                      mol_type = other DNA
                      organism = synthetic construct
SEQUENCE: 135
gcaaaagata atagtggcta cggtcactac tactacggaa tggacgtc                48

SEQ ID NO: 136        moltype = AA  length = 16
FEATURE               Location/Qualifiers
REGION                1..16
                      note = Synthetic
source                1..16
                      mol_type = protein
                      organism = synthetic construct
SEQUENCE: 136
AKDNSGYGHY YYGMDV                                                   16

SEQ ID NO: 137        moltype = DNA  length = 321
FEATURE               Location/Qualifiers
misc_feature          1..321
                      note = Synthetic
source                1..321
                      mol_type = other DNA
                      organism = synthetic construct
SEQUENCE: 137
gaaatagtga tgacgcagtc tccagccacc ctgtctgtgt ctccagggga aagagccacc  60
ctctcctgca gggccagtca gagtgttagc agcaacttag cctggtacca gcaaaaacct  120
ggccaggctc ccaggctcct catctatggt gcatccacca gggccactgg tatcccagcc  180
aggttcagtg gcagtgggtc tgggacagag ttcactctca ccatcagcag cctgcagtct  240
gaagattttg cagtttatta ctgtcagcac tatattaact ggcctctcac tttcggcgga  300
gggaccaagg tggagatcaa a                                             321

SEQ ID NO: 138        moltype = AA  length = 107
FEATURE               Location/Qualifiers
REGION                1..107
                      note = Synthetic
source                1..107
                      mol_type = protein
```

```
                         organism = synthetic construct
SEQUENCE: 138
EIVMTQSPAT LSVSPGERAT LSCRASQSVS SNLAWYQQKP GQAPRLLIYG ASTRATGIPA  60
RFSGSGSGTE FTLTISSLQS EDFAVYYCQH YINWPLTFGG GTKVEIK                107

SEQ ID NO: 139           moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 139
cagagtgtta gcagcaac                                                18

SEQ ID NO: 140           moltype = AA  length = 6
FEATURE                  Location/Qualifiers
REGION                   1..6
                         note = Synthetic
source                   1..6
                         mol_type = protein
                         organism = synthetic construct
SEQUENCE: 140
QSVSSN                                                             6

SEQ ID NO: 141           moltype =   length =
SEQUENCE: 141
000

SEQ ID NO: 142           moltype =   length =
SEQUENCE: 142
000

SEQ ID NO: 143           moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 143
cagcactata ttaactggcc tctcact                                      27

SEQ ID NO: 144           moltype = AA  length = 9
FEATURE                  Location/Qualifiers
REGION                   1..9
                         note = Synthetic
source                   1..9
                         mol_type = protein
                         organism = synthetic construct
SEQUENCE: 144
QHYINWPLT                                                          9

SEQ ID NO: 145           moltype = DNA  length = 354
FEATURE                  Location/Qualifiers
misc_feature             1..354
                         note = Synthetic
source                   1..354
                         mol_type = other DNA
                         organism = synthetic construct
SEQUENCE: 145
caggtgcagt tggtggagtc tgggggaggc gtggtccagc ctgggaggtc cctgagactc  60
tcctgtggtg cgtctggatt caccttcaga agttatggca tgcactgggt ccgccagact  120
ccaggcaggg ggctggagtg ggtggcaatg atatattatg atggaaataa taaatactat  180
gcagactccg tgaggggccg attcaccgtt tccagagaca attccaagaa caccctgtat  240
ctgcaaatga gcagcctgag agccgaggac acggctctat atttctgtgc gcgagggcct  300
gggtacaact ggctcgaccc ctggggccag ggaaccctgg tcaccgtctc ctca        354

SEQ ID NO: 146           moltype = AA  length = 118
FEATURE                  Location/Qualifiers
REGION                   1..118
                         note = Synthetic
source                   1..118
                         mol_type = protein
                         organism = synthetic construct
SEQUENCE: 146
QVQLVESGGG VVQPGRSLRL SCGASGFTFR SYGMHWVRQT PGRGLEWVAM IYYDGNNKYY  60
ADSVRGRFTV SRDNSKNTLY LQMSSLRAED TALYFCARGP GYNWLDPWGQ GTLVTVSS    118
```

```
SEQ ID NO: 147         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 147
ggattcacct tcagaagtta tggc                                         24

SEQ ID NO: 148         moltype = AA  length = 8
FEATURE                Location/Qualifiers
REGION                 1..8
                       note = Synthetic
source                 1..8
                       mol_type = protein
                       organism = synthetic construct
SEQUENCE: 148
GFTFRSYG                                                           8

SEQ ID NO: 149         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 149
atatattatg atggaaataa taaa                                         24

SEQ ID NO: 150         moltype = AA  length = 8
FEATURE                Location/Qualifiers
REGION                 1..8
                       note = Synthetic
source                 1..8
                       mol_type = protein
                       organism = synthetic construct
SEQUENCE: 150
IYYDGNNK                                                           8

SEQ ID NO: 151         moltype = DNA  length = 33
FEATURE                Location/Qualifiers
misc_feature           1..33
                       note = Synthetic
source                 1..33
                       mol_type = other DNA
                       organism = synthetic construct
SEQUENCE: 151
gcgcgagggc ctgggtacaa ctggctcgac ccc                               33

SEQ ID NO: 152         moltype = AA  length = 11
FEATURE                Location/Qualifiers
REGION                 1..11
                       note = Synthetic
source                 1..11
                       mol_type = protein
                       organism = synthetic construct
SEQUENCE: 152
ARGPGYNWLD P                                                       11

SEQ ID NO: 153         moltype = DNA  length = 321
FEATURE                Location/Qualifiers
misc_feature           1..321
                       note = Synthetic
source                 1..321
                       mol_type = other DNA
                       organism = synthetic construct
SEQUENCE: 153
gaaatagtga tgacgcagtc tccagccacc ctgtctgtgt ctccagggga aagagccacc  60
ctctcctgca gggccagtca gagtattagc aggaacttgg cctggtacca gcaraaacct  120
ggccaggctc ccaggctcct catctatggt gcatccacca gggccactgg tatcccagcc  180
aggttcagtg gcagtgggtc tgggacagag ttcactctca ccatcagcag cctgcagtct  240
gaagattttg cagtttatta ctgtcagcag tataataacc ggcctctcac tttcggcgga  300
gggaccgagg tggagatcaa a                                            321

SEQ ID NO: 154         moltype = AA  length = 107
FEATURE                Location/Qualifiers
REGION                 1..107
                       note = Synthetic
```

-continued

```
VARIANT                 38
                        note = Xaa = any amino acid
VARIANT                 38
                        note = Xaa = Any Amino Acid
source                  1..107
                        mol_type = protein
                        organism = synthetic construct
SEQUENCE: 154
EIVMTQSPAT LSVSPGERAT LSCRASQSIS RNLAWYQXKP GQAPRLLIYG ASTRATGIPA  60
RFSGSGSGTE FTLTISSLQS EDFAVYYCQQ YNNRPLTFGG GTEVEIK                107

SEQ ID NO: 155          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 155
cagagtatta gcaggaac                                                18

SEQ ID NO: 156          moltype = AA  length = 6
FEATURE                 Location/Qualifiers
REGION                  1..6
                        note = Synthetic
source                  1..6
                        mol_type = protein
                        organism = synthetic construct
SEQUENCE: 156
QSISRN                                                             6

SEQ ID NO: 157          moltype =   length =
SEQUENCE: 157
000

SEQ ID NO: 158          moltype =   length =
SEQUENCE: 158
000

SEQ ID NO: 159          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 159
cagcagtata ataaccggcc tctcact                                      27

SEQ ID NO: 160          moltype = AA  length = 9
FEATURE                 Location/Qualifiers
REGION                  1..9
                        note = Synthetic
source                  1..9
                        mol_type = protein
                        organism = synthetic construct
SEQUENCE: 160
QQYNNRPLT                                                          9

SEQ ID NO: 161          moltype = DNA  length = 354
FEATURE                 Location/Qualifiers
misc_feature            1..354
                        note = Synthetic
source                  1..354
                        mol_type = other DNA
                        organism = synthetic construct
SEQUENCE: 161
caggtgcagt tggtggagtc tgggggaggc gtggtccagc ctgggaggtc cctgagactc  60
gcctgtgttg cgtctggatt caccttcaga agttatggca tgcactgggt ccgccaggct  120
ccaggcaagg gactgcagtg ggtggcaatg atttactatg atggtaagaa taaatattat  180
gcagactccg tgaggggccg attcaccatc tccagagaca attccaagaa cacactgtat  240
ctgcaaatga acaatctgag agtcgaggac acggctatgt atttctgtgc gcgagggcct  300
gggtacaatt ggctcgaccc ctggggccag ggaaccctgg tcactgtttc ctca        354

SEQ ID NO: 162          moltype = AA  length = 118
FEATURE                 Location/Qualifiers
REGION                  1..118
                        note = Synthetic
source                  1..118
```

```
                        mol_type = protein
                        organism = synthetic construct
SEQUENCE: 162
QVQLVESGGG VVQPGRSLRL ACVASGFTFR SYGMHWVRQA PGKGLQWVAM IYYDGKNKYY  60
ADSVRGRFTI SRDNSKNTLY LQMNNLRVED TAMYFCARGP GYNWLDPWGQ GTLVTVSS    118

SEQ ID NO: 163          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 163
ggattcacct tcagaagtta tggc                                         24

SEQ ID NO: 164          moltype = AA  length = 8
FEATURE                 Location/Qualifiers
REGION                  1..8
                        note = Synthetic
source                  1..8
                        mol_type = protein
                        organism = synthetic construct
SEQUENCE: 164
GFTFRSYG                                                           8

SEQ ID NO: 165          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 165
atttactatg atggtaagaa taaa                                         24

SEQ ID NO: 166          moltype = AA  length = 8
FEATURE                 Location/Qualifiers
REGION                  1..8
                        note = Synthetic
source                  1..8
                        mol_type = protein
                        organism = synthetic construct
SEQUENCE: 166
IYYDGKNK                                                           8

SEQ ID NO: 167          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 167
gcgcgagggc ctgggtacaa ttggctcgac ccc                               33

SEQ ID NO: 168          moltype = AA  length = 11
FEATURE                 Location/Qualifiers
REGION                  1..11
                        note = Synthetic
source                  1..11
                        mol_type = protein
                        organism = synthetic construct
SEQUENCE: 168
ARGPGYNWLD P                                                       11

SEQ ID NO: 169          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 169
gaaatagtga tgacgcagtc tccagccacc ctgtctgtgt ctccagggga aagagccacc  60
ctctcctgca gggccagtca gagaattagc agcaacttgg cctggtacca gcaaaaacct  120
ggccaggctc ccaggctcct catctatggt gcatccacca gggccactgg tagcccagcc  180
aggttcagtg gcagtgggtc tgggacagac ttcactctca ccatcagcag cctgcagtct  240
gaggatgttg cagtttatta ctgtcagcaa catcataact ggcctctcac tttcggcgga  300
```

```
gggaccaagg tggagatcaa a                                           321

SEQ ID NO: 170         moltype = AA  length = 107
FEATURE                Location/Qualifiers
REGION                 1..107
                       note = Synthetic
source                 1..107
                       mol_type = protein
                       organism = synthetic construct
SEQUENCE: 170
EIVMTQSPAT LSVSPGERAT LSCRASQRIS SNLAWYQQKP GQAPRLLIYG ASTRATGSPA  60
RFSGSGSGTD FTLTISSLQS EDVAVYYCQQ HHNWPLTFGG GTKVEIK               107

SEQ ID NO: 171         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 171
cagagaatta gcagcaac                                               18

SEQ ID NO: 172         moltype = AA  length = 6
FEATURE                Location/Qualifiers
REGION                 1..6
                       note = Synthetic
source                 1..6
                       mol_type = protein
                       organism = synthetic construct
SEQUENCE: 172
QRISSN                                                            6

SEQ ID NO: 173         moltype =   length =
SEQUENCE: 173
000

SEQ ID NO: 174         moltype =   length =
SEQUENCE: 174
000

SEQ ID NO: 175         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 175
cagcaacatc ataactggcc tctcact                                     27

SEQ ID NO: 176         moltype = AA  length = 9
FEATURE                Location/Qualifiers
REGION                 1..9
                       note = Synthetic
source                 1..9
                       mol_type = protein
                       organism = synthetic construct
SEQUENCE: 176
QQHHNWPLT                                                         9

SEQ ID NO: 177         moltype = DNA  length = 354
FEATURE                Location/Qualifiers
misc_feature           1..354
                       note = Synthetic
source                 1..354
                       mol_type = other DNA
                       organism = synthetic construct
SEQUENCE: 177
caggtgcagc tggtggagtc tgggggaggc gtggtccagc ctgggaggtc cctgagactc  60
tcctgtgctg cgtctggatt caccttcaga agttatgcca tgcactgggt ccgccaggct  120
ccaggcaagg ggctggagtg ggtggcaatg gtatactatg atggaaataa tcaatactat  180
gcagactccg tgaggggccg attcaccatc tccagagaca attccaagaa cacgctgtat  240
ctgcaaatga acagcctgag agccgatgac acggctgtgt atttctgtgc gcgagggcct  300
gggtacaact ggctcgaccc ctggggccag ggaaccctgg tcaccgtctc ctca       354

SEQ ID NO: 178         moltype = AA  length = 118
FEATURE                Location/Qualifiers
REGION                 1..118
```

```
                        note = Synthetic
source                  1..118
                        mol_type = protein
                        organism = synthetic construct
SEQUENCE: 178
QVQLVESGGG VVQPGRSLRL SCAASGFTFR SYAMHWVRQA PGKGLEWVAM VYYDGNNQYY  60
ADSVRGRFTI SRDNSKNTLY LQMNSLRADD TAVYFCARGP GYNWLDPWGQ GTLVTVSS    118

SEQ ID NO: 179          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 179
ggatttacct tcagaagtta tgcc                                         24

SEQ ID NO: 180          moltype = AA  length = 8
FEATURE                 Location/Qualifiers
REGION                  1..8
                        note = Synthetic
source                  1..8
                        mol_type = protein
                        organism = synthetic construct
SEQUENCE: 180
GFTFRSYA                                                           8

SEQ ID NO: 181          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 181
gtatactatg atggaaataa tcaa                                         24

SEQ ID NO: 182          moltype = AA  length = 8
FEATURE                 Location/Qualifiers
REGION                  1..8
                        note = Synthetic
source                  1..8
                        mol_type = protein
                        organism = synthetic construct
SEQUENCE: 182
VYYDGNNQ                                                           8

SEQ ID NO: 183          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 183
gcgcgagggc ctgggtacaa ctggctcgac ccc                               33

SEQ ID NO: 184          moltype = AA  length = 11
FEATURE                 Location/Qualifiers
REGION                  1..11
                        note = Synthetic
source                  1..11
                        mol_type = protein
                        organism = synthetic construct
SEQUENCE: 184
ARGPGYNWLD P                                                       11

SEQ ID NO: 185          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 185
gaaatagtga tgacgcagtc tccagccacc ctgtctgtgt ctccagggga aagagccacc  60
ctctcctgca gggccagtca gagtgttagc aggaacttgg cctggtacca gcaaaaacct  120
ggccaggctc ccaggctcct catctatggt gcatccacca gggccactgg tatcccggcc  180
```

-continued

```
aggttcagtg gcagtgggtc tgggacagac ttcactctca ccatcagcag cctgcagtct  240
gaagattttg cagtttatta ctgtcagcag tataataact ggcctctcac tttcggcgga  300
gggaccaagg tggtgatcaa a                                            321

SEQ ID NO: 186          moltype = AA  length = 107
FEATURE                 Location/Qualifiers
REGION                  1..107
                        note = Synthetic
source                  1..107
                        mol_type = protein
                        organism = synthetic construct
SEQUENCE: 186
EIVMTQSPAT LSVSPGERAT LSCRASQSVS RNLAWYQQKP GQAPRLLIYG ASTRATGIPA  60
RFSGSGSGTD FTLTISSLQS EDFAVYYCQQ YNNWPLTFGG GTKVVIK                107

SEQ ID NO: 187          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 187
cagagtgtta gcaggaac                                                18

SEQ ID NO: 188          moltype = AA  length = 6
FEATURE                 Location/Qualifiers
REGION                  1..6
                        note = Synthetic
source                  1..6
                        mol_type = protein
                        organism = synthetic construct
SEQUENCE: 188
QSVSRN                                                             6

SEQ ID NO: 189          moltype =   length =
SEQUENCE: 189
000

SEQ ID NO: 190          moltype =   length =
SEQUENCE: 190
000

SEQ ID NO: 191          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 191
cagcagtata ataactggcc tctcact                                      27

SEQ ID NO: 192          moltype = AA  length = 9
FEATURE                 Location/Qualifiers
REGION                  1..9
                        note = Synthetic
source                  1..9
                        mol_type = protein
                        organism = synthetic construct
SEQUENCE: 192
QQYNNWPLT                                                          9

SEQ ID NO: 193          moltype = DNA  length = 354
FEATURE                 Location/Qualifiers
misc_feature            1..354
                        note = Synthetic
source                  1..354
                        mol_type = other DNA
                        organism = synthetic construct
SEQUENCE: 193
caggtgcagc tggtggagtc tgggggaggc gtggtccagc ctgggaggtc cctgagactc  60
tcctgtattg cgtctggatt taccttcaga agttatggca tgcactgggt ccgccaggct  120
ccaggcaagg ggctggagtg ggtggcaatg atatattatg atggaaacaa taaatactat  180
gcagactccg tgaggggccg attcaccatc tccagagaca actccaagaa cacgctgtat  240
ctgcaaatga acagcctgag agccgatgac acggctgtgt atttctgtgc gcgagggcct  300
gggtacaact ggctcgaccc ctggggccag ggaaccctgg tcaccgtctc ctca        354

SEQ ID NO: 194          moltype = AA  length = 118
```

-continued

```
FEATURE                Location/Qualifiers
REGION                 1..118
                       note = Synthetic
source                 1..118
                       mol_type = protein
                       organism = synthetic construct
SEQUENCE: 194
QVQLVESGGG VVQPGRSLRL SCIASGFTFR SYGMHWVRQA PGKGLEWVAM IYYDGNNKYY  60
ADSVRGRFTI SRDNSKNTLY LQMNSLRADD TAVYFCARGP GYNWLDPWGQ GTLVTVSS    118

SEQ ID NO: 195         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 195
ggatttacct tcagaagtta tggc                                          24

SEQ ID NO: 196         moltype = AA  length = 8
FEATURE                Location/Qualifiers
REGION                 1..8
                       note = Synthetic
source                 1..8
                       mol_type = protein
                       organism = synthetic construct
SEQUENCE: 196
GFTFRSYG                                                            8

SEQ ID NO: 197         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 197
atatattatg atggaaacaa taaa                                          24

SEQ ID NO: 198         moltype = AA  length = 8
FEATURE                Location/Qualifiers
REGION                 1..8
                       note = Synthetic
source                 1..8
                       mol_type = protein
                       organism = synthetic construct
SEQUENCE: 198
IYYDGNNK                                                            8

SEQ ID NO: 199         moltype = DNA  length = 33
FEATURE                Location/Qualifiers
misc_feature           1..33
                       note = Synthetic
source                 1..33
                       mol_type = other DNA
                       organism = synthetic construct
SEQUENCE: 199
gcgcgagggc ctgggtacaa ctggctcgac ccc                                33

SEQ ID NO: 200         moltype = AA  length = 11
FEATURE                Location/Qualifiers
REGION                 1..11
                       note = Synthetic
source                 1..11
                       mol_type = protein
                       organism = synthetic construct
SEQUENCE: 200
ARGPGYNWLD P                                                        11

SEQ ID NO: 201         moltype = DNA  length = 321
FEATURE                Location/Qualifiers
misc_feature           1..321
                       note = Synthetic
source                 1..321
                       mol_type = other DNA
                       organism = synthetic construct
SEQUENCE: 201
gaaatagtga tgacgcagtc tccagccaca ctgtctgtgt ctccagggga aagagccacc  60
```

-continued

```
ctctcctgca gggccagtca gagtgttagc agcaacttgg cctggtacca gcagaaacct  120
ggccaggctc ccaggctcct catctatggt gcatccacca gggccactgg tatcccagcc  180
aggttcagtg gcagtgggtc tgggacagag ttcactctca ccatcagcag cctgcagtct  240
gaagattttg cagtttatta ctgtcagcag tataataaca ggcctctcac tttcggcgga  300
gggaccaagg tggagatcaa a                                            321

SEQ ID NO: 202         moltype = AA  length = 107
FEATURE                Location/Qualifiers
REGION                 1..107
                       note = Synthetic
source                 1..107
                       mol_type = protein
                       organism = synthetic construct
SEQUENCE: 202
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNRPLTFGG GTKVEIK               107

SEQ ID NO: 203         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 203
cagagtgtta gcagcaac                                                18

SEQ ID NO: 204         moltype = AA  length = 6
FEATURE                Location/Qualifiers
REGION                 1..6
                       note = Synthetic
source                 1..6
                       mol_type = protein
                       organism = synthetic construct
SEQUENCE: 204
QSVSSN                                                             6

SEQ ID NO: 205         moltype =   length =
SEQUENCE: 205
000

SEQ ID NO: 206         moltype =   length =
SEQUENCE: 206
000

SEQ ID NO: 207         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 207
cagcagtata ataacaggcc tctcact                                      27

SEQ ID NO: 208         moltype = AA  length = 9
FEATURE                Location/Qualifiers
REGION                 1..9
                       note = Synthetic
source                 1..9
                       mol_type = protein
                       organism = synthetic construct
SEQUENCE: 208
QQYNNRPLT                                                          9

SEQ ID NO: 209         moltype = DNA  length = 354
FEATURE                Location/Qualifiers
misc_feature           1..354
                       note = Synthetic
source                 1..354
                       mol_type = other DNA
                       organism = synthetic construct
SEQUENCE: 209
caggtgcagc tggtggagtc tgggggaggc gtggtccagc cggggaggtc cctgagactc  60
tcctgtgctg cgtctggatt caccttcaga agttttggca tgcactgggt ccgccaggct  120
ccaggcaggg gactggagtg ggtggcaatg atatattttg atggaaaaaa taaatactat  180
gcagactccg tgaggggccg attcaccatt tccagagaca attccaagaa caccctgtat  240
ctggaaatga gtagcctgag agccgaggac acggctgtat atttctgtgc gcgagggcct  300
gggtacaact ggctcgaccc ctggggccag ggaaccctgg tcaccgtctc ctca        354
```

```
SEQ ID NO: 210          moltype = AA  length = 118
FEATURE                 Location/Qualifiers
REGION                  1..118
                        note = Synthetic
source                  1..118
                        mol_type = protein
                        organism = synthetic construct
SEQUENCE: 210
QVQLVESGGG VVQPGRSLRL SCAASGFTFR SFGMHWVRQA PGRGLEWVAM IYFDGKNKYY  60
ADSVRGRFTI SRDNSKNTLY LEMSSLRAED TAVYFCARGP GYNWLDPWGQ GTLVTVSS    118

SEQ ID NO: 211          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 211
ggattcacct tcagaagttt tggc                                          24

SEQ ID NO: 212          moltype = AA  length = 8
FEATURE                 Location/Qualifiers
REGION                  1..8
                        note = Synthetic
source                  1..8
                        mol_type = protein
                        organism = synthetic construct
SEQUENCE: 212
GFTFRSFG                                                            8

SEQ ID NO: 213          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 213
atatattttg atggaaaaaa taaa                                          24

SEQ ID NO: 214          moltype = AA  length = 8
FEATURE                 Location/Qualifiers
REGION                  1..8
                        note = Synthetic
source                  1..8
                        mol_type = protein
                        organism = synthetic construct
SEQUENCE: 214
IYFDGKNK                                                            8

SEQ ID NO: 215          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 215
gcgcgagggc ctgggtacaa ctggctcgac ccc                                33

SEQ ID NO: 216          moltype = AA  length = 11
FEATURE                 Location/Qualifiers
REGION                  1..11
                        note = Synthetic
source                  1..11
                        mol_type = protein
                        organism = synthetic construct
SEQUENCE: 216
ARGPGYNWLD P                                                        11

SEQ ID NO: 217          moltype = DNA  length = 321
FEATURE                 Location/Qualifiers
misc_feature            1..321
                        note = Synthetic
source                  1..321
                        mol_type = other DNA
                        organism = synthetic construct
```

SEQUENCE: 217
gaaatagtga tgacgcagtc tccagccacc ctgtctgtgt ctccagggga aagagtcacc 60
ctctcctgta gggccagtca gagtattagc aggaacttgg cctggtacca gcagaaacct 120
ggccaggctc ccaggctcct catctatggt gcatccacca gggccactgg tgtcccagcc 180
aggttcagtg gcagtgggtc tgggacagag ttcactctca ccatcagcag cctacagtct 240
gaagattttg cagtttttca ctgtcagcag tataataata ggcctctcac tttcggcgga 300
gggaccgagg tggagatcaa a 321

SEQ ID NO: 218 moltype = AA length = 107
FEATURE Location/Qualifiers
REGION 1..107
note = Synthetic
source 1..107
mol_type = protein
organism = synthetic construct
SEQUENCE: 218
EIVMTQSPAT LSVSPGERVT LSCRASQSIS RNLAWYQQKP GQAPRLLIYG ASTRATGVPA 60
RFSGSGSGTE FTLTISSLQS EDFAVFHCQQ YNNRPLTFGG GTEVEIK 107

SEQ ID NO: 219 moltype = DNA length = 18
FEATURE Location/Qualifiers
misc_feature 1..18
note = Synthetic
source 1..18
mol_type = other DNA
organism = synthetic construct
SEQUENCE: 219
cagagtatta gcaggaac 18

SEQ ID NO: 220 moltype = AA length = 6
FEATURE Location/Qualifiers
REGION 1..6
note = Synthetic
source 1..6
mol_type = protein
organism = synthetic construct
SEQUENCE: 220
QSISRN 6

SEQ ID NO: 221 moltype = length =
SEQUENCE: 221
000

SEQ ID NO: 222 moltype = length =
SEQUENCE: 222
000

SEQ ID NO: 223 moltype = DNA length = 27
FEATURE Location/Qualifiers
misc_feature 1..27
note = Synthetic
source 1..27
mol_type = other DNA
organism = synthetic construct
SEQUENCE: 223
cagcagtata ataataggcc tctcact 27

SEQ ID NO: 224 moltype = AA length = 9
FEATURE Location/Qualifiers
REGION 1..9
note = Synthetic
source 1..9
mol_type = protein
organism = synthetic construct
SEQUENCE: 224
QQYNNRPLT 9

SEQ ID NO: 225 moltype = DNA length = 354
FEATURE Location/Qualifiers
misc_feature 1..354
note = Synthetic
source 1..354
mol_type = other DNA
organism = synthetic construct
SEQUENCE: 225
caggtgcaat tggtggagtc tgggggaggc gtggtccagc cggggaggtc cctgagactc 60
tcctgtgctg cgtctggatt caccttcaga agttttggca tgcactgggt ccgccaggct 120
ccaggcaggg gactggagtg ggtggcaatg atatattttg atggaaaaaa taaatactat 180
gcagactccg tgaggggccg attcaccatt tccagagaca attccaagaa caccctgtat 240

```
ctggaaatga gtagcctgag agccgaggac acggctgtat atttctgtgc gcgagggcct  300
gggtacaact ggctcgaccc ctggggccag ggaaccctgg tcaccgtctc ctca        354

SEQ ID NO: 226         moltype = AA  length = 118
FEATURE                Location/Qualifiers
REGION                 1..118
                       note = Synthetic
source                 1..118
                       mol_type = protein
                       organism = synthetic construct
SEQUENCE: 226
QVQLVESGGG VVQPGRSLRL SCAASGFTFR SFGMHWVRQA PGRGLEWVAM IYFDGKNKYY  60
ADSVRGRFTI SRDNSKNTLY LEMSSLRAED TAVYFCARGP GYNWLDPWGQ GTLVTVSS    118

SEQ ID NO: 227         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 227
ggattcacct tcagaagttt tggc                                         24

SEQ ID NO: 228         moltype = AA  length = 8
FEATURE                Location/Qualifiers
REGION                 1..8
                       note = Synthetic
source                 1..8
                       mol_type = protein
                       organism = synthetic construct
SEQUENCE: 228
GFTFRSFG                                                           8

SEQ ID NO: 229         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 229
atatattttg atggaaaaaa taaa                                         24

SEQ ID NO: 230         moltype = AA  length = 8
FEATURE                Location/Qualifiers
REGION                 1..8
                       note = Synthetic
source                 1..8
                       mol_type = protein
                       organism = synthetic construct
SEQUENCE: 230
IYFDGKNK                                                           8

SEQ ID NO: 231         moltype = DNA  length = 33
FEATURE                Location/Qualifiers
misc_feature           1..33
                       note = Synthetic
source                 1..33
                       mol_type = other DNA
                       organism = synthetic construct
SEQUENCE: 231
gcgcgagggc ctgggtacaa ctggctcgac ccc                               33

SEQ ID NO: 232         moltype = AA  length = 11
FEATURE                Location/Qualifiers
REGION                 1..11
                       note = Synthetic
source                 1..11
                       mol_type = protein
                       organism = synthetic construct
SEQUENCE: 232
ARGPGYNWLD P                                                       11

SEQ ID NO: 233         moltype = DNA  length = 321
FEATURE                Location/Qualifiers
misc_feature           1..321
                       note = Synthetic
source                 1..321
```

-continued

```
                        mol_type = other DNA
                        organism = synthetic construct
SEQUENCE: 233
gaaatagtga tgacgcagtc tccagccacc ctgtctgtgt ctccagggga aagagtcacc  60
ctctcctgta gggccagtca gagtattagc aggaacttgg cctggtacca gcaraaacct  120
ggccaggctc ccaggctcct catctatggt gcatccacca gggccactgg tgtcccagcc  180
aggttcagtg gcagtgggtc tgggacagag ttcactctca ccatcagcag cctacagtct  240
gaagattttg cagtttttca ctgtcagcag tataataata ggcctctcac tttcggcgga  300
gggaccgagg tggagatcaa a                                            321

SEQ ID NO: 234          moltype = AA  length = 107
FEATURE                 Location/Qualifiers
REGION                  1..107
                        note = Synthetic
VARIANT                 38
                        note = Xaa = Any amino acid
VARIANT                 38
                        note = Xaa = Any Amino Acid
source                  1..107
                        mol_type = protein
                        organism = synthetic construct
SEQUENCE: 234
EIVMTQSPAT LSVSPGERVT LSCRASQSIS RNLAWYQXKP GQAPRLLIYG ASTRATGVPA  60
RFSGSGSGTE FTLTISSLQS EDFAVFHCQQ YNNRPLTFGG GTEVEIK                107

SEQ ID NO: 235          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 235
cagagtatta gcaggaac                                                18

SEQ ID NO: 236          moltype = AA  length = 6
FEATURE                 Location/Qualifiers
REGION                  1..6
                        note = Synthetic
source                  1..6
                        mol_type = protein
                        organism = synthetic construct
SEQUENCE: 236
QSISRN                                                             6

SEQ ID NO: 237          moltype =   length =
SEQUENCE: 237
000

SEQ ID NO: 238          moltype =   length =
SEQUENCE: 238
000

SEQ ID NO: 239          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 239
cagcagtata ataataggcc tctcact                                      27

SEQ ID NO: 240          moltype = AA  length = 9
FEATURE                 Location/Qualifiers
REGION                  1..9
                        note = Synthetic
source                  1..9
                        mol_type = protein
                        organism = synthetic construct
SEQUENCE: 240
QQYNNRPLT                                                          9

SEQ ID NO: 241          moltype = DNA  length = 354
FEATURE                 Location/Qualifiers
misc_feature            1..354
                        note = Synthetic
source                  1..354
                        mol_type = other DNA
```

```
                        organism = synthetic construct
SEQUENCE: 241
caggtgcaat tggtggagtc tgggggaggc gtggtccagc cggggaggtc cctgagactc  60
tcctgtgctg cgtctggatt caccttcaga agttttggca tgcactgggt ccgccaggct  120
ccaggcaggg gactggagtg ggtggcaatg atatattttg atggaaaaaa taaatactat  180
gcagactccg tgaggggccg attcaccatt tccagagaca attccaagaa caccctgtat  240
ctggaaatga gcagcctgag agccgaggac acggctgtat atttctgtgc gcgagggcct  300
gggtacaatt ggctcgaccc ctggggccag ggaaccctgg tcaccgtctc ctca        354

SEQ ID NO: 242          moltype = AA  length = 118
FEATURE                 Location/Qualifiers
REGION                  1..118
                        note = Synthetic
source                  1..118
                        mol_type = protein
                        organism = synthetic construct
SEQUENCE: 242
QVQLVESGGG VVQPGRSLRL SCAASGFTFR SFGMHWVRQA PGRGLEWVAM IYFDGKNKYY  60
ADSVRGRFTI SRDNSKNTLY LEMSSLRAED TAVYFCARGP GYNWLDPWGQ GTLVTVSS    118

SEQ ID NO: 243          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 243
ggattcacct tcagaagttt tggc                                         24

SEQ ID NO: 244          moltype = AA  length = 8
FEATURE                 Location/Qualifiers
REGION                  1..8
                        note = Synthetic
source                  1..8
                        mol_type = protein
                        organism = synthetic construct
SEQUENCE: 244
GFTFRSFG                                                           8

SEQ ID NO: 245          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 245
atatattttg atggaaaaaa taaa                                         24

SEQ ID NO: 246          moltype = AA  length = 8
FEATURE                 Location/Qualifiers
REGION                  1..8
                        note = Synthetic
source                  1..8
                        mol_type = protein
                        organism = synthetic construct
SEQUENCE: 246
IYFDGKNK                                                           8

SEQ ID NO: 247          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 247
gcgcgagggc ctgggtacaa ttggctcgac ccc                               33

SEQ ID NO: 248          moltype = AA  length = 11
FEATURE                 Location/Qualifiers
REGION                  1..11
                        note = Synthetic
source                  1..11
                        mol_type = protein
                        organism = synthetic construct
SEQUENCE: 248
ARGPGYNWLD P                                                       11
```

```
SEQ ID NO: 249          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 249
gaaatagtga tgacgcagtc tccagccacc ctgtctgtgt ctccagggga aagagccacc  60
ctctcctgta gggccagtca gagtgttagc aggaacttgg cctggtacca gcaaaaacct  120
ggccaggctc ccaggctcct catctatggt gcatccacca gggccactgg tgtcccagcc  180
aggttcagtg gcagtgggtc tgggacagag ttcactctca ccatcagcag cctacagtct  240
gaagattttg cagtttttca ctgtcagcag tataataata ggcctctcac tttcggcgga  300
gggaccgagg tggagatcaa a                                            321

SEQ ID NO: 250          moltype = AA  length = 107
FEATURE                 Location/Qualifiers
REGION                  1..107
                        note = Synthetic
source                  1..107
                        mol_type = protein
                        organism = synthetic construct
SEQUENCE: 250
EIVMTQSPAT LSVSPGERAT LSCRASQSVS RNLAWYQQKP GQAPRLLIYG ASTRATGVPA  60
RFSGSGSGTE FTLTISSLQS EDFAVFHCQQ YNNRPLTFGG GTEVEIK                107

SEQ ID NO: 251          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 251
cagagtgtta gcaggaac                                                18

SEQ ID NO: 252          moltype = AA  length = 6
FEATURE                 Location/Qualifiers
REGION                  1..6
                        note = Synthetic
source                  1..6
                        mol_type = protein
                        organism = synthetic construct
SEQUENCE: 252
QSVSRN                                                             6

SEQ ID NO: 253          moltype =   length =
SEQUENCE: 253
000

SEQ ID NO: 254          moltype =   length =
SEQUENCE: 254
000

SEQ ID NO: 255          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 255
cagcagtata ataataggcc tctcact                                      27

SEQ ID NO: 256          moltype = AA  length = 9
FEATURE                 Location/Qualifiers
REGION                  1..9
                        note = Synthetic
source                  1..9
                        mol_type = protein
                        organism = synthetic construct
SEQUENCE: 256
QQYNNRPLT                                                          9

SEQ ID NO: 257          moltype = DNA  length = 354
FEATURE                 Location/Qualifiers
misc_feature            1..354
                        note = Synthetic
```

-continued

```
source                  1..354
                        mol_type = other DNA
                        organism = synthetic construct
SEQUENCE: 257
caggtgcaat tggtggagtc tgggggaggc gtggtccagc cggggaggtc cctgagactc  60
tcctgtgctg cgtctggatt caccttcaga agttttggca tgcactgggt ccgccaggct  120
ccaggcaggg gactggagtg ggtggcaatg atatattttg atggaaaaaa taaatactat  180
gcagactccg tgaggggccg attcaccatt tccagagaca attccaagaa caccctgtat  240
ctggaaatga gcagcctgag agccgaggac acggctgtat atttctgtgc gcgagggcct  300
gggtacaatt ggctcgaccc ctggggccag ggaaccctgg tcaccgtctc ctca        354

SEQ ID NO: 258          moltype = AA  length = 118
FEATURE                 Location/Qualifiers
REGION                  1..118
                        note = Synthetic
source                  1..118
                        mol_type = protein
                        organism = synthetic construct
SEQUENCE: 258
QVQLVESGGG VVQPGRSLRL SCAASGFTFR SFGMHWVRQA PGRGLEWVAM IYFDGKNKYY  60
ADSVRGRFTI SRDNSKNTLY LEMSSLRAED TAVYFCARGP GYNWLDPWGQ GTLVTVSS    118

SEQ ID NO: 259          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 259
ggattcacct tcagaagttt tggc                                         24

SEQ ID NO: 260          moltype = AA  length = 8
FEATURE                 Location/Qualifiers
REGION                  1..8
                        note = Synthetic
source                  1..8
                        mol_type = protein
                        organism = synthetic construct
SEQUENCE: 260
GFTFRSFG                                                           8

SEQ ID NO: 261          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 261
atatattttg atggaaaaaa taaa                                         24

SEQ ID NO: 262          moltype = AA  length = 8
FEATURE                 Location/Qualifiers
REGION                  1..8
                        note = Synthetic
source                  1..8
                        mol_type = protein
                        organism = synthetic construct
SEQUENCE: 262
IYFDGKNK                                                           8

SEQ ID NO: 263          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 263
gcgcgagggc ctgggtacaa ttggctcgac ccc                               33

SEQ ID NO: 264          moltype = AA  length = 11
FEATURE                 Location/Qualifiers
REGION                  1..11
                        note = Synthetic
source                  1..11
                        mol_type = protein
                        organism = synthetic construct
```

```
SEQUENCE: 264
ARGPGYNWLD P                                                 11

SEQ ID NO: 265          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 265
gaaatagtga tgacgcagtc tccagccacc ctgtctgtgt ctccagggga aagagccacc  60
ctctcctgta gggccagtca gagtgttagc aggaacttgg cctggtacca gcaaaaacct  120
ggccaggctc ccaggctcct catctatggt gcatccacca gggccactgg tgtcccagcc  180
aggttcagtg gcagtgggtc tgggacagag ttcactctca ccatcagcag cctacagtct  240
gaagattttg cagtttttca ctgtcagcag tataataata ggcctctcac tttcggcgga  300
gggaccgagg tggagatcaa a                                      321

SEQ ID NO: 266          moltype = AA  length = 107
FEATURE                 Location/Qualifiers
REGION                  1..107
                        note = Synthetic
source                  1..107
                        mol_type = protein
                        organism = synthetic construct
SEQUENCE: 266
EIVMTQSPAT LSVSPGERAT LSCRASQSVS RNLAWYQQKP GQAPRLLIYG ASTRATGVPA  60
RFSGSGSGTE FTLTISSLQS EDFAVFHCQQ YNNRPLTFGG GTEVEIK              107

SEQ ID NO: 267          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 267
cagagtgtta gcaggaac                                          18

SEQ ID NO: 268          moltype = AA  length = 6
FEATURE                 Location/Qualifiers
REGION                  1..6
                        note = Synthetic
source                  1..6
                        mol_type = protein
                        organism = synthetic construct
SEQUENCE: 268
QSVSRN                                                       6

SEQ ID NO: 269          moltype =   length =
SEQUENCE: 269
000

SEQ ID NO: 270          moltype =   length =
SEQUENCE: 270
000

SEQ ID NO: 271          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 271
cagcagtata ataataggcc tctcact                                27

SEQ ID NO: 272          moltype = AA  length = 9
FEATURE                 Location/Qualifiers
REGION                  1..9
                        note = Synthetic
source                  1..9
                        mol_type = protein
                        organism = synthetic construct
SEQUENCE: 272
QQYNNRPLT                                                    9

SEQ ID NO: 273          moltype = DNA  length = 354
FEATURE                 Location/Qualifiers
```

-continued

```
misc_feature           1..354
                       note = Synthetic
source                 1..354
                       mol_type = other DNA
                       organism = synthetic construct
SEQUENCE: 273
caggtgcagt tggtggagtc tgggggaggc gtggtccagc ctgggaggtc cctgagactc  60
tcctgtgttg cgtctggatt caccttcaga agttatggca tgcactgggt ccgccaggct  120
ccaggcaagg gactgcagtg ggtggcaatg atttactatg atggtaagaa taaatattat  180
gcagactccg tgaggggccg attcaccatc tccagagaca attccaagaa cacgctgtat  240
ctgcaaatga acagtctgag agccgaagac acggctatgt atttctgtgc gcgagggcct  300
gggtacaact ggctcgaccc ctggggccag ggaaccctgg tcactgtctc ctca        354

SEQ ID NO: 274         moltype = AA  length = 118
FEATURE                Location/Qualifiers
REGION                 1..118
                       note = Synthetic
source                 1..118
                       mol_type = protein
                       organism = synthetic construct
SEQUENCE: 274
QVQLVESGGG VVQPGRSLRL SCVASGFTFR SYGMHWVRQA PGKGLQWVAM IYYDGKNKYY  60
ADSVRGRFTI SRDNSKNTLY LQMNSLRAED TAMYFCARGP GYNWLDPWGQ GTLVTVSS    118

SEQ ID NO: 275         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 275
ggattcacct tcagaagtta tggc                                          24

SEQ ID NO: 276         moltype = AA  length = 8
FEATURE                Location/Qualifiers
REGION                 1..8
                       note = Synthetic
source                 1..8
                       mol_type = protein
                       organism = synthetic construct
SEQUENCE: 276
GFTFRSYG                                                            8

SEQ ID NO: 277         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 277
atttactatg atggtaagaa taaa                                          24

SEQ ID NO: 278         moltype = AA  length = 8
FEATURE                Location/Qualifiers
REGION                 1..8
                       note = Synthetic
source                 1..8
                       mol_type = protein
                       organism = synthetic construct
SEQUENCE: 278
IYYDGKNK                                                            8

SEQ ID NO: 279         moltype = DNA  length = 33
FEATURE                Location/Qualifiers
misc_feature           1..33
                       note = Synthetic
source                 1..33
                       mol_type = other DNA
                       organism = synthetic construct
SEQUENCE: 279
gcgcgagggc ctgggtacaa ctggctcgac ccc                                33

SEQ ID NO: 280         moltype = AA  length = 11
FEATURE                Location/Qualifiers
REGION                 1..11
                       note = Synthetic
source                 1..11
```

```
                         mol_type = protein
                         organism = synthetic construct
SEQUENCE: 280
ARGPGYNWLD P                                                       11

SEQ ID NO: 281           moltype = DNA  length = 321
FEATURE                  Location/Qualifiers
misc_feature             1..321
                         note = Synthetic
source                   1..321
                         mol_type = other DNA
                         organism = synthetic construct
SEQUENCE: 281
gaaatagtga tgacgcagtc tccagccacc ctgtctgtgt ctccagggga aagagccacc  60
ctctcctgca gggccagtca gagaattagc agcaacttgg cctggtacca gcaaaaacct  120
ggccaggctc ccaggctcct catctatggt gcatccacca gggccactgg tagcccagcc  180
aggttcagtg gcagtgggtc tgggacagag ttcactctca ccatcagcag cctgcagtct  240
gaagatgttg cagtttatta ctgtcagcaa cataataact ggcctctcac tttcggcgga  300
gggaccaagg tggagatcaa a                                            321

SEQ ID NO: 282           moltype = AA  length = 107
FEATURE                  Location/Qualifiers
REGION                   1..107
                         note = Synthetic
source                   1..107
                         mol_type = protein
                         organism = synthetic construct
SEQUENCE: 282
EIVMTQSPAT LSVSPGERAT LSCRASQRIS SNLAWYQQKP GQAPRLLIYG ASTRATGSPA  60
RFSGSGSGTE FTLTISSLQS EDVAVYYCQQ HNNWPLTFGG GTKVEIK                107

SEQ ID NO: 283           moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 283
cagagaatta gcagcaac                                                18

SEQ ID NO: 284           moltype = AA  length = 6
FEATURE                  Location/Qualifiers
REGION                   1..6
                         note = Synthetic
source                   1..6
                         mol_type = protein
                         organism = synthetic construct
SEQUENCE: 284
QRISSN                                                             6

SEQ ID NO: 285           moltype =   length =
SEQUENCE: 285
000

SEQ ID NO: 286           moltype =   length =
SEQUENCE: 286
000

SEQ ID NO: 287           moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 287
cagcaacata ataactggcc tctcact                                      27

SEQ ID NO: 288           moltype = AA  length = 9
FEATURE                  Location/Qualifiers
REGION                   1..9
                         note = Synthetic
source                   1..9
                         mol_type = protein
                         organism = synthetic construct
SEQUENCE: 288
QQHNNWPLT                                                          9
```

-continued

```
SEQ ID NO: 289          moltype = DNA  length = 354
FEATURE                 Location/Qualifiers
misc_feature            1..354
                        note = Synthetic
source                  1..354
                        mol_type = other DNA
                        organism = synthetic construct
SEQUENCE: 289
caggtgcaat tggtggagtc tgggggaggc gtggtccagc cggggaggtc cctgagactc  60
tcctgtgctg cgtctggttt caccttcaga agttttggca tgcactgggt ccgccaggct  120
ccaggcaggg gactggagtg ggtggcaatg atatattttg atggaaaaaa taaatactat  180
gcagactccg tgaggggccg attcaccatt tccagagaca attccaagaa caccctgtat  240
ctggaaatga gtagcctgag agccgaggac acggctgtat atttctgtgc gcgagggcct  300
gggtacaact ggctcgaccc ctggggccag ggaaccctgg tcaccgtctc ctca        354

SEQ ID NO: 290          moltype = AA  length = 118
FEATURE                 Location/Qualifiers
REGION                  1..118
                        note = Synthetic
source                  1..118
                        mol_type = protein
                        organism = synthetic construct
SEQUENCE: 290
QVQLVESGGG VVQPGRSLRL SCAASGFTFR SFGMHWVRQA PGRGLEWVAM IYFDGKNKYY  60
ADSVRGRFTI SRDNSKNTLY LEMSSLRAED TAVYFCARGP GYNWLDPWGQ GTLVTVSS    118

SEQ ID NO: 291          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 291
ggtttcacct tcagaagttt tggc                                         24

SEQ ID NO: 292          moltype = AA  length = 8
FEATURE                 Location/Qualifiers
REGION                  1..8
                        note = Synthetic
source                  1..8
                        mol_type = protein
                        organism = synthetic construct
SEQUENCE: 292
GFTFRSFG                                                           8

SEQ ID NO: 293          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 293
atatattttg atggaaaaaa taaa                                         24

SEQ ID NO: 294          moltype = AA  length = 8
FEATURE                 Location/Qualifiers
REGION                  1..8
                        note = Synthetic
source                  1..8
                        mol_type = protein
                        organism = synthetic construct
SEQUENCE: 294
IYFDGKNK                                                           8

SEQ ID NO: 295          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 295
gcgcgagggc ctgggtacaa ctggctcgac ccc                               33

SEQ ID NO: 296          moltype = AA  length = 11
FEATURE                 Location/Qualifiers
REGION                  1..11
```

```
                        note = Synthetic
source                  1..11
                        mol_type = protein
                        organism = synthetic construct
SEQUENCE: 296
ARGPGYNWLD P                                                        11

SEQ ID NO: 297          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 297
gaaatagtga tgacgcagtc tccagccacc ctgtctgtgt ctccagggga aagagtcatc  60
ctctcctgta gggccagtca gagtattagc aggaacttgg cctggtacca gcaaaaacct  120
ggccaggctc ccaggctcct catctatggt gcaaccacca gggccactgg tgtcccagcc  180
aggttcagtg gcagtgggtc tgggacagag ttcactctca ccatcagcag cctacagtct  240
gaagattttg cagtttttta ctgtcagcag tataataata ggcctctcac tttcggcgga  300
gggaccgagg tggagatcaa a                                             321

SEQ ID NO: 298          moltype = AA  length = 107
FEATURE                 Location/Qualifiers
REGION                  1..107
                        note = Synthetic
source                  1..107
                        mol_type = protein
                        organism = synthetic construct
SEQUENCE: 298
EIVMTQSPAT LSVSPGERVI LSCRASQSIS RNLAWYQQKP GQAPRLLIYG ATTRATGVPA  60
RFSGSGSGTE FTLTISSLQS EDFAVFYCQQ YNNRPLTFGG GTEVEIK                107

SEQ ID NO: 299          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 299
cagagtatta gcaggaac                                                 18

SEQ ID NO: 300          moltype = AA  length = 6
FEATURE                 Location/Qualifiers
REGION                  1..6
                        note = Synthetic
source                  1..6
                        mol_type = protein
                        organism = synthetic construct
SEQUENCE: 300
QSISRN                                                              6

SEQ ID NO: 301          moltype =   length =
SEQUENCE: 301
000

SEQ ID NO: 302          moltype =   length =
SEQUENCE: 302
000

SEQ ID NO: 303          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 303
cagcagtata ataataggcc tctcact                                       27

SEQ ID NO: 304          moltype = AA  length = 9
FEATURE                 Location/Qualifiers
REGION                  1..9
                        note = Synthetic
source                  1..9
                        mol_type = protein
                        organism = synthetic construct
SEQUENCE: 304
```

```
QQYNNRPLT                                                  9

SEQ ID NO: 305         moltype = DNA  length = 354
FEATURE                Location/Qualifiers
misc_feature           1..354
                       note = Synthetic
source                 1..354
                       mol_type = other DNA
                       organism = synthetic construct
SEQUENCE: 305
caggtgcaat tggtggagtc tgggggaggc gtggtccagc cggggaggtc cctgagactc  60
tcctgtgctg cgtctggttt caccttcaga agttttggca tgcactgggt ccgccaggct  120
ccaggcaggg gactggagtg ggtggcaatg atatattttg atggaaaaaa taaatactat  180
gcagactccg tgaggggccg attcaccatt tccagagaca attccaagaa caccctgtat  240
ctggaaatga gtagcctgag agccgaggac acggctgtat atttctgtgc gcgagggcct  300
gggtacaact ggctcgaccc ctggggccag ggaaccctgg tcaccgtctc ctca        354

SEQ ID NO: 306         moltype = AA  length = 118
FEATURE                Location/Qualifiers
REGION                 1..118
                       note = Synthetic
source                 1..118
                       mol_type = protein
                       organism = synthetic construct
SEQUENCE: 306
QVQLVESGGG VVQPGRSLRL SCAASGFTFR SFGMHWVRQA PGRGLEWVAM IYFDGKNKYY  60
ADSVRGRFTI SRDNSKNTLY LEMSSLRAED TAVYFCARGP GYNWLDPWGQ GTLVTVSS    118

SEQ ID NO: 307         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 307
ggtttcacct tcagaagttt tggc                                 24

SEQ ID NO: 308         moltype = AA  length = 8
FEATURE                Location/Qualifiers
REGION                 1..8
                       note = Synthetic
source                 1..8
                       mol_type = protein
                       organism = synthetic construct
SEQUENCE: 308
GFTFRSFG                                                   8

SEQ ID NO: 309         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 309
atatattttg atggaaaaaa taaa                                 24

SEQ ID NO: 310         moltype = AA  length = 8
FEATURE                Location/Qualifiers
REGION                 1..8
                       note = Synthetic
source                 1..8
                       mol_type = protein
                       organism = synthetic construct
SEQUENCE: 310
IYFDGKNK                                                   8

SEQ ID NO: 311         moltype = DNA  length = 33
FEATURE                Location/Qualifiers
misc_feature           1..33
                       note = Synthetic
source                 1..33
                       mol_type = other DNA
                       organism = synthetic construct
SEQUENCE: 311
gcgcgagggc ctgggtacaa ctggctcgac ccc                       33

SEQ ID NO: 312         moltype = AA  length = 11
```

-continued

```
FEATURE                 Location/Qualifiers
REGION                  1..11
                        note = Synthetic
source                  1..11
                        mol_type = protein
                        organism = synthetic construct
SEQUENCE: 312
ARGPGYNWLD P                                                      11

SEQ ID NO: 313          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 313
gaaatagtga tgacgcagtc tccagccacc ctgtctgtgt ctccagggga aagagtcatc  60
ctctcctgta gggccagtca gagtattagc aggaacttgg cctggtacca gcaraaacct  120
ggccaggctc ccaggctcct catctatggt gcaaccacca gggccactgg tgtcccagcc  180
aggttcagtg gcagtgggtc tgggacagag ttcactctca ccatcagcag cctacagtct  240
gaagattttg cagtttttta ctgtcagcag tataataata ggcctctcac tttcggcgga  300
gggaccgagg tggagatcaa a                                           321

SEQ ID NO: 314          moltype = AA  length = 107
FEATURE                 Location/Qualifiers
REGION                  1..107
                        note = Synthetic
VARIANT                 38
                        note = Xaa = Any amino acid
VARIANT                 38
                        note = Xaa = Any Amino Acid
source                  1..107
                        mol_type = protein
                        organism = synthetic construct
SEQUENCE: 314
EIVMTQSPAT LSVSPGERVI LSCRASQSIS RNLAWYQXKP GQAPRLLIYG ATTRATGVPA  60
RFSGSGSGTE FTLTISSLQS EDFAVFYCQQ YNNRPLTFGG GTEVEIK               107

SEQ ID NO: 315          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 315
cagagtatta gcaggaac                                               18

SEQ ID NO: 316          moltype = AA  length = 6
FEATURE                 Location/Qualifiers
REGION                  1..6
                        note = Synthetic
source                  1..6
                        mol_type = protein
                        organism = synthetic construct
SEQUENCE: 316
QSISRN                                                            6

SEQ ID NO: 317          moltype =   length =
SEQUENCE: 317
000

SEQ ID NO: 318          moltype =   length =
SEQUENCE: 318
000

SEQ ID NO: 319          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 319
cagcagtata ataataggcc tctcact                                     27

SEQ ID NO: 320          moltype = AA  length = 9
FEATURE                 Location/Qualifiers
```

```
REGION                  1..9
                        note = Synthetic
source                  1..9
                        mol_type = protein
                        organism = synthetic construct
SEQUENCE: 320
QQYNNRPLT                                                          9

SEQ ID NO: 321          moltype = DNA  length = 354
FEATURE                 Location/Qualifiers
misc_feature            1..354
                        note = Synthetic
source                  1..354
                        mol_type = other DNA
                        organism = synthetic construct
SEQUENCE: 321
caggtgcagc tggtggagtc tgggggaggc gtggtccagc ctgggaggtc cctgagactc  60
tcctgtattg cgtctggatt taccttcaga agttatggca tgcactgggt ccgccaggct  120
ccaggcaagg ggctggagtg ggtggcaatg atatattatg atggaaacaa taaatactat  180
gcagactccg tgaggggccg attcaccatc tccagagaca actccaagaa cacgctgtat  240
ctgcaaatga acagcctgag agccgatgac acggctgtgt atttctgtgc gcgagggcct  300
gggtacaact ggctcgaccc ctggggccag ggaaccctgg tcaccgtctc ctca        354

SEQ ID NO: 322          moltype = AA  length = 118
FEATURE                 Location/Qualifiers
REGION                  1..118
                        note = Synthetic
source                  1..118
                        mol_type = protein
                        organism = synthetic construct
SEQUENCE: 322
QVQLVESGGG VVQPGRSLRL SCIASGFTFR SYGMHWVRQA PGKGLEWVAM IYYDGNNKYY  60
ADSVRGRFTI SRDNSKNTLY LQMNSLRADD TAVYFCARGP GYNWLDPWGQ GTLVTVSS    118

SEQ ID NO: 323          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 323
ggatttacct tcagaagtta tggc                                         24

SEQ ID NO: 324          moltype = AA  length = 8
FEATURE                 Location/Qualifiers
REGION                  1..8
                        note = Synthetic
source                  1..8
                        mol_type = protein
                        organism = synthetic construct
SEQUENCE: 324
GFTFRSYG                                                           8

SEQ ID NO: 325          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 325
atatattatg atggaaacaa taaa                                         24

SEQ ID NO: 326          moltype = AA  length = 8
FEATURE                 Location/Qualifiers
REGION                  1..8
                        note = Synthetic
source                  1..8
                        mol_type = protein
                        organism = synthetic construct
SEQUENCE: 326
IYYDGNNK                                                           8

SEQ ID NO: 327          moltype = DNA  length = 33
FEATURE                 Location/Qualifiers
misc_feature            1..33
                        note = Synthetic
source                  1..33
```

```
                        mol_type = other DNA
                        organism = synthetic construct
SEQUENCE: 327
gcgcgagggc ctgggtacaa ctggctcgac ccc                            33

SEQ ID NO: 328          moltype = AA  length = 11
FEATURE                 Location/Qualifiers
REGION                  1..11
                        note = Synthetic
source                  1..11
                        mol_type = protein
                        organism = synthetic construct
SEQUENCE: 328
ARGPGYNWLD P                                                    11

SEQ ID NO: 329          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 329
gaaatagtga tgacgcagtc tccagccaca ctgtctgtgt ctccagggga aagagccacc  60
ctctcctgca gggccagtca gagtgttagc agcaacttgg cctggtacca gcagaaacct  120
ggccaggctc ccaggctcct catctatggt gcatccacca gggccactgg tatcccagcc  180
aggttcagtg gcagtgggtc tgggacagag ttcactctca ccatcagcag cctgcagtct  240
gaagattttg cagtttatta ctgtcagcag tataataaca ggcctctcac tttcggcgga  300
gggaccaagg tggagatcaa a                                         321

SEQ ID NO: 330          moltype = AA  length = 107
FEATURE                 Location/Qualifiers
REGION                  1..107
                        note = Synthetic
source                  1..107
                        mol_type = protein
                        organism = synthetic construct
SEQUENCE: 330
EIVMTQSPAT LSVSPGERAT LSCRASQSVS SNLAWYQQKP GQAPRLLIYG ASTRATGIPA  60
RFSGSGSGTE FTLTISSLQS EDFAVYYCQQ YNNRPLTFGG GTKVEIK             107

SEQ ID NO: 331          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 331
cagagtgtta gcagcaac                                             18

SEQ ID NO: 332          moltype = AA  length = 6
FEATURE                 Location/Qualifiers
REGION                  1..6
                        note = Synthetic
source                  1..6
                        mol_type = protein
                        organism = synthetic construct
SEQUENCE: 332
QSVSSN                                                          6

SEQ ID NO: 333          moltype =   length =
SEQUENCE: 333
000

SEQ ID NO: 334          moltype =   length =
SEQUENCE: 334
000

SEQ ID NO: 335          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 335
cagcagtata ataacaggcc tctcact                                   27
```

```
SEQ ID NO: 336         moltype = AA  length = 9
FEATURE                Location/Qualifiers
REGION                 1..9
                       note = Synthetic
source                 1..9
                       mol_type = protein
                       organism = synthetic construct
SEQUENCE: 336
QQYNNRPLT                                                          9

SEQ ID NO: 337         moltype = DNA  length = 372
FEATURE                Location/Qualifiers
misc_feature           1..372
                       note = Synthetic
source                 1..372
                       mol_type = other DNA
                       organism = synthetic construct
SEQUENCE: 337
gaagtgcagc tggtggagtc tgggggaggc ttggtacagc ctggcaggtc cctgagactc  60
tcctgtgcag cctctggatt cacctttgat gattattcca tgcactgggt ccggcaagct  120
ccagggaagg gcctggagtg ggtctcaggt attagttgga atagtcgtag catagactat  180
gcggactctg tgaagggccg attcaccatc tccagagaca acgccaagaa ctccctgtat  240
ctgcaaatga acagtctgag agctgaggac acggccttgt attactgtgt aaaagataat  300
agtggctatg gccgctatta ctactacggg atggacgtct ggggccaagg gaccacggtc  360
tccgtctcct ca                                                      372

SEQ ID NO: 338         moltype = AA  length = 124
FEATURE                Location/Qualifiers
REGION                 1..124
                       note = Synthetic
source                 1..124
                       mol_type = protein
                       organism = synthetic construct
SEQUENCE: 338
EVQLVESGGG LVQPGRSLRL SCAASGFTFD DYSMHWVRQA PGKGLEWVSG ISWNSRSIDY  60
ADSVKGRFTI SRDNAKNSLY LQMNSLRAED TALYYCVKDN SGYGRYYYYG MDVWGQGTTV  120
SVSS                                                               124

SEQ ID NO: 339         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 339
ggattcacct ttgatgatta ttcc                                         24

SEQ ID NO: 340         moltype = AA  length = 8
FEATURE                Location/Qualifiers
REGION                 1..8
                       note = Synthetic
source                 1..8
                       mol_type = protein
                       organism = synthetic construct
SEQUENCE: 340
GFTFDDYS                                                           8

SEQ ID NO: 341         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 341
attagttgga atagtcgtag cata                                         24

SEQ ID NO: 342         moltype = AA  length = 8
FEATURE                Location/Qualifiers
REGION                 1..8
                       note = Synthetic
source                 1..8
                       mol_type = protein
                       organism = synthetic construct
SEQUENCE: 342
ISWNSRSI                                                           8

SEQ ID NO: 343         moltype = DNA  length = 51
```

```
FEATURE                 Location/Qualifiers
misc_feature            1..51
                        note = Synthetic
source                  1..51
                        mol_type = other DNA
                        organism = synthetic construct
SEQUENCE: 343
gtaaaagata atagtggcta tggccgctat tactactacg ggatggacgt c          51

SEQ ID NO: 344          moltype = AA  length = 17
FEATURE                 Location/Qualifiers
REGION                  1..17
                        note = Synthetic
source                  1..17
                        mol_type = protein
                        organism = synthetic construct
SEQUENCE: 344
VKDNSGYGRY YYYGMDV                                                17

SEQ ID NO: 345          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 345
aaaatagtga tgacgcagtc tcccgccacc ctgtctgtgt ctccagggga aagagccacc  60
ctctcctgca gggccagtca gagtgttagc ggcaacttag cctggtacca gcaaaaacct  120
ggccaggctc ccaggctcct catctatggt gcatccacca gggccactag tatcccagcc  180
aggttcagtg gcagtgggtc tgggacagag ttcactctca ccatcagcag cctgcagtct  240
gaagattttg cagtttattt ctgtcagcac tattataact ggcctctcac tttcggcgga  300
gggaccaagg tggagatcag a                                            321

SEQ ID NO: 346          moltype = AA  length = 107
FEATURE                 Location/Qualifiers
REGION                  1..107
                        note = Synthetic
source                  1..107
                        mol_type = protein
                        organism = synthetic construct
SEQUENCE: 346
KIVMTQSPAT LSVSPGERAT LSCRASQSVS GNLAWYQQKP GQAPRLLIYG ASTRATSIPA  60
RFSGSGSGTE FTLTISSLQS EDFAVYFCQH YYNWPLTFGG GTKVEIR                107

SEQ ID NO: 347          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 347
cagagtgtta gcggcaac                                               18

SEQ ID NO: 348          moltype = AA  length = 6
FEATURE                 Location/Qualifiers
REGION                  1..6
                        note = Synthetic
source                  1..6
                        mol_type = protein
                        organism = synthetic construct
SEQUENCE: 348
QSVSGN                                                            6

SEQ ID NO: 349          moltype =   length =
SEQUENCE: 349
000

SEQ ID NO: 350          moltype =   length =
SEQUENCE: 350
000

SEQ ID NO: 351          moltype = DNA  length = 27
FEATURE                 Location/Qualifiers
misc_feature            1..27
                        note = Synthetic
source                  1..27
                        mol_type = other DNA
```

-continued

```
                        organism = synthetic construct
SEQUENCE: 351
cagcactatt ataactggcc tctcact                                      27

SEQ ID NO: 352          moltype = AA  length = 9
FEATURE                 Location/Qualifiers
REGION                  1..9
                        note = Synthetic
source                  1..9
                        mol_type = protein
                        organism = synthetic construct
SEQUENCE: 352
QHYYNWPLT                                                          9

SEQ ID NO: 353          moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 353
gaagtgcaac tggtggagtc tgggggaggc ttagtacagc ctggcgggtc cctgagactc  60
tcctgtgcag ccactggatt cacctttgat gattttacca tgcactgggt ccggcaagct  120
ccagggaagg gcctggagtg ggtctcaggt atcagttgga atagtggtag cataggctat  180
gtggactctg tgaagggccg attcaccatc tccagagaca acgccaagaa ctccctgtat  240
ctgcaaatga acagtctgag agctgaggac acggccttgt actactgtgc aaaagataat  300
agtggctacg gctattatta ctacggtatg gacgtctggg gccaagggac cacggtcacc  360
gtctcctca                                                          369

SEQ ID NO: 354          moltype = AA  length = 123
FEATURE                 Location/Qualifiers
REGION                  1..123
                        note = Synthetic
source                  1..123
                        mol_type = protein
                        organism = synthetic construct
SEQUENCE: 354
EVQLVESGGG LVQPGGSLRL SCAATGFTFD DFTMHWVRQA PGKGLEWVSG ISWNSGSIGY  60
VDSVKGRFTI SRDNAKNSLY LQMNSLRAED TALYYCAKDN SGYGYYYYGM DVWGQGTTVT  120
VSS                                                                123

SEQ ID NO: 355          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 355
ggattcacct ttgatgattt tacc                                         24

SEQ ID NO: 356          moltype = AA  length = 8
FEATURE                 Location/Qualifiers
REGION                  1..8
                        note = Synthetic
source                  1..8
                        mol_type = protein
                        organism = synthetic construct
SEQUENCE: 356
GFTFDDFT                                                           8

SEQ ID NO: 357          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 357
atcagttgga atagtggtag cata                                         24

SEQ ID NO: 358          moltype = AA  length = 8
FEATURE                 Location/Qualifiers
REGION                  1..8
                        note = Synthetic
source                  1..8
                        mol_type = protein
                        organism = synthetic construct
```

```
SEQUENCE: 358
ISWNSGSI                                                     8

SEQ ID NO: 359          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 359
gcaaaagata atagtggcta cggctattat tactacggta tggacgtc         48

SEQ ID NO: 360          moltype = AA  length = 16
FEATURE                 Location/Qualifiers
REGION                  1..16
                        note = Synthetic
source                  1..16
                        mol_type = protein
                        organism = synthetic construct
SEQUENCE: 360
AKDNSGYGYY YYGMDV                                            16

SEQ ID NO: 361          moltype = DNA  length = 339
FEATURE                 Location/Qualifiers
misc_feature            1..339
                        note = Synthetic
source                  1..339
                        mol_type = other DNA
                        organism = synthetic construct
SEQUENCE: 361
gacatcgtga tgacccagtc tccagactcc ctggctgtgt ctctgggcga gagggccacc  60
atcaactgca agtccagcca gagtgtttta tacagctcca acaataagaa ctacttagct  120
tggtaccagc agaaaccagg acagcctcct aagctgctca tttactgggc atctacccgg  180
gaatccgggg tccctgaccg attcagtggc agcgggtctg ggacagattt cactctcacc  240
atcagcagcc tgcaggctga agatgtggca gtttattact gtcagcaata ttatagtact  300
ccgtacactt ttggccaggg gaccaagctg gagatcaaa                   339

SEQ ID NO: 362          moltype = AA  length = 113
FEATURE                 Location/Qualifiers
REGION                  1..113
                        note = Synthetic
source                  1..113
                        mol_type = protein
                        organism = synthetic construct
SEQUENCE: 362
DIVMTQSPDS LAVSLGERAT INCKSSQSVL YSSNNKNYLA WYQQKPGQPP KLLIYWASTR  60
ESGVPDRFSG SGSGTDFTLT ISSLQAEDVA VYYCQQYYST PYTFGQGTKL EIK        113

SEQ ID NO: 363          moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 363
cagagtgttt tatacagctc caacaataag aactac                      36

SEQ ID NO: 364          moltype = AA  length = 12
FEATURE                 Location/Qualifiers
REGION                  1..12
                        note = Synthetic
source                  1..12
                        mol_type = protein
                        organism = synthetic construct
SEQUENCE: 364
QSVLYSSNNK NY                                                12

SEQ ID NO: 365          moltype =   length =
SEQUENCE: 365
000

SEQ ID NO: 366          moltype =   length =
SEQUENCE: 366
000

SEQ ID NO: 367          moltype = DNA  length = 27
FEATURE                 Location/Qualifiers
```

```
misc_feature           1..27
                       note = Synthetic
source                 1..27
                       mol_type = other DNA
                       organism = synthetic construct
SEQUENCE: 367
cagcaatatt atagtactcc gtacact                                27

SEQ ID NO: 368         moltype = AA  length = 9
FEATURE                Location/Qualifiers
REGION                 1..9
                       note = Synthetic
source                 1..9
                       mol_type = protein
                       organism = synthetic construct
SEQUENCE: 368
QQYYSTPYT                                                    9

SEQ ID NO: 369         moltype = DNA  length = 369
FEATURE                Location/Qualifiers
misc_feature           1..369
                       note = Synthetic
source                 1..369
                       mol_type = other DNA
                       organism = synthetic construct
SEQUENCE: 369
caggtcacct tgaaggagtc tggtcctgcg ctggtgaaac ccacacagac cctcacactg  60
acctgcacct tctctgggtt ctcactcagc actagtggaa tgtgtgtgag ctggatccgt  120
cagcccccag ggaaggccct ggagtggctt gcacgcattg attgggatga tgataaatac  180
tacagcacat ctctgaagac caggctcacc atctccaagg acacctccaa aaaccaggtg  240
gtccttacaa tgaccaacat ggaccctgtg gacacagcca cgtattactg tgcacggatg  300
gatatagtgg gagctagagg ggggtggttc gacccctggg gccagggaac cctggtcacc  360
gtctcctca                                                    369

SEQ ID NO: 370         moltype = AA  length = 123
FEATURE                Location/Qualifiers
REGION                 1..123
                       note = Synthetic
source                 1..123
                       mol_type = protein
                       organism = synthetic construct
SEQUENCE: 370
QVTLKESGPA LVKPTQTLTL TCTFSGFSLS TSGMCVSWIR QPPGKALEWL ARIDWDDDKY  60
YSTSLKTRLT ISKDTSKNQV VLTMTNMDPV DTATYYCARM DIVGARGGWF DPWGQGTLVT  120
VSS                                                          123

SEQ ID NO: 371         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 371
gggttctcac tcagcactag tggaatgtgt                             30

SEQ ID NO: 372         moltype = AA  length = 10
FEATURE                Location/Qualifiers
REGION                 1..10
                       note = Synthetic
source                 1..10
                       mol_type = protein
                       organism = synthetic construct
SEQUENCE: 372
GFSLSTSGMC                                                   10

SEQ ID NO: 373         moltype = DNA  length = 21
FEATURE                Location/Qualifiers
misc_feature           1..21
                       note = Synthetic
source                 1..21
                       mol_type = other DNA
                       organism = synthetic construct
SEQUENCE: 373
attgattggg atgatgataa a                                      21

SEQ ID NO: 374         moltype = AA  length = 7
FEATURE                Location/Qualifiers
REGION                 1..7
```

```
                        note = Synthetic
source                  1..7
                        mol_type = protein
                        organism = synthetic construct
SEQUENCE: 374
IDWDDDK                                                             7

SEQ ID NO: 375          moltype = DNA  length = 45
FEATURE                 Location/Qualifiers
misc_feature            1..45
                        note = Synthetic
source                  1..45
                        mol_type = other DNA
                        organism = synthetic construct
SEQUENCE: 375
gcacggatgg atatagtggg agctagaggg gggtggttcg acccc                  45

SEQ ID NO: 376          moltype = AA  length = 15
FEATURE                 Location/Qualifiers
REGION                  1..15
                        note = Synthetic
source                  1..15
                        mol_type = protein
                        organism = synthetic construct
SEQUENCE: 376
ARMDIVGARG GWFDP                                                    15

SEQ ID NO: 377          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 377
gacatccaga tgacccagtc tccatcctca ctgtctgcat ctgtaggaga cagagtcacc  60
atcacttgtc gggcgagtca gggcattagc aattatttag cctggtttca gcagaaacca  120
gggaaagccc ctaagtccct gatctatgct gcatccagtt tgcaaagtgg ggtcccatca  180
aagttcagcg gcagtggatc tgggacagat ttcactctca ccatcagcag cctgcagcct  240
gaagattttg caacttatta ctgccaacag tataatagtt acccgctcac tttcggcgga  300
gggaccaagg tggagatcaa a                                             321

SEQ ID NO: 378          moltype = AA  length = 107
FEATURE                 Location/Qualifiers
REGION                  1..107
                        note = Synthetic
source                  1..107
                        mol_type = protein
                        organism = synthetic construct
SEQUENCE: 378
DIQMTQSPSS LSASVGDRVT ITCRASQGIS NYLAWFQQKP GKAPKSLIYA ASSLQSGVPS  60
KFSGSGSGTD FTLTISSLQP EDFATYYCQQ YNSYPLTFGG GTKVEIK                 107

SEQ ID NO: 379          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 379
cagggcatta gcaattat                                                 18

SEQ ID NO: 380          moltype = AA  length = 6
FEATURE                 Location/Qualifiers
REGION                  1..6
                        note = Synthetic
source                  1..6
                        mol_type = protein
                        organism = synthetic construct
SEQUENCE: 380
QGISNY                                                              6

SEQ ID NO: 381          moltype =   length =
SEQUENCE: 381
000

SEQ ID NO: 382          moltype =   length =
SEQUENCE: 382
```

```
000

SEQ ID NO: 383         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 383
caacagtata atagttaccc gctcact                                      27

SEQ ID NO: 384         moltype = AA  length = 9
FEATURE                Location/Qualifiers
REGION                 1..9
                       note = Synthetic
source                 1..9
                       mol_type = protein
                       organism = synthetic construct
SEQUENCE: 384
QQYNSYPLT                                                          9

SEQ ID NO: 385         moltype = DNA  length = 404
FEATURE                Location/Qualifiers
misc_feature           1..404
                       note = Synthetic
source                 1..404
                       mol_type = other DNA
                       organism = synthetic construct
SEQUENCE: 385
caggtgcagt tggtggagtc tgggggaggc gtggtccagc ctgggaggtc cctgagactc  60
tcctgtgctg cgtctggatt caccttcaga agttatggca tgcactgggt ccgccaggct  120
ccaggcaagg ggctggagtg ggtggcaatg atatattatg atggaaataa taaaaagtat  180
gcagactccg tgaggggccg attcaccatt tccagagaca attccaagaa cacgctgtat  240
ctgcaaatga acagcctgag agtcgaggac acggctgtgt atttctgtgc gcgagggcct  300
gggtacaact ggctcgaccc ctggggccag ggaaccctgg tcaccgtctc ctcagccaaa  360
acaacagccc cacccgttta tccactggcc cctggaagct tggg                   404

SEQ ID NO: 386         moltype = AA  length = 134
FEATURE                Location/Qualifiers
REGION                 1..134
                       note = Synthetic
source                 1..134
                       mol_type = protein
                       organism = synthetic construct
SEQUENCE: 386
QVQLVESGGG VVQPGRSLRL SCAASGFTFR SYGMHWVRQA PGKGLEWVAM IYYDGNNKKY  60
ADSVRGRFTI SRDNSKNTLY LQMNSLRVED TAVYFCARGP GYNWLDPWGQ GTLVTVSSAK  120
TTAPPVYPLA PGSL                                                    134

SEQ ID NO: 387         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 387
ggattcacct tcagaagtta tggc                                         24

SEQ ID NO: 388         moltype = AA  length = 8
FEATURE                Location/Qualifiers
REGION                 1..8
                       note = Synthetic
source                 1..8
                       mol_type = protein
                       organism = synthetic construct
SEQUENCE: 388
GFTFRSYG                                                           8

SEQ ID NO: 389         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 389
atatattatg atggaaataa taaa                                         24
```

```
SEQ ID NO: 390          moltype = AA  length = 8
FEATURE                 Location/Qualifiers
REGION                  1..8
                        note = Synthetic
source                  1..8
                        mol_type = protein
                        organism = synthetic construct
SEQUENCE: 390
IYYDGNNK                                                          8

SEQ ID NO: 391          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 391
gcgcgagggc ctgggtacaa ctggctcgac ccc                              33

SEQ ID NO: 392          moltype = AA  length = 11
FEATURE                 Location/Qualifiers
REGION                  1..11
                        note = Synthetic
source                  1..11
                        mol_type = protein
                        organism = synthetic construct
SEQUENCE: 392
ARGPGYNWLD P                                                      11

SEQ ID NO: 393          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 393
gaaatagtga tgacgcagtc tccagccacc ctgtctgtgt ctccagggga aagagccacc  60
ctctcctgca gggccagtca gagtgttagc aggaacttgg cctggtacca gcagaaacct  120
ggccaggctc ccaggctcct catctatggt gcatccacca gggccactga tatcccagcc  180
aggttcagtg gcagtgggtc tgggacagag ttcattctca acatcagcag cctgcagtct  240
gaagattttg cactttatta ctgtcaacaa tatagtaact ggcctctcac tttcggcgga  300
gggaccgagg tggagatcaa a                                           321

SEQ ID NO: 394          moltype = AA  length = 107
FEATURE                 Location/Qualifiers
REGION                  1..107
                        note = Synthetic
source                  1..107
                        mol_type = protein
                        organism = synthetic construct
SEQUENCE: 394
EIVMTQSPAT LSVSPGERAT LSCRASQSVS RNLAWYQQKP GQAPRLLIYG ASTRATDIPA  60
RFSGSGSGTE FILNISSLQS EDFALYYCQQ YSNWPLTFGG GTEVEIK               107

SEQ ID NO: 395          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 395
cagagtgtta gcaggaac                                               18

SEQ ID NO: 396          moltype = AA  length = 6
FEATURE                 Location/Qualifiers
REGION                  1..6
                        note = Synthetic
source                  1..6
                        mol_type = protein
                        organism = synthetic construct
SEQUENCE: 396
QSVSRN                                                            6

SEQ ID NO: 397          moltype =   length =
SEQUENCE: 397
```

```
000

SEQ ID NO: 398          moltype =   length =
SEQUENCE: 398
000

SEQ ID NO: 399          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 399
caacaatata gtaactggcc tctcact                                      27

SEQ ID NO: 400          moltype = AA  length = 9
FEATURE                 Location/Qualifiers
REGION                  1..9
                        note = Synthetic
source                  1..9
                        mol_type = protein
                        organism = synthetic construct
SEQUENCE: 400
QQYSNWPLT                                                          9

SEQ ID NO: 401          moltype = DNA  length = 354
FEATURE                 Location/Qualifiers
misc_feature            1..354
                        note = Synthetic
source                  1..354
                        mol_type = other DNA
                        organism = synthetic construct
SEQUENCE: 401
caggtgcaat tggtggagtc tgggggaggc gtggtccagc cggggaggtc cctgagactc  60
tcctgtgctg cgtctggttt caccttcaga agttttggca tgcactgggt ccgccaggct  120
ccaggcaggg gactggagtg ggtggcaatg atatattttg atggaaaaaa taaatactat  180
gcagactccg tgaggggccg attcaccatt tccagagaca attccaagaa caccctgtat  240
ctggaaatga gtagcctgag agccgaggac acggctgtat atttctgtgc gcgagggcct  300
gggtacaact ggctcgaccc ctggggccag ggaaccctgg tcaccgtctc ctca        354

SEQ ID NO: 402          moltype = AA  length = 118
FEATURE                 Location/Qualifiers
REGION                  1..118
                        note = Synthetic
source                  1..118
                        mol_type = protein
                        organism = synthetic construct
SEQUENCE: 402
QVQLVESGGG VVQPGRSLRL SCAASGFTFR SFGMHWVRQA PGRGLEWVAM IYFDGKNKYY  60
ADSVRGRFTI SRDNSKNTLY LEMSSLRAED TAVYFCARGP GYNWLDPWGQ GTLVTVSS    118

SEQ ID NO: 403          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 403
ggtttcacct tcagaagttt tggc                                         24

SEQ ID NO: 404          moltype = AA  length = 8
FEATURE                 Location/Qualifiers
REGION                  1..8
                        note = Synthetic
source                  1..8
                        mol_type = protein
                        organism = synthetic construct
SEQUENCE: 404
GFTFRSFG                                                           8

SEQ ID NO: 405          moltype = DNA  length = 24
FEATURE                 Location/Qualifiers
misc_feature            1..24
                        note = Synthetic
source                  1..24
                        mol_type = other DNA
                        organism = synthetic construct
```

```
SEQUENCE: 405
atatattttg atggaaaaaa taaa                                  24

SEQ ID NO: 406         moltype = AA  length = 8
FEATURE                Location/Qualifiers
REGION                 1..8
                       note = Synthetic
source                 1..8
                       mol_type = protein
                       organism = synthetic construct
SEQUENCE: 406
IYFDGKNK                                                    8

SEQ ID NO: 407         moltype = DNA  length = 33
FEATURE                Location/Qualifiers
misc_feature           1..33
                       note = Synthetic
source                 1..33
                       mol_type = other DNA
                       organism = synthetic construct
SEQUENCE: 407
gcgcgagggc ctgggtacaa ctggctcgac ccc                        33

SEQ ID NO: 408         moltype = AA  length = 11
FEATURE                Location/Qualifiers
REGION                 1..11
                       note = Synthetic
source                 1..11
                       mol_type = protein
                       organism = synthetic construct
SEQUENCE: 408
ARGPGYNWLD P                                                11

SEQ ID NO: 409         moltype = DNA  length = 321
FEATURE                Location/Qualifiers
misc_feature           1..321
                       note = Synthetic
source                 1..321
                       mol_type = other DNA
                       organism = synthetic construct
SEQUENCE: 409
gaaatagtga tgacgcagtc tccagccacc ctgtctgtgt ctccagggga aagagtcatc  60
ctctcctgta gggccagtca gagtattagc aggaacttgg cctggtacca gcagaaacct  120
ggccaggctc ccaggctcct catctatggt gcaaccacca gggccactgg tgtcccagcc  180
aggttcagtg gcagtgggtc tgggacagag ttcactctca ccatcagcag cctacagtct  240
gaagattttg cagtttttta ctgtcagcag tataataata ggcctctcac tttcggcgga  300
gggaccgagg tggagatcaa a                                     321

SEQ ID NO: 410         moltype = AA  length = 107
FEATURE                Location/Qualifiers
REGION                 1..107
                       note = Synthetic
source                 1..107
                       mol_type = protein
                       organism = synthetic construct
SEQUENCE: 410
EIVMTQSPAT LSVSPGERVI LSCRASQSIS RNLAWYQQKP GQAPRLLIYG ATTRATGVPA  60
RFSGSGSGTE FTLTISSLQS EDFAVFYCQQ YNNRPLTFGG GTEVEIK           107

SEQ ID NO: 411         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 411
cagagtatta gcaggaac                                         18

SEQ ID NO: 412         moltype = AA  length = 6
FEATURE                Location/Qualifiers
REGION                 1..6
                       note = Synthetic
source                 1..6
                       mol_type = protein
                       organism = synthetic construct
SEQUENCE: 412
QSISRN                                                      6
```

```
SEQ ID NO: 413         moltype =   length =
SEQUENCE: 413
000

SEQ ID NO: 414         moltype =   length =
SEQUENCE: 414
000

SEQ ID NO: 415         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 415
cagcagtata ataataggcc tctcact                                      27

SEQ ID NO: 416         moltype = AA  length = 9
FEATURE                Location/Qualifiers
REGION                 1..9
                       note = Synthetic
source                 1..9
                       mol_type = protein
                       organism = synthetic construct
SEQUENCE: 416
QQYNNRPLT                                                          9

SEQ ID NO: 417         moltype = DNA  length = 354
FEATURE                Location/Qualifiers
misc_feature           1..354
                       note = Synthetic
source                 1..354
                       mol_type = other DNA
                       organism = synthetic construct
SEQUENCE: 417
caggtgcaat tggtggagtc tgggggaggc gtggtccagc cggggaggtc cctgagactc  60
tcctgtgctg cgtctggttt caccttcaga agttttggca tgcactgggt ccgccaggct  120
ccaggcaggg gactggagtg ggtggcaatg atatattttg atggaaaaaa taaatactat  180
gcagactccg tgaggggccg attcaccatt tccagagaca attccaagaa caccctgtat  240
ctggaaatga gtagcctgag agccgaggac acggctgtat atttctgtgc gcgagggcct  300
gggtacaact ggctcgaccc ctggggccag ggaaccctgg tcaccgtctc ctca        354

SEQ ID NO: 418         moltype = AA  length = 118
FEATURE                Location/Qualifiers
REGION                 1..118
                       note = Synthetic
source                 1..118
                       mol_type = protein
                       organism = synthetic construct
SEQUENCE: 418
QVQLVESGGG VVQPGRSLRL SCAASGFTFR SFGMHWVRQA PGRGLEWVAM IYFDGKNKYY  60
ADSVRGRFTI SRDNSKNTLY LEMSSLRAED TAVYFCARGP GYNWLDPWGQ GTLVTVSS    118

SEQ ID NO: 419         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 419
ggtttcacct tcagaagttt tggc                                         24

SEQ ID NO: 420         moltype = AA  length = 8
FEATURE                Location/Qualifiers
REGION                 1..8
                       note = Synthetic
source                 1..8
                       mol_type = protein
                       organism = synthetic construct
SEQUENCE: 420
GFTFRSFG                                                           8

SEQ ID NO: 421         moltype = DNA  length = 24
FEATURE                Location/Qualifiers
misc_feature           1..24
                       note = Synthetic
source                 1..24
```

```
                        mol_type = other DNA
                        organism = synthetic construct
SEQUENCE: 421
atatattttg atggaaaaaa taaa                                            24

SEQ ID NO: 422          moltype = AA  length = 8
FEATURE                 Location/Qualifiers
REGION                  1..8
                        note = Synthetic
source                  1..8
                        mol_type = protein
                        organism = synthetic construct
SEQUENCE: 422
IYFDGKNK                                                              8

SEQ ID NO: 423          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 423
gcgcgagggc ctgggtacaa ctggctcgac ccc                                  33

SEQ ID NO: 424          moltype = AA  length = 11
FEATURE                 Location/Qualifiers
REGION                  1..11
                        note = Synthetic
source                  1..11
                        mol_type = protein
                        organism = synthetic construct
SEQUENCE: 424
ARGPGYNWLD P                                                          11

SEQ ID NO: 425          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 425
gaaatagtga tgacgcagtc tccagccacc ctgtctgtgt ctccagggga aagagtcatc  60
ctctcctgta gggccagtca gagtattagc aggaacttgg cctggtacca gcagaaacct  120
ggccaggctc ccaggctcct catctatggt gcaaccacca gggccactgg tgtcccagcc  180
aggttcagtg gcagtgggtc tgggacagag ttcactctca ccatcagcag cctacagtct  240
gaagattttg cagtttttta ctgtcagcag tataataata ggcctctcac tttcggcgga  300
gggaccgagg tggagatcaa a                                               321

SEQ ID NO: 426          moltype = AA  length = 107
FEATURE                 Location/Qualifiers
REGION                  1..107
                        note = Synthetic
source                  1..107
                        mol_type = protein
                        organism = synthetic construct
SEQUENCE: 426
EIVMTQSPAT LSVSPGERVI LSCRASQSIS RNLAWYQQKP GQAPRLLIYG ATTRATGVPA  60
RFSGSGSGTE FTLTISSLQS EDFAVFYCQQ YNNRPLTFGG GTEVEIK                  107

SEQ ID NO: 427          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 427
cagagtatta gcaggaac                                                   18

SEQ ID NO: 428          moltype = AA  length = 6
FEATURE                 Location/Qualifiers
REGION                  1..6
                        note = Synthetic
source                  1..6
                        mol_type = protein
                        organism = synthetic construct
SEQUENCE: 428
```

-continued

```
QSISRN                                                     6

SEQ ID NO: 429         moltype =   length =
SEQUENCE: 429
000

SEQ ID NO: 430         moltype =   length =
SEQUENCE: 430
000

SEQ ID NO: 431         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 431
cagcagtata ataataggcc tctcact                              27

SEQ ID NO: 432         moltype = AA  length = 9
FEATURE                Location/Qualifiers
REGION                 1..9
                       note = Synthetic
source                 1..9
                       mol_type = protein
                       organism = synthetic construct
SEQUENCE: 432
QQYNNRPLT                                                  9

SEQ ID NO: 433         moltype = DNA  length = 351
FEATURE                Location/Qualifiers
misc_feature           1..351
                       note = Synthetic
source                 1..351
                       mol_type = other DNA
                       organism = synthetic construct
SEQUENCE: 433
caggtgcacc tggaagagtc tgggggaggc gtggtccagc ctgggaggtc cctgagactc  60
tcctgttcag cgtctggttt caccttcagt agttatgcca tgcactgggt ccgccaggct  120
ccaggcaagg ggctggagtg ggtggcagtt atatggtatg atggaactaa taaatattat  180
ttagattccg tgaagggccg attcaccatc tccagagaca attccaagaa cacgctgttt  240
ctgcaaatga acagcctgag agccgaagac acggctgtgt attactgtgc gagagatcgg  300
ggaagtataa taacccactg gggccaggga accctggtca ccgtctcctc a           351

SEQ ID NO: 434         moltype = AA  length = 117
FEATURE                Location/Qualifiers
REGION                 1..117
                       note = Synthetic
source                 1..117
                       mol_type = protein
                       organism = synthetic construct
SEQUENCE: 434
QVHLEESGGG VVQPGRSLRL SCSASGFTFS SYAMHWVRQA PGKGLEWVAV IWYDGTNKYY  60
LDSVKGRFTI SRDNSKNTLF LQMNSLRAED TAVYYCARDR GSIITHWGQG TLVTVSS     117

SEQ ID NO: 435         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 435
ggtttcacct tcagtagtta tgcc                                 24

SEQ ID NO: 436         moltype = AA  length = 8
FEATURE                Location/Qualifiers
REGION                 1..8
                       note = Synthetic
source                 1..8
                       mol_type = protein
                       organism = synthetic construct
SEQUENCE: 436
GFTFSSYA                                                   8

SEQ ID NO: 437         moltype = DNA  length = 24
FEATURE                Location/Qualifiers
misc_feature           1..24
```

```
                        note = Synthetic
source                  1..24
                        mol_type = other DNA
                        organism = synthetic construct
SEQUENCE: 437
atatggtatg atggaactaa taaa                                        24

SEQ ID NO: 438          moltype = AA  length = 8
FEATURE                 Location/Qualifiers
REGION                  1..8
                        note = Synthetic
source                  1..8
                        mol_type = protein
                        organism = synthetic construct
SEQUENCE: 438
IWYDGTNK                                                          8

SEQ ID NO: 439          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 439
gcgagagatc ggggaagtat aataacccac                                  30

SEQ ID NO: 440          moltype = AA  length = 10
FEATURE                 Location/Qualifiers
REGION                  1..10
                        note = Synthetic
source                  1..10
                        mol_type = protein
                        organism = synthetic construct
SEQUENCE: 440
ARDRGSIITH                                                        10

SEQ ID NO: 441          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 441
gacatccaga tgacccagtc tccatcctcc ctgtctgcat ctataggaga cagagtcacc  60
atcacttgcc gggcaagtca gaacattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag acttacagta cccctccgat caccttcggc  300
caagggacac gactggagat taaa                                        324

SEQ ID NO: 442          moltype = AA  length = 108
FEATURE                 Location/Qualifiers
REGION                  1..108
                        note = Synthetic
source                  1..108
                        mol_type = protein
                        organism = synthetic construct
SEQUENCE: 442
DIQMTQSPSS LSASIGDRVT ITCRASQNIS SYLNWYQQKP GKAPKLLIYA ASSLQSGVPS  60
RFSGSGSGTD FTLTISSLQP EDFATYYCQQ TYSTPPITFG QGTRLEIK              108

SEQ ID NO: 443          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 443
cagaacatta gcagctat                                               18

SEQ ID NO: 444          moltype = AA  length = 6
FEATURE                 Location/Qualifiers
REGION                  1..6
                        note = Synthetic
source                  1..6
                        mol_type = protein
```

```
                       organism = synthetic construct
SEQUENCE: 444
QNISSY                                                            6

SEQ ID NO: 445         moltype =   length =
SEQUENCE: 445
000

SEQ ID NO: 446         moltype =   length =
SEQUENCE: 446
000

SEQ ID NO: 447         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 447
caacagactt acagtacccc tccgatcacc                                  30

SEQ ID NO: 448         moltype = AA  length = 10
FEATURE                Location/Qualifiers
REGION                 1..10
                       note = Synthetic
source                 1..10
                       mol_type = protein
                       organism = synthetic construct
SEQUENCE: 448
QQTYSTPPIT                                                        10

SEQ ID NO: 449         moltype = DNA  length = 372
FEATURE                Location/Qualifiers
misc_feature           1..372
                       note = Synthetic
source                 1..372
                       mol_type = other DNA
                       organism = synthetic construct
SEQUENCE: 449
gaagtacagc tggtggagtc tgggggaggc ttggtacggc ctggcaggtc cctgagactc  60
tcctgtgcag cctctggatt cacctttgat gattatacca tgcactgggt ccgccaagct  120
ccagggaagg gcctggagtg ggtctcagat attagttgga atagtgggac cataggctat  180
gcggactctg tgaagggccg attcaccatc tccagagaca acgccaagaa ctccctgtat  240
ctgcaaatga acagtctgag acctgaggac acggccttgt attactgtgc aaaagatatg  300
agtggctacg cccactacta ctactacggt atggacgtct ggggccaagg gaccacggtc  360
accgtctcct ca                                                     372

SEQ ID NO: 450         moltype = AA  length = 124
FEATURE                Location/Qualifiers
REGION                 1..124
                       note = Synthetic
source                 1..124
                       mol_type = protein
                       organism = synthetic construct
SEQUENCE: 450
EVQLVESGGG LVRPGRSLRL SCAASGFTFD DYTMHWVRQA PGKGLEWVSD ISWNSGTIGY  60
ADSVKGRFTI SRDNAKNSLY LQMNSLRPED TALYYCAKDM SGYAHYYYYG MDVWGQGTTV  120
TVSS                                                              124

SEQ ID NO: 451         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 451
ggattcacct ttgatgatta tacc                                        24

SEQ ID NO: 452         moltype = AA  length = 8
FEATURE                Location/Qualifiers
REGION                 1..8
                       note = Synthetic
source                 1..8
                       mol_type = protein
                       organism = synthetic construct
SEQUENCE: 452
GFTFDDYT                                                          8
```

```
SEQ ID NO: 453          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 453
attagttgga atagtgggac cata                                        24

SEQ ID NO: 454          moltype = AA  length = 8
FEATURE                 Location/Qualifiers
REGION                  1..8
                        note = Synthetic
source                  1..8
                        mol_type = protein
                        organism = synthetic construct
SEQUENCE: 454
ISWNSGTI                                                          8

SEQ ID NO: 455          moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 455
gcaaaagata tgagtggcta cgcccactac tactactacg gtatggacgt c          51

SEQ ID NO: 456          moltype = AA  length = 17
FEATURE                 Location/Qualifiers
REGION                  1..17
                        note = Synthetic
source                  1..17
                        mol_type = protein
                        organism = synthetic construct
SEQUENCE: 456
AKDMSGYAHY YYYGMDV                                                17

SEQ ID NO: 457          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 457
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                        324

SEQ ID NO: 458          moltype = AA  length = 108
FEATURE                 Location/Qualifiers
REGION                  1..108
                        note = Synthetic
source                  1..108
                        mol_type = protein
                        organism = synthetic construct
SEQUENCE: 458
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK              108

SEQ ID NO: 459          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 459
cagagcatta gcagctat                                               18

SEQ ID NO: 460          moltype = AA  length = 6
FEATURE                 Location/Qualifiers
```

```
REGION                  1..6
                        note = Synthetic
source                  1..6
                        mol_type = protein
                        organism = synthetic construct
SEQUENCE: 460
QSISSY                                                          6

SEQ ID NO: 461          moltype =   length =
SEQUENCE: 461
000

SEQ ID NO: 462          moltype =   length =
SEQUENCE: 462
000

SEQ ID NO: 463          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 463
caacagagtt acagtacccc tccgatcacc                                30

SEQ ID NO: 464          moltype = AA  length = 10
FEATURE                 Location/Qualifiers
REGION                  1..10
                        note = Synthetic
source                  1..10
                        mol_type = protein
                        organism = synthetic construct
SEQUENCE: 464
QQSYSTPPIT                                                      10

SEQ ID NO: 465          moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 465
gaagtgcagc tggtggagtc tgggggaggc ttggtacagc ctggcaggtc cctgagactc  60
tcctgtgcag cctctggatt cacctttgat gattatacca tgcactgggt ccggcaagct  120
ccagggaagg gcctggagtg ggtctccgat attagttgga atagtggtag cataggctat  180
gcggactctg tgaagggccg attcaccgtc tccagagaca acgccaagaa ctccctgtat  240
ctgcaaatga acagtctgag aggtgaggac acggccctgt attactgtgc aaaagatatg  300
agtggctacg cccactacgg ctactacggt atggacgtct ggggccaagg gaccacggtc  360
accgtctcct ca                                                   372

SEQ ID NO: 466          moltype = AA  length = 124
FEATURE                 Location/Qualifiers
REGION                  1..124
                        note = Synthetic
source                  1..124
                        mol_type = protein
                        organism = synthetic construct
SEQUENCE: 466
EVQLVESGGG LVQPGRSLRL SCAASGFTFD DYTMHWVRQA PGKGLEWVSD ISWNSGSIGY  60
ADSVKGRFTV SRDNAKNSLY LQMNSLRGED TALYYCAKDM SGYAHYGYYG MDVWGQGTTV  120
TVSS                                                            124

SEQ ID NO: 467          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 467
ggattcacct ttgatgatta tacc                                      24

SEQ ID NO: 468          moltype = AA  length = 8
FEATURE                 Location/Qualifiers
REGION                  1..8
                        note = Synthetic
source                  1..8
```

```
                        mol_type = protein
                        organism = synthetic construct
SEQUENCE: 468
GFTFDDYT                                                                    8

SEQ ID NO: 469          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 469
attagttgga atagtggtag cata                                                  24

SEQ ID NO: 470          moltype = AA  length = 8
FEATURE                 Location/Qualifiers
REGION                  1..8
                        note = Synthetic
source                  1..8
                        mol_type = protein
                        organism = synthetic construct
SEQUENCE: 470
ISWNSGSI                                                                    8

SEQ ID NO: 471          moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 471
gcaaaagata tgagtggcta cgcccactac ggctactacg gtatggacgt c                    51

SEQ ID NO: 472          moltype = AA  length = 17
FEATURE                 Location/Qualifiers
REGION                  1..17
                        note = Synthetic
source                  1..17
                        mol_type = protein
                        organism = synthetic construct
SEQUENCE: 472
AKDMSGYAHY GYYGMDV                                                          17

SEQ ID NO: 473          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 473
gacatccaga tgacccagtc tccatcctcc ctgtctgcat ctgtaggaga cagagtcacc  60
atcacttgcc gggcaagtca gagcattagg aactatttaa attggtatca gcagaaacca  120
gggaaagtcc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta accctccgat caccttcggc  300
caagggacac gactggagat taaa                                          324

SEQ ID NO: 474          moltype = AA  length = 108
FEATURE                 Location/Qualifiers
REGION                  1..108
                        note = Synthetic
source                  1..108
                        mol_type = protein
                        organism = synthetic construct
SEQUENCE: 474
DIQMTQSPSS LSASVGDRVT ITCRASQSIR NYLNWYQQKP GKVPKLLIYA ASSLQSGVPS  60
RFSGSGSGTD FTLTISSLQP EDFATYYCQQ SYSNPPITFG QGTRLEIK                108

SEQ ID NO: 475          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 475
```

```
cagagcatta ggaactat                                              18

SEQ ID NO: 476         moltype = AA  length = 6
FEATURE                Location/Qualifiers
REGION                 1..6
                       note = Synthetic
source                 1..6
                       mol_type = protein
                       organism = synthetic construct
SEQUENCE: 476
QSIRNY                                                           6

SEQ ID NO: 477         moltype =   length =
SEQUENCE: 477
000

SEQ ID NO: 478         moltype =   length =
SEQUENCE: 478
000

SEQ ID NO: 479         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 479
caacagagtt acagtaaccc tccgatcacc                                 30

SEQ ID NO: 480         moltype = AA  length = 10
FEATURE                Location/Qualifiers
REGION                 1..10
                       note = Synthetic
source                 1..10
                       mol_type = protein
                       organism = synthetic construct
SEQUENCE: 480
QQSYSNPPIT                                                       10

SEQ ID NO: 481         moltype = DNA  length = 369
FEATURE                Location/Qualifiers
misc_feature           1..369
                       note = Synthetic
source                 1..369
                       mol_type = other DNA
                       organism = synthetic construct
SEQUENCE: 481
gaagcgcagc tggtggaatc tgggggaggc ttggtacagc ctggcaggtc cctgagactc  60
tcctgtacaa cctctggatt cacctttgat gattatacca tgcactgggt ccggcaagct  120
ccagggaagg gcctggagtg gatctctgat attagttgga atggtggaac caaaggctat  180
gcggactctg tgaagggccg attcaccatc tccagagaca acgccaaaaa ctccctgtat  240
ctgcaaatgg acagtctgag aggtgaggac acggccttat attactgtgt aaaagataaa  300
agtggctacg ggcacttcta cttcggtttg gacgtctggg gccaagggac cacggtcacc  360
gtctcctca                                                        369

SEQ ID NO: 482         moltype = AA  length = 123
FEATURE                Location/Qualifiers
REGION                 1..123
                       note = Synthetic
source                 1..123
                       mol_type = protein
                       organism = synthetic construct
SEQUENCE: 482
EAQLVESGGG LVQPGRSLRL SCTTSGFTFD DYTMHWVRQA PGKGLEWISD ISWNGGTKGY  60
ADSVKGRFTI SRDNAKNSLY LQMDSLRGED TALYYCVKDK SGYGHFYFGL DVWGQGTTVT  120
VSS                                                              123

SEQ ID NO: 483         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 483
ggattcacct ttgatgatta tacc                                       24

SEQ ID NO: 484         moltype = AA  length = 8
```

```
FEATURE                Location/Qualifiers
REGION                 1..8
                       note = Synthetic
source                 1..8
                       mol_type = protein
                       organism = synthetic construct
SEQUENCE: 484
GFTFDDYT                                                             8

SEQ ID NO: 485         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 485
attagttgga atggtggaac caaa                                           24

SEQ ID NO: 486         moltype = AA  length = 8
FEATURE                Location/Qualifiers
REGION                 1..8
                       note = Synthetic
source                 1..8
                       mol_type = protein
                       organism = synthetic construct
SEQUENCE: 486
ISWNGGTK                                                             8

SEQ ID NO: 487         moltype = DNA  length = 48
FEATURE                Location/Qualifiers
misc_feature           1..48
                       note = Synthetic
source                 1..48
                       mol_type = other DNA
                       organism = synthetic construct
SEQUENCE: 487
gtaaaagata aaagtggcta cgggcacttc tacttcggtt tggacgtc                 48

SEQ ID NO: 488         moltype = AA  length = 16
FEATURE                Location/Qualifiers
REGION                 1..16
                       note = Synthetic
source                 1..16
                       mol_type = protein
                       organism = synthetic construct
SEQUENCE: 488
VKDKSGYGHF YFGLDV                                                    16

SEQ ID NO: 489         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 489
gacatccaga tgacccagtc tccatcctcc ctgactgcgt ctgtaggaga cagagtcacc  60
ttcacttgcc gggcaagtca gagcattagc aggcatttaa gttggtatca gcagaaacca  120
gggaaagccc ctaagctcct gatctatgct gcatccagtt tggaaagtgg ggtcccttca  180
aggttcagtg gcagtggatc tgggacagat ttcactctca ccatcagcag tctgcaccct  240
gaagattttg caacttacta ctgtcaacag agctacagta accctccgat caccttcggc  300
caagggacac gactggagat taaa                                           324

SEQ ID NO: 490         moltype = AA  length = 108
FEATURE                Location/Qualifiers
REGION                 1..108
                       note = Synthetic
source                 1..108
                       mol_type = protein
                       organism = synthetic construct
SEQUENCE: 490
DIQMTQSPSS LTASVGDRVT FTCRASQSIS RHLSWYQQKP GKAPKLLIYA ASSLESGVPS  60
RFSGSGSGTD FTLTISSLHP EDFATYYCQQ SYSNPPITFG QGTRLEIK                 108

SEQ ID NO: 491         moltype = DNA  length = 18
FEATURE                Location/Qualifiers
misc_feature           1..18
                       note = Synthetic
```

```
source                  1..18
                        mol_type = other DNA
                        organism = synthetic construct
SEQUENCE: 491
cagagcatta gcaggcat                                             18

SEQ ID NO: 492          moltype = AA  length = 6
FEATURE                 Location/Qualifiers
REGION                  1..6
                        note = Synthetic
source                  1..6
                        mol_type = protein
                        organism = synthetic construct
SEQUENCE: 492
QSISRH                                                          6

SEQ ID NO: 493          moltype =   length =
SEQUENCE: 493
000

SEQ ID NO: 494          moltype =   length =
SEQUENCE: 494
000

SEQ ID NO: 495          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 495
caacagagct acagtaaccc tccgatcacc                                30

SEQ ID NO: 496          moltype = AA  length = 10
FEATURE                 Location/Qualifiers
REGION                  1..10
                        note = Synthetic
source                  1..10
                        mol_type = protein
                        organism = synthetic construct
SEQUENCE: 496
QQSYSNPPIT                                                      10

SEQ ID NO: 497          moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 497
gaagtgcagt tggtggagtc tgggggaggc ttggtacagc ctggcaggtc cctgagactc  60
tcctgtgcag cctctggatt caagtttgct gattatgcca tgcactgggt ccggcaagct  120
ccagggaagg gcctggagtg ggtctcagag attagttgga atagtggtag cataggttat  180
gtggactctg tgaagggccg attcaccatc tccagagaca acgccaagaa ctccctgtat  240
ctgcaaatga acagtctgag agctgaggac acggccttgt attactgtgt aaaagataaa  300
agtggctacg ggcactacta tatcggtatg gacgtctggg gccaagggac cacggtcatc  360
gtctcctcc                                                       369

SEQ ID NO: 498          moltype = AA  length = 123
FEATURE                 Location/Qualifiers
REGION                  1..123
                        note = Synthetic
source                  1..123
                        mol_type = protein
                        organism = synthetic construct
SEQUENCE: 498
EVQLVESGGG LVQPGRSLRL SCAASGFKFA DYAMHWVRQA PGKGLEWVSE ISWNSGSIGY  60
VDSVKGRFTI SRDNAKNSLY LQMNSLRAED TALYYCVKDK SGYGHYYIGM DVWGQGTTVI  120
VSS                                                             123

SEQ ID NO: 499          moltype = DNA  length = 24
FEATURE                 Location/Qualifiers
misc_feature            1..24
                        note = Synthetic
source                  1..24
                        mol_type = other DNA
                        organism = synthetic construct
```

```
SEQUENCE: 499
ggattcaagt ttgctgatta tgcc                                    24

SEQ ID NO: 500         moltype = AA  length = 8
FEATURE                Location/Qualifiers
REGION                 1..8
                       note = Synthetic
source                 1..8
                       mol_type = protein
                       organism = synthetic construct
SEQUENCE: 500
GFKFADYA                                                      8

SEQ ID NO: 501         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 501
attagttgga atagtggtag cata                                    24

SEQ ID NO: 502         moltype = AA  length = 8
FEATURE                Location/Qualifiers
REGION                 1..8
                       note = Synthetic
source                 1..8
                       mol_type = protein
                       organism = synthetic construct
SEQUENCE: 502
ISWNSGSI                                                      8

SEQ ID NO: 503         moltype = DNA  length = 48
FEATURE                Location/Qualifiers
misc_feature           1..48
                       note = Synthetic
source                 1..48
                       mol_type = other DNA
                       organism = synthetic construct
SEQUENCE: 503
gtaaaagata aaagtggcta cgggcactac tatatcggta tggacgtc          48

SEQ ID NO: 504         moltype = AA  length = 16
FEATURE                Location/Qualifiers
REGION                 1..16
                       note = Synthetic
source                 1..16
                       mol_type = protein
                       organism = synthetic construct
SEQUENCE: 504
VKDKSGYGHY YIGMDV                                             16

SEQ ID NO: 505         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 505
gacatccaga tgacccagtc tccatcctcc ctgtctgcat ctgtaggaga cagagtcacc  60
atcacttgcc gggcaagtca gagtattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                    324

SEQ ID NO: 506         moltype = AA  length = 108
FEATURE                Location/Qualifiers
REGION                 1..108
                       note = Synthetic
source                 1..108
                       mol_type = protein
                       organism = synthetic construct
SEQUENCE: 506
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK          108
```

```
SEQ ID NO: 507         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 507
cagagtatta gcagctat                                                18

SEQ ID NO: 508         moltype = AA  length = 6
FEATURE                Location/Qualifiers
REGION                 1..6
                       note = Synthetic
source                 1..6
                       mol_type = protein
                       organism = synthetic construct
SEQUENCE: 508
QSISSY                                                             6

SEQ ID NO: 509         moltype =   length =
SEQUENCE: 509
000

SEQ ID NO: 510         moltype =   length =
SEQUENCE: 510
000

SEQ ID NO: 511         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 511
caacagagtt acagtacccc tccgatcacc                                   30

SEQ ID NO: 512         moltype = AA  length = 10
FEATURE                Location/Qualifiers
REGION                 1..10
                       note = Synthetic
source                 1..10
                       mol_type = protein
                       organism = synthetic construct
SEQUENCE: 512
QQSYSTPPIT                                                         10

SEQ ID NO: 513         moltype = DNA  length = 372
FEATURE                Location/Qualifiers
misc_feature           1..372
                       note = Synthetic
source                 1..372
                       mol_type = other DNA
                       organism = synthetic construct
SEQUENCE: 513
gaagtgcacc tggtggagtc tgggggaggc ttggtacagc ctggcaggtc cctgagactc  60
tcctgtgcag cctctggatt cacctttgat gattatacca tgcactgggt ccggcaagct  120
ccagggaagg gcctggagtg ggtctccgat attagttgga atagtggtag cataggctat  180
gcggactctg tgaagggccg attcaccgtc tccagagaca acgccaagaa ctccctgtat  240
ctgcaaatga acagtctgag aggtgaggac acggccttgt attactgtgc aaaagatatg  300
agtggctacg gccactacgg caagtacggt atggacgtct ggggccaagg gaccacggtc  360
accgtctcct ca                                                      372

SEQ ID NO: 514         moltype = AA  length = 124
FEATURE                Location/Qualifiers
REGION                 1..124
                       note = Synthetic
source                 1..124
                       mol_type = protein
                       organism = synthetic construct
SEQUENCE: 514
EVHLVESGGG LVQPGRSLRL SCAASGFTFD DYTMHWVRQA PGKGLEWVSD ISWNSGSIGY  60
ADSVKGRFTV SRDNAKNSLY LQMNSLRGED TALYYCAKDM SGYGHYGKYG MDVWGQGTTV  120
TVSS                                                               124

SEQ ID NO: 515         moltype = DNA  length = 24
FEATURE                Location/Qualifiers
misc_feature           1..24
```

```
                        note = Synthetic
source                  1..24
                        mol_type = other DNA
                        organism = synthetic construct
SEQUENCE: 515
ggattcacct ttgatgatta tacc                                        24

SEQ ID NO: 516          moltype = AA  length = 8
FEATURE                 Location/Qualifiers
REGION                  1..8
                        note = Synthetic
source                  1..8
                        mol_type = protein
                        organism = synthetic construct
SEQUENCE: 516
GFTFDDYT                                                          8

SEQ ID NO: 517          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 517
attagttgga atagtggtag cata                                        24

SEQ ID NO: 518          moltype = AA  length = 8
FEATURE                 Location/Qualifiers
REGION                  1..8
                        note = Synthetic
source                  1..8
                        mol_type = protein
                        organism = synthetic construct
SEQUENCE: 518
ISWNSGSI                                                          8

SEQ ID NO: 519          moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 519
gcaaaagata tgagtggcta cggccactac ggcaagtacg gtatggacgt c          51

SEQ ID NO: 520          moltype = AA  length = 17
FEATURE                 Location/Qualifiers
REGION                  1..17
                        note = Synthetic
source                  1..17
                        mol_type = protein
                        organism = synthetic construct
SEQUENCE: 520
AKDMSGYGHY GKYGMDV                                                17

SEQ ID NO: 521          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 521
gacatccaga tgacccagtc tccatcctcc ctgtctgcat ctgtaggaga cagagtcacc  60
atcacttgcc gggcaagtca gagcattagg agctatttaa attggtatca gcagaaacca  120
gggaaagtcc ctaagctcct gatctatgct gcatccagtt tgcaaagtgg ggtcccatca  180
aggttcagtg gcagtggatc tgggacagat ttcactctca ccatcaacag tctgcaacct  240
gacgattttg caacttacta ctgtcaacag acttacagta accctccgat caccttcggc  300
caagggacac gactggagat taaa                                        324

SEQ ID NO: 522          moltype = AA  length = 108
FEATURE                 Location/Qualifiers
REGION                  1..108
                        note = Synthetic
source                  1..108
                        mol_type = protein
                        organism = synthetic construct
```

```
SEQUENCE: 522
DIQMTQSPSS LSASVGDRVT ITCRASQSIR SYLNWYQQKP GKVPKLLIYA ASSLQSGVPS  60
RFSGSGSGTD FTLTINSLQP DDFATYYCQQ TYSNPPITFG QGTRLEIK               108

SEQ ID NO: 523         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 523
cagagcatta ggagctat                                                18

SEQ ID NO: 524         moltype = AA  length = 6
FEATURE                Location/Qualifiers
REGION                 1..6
                       note = Synthetic
source                 1..6
                       mol_type = protein
                       organism = synthetic construct
SEQUENCE: 524
QSIRSY                                                             6

SEQ ID NO: 525         moltype =   length =
SEQUENCE: 525
000

SEQ ID NO: 526         moltype =   length =
SEQUENCE: 526
000

SEQ ID NO: 527         moltype = DNA  length = 30
FEATURE                Location/Qualifiers
misc_feature           1..30
                       note = Synthetic
source                 1..30
                       mol_type = other DNA
                       organism = synthetic construct
SEQUENCE: 527
caacagactt acagtaaccc tccgatcacc                                   30

SEQ ID NO: 528         moltype = AA  length = 10
FEATURE                Location/Qualifiers
REGION                 1..10
                       note = Synthetic
source                 1..10
                       mol_type = protein
                       organism = synthetic construct
SEQUENCE: 528
QQTYSNPPIT                                                         10

SEQ ID NO: 529         moltype = DNA  length = 372
FEATURE                Location/Qualifiers
misc_feature           1..372
                       note = Synthetic
source                 1..372
                       mol_type = other DNA
                       organism = synthetic construct
SEQUENCE: 529
gaggtgcagc tggtggagtc tgggggagac ttggtacagc ctggcaggtc cctgagactc  60
tcctgtgcag cctctggatt cacctttgat gattatacca tgcactgggt ccggcaagct  120
ccagggaagg gcctggagtg ggtctcaatt attagttgga atggtaatac cattgactat  180
gcggactctg tgaagggccg attcaccatc tccagagaca acgccaagaa ctccctgtat  240
cttcaaatga acagtctgag agctgaggac acggccttgt attactgtgc aaaagataag  300
agtggctacg gacacttcta ctattacgtt ttggacgtct ggggccaagg gaccacggtc  360
accgtctcct ca                                                      372

SEQ ID NO: 530         moltype = AA  length = 124
FEATURE                Location/Qualifiers
REGION                 1..124
                       note = Synthetic
source                 1..124
                       mol_type = protein
                       organism = synthetic construct
SEQUENCE: 530
EVQLVESGGD LVQPGRSLRL SCAASGFTFD DYTMHWVRQA PGKGLEWVSI ISWNGNTIDY  60
ADSVKGRFTI SRDNAKNSLY LQMNSLRAED TALYYCAKDK SGYGHFYYYV LDVWGQGTTV  120
TVSS                                                               124
```

```
SEQ ID NO: 531          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 531
ggattcacct ttgatgatta tacc                                        24

SEQ ID NO: 532          moltype = AA  length = 8
FEATURE                 Location/Qualifiers
REGION                  1..8
                        note = Synthetic
source                  1..8
                        mol_type = protein
                        organism = synthetic construct
SEQUENCE: 532
GFTFDDYT                                                          8

SEQ ID NO: 533          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 533
attagttgga atggtaatac catt                                        24

SEQ ID NO: 534          moltype = AA  length = 8
FEATURE                 Location/Qualifiers
REGION                  1..8
                        note = Synthetic
source                  1..8
                        mol_type = protein
                        organism = synthetic construct
SEQUENCE: 534
ISWNGNTI                                                          8

SEQ ID NO: 535          moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 535
gcaaaagata agagtggcta cggacacttc tactattacg ttttggacgt c          51

SEQ ID NO: 536          moltype = AA  length = 17
FEATURE                 Location/Qualifiers
REGION                  1..17
                        note = Synthetic
source                  1..17
                        mol_type = protein
                        organism = synthetic construct
SEQUENCE: 536
AKDKSGYGHF YYYVLDV                                                17

SEQ ID NO: 537          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 537
gacatccaga tgacccagtc tccatcctcc ctgtctgcat ctgtaggaga cagagtcacc  60
atcacttgcc gggcaagtca gagcattaac aactatttaa attggtatca gcagaaacca  120
gggaaagccc ctaaactcct gatctatgct gcttccagtt tgcaaagtgg ggtcccgtca  180
aggttcagtg gcagtggttc tgggacagat ttcactctca ccatcagcag tctgcaacct  240
gaagattttg caacttacta ctctcaacag agttacagtt tcccgtggac gttcggccaa  300
gggaccaagg tggaaatcaa a                                           321

SEQ ID NO: 538          moltype = AA  length = 107
FEATURE                 Location/Qualifiers
REGION                  1..107
```

```
                        note = Synthetic
source                  1..107
                        mol_type = protein
                        organism = synthetic construct
SEQUENCE: 538
DIQMTQSPSS LSASVGDRVT ITCRASQSIN NYLNWYQQKP GKAPKLLIYA ASSLQSGVPS  60
RFSGSGSGTD FTLTISSLQP EDFATYYSQQ SYSFPWTFGQ GTKVEIK               107

SEQ ID NO: 539          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 539
cagagcatta acaactat                                               18

SEQ ID NO: 540          moltype = AA  length = 6
FEATURE                 Location/Qualifiers
REGION                  1..6
                        note = Synthetic
source                  1..6
                        mol_type = protein
                        organism = synthetic construct
SEQUENCE: 540
QSINNY                                                            6

SEQ ID NO: 541          moltype =   length =
SEQUENCE: 541
000

SEQ ID NO: 542          moltype =   length =
SEQUENCE: 542
000

SEQ ID NO: 543          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 543
caacagagtt acagtttccc gtggacg                                     27

SEQ ID NO: 544          moltype = AA  length = 9
FEATURE                 Location/Qualifiers
REGION                  1..9
                        note = Synthetic
source                  1..9
                        mol_type = protein
                        organism = synthetic construct
SEQUENCE: 544
QQSYSFPWT                                                         9

SEQ ID NO: 545          moltype = DNA  length = 363
FEATURE                 Location/Qualifiers
misc_feature            1..363
                        note = Synthetic
source                  1..363
                        mol_type = other DNA
                        organism = synthetic construct
SEQUENCE: 545
caggtgcagc tggtggagtc gggggaggc gtggtccagc ctgggaggtc cctgagaccc  60
tcctgtgcag cgtctggatt tagtttcagg gactatggca tgcactgggt ccgccaggct  120
ccaggtaagg gactagagtg gatggcacac atatggtata atggaaagaa taaatattat  180
gcagactccg tgaagggccg attcaccatc tccagagaca attccaagaa cacgctatat  240
ctgcaaatga acagcctgag acccgaggac acggctgtat attattgtgc gagagatggt  300
gtatcagcac gtggtactcc atttgactac tggggccagg gaaccctggt caccgtctcc  360
tca                                                               363

SEQ ID NO: 546          moltype = AA  length = 121
FEATURE                 Location/Qualifiers
REGION                  1..121
                        note = Synthetic
source                  1..121
                        mol_type = protein
                        organism = synthetic construct
```

```
SEQUENCE: 546
QVQLVESGGG VVQPGRSLRP SCAASGFSFR DYGMHWVRQA PGKGLEWMAH IWYNGKNKYY  60
ADSVKGRFTI SRDNSKNTLY LQMNSLRPED TAVYYCARDG VSARGTPFDY WGQGTLVTVS  120
S                                                                  121

SEQ ID NO: 547          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 547
ggatttagtt tcagggacta tggc                                        24

SEQ ID NO: 548          moltype = AA  length = 8
FEATURE                 Location/Qualifiers
REGION                  1..8
                        note = Synthetic
source                  1..8
                        mol_type = protein
                        organism = synthetic construct
SEQUENCE: 548
GFSFRDYG                                                          8

SEQ ID NO: 549          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 549
atatggtata atggaaagaa taaa                                        24

SEQ ID NO: 550          moltype = AA  length = 8
FEATURE                 Location/Qualifiers
REGION                  1..8
                        note = Synthetic
source                  1..8
                        mol_type = protein
                        organism = synthetic construct
SEQUENCE: 550
IWYNGKNK                                                          8

SEQ ID NO: 551          moltype = DNA  length = 42
FEATURE                 Location/Qualifiers
misc_feature            1..42
                        note = Synthetic
source                  1..42
                        mol_type = other DNA
                        organism = synthetic construct
SEQUENCE: 551
gcgagagatg gtgtatcagc acgtggtact ccatttgact ac                    42

SEQ ID NO: 552          moltype = AA  length = 14
FEATURE                 Location/Qualifiers
REGION                  1..14
                        note = Synthetic
source                  1..14
                        mol_type = protein
                        organism = synthetic construct
SEQUENCE: 552
ARDGVSARGT PFDY                                                   14

SEQ ID NO: 553          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 553
gaaacgacac tcacgcagtc tccagcattc atgtcagcgg ctccaggaga caaagtcagc  60
atctcctgca ttgccagcca gtacattgat gatgatgtga actggtacca acagaaacca  120
ggagaaactg ctattttcat tattcaagaa gcttctactc tcgttcctgg aatctcacct  180
cgattcagtg gcagcgggta tggaacacat tttaccctca caattaataa catagattct  240
gaggatgctg cattttactt ctgtctccaa catgataatt tcccgtacac ttttggccag  300
gggaccaagc tggagatcaa a                                            321
```

```
SEQ ID NO: 554          moltype = AA  length = 107
FEATURE                 Location/Qualifiers
REGION                  1..107
                        note = Synthetic
source                  1..107
                        mol_type = protein
                        organism = synthetic construct
SEQUENCE: 554
ETTLTQSPAF MSAAPGDKVS ISCIASQYID DDVNWYQQKP GETAIFIIQE ASTLVPGISP  60
RFSGSGYGTH FTLTINNIDS EDAAFYFCLQ HDNFPYTFGQ GTKLEIK                107

SEQ ID NO: 555          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 555
cagtacattg atgatgat                                                18

SEQ ID NO: 556          moltype = AA  length = 6
FEATURE                 Location/Qualifiers
REGION                  1..6
                        note = Synthetic
source                  1..6
                        mol_type = protein
                        organism = synthetic construct
SEQUENCE: 556
QYIDDD                                                             6

SEQ ID NO: 557          moltype =   length =
SEQUENCE: 557
000

SEQ ID NO: 558          moltype =   length =
SEQUENCE: 558
000

SEQ ID NO: 559          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 559
ctccaacatg ataatttccc gtacact                                      27

SEQ ID NO: 560          moltype = AA  length = 9
FEATURE                 Location/Qualifiers
REGION                  1..9
                        note = Synthetic
source                  1..9
                        mol_type = protein
                        organism = synthetic construct
SEQUENCE: 560
LQHDNFPYT                                                          9

SEQ ID NO: 561          moltype = DNA  length = 384
FEATURE                 Location/Qualifiers
misc_feature            1..384
                        note = Synthetic
source                  1..384
                        mol_type = other DNA
                        organism = synthetic construct
SEQUENCE: 561
caggtgcagc tggtggagtc tgggggaggc ttggtacagc ctgggggggtc cctgagactc  60
tcctgtgcag cctcttattt cacctttagc agttttgcca tgaactgggt ccgccaggct  120
ccagggcagg gcctggagtg ggtctcagct attagtggta gggtctcagc tattagtggt  180
agtggtggta tcacatacta cgcagactcc gtgaagggcc ggttcatcat ctccagagac  240
aattccaaga acacgctgta tctgcaaatg agcggcctga gagccgagga cacggccgta  300
tattactgtg cgaaaggccc ctatttgact acagtcaccc cctttgacta ctggggccag  360
ggaaccctgg tcaccgtctc ctca                                         384

SEQ ID NO: 562          moltype = AA  length = 128
FEATURE                 Location/Qualifiers
REGION                  1..128
```

```
                        note = Synthetic
source                  1..128
                        mol_type = protein
                        organism = synthetic construct
SEQUENCE: 562
QVQLVESGGG LVQPGGSLRL SCAASYFTFS SFAMNWVRQA PGQGLEWVSA ISGRVSAISG  60
SGGITYYADS VKGRFIISRD NSKNTLYLQM SGLRAEDTAV YYCAKGPYLT TVTPFDYWGQ  120
GTLVTVSS                                                           128

SEQ ID NO: 563          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 563
tatttcacct ttagcagttt tgcc                                         24

SEQ ID NO: 564          moltype = AA  length = 8
FEATURE                 Location/Qualifiers
REGION                  1..8
                        note = Synthetic
source                  1..8
                        mol_type = protein
                        organism = synthetic construct
SEQUENCE: 564
YFTFSSFA                                                           8

SEQ ID NO: 565          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 565
attagtggta gtggtggtat caca                                         24

SEQ ID NO: 566          moltype = AA  length = 8
FEATURE                 Location/Qualifiers
REGION                  1..8
                        note = Synthetic
source                  1..8
                        mol_type = protein
                        organism = synthetic construct
SEQUENCE: 566
ISGSGGIT                                                           8

SEQ ID NO: 567          moltype = DNA  length = 42
FEATURE                 Location/Qualifiers
misc_feature            1..42
                        note = Synthetic
source                  1..42
                        mol_type = other DNA
                        organism = synthetic construct
SEQUENCE: 567
gcgaaaggcc cctatttgac tacagtcacc ccctttgact ac                     42

SEQ ID NO: 568          moltype = AA  length = 14
FEATURE                 Location/Qualifiers
REGION                  1..14
                        note = Synthetic
source                  1..14
                        mol_type = protein
                        organism = synthetic construct
SEQUENCE: 568
AKGPYLTTVT PFDY                                                    14

SEQ ID NO: 569          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 569
gacatccagt tgacccagtc tccatcttcc gtgtctgcat ctgtcggaga cagagtcacc  60
atcacttgtc gggcgagtca ggggattagc agctggttag cctggtatca gcagaaacca  120
```

```
gggaaagccc ctaaactcct gatctatgct gtatccagtt tgcaaaatgg ggtcccatca  180
aggttcagcg gcagtggatc tgggacagat ttcaccctca ccatcagcag cctgcagcct  240
gaagactttg caacttacta ttgtcaacag gctaacagtt tcccattcac tttcggccct  300
gggaccaagc tggagatcaa acga                                          324

SEQ ID NO: 570         moltype = AA  length = 108
FEATURE                Location/Qualifiers
REGION                 1..108
                       note = Synthetic
source                 1..108
                       mol_type = protein
                       organism = synthetic construct
SEQUENCE: 570
DIQLTQSPSS VSASVGDRVT ITCRASQGIS SWLAWYQQKP GKAPKLLIYA VSSLQNGVPS  60
RFSGSGSGTD FTLTISSLQP EDFATYYCQQ ANSFPFTFGP GTKLEIKR                108

SEQ ID NO: 571         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 571
caggggatta gcagctgg                                                 18

SEQ ID NO: 572         moltype = AA  length = 6
FEATURE                Location/Qualifiers
REGION                 1..6
                       note = Synthetic
source                 1..6
                       mol_type = protein
                       organism = synthetic construct
SEQUENCE: 572
QGISSW                                                              6

SEQ ID NO: 573         moltype =   length =
SEQUENCE: 573
000

SEQ ID NO: 574         moltype =   length =
SEQUENCE: 574
000

SEQ ID NO: 575         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 575
caacaggcta acagtttccc attcact                                       27

SEQ ID NO: 576         moltype = AA  length = 9
FEATURE                Location/Qualifiers
REGION                 1..9
                       note = Synthetic
source                 1..9
                       mol_type = protein
                       organism = synthetic construct
SEQUENCE: 576
QQANSFPFT                                                           9

SEQ ID NO: 577         moltype = DNA  length = 369
FEATURE                Location/Qualifiers
misc_feature           1..369
                       note = Synthetic
source                 1..369
                       mol_type = other DNA
                       organism = synthetic construct
SEQUENCE: 577
gaggtgcagc tggtggagtc tgggggaggc ttggtacagc ctggcaggtc cctgagactc  60
tcctgtgcag cctctggatt cacctttgct gattatgcca tgcactgggt ccggcaagct  120
ccagggaagg gcctggagtg ggtctcaggt attagttgga atagtggtag tataggttat  180
gcggactctg tgaagggccg attcaccatc tccagagaca acgccaagaa ctccctgtat  240
ctgcaaatga acagtctgag agctgaggac acggccttat attactgtgt aaaagataat  300
agtggctacg catcctacta ctacggtatg gacgtctggg gccaagggac cacggtcacc  360
gtctcctca                                                           369
```

```
SEQ ID NO: 578         moltype = AA  length = 123
FEATURE                Location/Qualifiers
REGION                 1..123
                       note = Synthetic
source                 1..123
                       mol_type = protein
                       organism = synthetic construct
SEQUENCE: 578
EVQLVESGGG LVQPGRSLRL SCAASGFTFA DYAMHWVRQA PGKGLEWVSG ISWNSGSIGY  60
ADSVKGRFTI SRDNAKNSLY LQMNSLRAED TALYYCVKDN SGYASYYYGM DVWGQGTTVT  120
VSS                                                               123

SEQ ID NO: 579         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 579
ggattcacct ttgctgatta tgcc                                        24

SEQ ID NO: 580         moltype = AA  length = 8
FEATURE                Location/Qualifiers
REGION                 1..8
                       note = Synthetic
source                 1..8
                       mol_type = protein
                       organism = synthetic construct
SEQUENCE: 580
GFTFADYA                                                          8

SEQ ID NO: 581         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 581
attagttgga atagtggtag tata                                        24

SEQ ID NO: 582         moltype = AA  length = 8
FEATURE                Location/Qualifiers
REGION                 1..8
                       note = Synthetic
source                 1..8
                       mol_type = protein
                       organism = synthetic construct
SEQUENCE: 582
ISWNSGSI                                                          8

SEQ ID NO: 583         moltype = DNA  length = 48
FEATURE                Location/Qualifiers
misc_feature           1..48
                       note = Synthetic
source                 1..48
                       mol_type = other DNA
                       organism = synthetic construct
SEQUENCE: 583
gtaaaagata atagtggcta cgcatcctac tactacggta tggacgtc              48

SEQ ID NO: 584         moltype = AA  length = 16
FEATURE                Location/Qualifiers
REGION                 1..16
                       note = Synthetic
source                 1..16
                       mol_type = protein
                       organism = synthetic construct
SEQUENCE: 584
VKDNSGYASY YYGMDV                                                 16

SEQ ID NO: 585         moltype = DNA  length = 324
FEATURE                Location/Qualifiers
misc_feature           1..324
                       note = Synthetic
source                 1..324
                       mol_type = other DNA
```

```
                         organism = synthetic construct
SEQUENCE: 585
gacatccagt tgacccagtc cccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctacgat gcatccaatt tggaaacagg ggtcccatca  180
aggttcagtg gaagtggatc tgggacagat tttactttca ccatcagcag cctgcagcct  240
gaagatattg caacatatta ctgtcaacag tatgataatc tcccattcac tttcggccct  300
gggaccaaag tggatatcaa acga                                          324

SEQ ID NO: 586           moltype = AA  length = 108
FEATURE                  Location/Qualifiers
REGION                   1..108
                         note = Synthetic
source                   1..108
                         mol_type = protein
                         organism = synthetic construct
SEQUENCE: 586
DIQLTQSPSS LSASVGDRVT ITCRASQSIS SYLNWYQQKP GKAPKLLIYD ASNLETGVPS  60
RFSGSGSGTD FTFTISSLQP EDIATYYCQQ YDNLPFTFGP GTKVDIKR              108

SEQ ID NO: 587           moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 587
cagagcatta gcagctat                                                 18

SEQ ID NO: 588           moltype = AA  length = 6
FEATURE                  Location/Qualifiers
REGION                   1..6
                         note = Synthetic
source                   1..6
                         mol_type = protein
                         organism = synthetic construct
SEQUENCE: 588
QSISSY                                                              6

SEQ ID NO: 589           moltype =   length =
SEQUENCE: 589
000

SEQ ID NO: 590           moltype =   length =
SEQUENCE: 590
000

SEQ ID NO: 591           moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 591
caacagtatg ataatctccc attcact                                       27

SEQ ID NO: 592           moltype = AA  length = 9
FEATURE                  Location/Qualifiers
REGION                   1..9
                         note = Synthetic
source                   1..9
                         mol_type = protein
                         organism = synthetic construct
SEQUENCE: 592
QQYDNLPFT                                                           9

SEQ ID NO: 593           moltype = DNA  length = 378
FEATURE                  Location/Qualifiers
misc_feature             1..378
                         note = Synthetic
source                   1..378
                         mol_type = other DNA
                         organism = synthetic construct
SEQUENCE: 593
gaggtgcagc tggtggagtc tgggggaggc gtggtccagc ctgggaggtc cctgagactc  60
tcctgtgcag cctctggatt caccttcagt aactatggca tgcactgggt ccgccaggct  120
ccaggcaaag ggctggagtg ggtgacagtt atattacatg atggaagtta taaatactat  180
```

```
gcagactccg tgaagggccg attcaccatc tccagagaca attccaagaa cacgctacat  240
ctgcaaatga acagcctgag aactgaggac acggctgtat attactgtgc gaaagggcct  300
atgtttcggg gagtccctta caaccactac tatggtatgg acgtctgggg ccaagggacc  360
acggtcaccg tctcctca                                                 378

SEQ ID NO: 594          moltype = AA  length = 126
FEATURE                 Location/Qualifiers
REGION                  1..126
                        note = Synthetic
source                  1..126
                        mol_type = protein
                        organism = synthetic construct
SEQUENCE: 594
EVQLVESGGG VVQPGRSLRL SCAASGFTFS NYGMHWVRQA PGKGLEWVTV ILHDGSYKYY  60
ADSVKGRFTI SRDNSKNTLH LQMNSLRTED TAVYYCAKGP MFRGVPYNHY YGMDVWGQGT  120
TVTVSS                                                              126

SEQ ID NO: 595          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 595
ggattcacct tcagtaacta tggc                                          24

SEQ ID NO: 596          moltype = AA  length = 8
FEATURE                 Location/Qualifiers
REGION                  1..8
                        note = Synthetic
source                  1..8
                        mol_type = protein
                        organism = synthetic construct
SEQUENCE: 596
GFTFSNYG                                                            8

SEQ ID NO: 597          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 597
atattacatg atggaagtta taaa                                          24

SEQ ID NO: 598          moltype = AA  length = 8
FEATURE                 Location/Qualifiers
REGION                  1..8
                        note = Synthetic
source                  1..8
                        mol_type = protein
                        organism = synthetic construct
SEQUENCE: 598
ILHDGSYK                                                            8

SEQ ID NO: 599          moltype = DNA  length = 57
FEATURE                 Location/Qualifiers
misc_feature            1..57
                        note = Synthetic
source                  1..57
                        mol_type = other DNA
                        organism = synthetic construct
SEQUENCE: 599
gcgaaagggc ctatgtttcg gggagtccct tacaaccact actatggtat ggacgtc     57

SEQ ID NO: 600          moltype = AA  length = 19
FEATURE                 Location/Qualifiers
REGION                  1..19
                        note = Synthetic
source                  1..19
                        mol_type = protein
                        organism = synthetic construct
SEQUENCE: 600
AKGPMFRGVP YNHYYGMDV                                                19

SEQ ID NO: 601          moltype = DNA  length = 324
FEATURE                 Location/Qualifiers
```

```
misc_feature            1..324
                        note = Synthetic
source                  1..324
                        mol_type = other DNA
                        organism = synthetic construct
SEQUENCE: 601
gacatccaga tgacccagtc tccatcctcc ctgtctgcat ctgtaggaga cagagtcacc  60
atcacttgcc gggcaagtca gggcatcaga aatgatttag gctggtatca gcagaaacca  120
gggaaagccc ctaagcgcct gatctatgct gcatccagtt tgcaaagtgg ggtctcatca  180
aggttcagcg gcagtggatc tgggacagaa ttcactctca caatcagcag cctgcagcct  240
gaagattttg caacttatta ctgtctacag cataatagtt acccgtacac ttttggccag  300
gggaccaagg tggaaatcaa acga                                          324

SEQ ID NO: 602          moltype = AA  length = 108
FEATURE                 Location/Qualifiers
REGION                  1..108
                        note = Synthetic
source                  1..108
                        mol_type = protein
                        organism = synthetic construct
SEQUENCE: 602
DIQMTQSPSS LSASVGDRVT ITCRASQGIR NDLGWYQQKP GKAPKRLIYA ASSLQSGVSS  60
RFSGSGSGTE FTLTISSLQP EDFATYYCLQ HNSYPYTFGQ GTKVEIKR                108

SEQ ID NO: 603          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 603
cagggcatca gaaatgat                                                 18

SEQ ID NO: 604          moltype = AA  length = 6
FEATURE                 Location/Qualifiers
REGION                  1..6
                        note = Synthetic
source                  1..6
                        mol_type = protein
                        organism = synthetic construct
SEQUENCE: 604
QGIRND                                                              6

SEQ ID NO: 605          moltype =   length =
SEQUENCE: 605
000

SEQ ID NO: 606          moltype =   length =
SEQUENCE: 606
000

SEQ ID NO: 607          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 607
ctacagcata atagttaccc gtacact                                       27

SEQ ID NO: 608          moltype = AA  length = 9
FEATURE                 Location/Qualifiers
REGION                  1..9
                        note = Synthetic
source                  1..9
                        mol_type = protein
                        organism = synthetic construct
SEQUENCE: 608
LQHNSYPYT                                                           9

SEQ ID NO: 609          moltype = DNA  length = 357
FEATURE                 Location/Qualifiers
misc_feature            1..357
                        note = Synthetic
source                  1..357
                        mol_type = other DNA
                        organism = synthetic construct
```

```
SEQUENCE: 609
gaggtgcagc tggtggagtc tgggggaggc gtggtccagc ctgggaggtc cctgagactc  60
tcctgtacag cgtcaggttt ccccttcagt cgctatggca tgcactgggt ccgccaggct  120
ccaggcaagg ggctggaatg ggtgacattt atatggtatg atggaagtaa taaatactat  180
gcagactccg cgaagggccg attcaccatc accagagaca attccaagaa cacggtgtat  240
ctgcaaatgg acagcctgag agccgatgac acggctgttt attattgtgt gagagatcag  300
gcagctctct actattttga ctcttggggc cagggaaccc tggtcaccgt ctcctca     357

SEQ ID NO: 610          moltype = AA  length = 119
FEATURE                 Location/Qualifiers
REGION                  1..119
                        note = Synthetic
source                  1..119
                        mol_type = protein
                        organism = synthetic construct
SEQUENCE: 610
EVQLVESGGG VVQPGRSLRL SCTASGFPFS RYGMHWVRQA PGKGLEWVTF IWYDGSNKYY  60
ADSAKGRFTI TRDNSKNTVY LQMDSLRADD TAVYYCVRDQ AALYYFDSWG QGTLVTVSS   119

SEQ ID NO: 611          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 611
ggtttcccct tcagtcgcta tggc                                          24

SEQ ID NO: 612          moltype = AA  length = 8
FEATURE                 Location/Qualifiers
REGION                  1..8
                        note = Synthetic
source                  1..8
                        mol_type = protein
                        organism = synthetic construct
SEQUENCE: 612
GFPFSRYG                                                            8

SEQ ID NO: 613          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 613
atatggtatg atggaagtaa taaa                                          24

SEQ ID NO: 614          moltype = AA  length = 8
FEATURE                 Location/Qualifiers
REGION                  1..8
                        note = Synthetic
source                  1..8
                        mol_type = protein
                        organism = synthetic construct
SEQUENCE: 614
IWYDGSNK                                                            8

SEQ ID NO: 615          moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 615
gtgagagatc aggcagctct ctactatttt gactct                             36

SEQ ID NO: 616          moltype = AA  length = 12
FEATURE                 Location/Qualifiers
REGION                  1..12
                        note = Synthetic
source                  1..12
                        mol_type = protein
                        organism = synthetic construct
SEQUENCE: 616
VRDQAALYYF DS                                                       12
```

-continued

```
SEQ ID NO: 617         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 617
gacatccaga tgacccagtc tccatcttcc gtgtctgcat ctgtaggaga cagagtcacc  60
atcacttgtc gggcgagtca gggtattagc aggtggttag cctggtatca gcagaaacca  120
gggaaagccc ctaagctcct gatctctgct gcatccagtt tgcaaagtgg agtcccatca  180
aggttcagcg gcagtggatc tgggacagat ttcactctca ccatcagcgg cctgcagcct  240
gaagattttg caacttacta ttgtcaaaag gctaacagtt tccctttcac tttcggccct  300
gggaccaagc tggagatcaa acga                                        324

SEQ ID NO: 618         moltype = AA  length = 108
FEATURE                Location/Qualifiers
REGION                 1..108
                       note = Synthetic
source                 1..108
                       mol_type = protein
                       organism = synthetic construct
SEQUENCE: 618
DIQMTQSPSS VSASVGDRVT ITCRASQGIS RWLAWYQQKP GKAPKLLISA ASSLQSGVPS  60
RFSGSGSGTD FTLTISGLQP EDFATYYCQK ANSFPFTFGP GTKLEIKR              108

SEQ ID NO: 619         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 619
cagggtatta gcaggtgg                                                18

SEQ ID NO: 620         moltype = AA  length = 6
FEATURE                Location/Qualifiers
REGION                 1..6
                       note = Synthetic
source                 1..6
                       mol_type = protein
                       organism = synthetic construct
SEQUENCE: 620
QGISRW                                                             6

SEQ ID NO: 621         moltype =   length =
SEQUENCE: 621
000

SEQ ID NO: 622         moltype =   length =
SEQUENCE: 622
000

SEQ ID NO: 623         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 623
caaaaggcta acagtttccc tttcact                                     27

SEQ ID NO: 624         moltype = AA  length = 9
FEATURE                Location/Qualifiers
REGION                 1..9
                       note = Synthetic
source                 1..9
                       mol_type = protein
                       organism = synthetic construct
SEQUENCE: 624
QKANSFPFT                                                          9

SEQ ID NO: 625         moltype = DNA  length = 378
FEATURE                Location/Qualifiers
misc_feature           1..378
                       note = Synthetic
source                 1..378
```

```
                        mol_type = other DNA
                        organism = synthetic construct
SEQUENCE: 625
gaggtgcagc tggtggagtc tgggggaggc gtggtccagc ctgggaggtc cctgagactc  60
tcctgtgcag cctctggatt caccttcagt agttatggca tgcactgggt ccgccaggct  120
ccaggcaagg ggctggagtg ggtgacagtt atattacatg atggaagtaa tagatactct  180
gcagactccg tgaagggccg attcaccatc tccagagaca attccaagaa cacgctttat  240
ctgcaaatga acatcctgag agttgaggac acggctgtgt attactgtac gaaaggggct  300
atggttcggg gagtccctta caatcactac tacggcatgg acgtctgggg ccaagggacc  360
acggtcaccg tctcctca                                                 378

SEQ ID NO: 626          moltype = AA  length = 126
FEATURE                 Location/Qualifiers
REGION                  1..126
                        note = Synthetic
source                  1..126
                        mol_type = protein
                        organism = synthetic construct
SEQUENCE: 626
EVQLVESGGG VVQPGRSLRL SCAASGFTFS SYGMHWVRQA PGKGLEWVTV ILHDGSNRYS  60
ADSVKGRFTI SRDNSKNTLY LQMNILRVED TAVYYCTKGA MVRGVPYNHY YGMDVWGQGT  120
TVTVSS                                                              126

SEQ ID NO: 627          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 627
ggattcacct tcagtagtta tggc                                          24

SEQ ID NO: 628          moltype = AA  length = 8
FEATURE                 Location/Qualifiers
REGION                  1..8
                        note = Synthetic
source                  1..8
                        mol_type = protein
                        organism = synthetic construct
SEQUENCE: 628
GFTFSSYG                                                            8

SEQ ID NO: 629          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 629
atattacatg atggaagtaa taga                                          24

SEQ ID NO: 630          moltype = AA  length = 8
FEATURE                 Location/Qualifiers
REGION                  1..8
                        note = Synthetic
source                  1..8
                        mol_type = protein
                        organism = synthetic construct
SEQUENCE: 630
ILHDGSNR                                                            8

SEQ ID NO: 631          moltype = DNA  length = 57
FEATURE                 Location/Qualifiers
misc_feature            1..57
                        note = Synthetic
source                  1..57
                        mol_type = other DNA
                        organism = synthetic construct
SEQUENCE: 631
acgaaagggg ctatggttcg gggagtccct tacaatcact actacggcat ggacgtc      57

SEQ ID NO: 632          moltype = AA  length = 19
FEATURE                 Location/Qualifiers
REGION                  1..19
                        note = Synthetic
source                  1..19
                        mol_type = protein
```

-continued

```
                      organism = synthetic construct
SEQUENCE: 632
TKGAMVRGVP YNHYYGMDV                                              19

SEQ ID NO: 633        moltype = DNA  length = 324
FEATURE               Location/Qualifiers
misc_feature          1..324
                      note = Synthetic
source                1..324
                      mol_type = other DNA
                      organism = synthetic construct
SEQUENCE: 633
gacatccaga tgacccagtc tccatcctcc ctgtctgcat ctgtaggaga cagagtcacc  60
atcacttgcc gggcaagtca gggcattaga aatgatttag gctggtatca gcagaaacca  120
gggaaagccc ctaagcgcct aatctatgct gcatccattt tgcaaagtgg ggtcccatca  180
aggttcagcg gcagtggatc tgggacagaa ttcactctca caatcagcag cctgcagcct  240
gaagattttg caacttatta ctgtctacag cataatagtt acccgtacac ttttggccag  300
gggaccaagc tggagatcaa acga                                        324

SEQ ID NO: 634        moltype = AA  length = 108
FEATURE               Location/Qualifiers
REGION                1..108
                      note = Synthetic
source                1..108
                      mol_type = protein
                      organism = synthetic construct
SEQUENCE: 634
DIQMTQSPSS LSASVGDRVT ITCRASQGIR NDLGWYQQKP GKAPKRLIYA ASILQSGVPS  60
RFSGSGSGTE FTLTISSLQP EDFATYYCLQ HNSYPYTFGQ GTKLEIKR              108

SEQ ID NO: 635        moltype = DNA  length = 18
FEATURE               Location/Qualifiers
misc_feature          1..18
                      note = Synthetic
source                1..18
                      mol_type = other DNA
                      organism = synthetic construct
SEQUENCE: 635
cagggcatta gaaatgat                                               18

SEQ ID NO: 636        moltype = AA  length = 6
FEATURE               Location/Qualifiers
REGION                1..6
                      note = Synthetic
source                1..6
                      mol_type = protein
                      organism = synthetic construct
SEQUENCE: 636
QGIRND                                                            6

SEQ ID NO: 637        moltype =   length =
SEQUENCE: 637
000

SEQ ID NO: 638        moltype =   length =
SEQUENCE: 638
000

SEQ ID NO: 639        moltype = DNA  length = 27
FEATURE               Location/Qualifiers
misc_feature          1..27
                      note = Synthetic
source                1..27
                      mol_type = other DNA
                      organism = synthetic construct
SEQUENCE: 639
ctacagcata atagttaccc gtacact                                     27

SEQ ID NO: 640        moltype = AA  length = 9
FEATURE               Location/Qualifiers
REGION                1..9
                      note = Synthetic
source                1..9
                      mol_type = protein
                      organism = synthetic construct
SEQUENCE: 640
LQHNSYPYT                                                         9

SEQ ID NO: 641        moltype = DNA  length = 378
```

```
FEATURE                 Location/Qualifiers
misc_feature            1..378
                        note = Synthetic
source                  1..378
                        mol_type = other DNA
                        organism = synthetic construct
SEQUENCE: 641
gaggtgcagc tggtggagtc tgggggaggc gtggtccagc ctgggaggtc cctgagactc  60
tcctgtgcag cctctggatt caccttcagt agctatggca tgcactgggt ccgccaggct  120
ccaggcaagg ggctggagtg ggtgacagtt atattacatg atggaagtaa tagatactat  180
gcagactccg tgaagggccg attcaccatc tccagagaca attccaagaa cacgctttat  240
ctgcaaatga acatcctgag agctgaggac acggctgtgt attactgtac gaaaggggct  300
atggttcggg gagtccctta caatcactac tacggcatgg acgtctgggg ccaagggacc  360
acggtcaccg tctcctca                                                 378

SEQ ID NO: 642          moltype = AA  length = 126
FEATURE                 Location/Qualifiers
REGION                  1..126
                        note = Synthetic
source                  1..126
                        mol_type = protein
                        organism = synthetic construct
SEQUENCE: 642
EVQLVESGGG VVQPGRSLRL SCAASGFTFS SYGMHWVRQA PGKGLEWVTV ILHDGSNRYY  60
ADSVKGRFTI SRDNSKNTLY LQMNILRAED TAVYYCTKGA MVRGVPYNHY YGMDVWGQGT  120
TVTVSS                                                              126

SEQ ID NO: 643          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 643
ggattcacct tcagtagcta tggc                                          24

SEQ ID NO: 644          moltype = AA  length = 8
FEATURE                 Location/Qualifiers
REGION                  1..8
                        note = Synthetic
source                  1..8
                        mol_type = protein
                        organism = synthetic construct
SEQUENCE: 644
GFTFSSYG                                                            8

SEQ ID NO: 645          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 645
atattacatg atggaagtaa taga                                          24

SEQ ID NO: 646          moltype = AA  length = 8
FEATURE                 Location/Qualifiers
REGION                  1..8
                        note = Synthetic
source                  1..8
                        mol_type = protein
                        organism = synthetic construct
SEQUENCE: 646
ILHDGSNR                                                            8

SEQ ID NO: 647          moltype = DNA  length = 57
FEATURE                 Location/Qualifiers
misc_feature            1..57
                        note = Synthetic
source                  1..57
                        mol_type = other DNA
                        organism = synthetic construct
SEQUENCE: 647
acgaaagggg ctatggttcg gggagtccct tacaatcact actacggcat ggacgtc     57

SEQ ID NO: 648          moltype = AA  length = 19
FEATURE                 Location/Qualifiers
```

```
REGION                  1..19
                        note = Synthetic
source                  1..19
                        mol_type = protein
                        organism = synthetic construct
SEQUENCE: 648
TKGAMVRGVP YNHYYGMDV                                            19

SEQ ID NO: 649          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 649
gacatcgtga tgacccagtc tccatcctcc ctgtctgcat ctgtaggaga cagagtcacc  60
atcacttgcc gggcaagtca gggcattaga aatgatttag gctggtatca gcagaaacca  120
gggaaagccc ctaagcgcct gatctatgct gcatccaatt tgcaaagtgg ggtcccatca  180
aggttcagcg gcagtggatc tgggacagaa ttcactctca caatcagcag cctgcagcct  240
gaagattttg caacttatta ctgtctacag cataatagtt acccgtacac ttttggccag  300
gggaccaagc tggagatcaa acga                                      324

SEQ ID NO: 650          moltype = AA  length = 108
FEATURE                 Location/Qualifiers
REGION                  1..108
                        note = Synthetic
source                  1..108
                        mol_type = protein
                        organism = synthetic construct
SEQUENCE: 650
DIVMTQSPSS LSASVGDRVT ITCRASQGIR NDLGWYQQKP GKAPKRLIYA ASNLQSGVPS  60
RFSGSGSGTE FTLTISSLQP EDFATYYCLQ HNSYPYTFGQ GTKLEIKR            108

SEQ ID NO: 651          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 651
cagggcatta gaaatgat                                             18

SEQ ID NO: 652          moltype = AA  length = 6
FEATURE                 Location/Qualifiers
REGION                  1..6
                        note = Synthetic
source                  1..6
                        mol_type = protein
                        organism = synthetic construct
SEQUENCE: 652
QGIRND                                                          6

SEQ ID NO: 653          moltype =   length =
SEQUENCE: 653
000

SEQ ID NO: 654          moltype =   length =
SEQUENCE: 654
000

SEQ ID NO: 655          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 655
ctacagcata atagttaccc gtacact                                   27

SEQ ID NO: 656          moltype = AA  length = 9
FEATURE                 Location/Qualifiers
REGION                  1..9
                        note = Synthetic
source                  1..9
                        mol_type = protein
                        organism = synthetic construct
```

```
SEQUENCE: 656
LQHNSYPYT                                                        9

SEQ ID NO: 657         moltype = DNA  length = 378
FEATURE                Location/Qualifiers
misc_feature           1..378
                       note = Synthetic
source                 1..378
                       mol_type = other DNA
                       organism = synthetic construct
SEQUENCE: 657
caggtgcagc tggtggagtc tgggggaggc gtggtccagc ctgggaggtc cctgagactc  60
tcctgtgcag cctctggatt caccttcagt agctatggca tgcactgggt ccgccaggct  120
ccaggcaagg ggctggagtg ggtggcagtt atatcatatg atggaagtaa taaatactat  180
gcagactccg tgaagggccg attcaccatc tccagagact attccaagaa cacgctgtat  240
ctgcaaatga acagcctgag agctgaggac acggctgtgt tttactgtgc gaaaggggct  300
atggttcggg gagtccctta caactactac tacggtatgg acgtctgggg ccaagggacc  360
acggtcaccg tctcctca                                                378

SEQ ID NO: 658         moltype = AA  length = 126
FEATURE                Location/Qualifiers
REGION                 1..126
                       note = Synthetic
source                 1..126
                       mol_type = protein
                       organism = synthetic construct
SEQUENCE: 658
QVQLVESGGG VVQPGRSLRL SCAASGFTFS SYGMHWVRQA PGKGLEWVAV ISYDGSNKYY  60
ADSVKGRFTI SRDYSKNTLY LQMNSLRAED TAVFYCAKGA MVRGVPYNYY YGMDVWGQGT  120
TVTVSS                                                             126

SEQ ID NO: 659         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 659
ggattcacct tcagtagcta tggc                                        24

SEQ ID NO: 660         moltype = AA  length = 8
FEATURE                Location/Qualifiers
REGION                 1..8
                       note = Synthetic
source                 1..8
                       mol_type = protein
                       organism = synthetic construct
SEQUENCE: 660
GFTFSSYG                                                          8

SEQ ID NO: 661         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 661
atatcatatg atggaagtaa taaa                                        24

SEQ ID NO: 662         moltype = AA  length = 8
FEATURE                Location/Qualifiers
REGION                 1..8
                       note = Synthetic
source                 1..8
                       mol_type = protein
                       organism = synthetic construct
SEQUENCE: 662
ISYDGSNK                                                          8

SEQ ID NO: 663         moltype = DNA  length = 57
FEATURE                Location/Qualifiers
misc_feature           1..57
                       note = Synthetic
source                 1..57
                       mol_type = other DNA
                       organism = synthetic construct
SEQUENCE: 663
```

```
gcgaaagggg ctatggttcg gggagtccct tacaactact actacggtat ggacgtc     57

SEQ ID NO: 664          moltype = AA  length = 19
FEATURE                 Location/Qualifiers
REGION                  1..19
                        note = Synthetic
source                  1..19
                        mol_type = protein
                        organism = synthetic construct
SEQUENCE: 664
AKGAMVRGVP YNYYYGMDV                                               19

SEQ ID NO: 665          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 665
gacatccaga tgacccagtc tccatcctcc ctgtctgcat ctgtaggaga cagagtcacc  60
atcacttgcc gggcaagtca gggcattaga aatgatttag gctggtttca gcagaaacca  120
gggaaagccc ctaagcgcct gatctatgct gcatccagtt tgcaaagtgg ggtcccatca  180
aggttcagcg gcagtggatc tgggacagaa ttcactctca caatcagcag cctgcagcct  240
gaagattttg caacttatta ctgtctacag cataatagtt acccgtacac ttttggccag  300
gggaccaagc tggagatcaa a                                            321

SEQ ID NO: 666          moltype = AA  length = 107
FEATURE                 Location/Qualifiers
REGION                  1..107
                        note = Synthetic
source                  1..107
                        mol_type = protein
                        organism = synthetic construct
SEQUENCE: 666
DIQMTQSPSS LSASVGDRVT ITCRASQGIR NDLGWFQQKP GKAPKRLIYA ASSLQSGVPS  60
RFSGSGSGTE FTLTISSLQP EDFATYYCLQ HNSYPYTFGQ GTKLEIK                107

SEQ ID NO: 667          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 667
cagggcatta gaaatgat                                                18

SEQ ID NO: 668          moltype = AA  length = 6
FEATURE                 Location/Qualifiers
REGION                  1..6
                        note = Synthetic
source                  1..6
                        mol_type = protein
                        organism = synthetic construct
SEQUENCE: 668
QGIRND                                                             6

SEQ ID NO: 669          moltype =   length =
SEQUENCE: 669
000

SEQ ID NO: 670          moltype =   length =
SEQUENCE: 670
000

SEQ ID NO: 671          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 671
ctacagcata atagttaccc gtacact                                      27

SEQ ID NO: 672          moltype = AA  length = 9
FEATURE                 Location/Qualifiers
REGION                  1..9
```

```
                        note = Synthetic
source                  1..9
                        mol_type = protein
                        organism = synthetic construct
SEQUENCE: 672
LQHNSYPYT                                                             9

SEQ ID NO: 673          moltype = DNA  length = 378
FEATURE                 Location/Qualifiers
misc_feature            1..378
                        note = Synthetic
source                  1..378
                        mol_type = other DNA
                        organism = synthetic construct
SEQUENCE: 673
caggtgcagc tggtggagtc tgggggaggc gtggtccagc ctgggaggtc cctgagactc  60
tcctgtgcag cctctggact caccttcagt agctatggca tgcactgggt ccgccaggct  120
ccaggcaagg ggctggagtg ggtggcagtt atatcatatg atggaagtaa taaatactat  180
acagactccg tgaagggccg attcaccatc tccagagaca attctaagaa cacgctgtat  240
ctgcaaatga acagcctgag agctgaggac acggctgtgt attactgtgc gaaaggggcc  300
atggttcggg gagtccctta caactactac tacggtatgg acgtctgggg ccaagggacc  360
acggtcaccg tctcctca                                                   378

SEQ ID NO: 674          moltype = AA  length = 126
FEATURE                 Location/Qualifiers
REGION                  1..126
                        note = Synthetic
source                  1..126
                        mol_type = protein
                        organism = synthetic construct
SEQUENCE: 674
QVQLVESGGG VVQPGRSLRL SCAASGLTFS SYGMHWVRQA PGKGLEWVAV ISYDGSNKYY  60
TDSVKGRFTI SRDNSKNTLY LQMNSLRAED TAVYYCAKGA MVRGVPYNYY YGMDVWGQGT  120
TVTVSS                                                                126

SEQ ID NO: 675          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 675
ggactcacct tcagtagcta tggc                                            24

SEQ ID NO: 676          moltype = AA  length = 8
FEATURE                 Location/Qualifiers
REGION                  1..8
                        note = Synthetic
source                  1..8
                        mol_type = protein
                        organism = synthetic construct
SEQUENCE: 676
GLTFSSYG                                                              8

SEQ ID NO: 677          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 677
atatcatatg atggaagtaa taaa                                            24

SEQ ID NO: 678          moltype = AA  length = 8
FEATURE                 Location/Qualifiers
REGION                  1..8
                        note = Synthetic
source                  1..8
                        mol_type = protein
                        organism = synthetic construct
SEQUENCE: 678
ISYDGSNK                                                              8

SEQ ID NO: 679          moltype = DNA  length = 57
FEATURE                 Location/Qualifiers
misc_feature            1..57
                        note = Synthetic
```

```
source                  1..57
                        mol_type = other DNA
                        organism = synthetic construct
SEQUENCE: 679
gcgaaagggg ccatggttcg gggagtccct tacaactact actacggtat ggacgtc     57

SEQ ID NO: 680          moltype = AA  length = 19
FEATURE                 Location/Qualifiers
REGION                  1..19
                        note = Synthetic
source                  1..19
                        mol_type = protein
                        organism = synthetic construct
SEQUENCE: 680
AKGAMVRGVP YNYYYGMDV                                               19

SEQ ID NO: 681          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 681
gacatccaga tgacccagtc tccatcctcc ctgtctgcat ctgtaggaga cagagtcacc  60
atcacttgcc gggcaagtca gggcattaga aatgatttag gctggtatca gcagaaacca  120
gggaaagccc ctaagcgcct gatctatgct gcgtccagtt tgcaaagtgg ggtcccatca  180
aggttcagcg gcagtggatc tgggacagaa ttcactctca caatcagcag cctgcagcct  240
gaagattttg caacttatta ctgtctacag cataatagtt acccgtacac ttttggccag  300
gggaccaagc tggagatcaa a                                            321

SEQ ID NO: 682          moltype = AA  length = 107
FEATURE                 Location/Qualifiers
REGION                  1..107
                        note = Synthetic
source                  1..107
                        mol_type = protein
                        organism = synthetic construct
SEQUENCE: 682
DIQMTQSPSS LSASVGDRVT ITCRASQGIR NDLGWYQQKP GKAPKRLIYA ASSLQSGVPS  60
RFSGSGSGTE FTLTISSLQP EDFATYYCLQ HNSYPYTFGQ GTKLEIK                107

SEQ ID NO: 683          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 683
cagggcatta gaaatgat                                                18

SEQ ID NO: 684          moltype = AA  length = 6
FEATURE                 Location/Qualifiers
REGION                  1..6
                        note = Synthetic
source                  1..6
                        mol_type = protein
                        organism = synthetic construct
SEQUENCE: 684
QGIRND                                                             6

SEQ ID NO: 685          moltype =   length =
SEQUENCE: 685
000

SEQ ID NO: 686          moltype =   length =
SEQUENCE: 686
000

SEQ ID NO: 687          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 687
ctacagcata atagttaccc gtacact                                      27
```

```
SEQ ID NO: 688          moltype = AA  length = 9
FEATURE                 Location/Qualifiers
REGION                  1..9
                        note = Synthetic
source                  1..9
                        mol_type = protein
                        organism = synthetic construct
SEQUENCE: 688
LQHNSYPYT                                                          9

SEQ ID NO: 689          moltype = DNA  length = 378
FEATURE                 Location/Qualifiers
misc_feature            1..378
                        note = Synthetic
source                  1..378
                        mol_type = other DNA
                        organism = synthetic construct
SEQUENCE: 689
caggtgcagc tggtggagtc tgggggaggc gtggtccagc ctgggaggtc cctgagactc  60
tcctgtgcag cctctggatt caccttcagg agctttggca tgcactgggt ccgccaggct  120
ccaggcaagg ggctggagtg ggtggcagtt atttcatatg atggaaatta taaatactat  180
gcagactccg tgaagggccg attcaccatc tccagagaca attccaagaa cacgctgtat  240
ctgcaaatga acagcctgag agctgaggac acggctgtac attactgtgc gaaaggggct  300
atggttcggg gagtccctta caacttctac tacggtatgg acgtctgggg ccaagggacc  360
acggtcaccg tctcctca                                                378

SEQ ID NO: 690          moltype = AA  length = 126
FEATURE                 Location/Qualifiers
REGION                  1..126
                        note = Synthetic
source                  1..126
                        mol_type = protein
                        organism = synthetic construct
SEQUENCE: 690
QVQLVESGGG VVQPGRSLRL SCAASGFTFR SFGMHWVRQA PGKGLEWVAV ISYDGNYKYY  60
ADSVKGRFTI SRDNSKNTLY LQMNSLRAED TAVHYCAKGA MVRGVPYNFY YGMDVWGQGT  120
TVTVSS                                                             126

SEQ ID NO: 691          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 691
ggattcacct tcaggagctt tggc                                         24

SEQ ID NO: 692          moltype = AA  length = 8
FEATURE                 Location/Qualifiers
REGION                  1..8
                        note = Synthetic
source                  1..8
                        mol_type = protein
                        organism = synthetic construct
SEQUENCE: 692
GFTFRSFG                                                           8

SEQ ID NO: 693          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 693
atttcatatg atggaaatta taaa                                         24

SEQ ID NO: 694          moltype = AA  length = 8
FEATURE                 Location/Qualifiers
REGION                  1..8
                        note = Synthetic
source                  1..8
                        mol_type = protein
                        organism = synthetic construct
SEQUENCE: 694
ISYDGNYK                                                           8
```

-continued

```
SEQ ID NO: 695         moltype = DNA  length = 57
FEATURE                Location/Qualifiers
misc_feature           1..57
                       note = Synthetic
source                 1..57
                       mol_type = other DNA
                       organism = synthetic construct
SEQUENCE: 695
gcgaaagggg ctatggttcg gggagtccct tacaacttct actacggtat ggacgtc     57

SEQ ID NO: 696         moltype = AA  length = 19
FEATURE                Location/Qualifiers
REGION                 1..19
                       note = Synthetic
source                 1..19
                       mol_type = protein
                       organism = synthetic construct
SEQUENCE: 696
AKGAMVRGVP YNFYYGMDV                                               19

SEQ ID NO: 697         moltype = DNA  length = 321
FEATURE                Location/Qualifiers
misc_feature           1..321
                       note = Synthetic
source                 1..321
                       mol_type = other DNA
                       organism = synthetic construct
SEQUENCE: 697
gacatccaga tgacccagtc tccatcctcc ctgtctgcat ctgtaggaga cagagtcacc  60
atcacttgcc gggcaagtca ggtcattaga aatgatttag gctggtatca gcagaaacca  120
gggaaagccc ctaagcgcct gatctatgct gcatccagtt tgcaaagtgg gatcccatca  180
aggttcagcg gcagtggatc tgggacagaa ttcactctca caatcagcag cctgcagcct  240
gaagattttg caacttatta ctgtctacag cataatagtt acccgtacac ttttggccag  300
gggaccaagc tggagatcaa a                                            321

SEQ ID NO: 698         moltype = AA  length = 107
FEATURE                Location/Qualifiers
REGION                 1..107
                       note = Synthetic
source                 1..107
                       mol_type = protein
                       organism = synthetic construct
SEQUENCE: 698
DIQMTQSPSS LSASVGDRVT ITCRASQVIR NDLGWYQQKP GKAPKRLIYA ASSLQSGIPS  60
RFSGSGSGTE FTLTISSLQP EDFATYYCLQ HNSYPYTFGQ GTKLEIK                107

SEQ ID NO: 699         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 699
caggtcatta gaaatgat                                                18

SEQ ID NO: 700         moltype = AA  length = 6
FEATURE                Location/Qualifiers
REGION                 1..6
                       note = Synthetic
source                 1..6
                       mol_type = protein
                       organism = synthetic construct
SEQUENCE: 700
QVIRND                                                             6

SEQ ID NO: 701         moltype =   length =
SEQUENCE: 701
000

SEQ ID NO: 702         moltype =   length =
SEQUENCE: 702
000

SEQ ID NO: 703         moltype = DNA  length = 27
FEATURE                Location/Qualifiers
misc_feature           1..27
                       note = Synthetic
source                 1..27
```

```
                        mol_type = other DNA
                        organism = synthetic construct
SEQUENCE: 703
ctacagcata atagttaccc gtacact                                           27

SEQ ID NO: 704          moltype = AA  length = 9
FEATURE                 Location/Qualifiers
REGION                  1..9
                        note = Synthetic
source                  1..9
                        mol_type = protein
                        organism = synthetic construct
SEQUENCE: 704
LQHNSYPYT                                                               9

SEQ ID NO: 705          moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 705
gaggtgcagc tggtggagtc tgggggaggc ttggtacagc ctggcaggtc cctgagactc  60
tcctgtgcag cctctggatt cacctttgat gattatacca tgcactgggt ccggcaagtt  120
ccaggaaagg gcctggagtg gatctcaggt attagttgga atagtggtag catggactat  180
gcggactctg tgaagggccg attcaccatc tctagagaca acgccaggaa ctccctgttt  240
ctgcaaatga acagtgtgag aactgaggac acggccttgt attactgtgc aaaagataag  300
agtggctacg gctccttcta ctacggtatg gacgtctggg gccaggggac cacggtcacc  360
gtctcctca                                                               369

SEQ ID NO: 706          moltype = AA  length = 123
FEATURE                 Location/Qualifiers
REGION                  1..123
                        note = Synthetic
source                  1..123
                        mol_type = protein
                        organism = synthetic construct
SEQUENCE: 706
EVQLVESGGG LVQPGRSLRL SCAASGFTFD DYTMHWVRQV PGKGLEWISG ISWNSGSMDY  60
ADSVKGRFTI SRDNARNSLF LQMNSVRTED TALYYCAKDK SGYGSFYYGM DVWGQGTTVT  120
VSS                                                                     123

SEQ ID NO: 707          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 707
ggattcacct ttgatgatta tacc                                              24

SEQ ID NO: 708          moltype = AA  length = 8
FEATURE                 Location/Qualifiers
REGION                  1..8
                        note = Synthetic
source                  1..8
                        mol_type = protein
                        organism = synthetic construct
SEQUENCE: 708
GFTFDDYT                                                                8

SEQ ID NO: 709          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 709
attagttgga atagtggtag catg                                              24

SEQ ID NO: 710          moltype = AA  length = 8
FEATURE                 Location/Qualifiers
REGION                  1..8
                        note = Synthetic
source                  1..8
                        mol_type = protein
```

```
                        organism = synthetic construct
SEQUENCE: 710
ISWNSGSM                                                          8

SEQ ID NO: 711          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 711
gcaaaagata agagtggcta cggctccttc tactacggta tggacgtc             48

SEQ ID NO: 712          moltype = AA  length = 16
FEATURE                 Location/Qualifiers
REGION                  1..16
                        note = Synthetic
source                  1..16
                        mol_type = protein
                        organism = synthetic construct
SEQUENCE: 712
AKDKSGYGSF YYGMDV                                                 16

SEQ ID NO: 713          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 713
gaaattgtgt tgacgcagtc tccaggcacc ctgtctttgt ctccagggga cagagccacc  60
ctctcctgca gggccagtca gagtgtcagc agcatctact tagcctggta ccagcagaaa  120
cctggccagg ctcccaggct cctcatccat ggtgcgtcca ccagggccac tggcatccca  180
gacaggttca gtggcagtgg gtcagggaca gacttcactc tcaccatcag cagactggag  240
cctgaagatt ttgcagttta ttactgtcag cagcgtgctc actcaccgta cacttttggc  300
caggggacca agctggagat caaa                                        324

SEQ ID NO: 714          moltype = AA  length = 108
FEATURE                 Location/Qualifiers
REGION                  1..108
                        note = Synthetic
source                  1..108
                        mol_type = protein
                        organism = synthetic construct
SEQUENCE: 714
EIVLTQSPGT LSLSPGDRAT LSCRASQSVS SIYLAWYQQK PGQAPRLLIH GASTRATGIP  60
DRFSGSGSGT DFTLTISRLE PEDFAVYYCQ QRAHSPYTFG QGTKLEIK              108

SEQ ID NO: 715          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 715
cagagtgtca gcagcatcta c                                           21

SEQ ID NO: 716          moltype = AA  length = 7
FEATURE                 Location/Qualifiers
REGION                  1..7
                        note = Synthetic
source                  1..7
                        mol_type = protein
                        organism = synthetic construct
SEQUENCE: 716
QSVSSIY                                                           7

SEQ ID NO: 717          moltype =   length =
SEQUENCE: 717
000

SEQ ID NO: 718          moltype =   length =
SEQUENCE: 718
000

SEQ ID NO: 719          moltype = DNA  length = 27
```

```
FEATURE                Location/Qualifiers
misc_feature           1..27
                       note = Synthetic
source                 1..27
                       mol_type = other DNA
                       organism = synthetic construct
SEQUENCE: 719
cagcagcgtg ctcactcacc gtacact                                      27

SEQ ID NO: 720         moltype = AA  length = 9
FEATURE                Location/Qualifiers
REGION                 1..9
                       note = Synthetic
source                 1..9
                       mol_type = protein
                       organism = synthetic construct
SEQUENCE: 720
QQRAHSPYT                                                          9

SEQ ID NO: 721         moltype = DNA  length = 369
FEATURE                Location/Qualifiers
misc_feature           1..369
                       note = Synthetic
source                 1..369
                       mol_type = other DNA
                       organism = synthetic construct
SEQUENCE: 721
gaagtgcagc tggtggagtc tgggggaggc ttggtacagc ctggcaggtc cctgagactc  60
tcctgtgcag cctctggctt cagctttgat aattatgcca tgcactgggt ccggcaagct  120
ccaggacagg gcctggagtg ggtctcaggt attagttgga atagtggtag cagagactat  180
gcggactctg tgaagggccg attcaccatc tccagagaca atgccaggaa ctccctgttt  240
ctgcaaatga acagtctgag taatgaggac acggccatgt attactgcgc aaaagataag  300
agtggctacg gctcctactt ctacggtatg gacgtctggg gccaagggac cacggtcacc  360
gtctcctca                                                          369

SEQ ID NO: 722         moltype = AA  length = 123
FEATURE                Location/Qualifiers
REGION                 1..123
                       note = Synthetic
source                 1..123
                       mol_type = protein
                       organism = synthetic construct
SEQUENCE: 722
EVQLVESGGG LVQPGRSLRL SCAASGFSFD NYAMHWVRQA PGQGLEWVSG ISWNSGSRDY  60
ADSVKGRFTI SRDNARNSLF LQMNSLSNED TAMYYCAKDK SGYGSYFYGM DVWGQGTTVT  120
VSS                                                                123

SEQ ID NO: 723         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 723
ggcttcagct ttgataatta tgcc                                         24

SEQ ID NO: 724         moltype = AA  length = 8
FEATURE                Location/Qualifiers
REGION                 1..8
                       note = Synthetic
source                 1..8
                       mol_type = protein
                       organism = synthetic construct
SEQUENCE: 724
GFSFDNYA                                                           8

SEQ ID NO: 725         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 725
attagttgga atagtggtag caga                                         24

SEQ ID NO: 726         moltype = AA  length = 8
FEATURE                Location/Qualifiers
```

```
REGION                  1..8
                        note = Synthetic
source                  1..8
                        mol_type = protein
                        organism = synthetic construct
SEQUENCE: 726
ISWNSGSR                                                        8

SEQ ID NO: 727          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 727
gcaaaagata agagtggcta cggctcctac ttctacggta tggacgtc            48

SEQ ID NO: 728          moltype = AA  length = 16
FEATURE                 Location/Qualifiers
REGION                  1..16
                        note = Synthetic
source                  1..16
                        mol_type = protein
                        organism = synthetic construct
SEQUENCE: 728
AKDKSGYGSY FYGMDV                                               16

SEQ ID NO: 729          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 729
gaaattgtgt tgacgcagtc tccaggcacc ctgtctttgt ctccagggga cagagccacc  60
ctctcctgca gggccagtca gagtattaga aacatctatt tagcctggta ccagcagaaa  120
cctggccagg ctcccaggct cctcatccat ggtgcgtcca ccagggccac tggcatccca  180
gacaggttca gtggcagtgg gtcagggaca gacttcactc tcaccatcag cagactggag  240
cctgaagatt ttgcagttta ttactgtcag cagcgtgtta gtttaccgta cacttttggc  300
caggggacca agctggagat caaa                                      324

SEQ ID NO: 730          moltype = AA  length = 108
FEATURE                 Location/Qualifiers
REGION                  1..108
                        note = Synthetic
source                  1..108
                        mol_type = protein
                        organism = synthetic construct
SEQUENCE: 730
EIVLTQSPGT LSLSPGDRAT LSCRASQSIR NIYLAWYQQK PGQAPRLLIH GASTRATGIP  60
DRFSGSGSGT DFTLTISRLE PEDFAVYYCQ QRVSLPYTFG QGTKLEIK            108

SEQ ID NO: 731          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 731
cagagtatta gaaacatcta t                                         21

SEQ ID NO: 732          moltype = AA  length = 7
FEATURE                 Location/Qualifiers
REGION                  1..7
                        note = Synthetic
source                  1..7
                        mol_type = protein
                        organism = synthetic construct
SEQUENCE: 732
QSIRNIY                                                         7

SEQ ID NO: 733          moltype =   length =
SEQUENCE: 733
000

SEQ ID NO: 734          moltype =   length =
```

```
SEQUENCE: 734
000

SEQ ID NO: 735          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 735
cagcagcgtg ttagtttacc gtacact                                      27

SEQ ID NO: 736          moltype = AA  length = 9
FEATURE                 Location/Qualifiers
REGION                  1..9
                        note = Synthetic
source                  1..9
                        mol_type = protein
                        organism = synthetic construct
SEQUENCE: 736
QQRVSLPYT                                                          9

SEQ ID NO: 737          moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 737
caggtgcagc tggtggagtc tgggggaggc ttggtacagc ctggcaggtc cctgagactc  60
tcctgtgcag cctctggctt cagctttgat gattatgcca tgcactgggt ccggcaagct  120
ccaggacagg gcctggagtg ggtctcaggt attagttgga atggtggtag cagagactat  180
gcggactctg tgaagggccg attcaccatc tccagagaca acgccaggaa ctccctgttt  240
ctgcaaatga acagtctgtt tactgaggac acggccttgt attactgtgc aaaagataag  300
agtggctacg gctcctactt ctacggtatg gacgtctggg gccaagggac cacggtcacc  360
gtctcctca                                                          369

SEQ ID NO: 738          moltype = AA  length = 123
FEATURE                 Location/Qualifiers
REGION                  1..123
                        note = Synthetic
source                  1..123
                        mol_type = protein
                        organism = synthetic construct
SEQUENCE: 738
QVQLVESGGG LVQPGRSLRL SCAASGFSFD DYAMHWVRQA PGQGLEWVSG ISWNGGSRDY  60
ADSVKGRFTI SRDNARNSLF LQMNSLFTED TALYYCAKDK SGYGSYFYGM DVWGQGTTVT  120
VSS                                                                123

SEQ ID NO: 739          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 739
ggcttcagct ttgatgatta tgcc                                         24

SEQ ID NO: 740          moltype = AA  length = 8
FEATURE                 Location/Qualifiers
REGION                  1..8
                        note = Synthetic
source                  1..8
                        mol_type = protein
                        organism = synthetic construct
SEQUENCE: 740
GFSFDDYA                                                           8

SEQ ID NO: 741          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 741
```

```
attagttgga atggtggtag caga                                        24

SEQ ID NO: 742         moltype = AA  length = 8
FEATURE                Location/Qualifiers
REGION                 1..8
                       note = Synthetic
source                 1..8
                       mol_type = protein
                       organism = synthetic construct
SEQUENCE: 742
ISWNGGSR                                                          8

SEQ ID NO: 743         moltype = DNA  length = 48
FEATURE                Location/Qualifiers
misc_feature           1..48
                       note = Synthetic
source                 1..48
                       mol_type = other DNA
                       organism = synthetic construct
SEQUENCE: 743
gcaaaagata agagtggcta cggctcctac ttctacggta tggacgtc              48

SEQ ID NO: 744         moltype = AA  length = 16
FEATURE                Location/Qualifiers
REGION                 1..16
                       note = Synthetic
source                 1..16
                       mol_type = protein
                       organism = synthetic construct
SEQUENCE: 744
AKDKSGYGSY FYGMDV                                                 16

SEQ ID NO: 745         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 745
gaaattgtgt tgacgcagtc tccaggcatt ctgtctttgt ctccagggga cagagccacc  60
ctctcctgca gggccagtca gagtattaga aacatctatt tagcctggta ccagcagaaa  120
cctggccagg ctcccaggct cctcatccat ggtgcgtcca ccagggccac tggcatccca  180
gacaggttca gtggcagtgg gtcagggaca gacttcactc tcaccatcag cagactggag  240
cctgaagatt ttgcagttta ttactgtcag cagcgtgtta gttcaccgta cacttttggc  300
caggggacca agctggagat caaa                                        324

SEQ ID NO: 746         moltype = AA  length = 108
FEATURE                Location/Qualifiers
REGION                 1..108
                       note = Synthetic
source                 1..108
                       mol_type = protein
                       organism = synthetic construct
SEQUENCE: 746
EIVLTQSPGI LSLSPGDRAT LSCRASQSIR NIYLAWYQQK PGQAPRLLIH GASTRATGIP  60
DRFSGSGSGT DFTLTISRLE PEDFAVYYCQ QRVSSPYTFG QGTKLEIK              108

SEQ ID NO: 747         moltype = DNA  length = 21
FEATURE                Location/Qualifiers
misc_feature           1..21
                       note = Synthetic
source                 1..21
                       mol_type = other DNA
                       organism = synthetic construct
SEQUENCE: 747
cagagtatta gaaacatcta t                                           21

SEQ ID NO: 748         moltype = AA  length = 7
FEATURE                Location/Qualifiers
REGION                 1..7
                       note = Synthetic
source                 1..7
                       mol_type = protein
                       organism = synthetic construct
SEQUENCE: 748
QSIRNIY                                                           7

SEQ ID NO: 749         moltype =   length =
```

```
SEQUENCE: 749
000

SEQ ID NO: 750         moltype =   length =
SEQUENCE: 750
000

SEQ ID NO: 751         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 751
cagcagcgtg ttagttcacc gtacact                                      27

SEQ ID NO: 752         moltype = AA  length = 9
FEATURE                Location/Qualifiers
REGION                 1..9
                       note = Synthetic
source                 1..9
                       mol_type = protein
                       organism = synthetic construct
SEQUENCE: 752
QQRVSSPYT                                                          9

SEQ ID NO: 753         moltype = DNA  length = 369
FEATURE                Location/Qualifiers
misc_feature           1..369
                       note = Synthetic
source                 1..369
                       mol_type = other DNA
                       organism = synthetic construct
SEQUENCE: 753
gaggtgcagc tggtggagtc tgggggaggc ttggtacagc ctggcaggtc cctgagactc  60
tcctgtgcag cctctggatt cacctttgat gattatgcca tgcactgggt ccggcaagct  120
ccaggaaagg gcctggagtg ggtctcaggt attagttgga atagtggtag cagagactat  180
gcggactctg tgaagggccg attcaccatc tccagagaca acgccaggaa ctccctgttt  240
ctgcaaatga acagtctgag tactgaggac acggccttgt attactgtgc aaaagataag  300
agtggctacg gctcctacta ctacggtatg gacgtctggg gccaagggac cacggtcacc  360
gtctcctca                                                          369

SEQ ID NO: 754         moltype = AA  length = 123
FEATURE                Location/Qualifiers
REGION                 1..123
                       note = Synthetic
source                 1..123
                       mol_type = protein
                       organism = synthetic construct
SEQUENCE: 754
EVQLVESGGG LVQPGRSLRL SCAASGFTFD DYAMHWVRQA PGKGLEWVSG ISWNSGSRDY  60
ADSVKGRFTI SRDNARNSLF LQMNSLSTED TALYYCAKDK SGYGSYYYGM DVWGQGTTVT  120
VSS                                                                123

SEQ ID NO: 755         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 755
ggattcacct ttgatgatta tgcc                                         24

SEQ ID NO: 756         moltype = AA  length = 8
FEATURE                Location/Qualifiers
REGION                 1..8
                       note = Synthetic
source                 1..8
                       mol_type = protein
                       organism = synthetic construct
SEQUENCE: 756
GFTFDDYA                                                           8

SEQ ID NO: 757         moltype = DNA  length = 24
FEATURE                Location/Qualifiers
misc_feature           1..24
                       note = Synthetic
```

```
source                1..24
                      mol_type = other DNA
                      organism = synthetic construct
SEQUENCE: 757
attagttgga atagtggtag caga                                        24

SEQ ID NO: 758        moltype = AA  length = 8
FEATURE               Location/Qualifiers
REGION                1..8
                      note = Synthetic
source                1..8
                      mol_type = protein
                      organism = synthetic construct
SEQUENCE: 758
ISWNSGSR                                                          8

SEQ ID NO: 759        moltype = DNA  length = 48
FEATURE               Location/Qualifiers
misc_feature          1..48
                      note = Synthetic
source                1..48
                      mol_type = other DNA
                      organism = synthetic construct
SEQUENCE: 759
gcaaaagata agagtggcta cggctcctac tactacggta tggacgtc              48

SEQ ID NO: 760        moltype = AA  length = 16
FEATURE               Location/Qualifiers
REGION                1..16
                      note = Synthetic
source                1..16
                      mol_type = protein
                      organism = synthetic construct
SEQUENCE: 760
AKDKSGYGSY YYGMDV                                                 16

SEQ ID NO: 761        moltype = DNA  length = 324
FEATURE               Location/Qualifiers
misc_feature          1..324
                      note = Synthetic
source                1..324
                      mol_type = other DNA
                      organism = synthetic construct
SEQUENCE: 761
gaaattgtgt tgacgcagtc tccaggcacc ctgtctttgt ctccagggga cagagccacc  60
ctctcctgca gggccagtca gagtattaga agcatctact tagcctggta ccagcagaaa  120
cctggccagg ctcccaggct cctcatccat ggtgcgtcca ccagggccac tggcatccca  180
gacaggttca gtggcagtgg gtcagggaca gacttcactc tcaccatcag cagactggag  240
cctgaagatt ttgcagttta ttactgtcag cagcgtgtta gctcaccgta cacttttggc  300
caggggacca agctggagat caaa                                        324

SEQ ID NO: 762        moltype = AA  length = 108
FEATURE               Location/Qualifiers
REGION                1..108
                      note = Synthetic
source                1..108
                      mol_type = protein
                      organism = synthetic construct
SEQUENCE: 762
EIVLTQSPGT LSLSPGDRAT LSCRASQSIR SIYLAWYQQK PGQAPRLLIH GASTRATGIP  60
DRFSGSGSGT DFTLTISRLE PEDFAVYYCQ QRVSSPYTFG QGTKLEIK              108

SEQ ID NO: 763        moltype = DNA  length = 21
FEATURE               Location/Qualifiers
misc_feature          1..21
                      note = Synthetic
source                1..21
                      mol_type = other DNA
                      organism = synthetic construct
SEQUENCE: 763
cagagtatta gaagcatcta c                                           21

SEQ ID NO: 764        moltype = AA  length = 7
FEATURE               Location/Qualifiers
REGION                1..7
                      note = Synthetic
source                1..7
                      mol_type = protein
                      organism = synthetic construct
```

```
SEQUENCE: 764
QSIRSIY                                                          7

SEQ ID NO: 765         moltype =   length =
SEQUENCE: 765
000

SEQ ID NO: 766         moltype =   length =
SEQUENCE: 766
000

SEQ ID NO: 767         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 767
cagcagcgtg ttagctcacc gtacact                                    27

SEQ ID NO: 768         moltype = AA  length = 9
FEATURE                Location/Qualifiers
REGION                 1..9
                       note = Synthetic
source                 1..9
                       mol_type = protein
                       organism = synthetic construct
SEQUENCE: 768
QQRVSSPYT                                                        9

SEQ ID NO: 769         moltype = DNA  length = 369
FEATURE                Location/Qualifiers
misc_feature           1..369
                       note = Synthetic
source                 1..369
                       mol_type = other DNA
                       organism = synthetic construct
SEQUENCE: 769
gaagtgcagc tggtggagtc tgggggaggc ttggtacagc ctggcaggtc cctgagactc  60
tcctgtgtag cctctggatt cacctttgct gattttacca tgcactgggt ccggcaagcg  120
ccagggaagg gccttgagtg ggtctcaggt attagttgga atagtaatag tatagactat  180
gcggactctg tgaagggccg attcaccatc tccagagaca acgccaagaa atccctgttt  240
ctgcaaatgt ccagtctgag agctgaggac acggccttat attactgtgt caaagacaga  300
agcggatata gcagattcta ctacggtatg gacgtctggg gccaagggac cacggtcacc  360
gtctcctca                                                        369

SEQ ID NO: 770         moltype = AA  length = 123
FEATURE                Location/Qualifiers
REGION                 1..123
                       note = Synthetic
source                 1..123
                       mol_type = protein
                       organism = synthetic construct
SEQUENCE: 770
EVQLVESGGG LVQPGRSLRL SCVASGFTFA DFTMHWVRQA PGKGLEWVSG ISWNSNSIDY  60
ADSVKGRFTI SRDNAKKSLF LQMSSLRAED TALYYCVKDR SGYSRFYYGM DVWGQGTTVT  120
VSS                                                              123

SEQ ID NO: 771         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 771
ggattcacct ttgctgattt tacc                                       24

SEQ ID NO: 772         moltype = AA  length = 8
FEATURE                Location/Qualifiers
REGION                 1..8
                       note = Synthetic
source                 1..8
                       mol_type = protein
                       organism = synthetic construct
SEQUENCE: 772
GFTFADFT                                                         8
```

```
SEQ ID NO: 773          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 773
attagttgga atagtaatag tata                                        24

SEQ ID NO: 774          moltype = AA  length = 8
FEATURE                 Location/Qualifiers
REGION                  1..8
                        note = Synthetic
source                  1..8
                        mol_type = protein
                        organism = synthetic construct
SEQUENCE: 774
ISWNSNSI                                                          8

SEQ ID NO: 775          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 775
gtcaaagaca gaagcggata tagcagattc tactacggta tggacgtc              48

SEQ ID NO: 776          moltype = AA  length = 16
FEATURE                 Location/Qualifiers
REGION                  1..16
                        note = Synthetic
source                  1..16
                        mol_type = protein
                        organism = synthetic construct
SEQUENCE: 776
VKDRSGYSRF YYGMDV                                                 16

SEQ ID NO: 777          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 777
gaaattgtga tgacgcagtc tccagccacc ctgtctgtgt ctccagggga aagagccatc  60
ctctcctgca gggccagtca gaatattaat agcaacttgg cctggtacca gcagaaacct  120
ggccaggctc ccaggctcct catctatggt gcatccacca gggccactgg tgtcccagcc  180
aggttcagtg gcagtgggtc tgggacagag ttcactctca ccatccgcag cctgcaatct  240
gaagattttg cagtttatta ctgtcaacaa tattataatt ggccgatcac tttcggccac  300
gggacacgac tggagattaa a                                           321

SEQ ID NO: 778          moltype = AA  length = 107
FEATURE                 Location/Qualifiers
REGION                  1..107
                        note = Synthetic
source                  1..107
                        mol_type = protein
                        organism = synthetic construct
SEQUENCE: 778
EIVMTQSPAT LSVSPGERAI LSCRASQNIN SNLAWYQQKP GQAPRLLIYG ASTRATGVPA  60
RFSGSGSGTE FTLTIRSLQS EDFAVYYCQQ YYNWPITFGH GTRLEIK                107

SEQ ID NO: 779          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 779
cagaatatta atagcaac                                               18

SEQ ID NO: 780          moltype = AA  length = 6
FEATURE                 Location/Qualifiers
REGION                  1..6
```

```
                        note = Synthetic
source                  1..6
                        mol_type = protein
                        organism = synthetic construct
SEQUENCE: 780
QNINSN                                                                 6

SEQ ID NO: 781          moltype =   length =
SEQUENCE: 781
000

SEQ ID NO: 782          moltype =   length =
SEQUENCE: 782
000

SEQ ID NO: 783          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 783
caacaatatt ataattggcc gatcact                                          27

SEQ ID NO: 784          moltype = AA  length = 9
FEATURE                 Location/Qualifiers
REGION                  1..9
                        note = Synthetic
source                  1..9
                        mol_type = protein
                        organism = synthetic construct
SEQUENCE: 784
QQYYNWPIT                                                              9

SEQ ID NO: 785          moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 785
gaggtgcagc tggtggagtc tgggggaggc ttggtacagc ctggcaggtc cctgagactc  60
tcctgtgcag cctctggatt cacctttgat gattatgcca tgcactgggt ccggcaagct  120
ccaggaaagg gcctggagtg ggtctcaggt attagttgga atggtggtag taaagactat  180
gcggactctg tgaagggccg attcaccatc tccagagaca acaccaggaa ctccctgtct  240
ctgcaaatga acagtctgag aattgaagac acggccttat attactgtgc aaaagataag  300
agtggctacg gctccttcta ctacggtttg gacgtctggg gccaagggac cacggtcacc  360
gtctcctca                                                              369

SEQ ID NO: 786          moltype = AA  length = 123
FEATURE                 Location/Qualifiers
REGION                  1..123
                        note = Synthetic
source                  1..123
                        mol_type = protein
                        organism = synthetic construct
SEQUENCE: 786
EVQLVESGGG LVQPGRSLRL SCAASGFTFD DYAMHWVRQA PGKGLEWVSG ISWNGGSKDY  60
ADSVKGRFTI SRDNTRNSLS LQMNSLRIED TALYYCAKDK SGYGSFYYGL DVWGQGTTVT  120
VSS                                                                    123

SEQ ID NO: 787          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 787
ggattcacct ttgatgatta tgcc                                             24

SEQ ID NO: 788          moltype = AA  length = 8
FEATURE                 Location/Qualifiers
REGION                  1..8
                        note = Synthetic
source                  1..8
                        mol_type = protein
```

```
                        organism = synthetic construct
SEQUENCE: 788
GFTFDDYA                                                            8

SEQ ID NO: 789          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 789
attagttgga atggtggtag taaa                                          24

SEQ ID NO: 790          moltype = AA  length = 8
FEATURE                 Location/Qualifiers
REGION                  1..8
                        note = Synthetic
source                  1..8
                        mol_type = protein
                        organism = synthetic construct
SEQUENCE: 790
ISWNGGSK                                                            8

SEQ ID NO: 791          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 791
gcaaaagata agagtggcta cggctccttc tactacggtt tggacgtc                48

SEQ ID NO: 792          moltype = AA  length = 16
FEATURE                 Location/Qualifiers
REGION                  1..16
                        note = Synthetic
source                  1..16
                        mol_type = protein
                        organism = synthetic construct
SEQUENCE: 792
AKDKSGYGSF YYGLDV                                                   16

SEQ ID NO: 793          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 793
gaaatagtgt tgacacagtc tccaggcacc ctgtctttgt ctccagggga cagagccacc  60
ctctcctgca gggccagtca gagtattaga agcatctact tagcctggta ccagcagaaa  120
cctggccagg ctcccaggct cctcatccat ggtgcgtcca ccagggccac tggcatccca  180
gacaggttca gtggcagtgg gtcagggaca gacttcactc tcaccatcag cagactggag  240
cctgaagatt ttgcagttta ttactgtcag cagcgtgtta gctcaccgta cacttttggc  300
caggggacca agctggagat caaa                                          324

SEQ ID NO: 794          moltype = AA  length = 108
FEATURE                 Location/Qualifiers
REGION                  1..108
                        note = Synthetic
source                  1..108
                        mol_type = protein
                        organism = synthetic construct
SEQUENCE: 794
EIVLTQSPGT LSLSPGDRAT LSCRASQSIR SIYLAWYQQK PGQAPRLLIH GASTRATGIP  60
DRFSGSGSGT DFTLTISRLE PEDFAVYYCQ QRVSSPYTFG QGTKLEIK                108

SEQ ID NO: 795          moltype = DNA  length = 21
FEATURE                 Location/Qualifiers
misc_feature            1..21
                        note = Synthetic
source                  1..21
                        mol_type = other DNA
                        organism = synthetic construct
SEQUENCE: 795
cagagtatta gaagcatcta c                                             21
```

```
SEQ ID NO: 796          moltype = AA  length = 7
FEATURE                 Location/Qualifiers
REGION                  1..7
                        note = Synthetic
source                  1..7
                        mol_type = protein
                        organism = synthetic construct
SEQUENCE: 796
QSIRSIY                                                           7

SEQ ID NO: 797          moltype =   length =
SEQUENCE: 797
000

SEQ ID NO: 798          moltype =   length =
SEQUENCE: 798
000

SEQ ID NO: 799          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 799
cagcagcgtg ttagctcacc gtacact                                     27

SEQ ID NO: 800          moltype = AA  length = 9
FEATURE                 Location/Qualifiers
REGION                  1..9
                        note = Synthetic
source                  1..9
                        mol_type = protein
                        organism = synthetic construct
SEQUENCE: 800
QQRVSSPYT                                                         9

SEQ ID NO: 801          moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 801
gaggtgcagc tggtggagtc tgggggaggc ttggtacagc ctggcaggtc cctgagactc  60
tcctgtgcag cctctggatt cacctttgat gatttcacca tgcactgggt ccggcaagct  120
ccaggaaagg gcctggagtg ggtctcagat attagttgga atagtggtag catagactat  180
gcggactctg tgaagggccg attcaccatt tccagagaca atgccaggaa ctccctgttt  240
ctacaaatga gcagtctgag aactgaggac acggcctcgt attactgtat aaaagataag  300
agtggctacg gctcctacaa ctacggtctg gacgtctggg gccaagggac cacggtcacc  360
gtctcctca                                                         369

SEQ ID NO: 802          moltype = AA  length = 123
FEATURE                 Location/Qualifiers
REGION                  1..123
                        note = Synthetic
source                  1..123
                        mol_type = protein
                        organism = synthetic construct
SEQUENCE: 802
EVQLVESGGG LVQPGRSLRL SCAASGFTFD DFTMHWVRQA PGKGLEWVSD ISWNSGSIDY  60
ADSVKGRFTI SRDNARNSLF LQMSSLRTED TASYYCIKDK SGYGSYNYGL DVWGQGTTVT  120
VSS                                                               123

SEQ ID NO: 803          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 803
ggattcacct ttgatgattt cacc                                        24

SEQ ID NO: 804          moltype = AA  length = 8
FEATURE                 Location/Qualifiers
```

```
REGION                  1..8
                        note = Synthetic
source                  1..8
                        mol_type = protein
                        organism = synthetic construct
SEQUENCE: 804
GFTFDDFT                                                                  8

SEQ ID NO: 805          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 805
attagttgga atagtggtag cata                                                24

SEQ ID NO: 806          moltype = AA  length = 8
FEATURE                 Location/Qualifiers
REGION                  1..8
                        note = Synthetic
source                  1..8
                        mol_type = protein
                        organism = synthetic construct
SEQUENCE: 806
ISWNSGSI                                                                  8

SEQ ID NO: 807          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 807
ataaaagata agagtggcta cggctcctac aactacggtc tggacgtc                      48

SEQ ID NO: 808          moltype = AA  length = 16
FEATURE                 Location/Qualifiers
REGION                  1..16
                        note = Synthetic
source                  1..16
                        mol_type = protein
                        organism = synthetic construct
SEQUENCE: 808
IKDKSGYGSY NYGLDV                                                         16

SEQ ID NO: 809          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 809
gaaattgtgt tgacgcagtc tccaggcacc ctgtctttgt ctccagggga cagagccacc  60
ctctcctgca gggccagtca gagtgttagc agcatctact tagcctggta ccagcagaaa  120
cctggccagg ctcccaggct cctcatccat ggtgcgtcca ccagggccac tggcatccca  180
gacaggttca gtggcagtgg gtcggggaca gacttcactc tcaccatcag cagactggag  240
cctgaagatt ttgcacttta ttactgtcac cagcgtgtta gttcaccgta cacttttggc  300
caggggacca agctggagat caaa                                         324

SEQ ID NO: 810          moltype = AA  length = 108
FEATURE                 Location/Qualifiers
REGION                  1..108
                        note = Synthetic
source                  1..108
                        mol_type = protein
                        organism = synthetic construct
SEQUENCE: 810
EIVLTQSPGT LSLSPGDRAT LSCRASQSVS SIYLAWYQQK PGQAPRLLIH GASTRATGIP  60
DRFSGSGSGT DFTLTISRLE PEDFALYYCH QRVSSPYTFG QGTKLEIK                108

SEQ ID NO: 811          moltype = DNA  length = 21
FEATURE                 Location/Qualifiers
misc_feature            1..21
                        note = Synthetic
source                  1..21
```

```
                        mol_type = other DNA
                        organism = synthetic construct
SEQUENCE: 811
cagagtgtta gcagcatcta c                                      21

SEQ ID NO: 812          moltype = AA  length = 7
FEATURE                 Location/Qualifiers
REGION                  1..7
                        note = Synthetic
source                  1..7
                        mol_type = protein
                        organism = synthetic construct
SEQUENCE: 812
QSVSSIY                                                      7

SEQ ID NO: 813          moltype =   length =
SEQUENCE: 813
000

SEQ ID NO: 814          moltype =   length =
SEQUENCE: 814
000

SEQ ID NO: 815          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 815
caccagcgtg ttagttcacc gtacact                                27

SEQ ID NO: 816          moltype = AA  length = 9
FEATURE                 Location/Qualifiers
REGION                  1..9
                        note = Synthetic
source                  1..9
                        mol_type = protein
                        organism = synthetic construct
SEQUENCE: 816
HQRVSSPYT                                                    9

SEQ ID NO: 817          moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 817
gaggtgcagc tggtggagtc tgggggaggc ttggtacagc ctggcaggtc cctgagactc  60
tcctgtgcag cctctggatt cacctttgat gattatgcca tgcactgggt ccggcaagct  120
ccaggaaagg gcctggagtg ggtctcaggt attagttgga atagtggtag taaagactat  180
gcggactctg tgaagggccg attcaccatc tccagagaca acaccaggaa ctccctgttt  240
ctgcaaatga acagtctgag aactgaagac acggccttat attactgtgc aaaagataag  300
agtggctacg gctccttcta ctacggtatg gacgtctggg gccaagggac cacggtcacc  360
gtctcctca                                                    369

SEQ ID NO: 818          moltype = AA  length = 123
FEATURE                 Location/Qualifiers
REGION                  1..123
                        note = Synthetic
source                  1..123
                        mol_type = protein
                        organism = synthetic construct
SEQUENCE: 818
EVQLVESGGG LVQPGRSLRL SCAASGFTFD DYAMHWVRQA PGKGLEWVSG ISWNSGSKDY  60
ADSVKGRFTI SRDNTRNSLF LQMNSLRTED TALYYCAKDK SGYGSFYYGM DVWGQGTTVT  120
VSS                                                          123

SEQ ID NO: 819          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 819
```

```
ggattcacct ttgatgatta tgcc                                        24

SEQ ID NO: 820         moltype = AA  length = 8
FEATURE                Location/Qualifiers
REGION                 1..8
                       note = Synthetic
source                 1..8
                       mol_type = protein
                       organism = synthetic construct
SEQUENCE: 820
GFTFDDYA                                                          8

SEQ ID NO: 821         moltype = DNA  length = 24
FEATURE                Location/Qualifiers
misc_feature           1..24
                       note = Synthetic
source                 1..24
                       mol_type = other DNA
                       organism = synthetic construct
SEQUENCE: 821
attagttgga atagtggtag taaa                                        24

SEQ ID NO: 822         moltype = AA  length = 8
FEATURE                Location/Qualifiers
REGION                 1..8
                       note = Synthetic
source                 1..8
                       mol_type = protein
                       organism = synthetic construct
SEQUENCE: 822
ISWNSGSK                                                          8

SEQ ID NO: 823         moltype = DNA  length = 48
FEATURE                Location/Qualifiers
misc_feature           1..48
                       note = Synthetic
source                 1..48
                       mol_type = other DNA
                       organism = synthetic construct
SEQUENCE: 823
gcaaaagata agagtggcta cggctccttc tactacggta tggacgtc              48

SEQ ID NO: 824         moltype = AA  length = 16
FEATURE                Location/Qualifiers
REGION                 1..16
                       note = Synthetic
source                 1..16
                       mol_type = protein
                       organism = synthetic construct
SEQUENCE: 824
AKDKSGYGSF YYGMDV                                                 16

SEQ ID NO: 825         moltype = DNA  length = 318
FEATURE                Location/Qualifiers
misc_feature           1..318
                       note = Synthetic
source                 1..318
                       mol_type = other DNA
                       organism = synthetic construct
SEQUENCE: 825
gacatccaga tgacccagtc tccttccacc ctgtctgcat ctgtaggaga cagagtcacc  60
atcacttgcc gggccagtca gagtattagt agctggttgg cctggtatca gcagaaacca  120
gggaaagccc ctaagctcct gatctataag gcgtctagtt tagaaagtgg ggtcccatca  180
aggttcagcg gcagtggatc tgggacagaa ttcactctca ccatcagcag cctgcagcct  240
gatgattttg caacttatta ctgccaacag tataatagtt attctccgtt cggccaaggg  300
accaaggtgg aaatcaaa                                               318

SEQ ID NO: 826         moltype = AA  length = 106
FEATURE                Location/Qualifiers
REGION                 1..106
                       note = Synthetic
source                 1..106
                       mol_type = protein
                       organism = synthetic construct
SEQUENCE: 826
DIQMTQSPST LSASVGDRVT ITCRASQSIS SWLAWYQQKP GKAPKLLIYK ASSLESGVPS  60
RFSGSGSGTE FTLTISSLQP DDFATYYCQQ YNSYSPFGQG TKVEIK                106

SEQ ID NO: 827         moltype = DNA  length = 18
```

```
FEATURE                 Location/Qualifiers
misc_feature            1..18
                        note = Synthetic
source                  1..18
                        mol_type = other DNA
                        organism = synthetic construct
SEQUENCE: 827
cagagtatta gtagctgg                                                18

SEQ ID NO: 828          moltype = AA  length = 6
FEATURE                 Location/Qualifiers
REGION                  1..6
                        note = Synthetic
source                  1..6
                        mol_type = protein
                        organism = synthetic construct
SEQUENCE: 828
QSISSW                                                             6

SEQ ID NO: 829          moltype =   length =
SEQUENCE: 829
000

SEQ ID NO: 830          moltype =   length =
SEQUENCE: 830
000

SEQ ID NO: 831          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 831
caacagtata atagttattc tccg                                         24

SEQ ID NO: 832          moltype = AA  length = 8
FEATURE                 Location/Qualifiers
REGION                  1..8
                        note = Synthetic
source                  1..8
                        mol_type = protein
                        organism = synthetic construct
SEQUENCE: 832
QQYNSYSP                                                           8

SEQ ID NO: 833          moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 833
caggtgcaac tggtggagtc tgggggaggc gtggtccagc ctgggaggtc cctgagactc  60
tcctgtgcag cctctggact caccttcagt acctatgtca tgcactgggt ccgccaggct  120
ccaggcaagg ggctggcgtg ggtggcagtt atagcaaatg atggaagtaa taaatattat  180
gcagactccg tgaagggccg attcaccatc tccagagaca actccaagaa cacgctgtat  240
ctgcaaatga atagcctgag acctgaggac acggctgtgt atttttgtgc gaaagagggg  300
ggtaccagtg ggtcctacta ttactatgga atggacgtct ggggtcaagg gactacggtc  360
accgtctcct ca                                                      372

SEQ ID NO: 834          moltype = AA  length = 124
FEATURE                 Location/Qualifiers
REGION                  1..124
                        note = Synthetic
source                  1..124
                        mol_type = protein
                        organism = synthetic construct
SEQUENCE: 834
QVQLVESGGG VVQPGRSLRL SCAASGLTFS TYVMHWVRQA PGKGLAWVAV IANDGSNKYY  60
ADSVKGRFTI SRDNSKNTLY LQMNSLRPED TAVYFCAKEG GTSGSYYYYG MDVWGQGTTV  120
TVSS                                                               124

SEQ ID NO: 835          moltype = DNA  length = 24
FEATURE                 Location/Qualifiers
misc_feature            1..24
                        note = Synthetic
```

```
source                1..24
                      mol_type = other DNA
                      organism = synthetic construct
SEQUENCE: 835
ggactcacct tcagtaccta tgtc                                        24

SEQ ID NO: 836        moltype = AA  length = 8
FEATURE               Location/Qualifiers
REGION                1..8
                      note = Synthetic
source                1..8
                      mol_type = protein
                      organism = synthetic construct
SEQUENCE: 836
GLTFSTYV                                                          8

SEQ ID NO: 837        moltype = DNA  length = 24
FEATURE               Location/Qualifiers
misc_feature          1..24
                      note = Synthetic
source                1..24
                      mol_type = other DNA
                      organism = synthetic construct
SEQUENCE: 837
atagcaaatg atggaagtaa taaa                                        24

SEQ ID NO: 838        moltype = AA  length = 8
FEATURE               Location/Qualifiers
REGION                1..8
                      note = Synthetic
source                1..8
                      mol_type = protein
                      organism = synthetic construct
SEQUENCE: 838
IANDGSNK                                                          8

SEQ ID NO: 839        moltype = DNA  length = 51
FEATURE               Location/Qualifiers
misc_feature          1..51
                      note = Synthetic
source                1..51
                      mol_type = other DNA
                      organism = synthetic construct
SEQUENCE: 839
gcgaaagagg ggggtaccag tgggtcctac tattactatg gaatggacgt c          51

SEQ ID NO: 840        moltype = AA  length = 17
FEATURE               Location/Qualifiers
REGION                1..17
                      note = Synthetic
source                1..17
                      mol_type = protein
                      organism = synthetic construct
SEQUENCE: 840
AKEGGTSGSY YYYGMDV                                                17

SEQ ID NO: 841        moltype = DNA  length = 342
FEATURE               Location/Qualifiers
misc_feature          1..342
                      note = Synthetic
source                1..342
                      mol_type = other DNA
                      organism = synthetic construct
SEQUENCE: 841
gacatccaga tgacccagtc tccagactcc ctggctgtgt ctctgggcga gagggccacc  60
atcaactgca agtccagcca gagtctttta ttcaactcca tcaataagaa ctacttagct  120
tggtaccagc agaaaccagg acagcctcct aagcttctcc tttactgggc atctacccgg  180
gaatccggga tccctgaccg attcagtggc agcgggtctg ggacagattt cactctcacc  240
atcaccagcc tgcaggctga agatgtggca ctttattact gtcagcaata ttatagtatt  300
ccgtggacgt tcggccaagg gaccaaggtg gaaatcaaac ga                    342

SEQ ID NO: 842        moltype = AA  length = 114
FEATURE               Location/Qualifiers
REGION                1..114
                      note = Synthetic
source                1..114
                      mol_type = protein
                      organism = synthetic construct
SEQUENCE: 842
```

```
DIQMTQSPDS LAVSLGERAT INCKSSQSLL FNSINKNYLA WYQQKPGQPP KLLLYWASTR  60
ESGIPDRFSG SGSGTDFTLT ITSLQAEDVA LYYCQQYYSI PWTFGQGTKV EIKR        114

SEQ ID NO: 843          moltype = DNA  length = 36
FEATURE                 Location/Qualifiers
misc_feature            1..36
                        note = Synthetic
source                  1..36
                        mol_type = other DNA
                        organism = synthetic construct
SEQUENCE: 843
cagagtcttt tattcaactc catcaataag aactac                            36

SEQ ID NO: 844          moltype = AA  length = 12
FEATURE                 Location/Qualifiers
REGION                  1..12
                        note = Synthetic
source                  1..12
                        mol_type = protein
                        organism = synthetic construct
SEQUENCE: 844
QSLLFNSINK NY                                                      12

SEQ ID NO: 845          moltype =   length =
SEQUENCE: 845
000

SEQ ID NO: 846          moltype =   length =
SEQUENCE: 846
000

SEQ ID NO: 847          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 847
cagcaatatt atagtattcc gtggacg                                      27

SEQ ID NO: 848          moltype = AA  length = 9
FEATURE                 Location/Qualifiers
REGION                  1..9
                        note = Synthetic
source                  1..9
                        mol_type = protein
                        organism = synthetic construct
SEQUENCE: 848
QQYYSIPWT                                                          9

SEQ ID NO: 849          moltype = DNA  length = 354
FEATURE                 Location/Qualifiers
misc_feature            1..354
                        note = Synthetic
source                  1..354
                        mol_type = other DNA
                        organism = synthetic construct
SEQUENCE: 849
caggtgcagc tggtggagtc tggggctgaa gtgaagaagc ctggggcctc agtgaaggtc  60
tcctgcaaga cttctggata caccttcacc ggctactata tgcactggat acgacaggcc  120
cctggacaag ggcttgagtg gatgggatgg atcaacccta aaagtggtgg cacaaattat  180
gcacagaagt ttcagggcag ggtcaccatg accagggaca cgtccatcag cacagcctac  240
atggaactga gcaggctgag atccgacgac atggccgtgt attattgtgc gagaatgggg  300
gacggtgcag tgtttgactt ctggggccag ggaaccctgg tcaccgtctc ctca        354

SEQ ID NO: 850          moltype = AA  length = 118
FEATURE                 Location/Qualifiers
REGION                  1..118
                        note = Synthetic
source                  1..118
                        mol_type = protein
                        organism = synthetic construct
SEQUENCE: 850
QVQLVESGAE VKKPGASVKV SCKTSGYTFT GYYMHWIRQA PGQGLEWMGW INPKSGGTNY  60
AQKFQGRVTM TRDTSISTAY MELSRLRSDD MAVYYCARMG DGAVFDFWGQ GTLVTVSS    118

SEQ ID NO: 851          moltype = DNA  length = 24
FEATURE                 Location/Qualifiers
```

```
misc_feature          1..24
                      note = Synthetic
source                1..24
                      mol_type = other DNA
                      organism = synthetic construct
SEQUENCE: 851
ggatacacct tcaccggcta ctat                                         24

SEQ ID NO: 852        moltype = AA  length = 8
FEATURE               Location/Qualifiers
REGION                1..8
                      note = Synthetic
source                1..8
                      mol_type = protein
                      organism = synthetic construct
SEQUENCE: 852
GYTFTGYY                                                           8

SEQ ID NO: 853        moltype = DNA  length = 24
FEATURE               Location/Qualifiers
misc_feature          1..24
                      note = Synthetic
source                1..24
                      mol_type = other DNA
                      organism = synthetic construct
SEQUENCE: 853
atcaacccta aaagtggtgg caca                                         24

SEQ ID NO: 854        moltype = AA  length = 8
FEATURE               Location/Qualifiers
REGION                1..8
                      note = Synthetic
source                1..8
                      mol_type = protein
                      organism = synthetic construct
SEQUENCE: 854
INPKSGGT                                                           8

SEQ ID NO: 855        moltype = DNA  length = 33
FEATURE               Location/Qualifiers
misc_feature          1..33
                      note = Synthetic
source                1..33
                      mol_type = other DNA
                      organism = synthetic construct
SEQUENCE: 855
gcgagaatgg gggacggtgc agtgtttgac ttc                               33

SEQ ID NO: 856        moltype = AA  length = 11
FEATURE               Location/Qualifiers
REGION                1..11
                      note = Synthetic
source                1..11
                      mol_type = protein
                      organism = synthetic construct
SEQUENCE: 856
ARMGDGAVFD F                                                       11

SEQ ID NO: 857        moltype = DNA  length = 324
FEATURE               Location/Qualifiers
misc_feature          1..324
                      note = Synthetic
source                1..324
                      mol_type = other DNA
                      organism = synthetic construct
SEQUENCE: 857
gccatccaga tgacccagtc tccatcctcc ctgtctgcat ctgtaggaga cagagtcacc  60
atcacttgcc gggcaagtca gaggattagc agctttttaa attggtatca gcagaaacca  120
gggaaagccc ctaagctcct gatctatact gcatccaatt tacaaaatgg ggtcccatca  180
aggttcagtg gcagtggatc tgggacagat ttcactctca ctatcagcag tctgcaacct  240
gaagattttg ctacttacta ctgtcaacag agttacagga ccccgctcac tttcggcgga  300
gggaccaagg tggaaatcaa acga                                         324

SEQ ID NO: 858        moltype = AA  length = 108
FEATURE               Location/Qualifiers
REGION                1..108
                      note = Synthetic
source                1..108
                      mol_type = protein
```

```
                          organism = synthetic construct
SEQUENCE: 858
AIQMTQSPSS LSASVGDRVT ITCRASQRIS SFLNWYQQKP GKAPKLLIYT ASNLQNGVPS  60
RFSGSGSGTD FTLTISSLQP EDFATYYCQQ SYRTPLTFGG GTKVEIKR               108

SEQ ID NO: 859            moltype = DNA  length = 18
FEATURE                   Location/Qualifiers
misc_feature              1..18
                          note = Synthetic
source                    1..18
                          mol_type = other DNA
                          organism = synthetic construct
SEQUENCE: 859
cagaggatta gcagcttt                                                18

SEQ ID NO: 860            moltype = AA  length = 6
FEATURE                   Location/Qualifiers
REGION                    1..6
                          note = Synthetic
source                    1..6
                          mol_type = protein
                          organism = synthetic construct
SEQUENCE: 860
QRISSF                                                             6

SEQ ID NO: 861            moltype =   length =
SEQUENCE: 861
000

SEQ ID NO: 862            moltype =   length =
SEQUENCE: 862
000

SEQ ID NO: 863            moltype = DNA  length = 27
FEATURE                   Location/Qualifiers
misc_feature              1..27
                          note = Synthetic
source                    1..27
                          mol_type = other DNA
                          organism = synthetic construct
SEQUENCE: 863
caacagagtt acaggacccc gctcact                                      27

SEQ ID NO: 864            moltype = AA  length = 9
FEATURE                   Location/Qualifiers
REGION                    1..9
                          note = Synthetic
source                    1..9
                          mol_type = protein
                          organism = synthetic construct
SEQUENCE: 864
QQSYRTPLT                                                          9

SEQ ID NO: 865            moltype = DNA  length = 369
FEATURE                   Location/Qualifiers
misc_feature              1..369
                          note = Synthetic
source                    1..369
                          mol_type = other DNA
                          organism = synthetic construct
SEQUENCE: 865
gaggtgcagc tggtggagtc tgggggaggc ttggtacagc ctggcaggtc cctgagactc  60
tcctgtgcag cctctggatt cacctttgat gattatacca tgcactgggt ccggcaagct  120
ccagggaagg gcctggagtg ggtctcaggt attagttgga acagtggtag cataggctat  180
gcggactctg tgaagggccg attcaccatt tccagagaca acgccaagaa ctccctgtat  240
ttgcaaatga acagtctgag agctgaggac acggccttgt tttactgtgc aaaagatcaa  300
agtggttacg gccactacta ctacggtatg gacgtctggg gccaagggac cacggtcacc  360
gtctcctca                                                          369

SEQ ID NO: 866            moltype = AA  length = 123
FEATURE                   Location/Qualifiers
REGION                    1..123
                          note = Synthetic
source                    1..123
                          mol_type = protein
                          organism = synthetic construct
SEQUENCE: 866
EVQLVESGGG LVQPGRSLRL SCAASGFTFD DYTMHWVRQA PGKGLEWVSG ISWNSGSIGY  60
ADSVKGRFTI SRDNAKNSLY LQMNSLRAED TALFYCAKDQ SGYGHYYYGM DVWGQGTTVT  120
```

```
VSS                                                          123

SEQ ID NO: 867          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 867
ggattcacct ttgatgatta tacc                                   24

SEQ ID NO: 868          moltype = AA  length = 8
FEATURE                 Location/Qualifiers
REGION                  1..8
                        note = Synthetic
source                  1..8
                        mol_type = protein
                        organism = synthetic construct
SEQUENCE: 868
GFTFDDYT                                                     8

SEQ ID NO: 869          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 869
attagttgga acagtggtag cata                                   24

SEQ ID NO: 870          moltype = AA  length = 8
FEATURE                 Location/Qualifiers
REGION                  1..8
                        note = Synthetic
source                  1..8
                        mol_type = protein
                        organism = synthetic construct
SEQUENCE: 870
ISWNSGSI                                                     8

SEQ ID NO: 871          moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 871
gcaaaagatc aaagtggtta cggccactac tactacggta tggacgtc         48

SEQ ID NO: 872          moltype = AA  length = 16
FEATURE                 Location/Qualifiers
REGION                  1..16
                        note = Synthetic
source                  1..16
                        mol_type = protein
                        organism = synthetic construct
SEQUENCE: 872
AKDQSGYGHY YYGMDV                                            16

SEQ ID NO: 873          moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 873
gaaatagtga tgacgcagtc tccagccacc ctgtctgtgt ctccagggga aagagccacc  60
ctctcctgta gggccagtca gagtgttagc agcaacttag cctggtacca gcagaaacct  120
ggccaggctc ccaggctcct catctatggt gcatccacca gggccactga tatcccagcc  180
aggttcagtg gcagtgggtc tgggacagag ttcactctca ccatcagcag cctgcagtct  240
gaagattttg cagtttatca ctgtcagcag tataataact ggccgctcac tttcggcgga  300
gggaccaagg tggagatcaa a                                      321

SEQ ID NO: 874          moltype = AA  length = 107
FEATURE                 Location/Qualifiers
```

```
REGION                 1..107
                       note = Synthetic
source                 1..107
                       mol_type = protein
                       organism = synthetic construct
SEQUENCE: 874
EIVMTQSPAT LSVSPGERAT LSCRASQSVS SNLAWYQQKP GQAPRLLIYG ASTRATDIPA  60
RFSGSGSGTE FTLTISSLQS EDFAVYHCQQ YNNWPLTFGG GTKVEIK               107

SEQ ID NO: 875         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 875
cagagtgtta gcagcaac                                               18

SEQ ID NO: 876         moltype = AA  length = 6
FEATURE                Location/Qualifiers
REGION                 1..6
                       note = Synthetic
source                 1..6
                       mol_type = protein
                       organism = synthetic construct
SEQUENCE: 876
QSVSSN                                                            6

SEQ ID NO: 877         moltype =   length =
SEQUENCE: 877
000

SEQ ID NO: 878         moltype =   length =
SEQUENCE: 878
000

SEQ ID NO: 879         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 879
cagcagtata ataactggcc gctcact                                     27

SEQ ID NO: 880         moltype = AA  length = 9
FEATURE                Location/Qualifiers
REGION                 1..9
                       note = Synthetic
source                 1..9
                       mol_type = protein
                       organism = synthetic construct
SEQUENCE: 880
QQYNNWPLT                                                         9

SEQ ID NO: 881         moltype = DNA  length = 387
FEATURE                Location/Qualifiers
misc_feature           1..387
                       note = Synthetic
source                 1..387
                       mol_type = other DNA
                       organism = synthetic construct
SEQUENCE: 881
gaggtgcagc tggtggagtc tgggggaggc gtggtccagc ctgggaggtc cctgagactc  60
tcctgtgcag cctctggatt caccttcagt tactatggca tgcactgggt ccgccaggct  120
ccaggcaagg ggctggagtg ggtggcagtt atatcatttg atggaaagaa taaatattat  180
gcagactccg tgatgggccg attcaccatc tccagagaca attccaagaa tacactgtat  240
ctgcaaatga acagcctgag agctgaggac tcggctgtgt ttttctgtgc gaggtcttac  300
gacattttga ctggttatgg agccggttac agctaccact acggtatgga cgtctggggc  360
caagggacca cggtcaccgt ctcctca                                     387

SEQ ID NO: 882         moltype = AA  length = 129
FEATURE                Location/Qualifiers
REGION                 1..129
                       note = Synthetic
source                 1..129
                       mol_type = protein
```

```
                         organism = synthetic construct
SEQUENCE: 882
EVQLVESGGG VVQPGRSLRL SCAASGFTFS YYGMHWVRQA PGKGLEWVAV ISFDGKNKYY  60
ADSVMGRFTI SRDNSKNTLY LQMNSLRAED SAVFFCARSY DILTGYGAGY SYHYGMDVWG  120
QGTTVTVSS                                                         129

SEQ ID NO: 883          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 883
ggattcacct tcagttacta tggc                                        24

SEQ ID NO: 884          moltype = AA  length = 8
FEATURE                 Location/Qualifiers
REGION                  1..8
                        note = Synthetic
source                  1..8
                        mol_type = protein
                        organism = synthetic construct
SEQUENCE: 884
GFTFSYYG                                                          8

SEQ ID NO: 885          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 885
atatcatttg atggaaagaa taaa                                        24

SEQ ID NO: 886          moltype = AA  length = 8
FEATURE                 Location/Qualifiers
REGION                  1..8
                        note = Synthetic
source                  1..8
                        mol_type = protein
                        organism = synthetic construct
SEQUENCE: 886
ISFDGKNK                                                          8

SEQ ID NO: 887          moltype = DNA  length = 66
FEATURE                 Location/Qualifiers
misc_feature            1..66
                        note = Synthetic
source                  1..66
                        mol_type = other DNA
                        organism = synthetic construct
SEQUENCE: 887
gcgaggtctt acgacatttt gactggttat ggagccggtt acagctacca ctacggtatg  60
gacgtc                                                            66

SEQ ID NO: 888          moltype = AA  length = 22
FEATURE                 Location/Qualifiers
REGION                  1..22
                        note = Synthetic
source                  1..22
                        mol_type = protein
                        organism = synthetic construct
SEQUENCE: 888
ARSYDILTGY GAGYSYHYGM DV                                          22

SEQ ID NO: 889          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 889
gccatccaga tgacccagtc tccatcctcc ctgtctgcat ctgtaggaga cagagtcacc  60
atcacttgcc gggcaagtca gaggattagc agctttttaa attggtatca gcagaaacca  120
gggaaagccc ctaagctcct aatctatact gcatccaatt tacaaaatgg ggtcccatca  180
aggttcagtg gcagtggatc tgggacagat ttcactctca ccatcagcag tctgcaacct  240
```

```
gaagattttg caacttacta ctgtcaacag agttacagga ccccgctcac tttcggcgga  300
gggaccaagg tggagatcaa acga                                         324

SEQ ID NO: 890         moltype = AA  length = 108
FEATURE                Location/Qualifiers
REGION                 1..108
                       note = Synthetic
source                 1..108
                       mol_type = protein
                       organism = synthetic construct
SEQUENCE: 890
AIQMTQSPSS LSASVGDRVT ITCRASQRIS SFLNWYQQKP GKAPKLLIYT ASNLQNGVPS  60
RFSGSGSGTD FTLTISSLQP EDFATYYCQQ SYRTPLTFGG GTKVEIKR               108

SEQ ID NO: 891         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 891
cagaggatta gcagcttt                                                18

SEQ ID NO: 892         moltype = AA  length = 6
FEATURE                Location/Qualifiers
REGION                 1..6
                       note = Synthetic
source                 1..6
                       mol_type = protein
                       organism = synthetic construct
SEQUENCE: 892
QRISSF                                                             6

SEQ ID NO: 893         moltype =   length =
SEQUENCE: 893
000

SEQ ID NO: 894         moltype =   length =
SEQUENCE: 894
000

SEQ ID NO: 895         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 895
caacagagtt acaggacccc gctcact                                      27

SEQ ID NO: 896         moltype = AA  length = 9
FEATURE                Location/Qualifiers
REGION                 1..9
                       note = Synthetic
source                 1..9
                       mol_type = protein
                       organism = synthetic construct
SEQUENCE: 896
QQSYRTPLT                                                          9

SEQ ID NO: 897         moltype = DNA  length = 354
FEATURE                Location/Qualifiers
misc_feature           1..354
                       note = Synthetic
source                 1..354
                       mol_type = other DNA
                       organism = synthetic construct
SEQUENCE: 897
caggtgcagc tggtggagtc tggggctgaa gtgaagaagc ctggggcctc agtgaaggtc  60
tcctgcaaga cttctggata caccctctcc ggctattata tgcactggat gcgacaggcc  120
cctggacaag ggcttgagtg gatgggatgg attaacccta aaagtggtgt cacaaattat  180
gcacagaagt ttcaggacag agtcgccatg accagggaca cgtccatcag cacagcctac  240
atggaactga gcaggctgag atctgacgac acggccgtgt attactgtgc gagaatgggg  300
gacggtgcag tgtttgactt ctgggcccag ggaaccctgg tcaccgtctc ctca        354

SEQ ID NO: 898         moltype = AA  length = 118
FEATURE                Location/Qualifiers
```

```
REGION                  1..118
                        note = Synthetic
source                  1..118
                        mol_type = protein
                        organism = synthetic construct
SEQUENCE: 898
QVQLVESGAE VKKPGASVKV SCKTSGYTLS GYYMHWMRQA PGQGLEWMGW INPKSGVTNY  60
AQKFQDRVAM TRDTSISTAY MELSRLRSDD TAVYYCARMG DGAVFDFWAQ GTLVTVSS    118

SEQ ID NO: 899          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 899
ggatacaccc tctccggcta ttat                                         24

SEQ ID NO: 900          moltype = AA  length = 8
FEATURE                 Location/Qualifiers
REGION                  1..8
                        note = Synthetic
source                  1..8
                        mol_type = protein
                        organism = synthetic construct
SEQUENCE: 900
GYTLSGYY                                                           8

SEQ ID NO: 901          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 901
attaacccta aaagtggtgt caca                                         24

SEQ ID NO: 902          moltype = AA  length = 8
FEATURE                 Location/Qualifiers
REGION                  1..8
                        note = Synthetic
source                  1..8
                        mol_type = protein
                        organism = synthetic construct
SEQUENCE: 902
INPKSGVT                                                           8

SEQ ID NO: 903          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 903
gcgagaatgg gggacggtgc agtgtttgac ttc                               33

SEQ ID NO: 904          moltype = AA  length = 11
FEATURE                 Location/Qualifiers
REGION                  1..11
                        note = Synthetic
source                  1..11
                        mol_type = protein
                        organism = synthetic construct
SEQUENCE: 904
ARMGDGAVFD F                                                       11

SEQ ID NO: 905          moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 905
gacatccagt tgacccagtc tccatcctcc ctgtctgcat ctgtaggaga cagagtcacc  60
atcacttgcc gggcaagtca gaggattagc agctttttaa attggtatca gcagaaacca  120
```

-continued

```
gggaaagccc ctaagctcct aatctatact gcatccaatt tacaaaatgg ggtcccatca  180
aggttcagtg gcagtggatc tgggacagat ttcactctca ccatcagcag tctgcaacct  240
gaagattttg caacttacta ctgtcaacag agttacagga ccccgctcac tttcggcgga  300
gggaccaagc tggagatcaa acga                                          324

SEQ ID NO: 906         moltype = AA  length = 108
FEATURE                Location/Qualifiers
REGION                 1..108
                       note = Synthetic
source                 1..108
                       mol_type = protein
                       organism = synthetic construct
SEQUENCE: 906
DIQLTQSPSS LSASVGDRVT ITCRASQRIS SFLNWYQQKP GKAPKLLIYT ASNLQNGVPS  60
RFSGSGSGTD FTLTISSLQP EDFATYYCQQ SYRTPLTFGG GTKLEIKR                108

SEQ ID NO: 907         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 907
cagaggatta gcagcttt                                                 18

SEQ ID NO: 908         moltype = AA  length = 6
FEATURE                Location/Qualifiers
REGION                 1..6
                       note = Synthetic
source                 1..6
                       mol_type = protein
                       organism = synthetic construct
SEQUENCE: 908
QRISSF                                                              6

SEQ ID NO: 909         moltype =   length =
SEQUENCE: 909
000

SEQ ID NO: 910         moltype =   length =
SEQUENCE: 910
000

SEQ ID NO: 911         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 911
caacagagtt acaggacccc gctcact                                       27

SEQ ID NO: 912         moltype = AA  length = 9
FEATURE                Location/Qualifiers
REGION                 1..9
                       note = Synthetic
source                 1..9
                       mol_type = protein
                       organism = synthetic construct
SEQUENCE: 912
QQSYRTPLT                                                           9

SEQ ID NO: 913         moltype = DNA  length = 372
FEATURE                Location/Qualifiers
misc_feature           1..372
                       note = Synthetic
source                 1..372
                       mol_type = other DNA
                       organism = synthetic construct
SEQUENCE: 913
caggtgcagc tggtggagtc tgggggaggc gtggtccagc ctgggaggtc cctgagactc  60
tcctgtgcag cctctggatt caccttcagt agctatggca tgcactgggt ccgccaggct  120
ccaggcaagg ggctggagtg ggtgtcaact atatcatttg atggaagtaa caaatactat  180
gcagactccg tgaagggccg attcaccatc tccagagaca attccaagaa cacgctgtat  240
ctgcaaatga acagcctgag acctgaggac acggctgtgt attactgtgc gaaagggggg  300
ggtaccagtg ggtcctactt ttactacggt atggacgtct ggggccaagg gaccacggtc  360
accgtctcct ca                                                       372
```

-continued

```
SEQ ID NO: 914          moltype = AA  length = 124
FEATURE                 Location/Qualifiers
REGION                  1..124
                        note = Synthetic
source                  1..124
                        mol_type = protein
                        organism = synthetic construct
SEQUENCE: 914
QVQLVESGGG VVQPGRSLRL SCAASGFTFS SYGMHWVRQA PGKGLEWVST ISFDGSNKYY   60
ADSVKGRFTI SRDNSKNTLY LQMNSLRPED TAVYYCAKGG GTSGSYFYYG MDVWGQGTTV  120
TVSS                                                               124

SEQ ID NO: 915          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 915
ggattcacct tcagtagcta tggc                                          24

SEQ ID NO: 916          moltype = AA  length = 8
FEATURE                 Location/Qualifiers
REGION                  1..8
                        note = Synthetic
source                  1..8
                        mol_type = protein
                        organism = synthetic construct
SEQUENCE: 916
GFTFSSYG                                                             8

SEQ ID NO: 917          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 917
atatcatttg atggaagtaa caaa                                          24

SEQ ID NO: 918          moltype = AA  length = 8
FEATURE                 Location/Qualifiers
REGION                  1..8
                        note = Synthetic
source                  1..8
                        mol_type = protein
                        organism = synthetic construct
SEQUENCE: 918
ISFDGSNK                                                             8

SEQ ID NO: 919          moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 919
gcgaaagggg ggggtaccag tgggtcctac ttttactacg gtatggacgt c            51

SEQ ID NO: 920          moltype = AA  length = 17
FEATURE                 Location/Qualifiers
REGION                  1..17
                        note = Synthetic
source                  1..17
                        mol_type = protein
                        organism = synthetic construct
SEQUENCE: 920
AKGGGTSGSY FYYGMDV                                                   17

SEQ ID NO: 921          moltype = DNA  length = 324
FEATURE                 Location/Qualifiers
misc_feature            1..324
                        note = Synthetic
source                  1..324
                        mol_type = other DNA
```

```
                         organism = synthetic construct
SEQUENCE: 921
gccatccaga tgacccagtc tccatcctcc ctgtctgcat ctgtaggaga cagagtcacc  60
atcacttgcc gggcaagtca gaggattagc agctttttaa attggtatca gcagaaacca  120
gggaaagccc ctaagctcct aatctatact gcatccaatt tacaaaatgg ggtcccatca  180
aggttcagtg gcagtggatc tgggacagat ttcactctca ccatcagcag tctgcaacct  240
gaagattttg caacttacta ctgtcaacag agttacagga ccccgctcac tttcggcgga  300
gggaccaagc tggagatcaa acga                                         324

SEQ ID NO: 922           moltype = AA  length = 108
FEATURE                  Location/Qualifiers
REGION                   1..108
                         note = Synthetic
source                   1..108
                         mol_type = protein
                         organism = synthetic construct
SEQUENCE: 922
AIQMTQSPSS LSASVGDRVT ITCRASQRIS SFLNWYQQKP GKAPKLLIYT ASNLQNGVPS  60
RFSGSGSGTD FTLTISSLQP EDFATYYCQQ SYRTPLTFGG GTKLEIKR               108

SEQ ID NO: 923           moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 923
cagaggatta gcagcttt                                                18

SEQ ID NO: 924           moltype = AA  length = 6
FEATURE                  Location/Qualifiers
REGION                   1..6
                         note = Synthetic
source                   1..6
                         mol_type = protein
                         organism = synthetic construct
SEQUENCE: 924
QRISSF                                                             6

SEQ ID NO: 925           moltype =   length =
SEQUENCE: 925
000

SEQ ID NO: 926           moltype =   length =
SEQUENCE: 926
000

SEQ ID NO: 927           moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 927
caacagagtt acaggacccc gctcact                                      27

SEQ ID NO: 928           moltype = AA  length = 9
FEATURE                  Location/Qualifiers
REGION                   1..9
                         note = Synthetic
source                   1..9
                         mol_type = protein
                         organism = synthetic construct
SEQUENCE: 928
QQSYRTPLT                                                          9

SEQ ID NO: 929           moltype = DNA  length = 354
FEATURE                  Location/Qualifiers
misc_feature             1..354
                         note = Synthetic
source                   1..354
                         mol_type = other DNA
                         organism = synthetic construct
SEQUENCE: 929
caggttcagc tggtgcagtc tggactgag gtgaagaagc ctggggcctc aatgaaggtc  60
tcctgcaagg cttctggata caccttcacc ggctactata ttcactgggt gcgacaggcc  120
cctggacaag ggcttgagtg gatgggatgg atcaacccta acagtgatgt cacaaagtat  180
```

-continued

```
gcacagaagt ttcagggcag ggtcaccttg accagggaca cgtccatcag tgcagcctat  240
attgacctga gcaggctgag atctgacgac acggccattt attactgtgc gagaatgggg  300
gacggtgcag tgtttgacta ctggggccag ggaaccctgg tcaccgtctc ctca        354

SEQ ID NO: 930          moltype = AA  length = 118
FEATURE                 Location/Qualifiers
REGION                  1..118
                        note = Synthetic
source                  1..118
                        mol_type = protein
                        organism = synthetic construct
SEQUENCE: 930
QVQLVQSGTE VKKPGASMKV SCKASGYTFT GYYIHWVRQA PGQGLEWMGW INPNSDVTKY  60
AQKFQGRVTL TRDTSISAAY IDLSRLRSDD TAIYYCARMG DGAVFDYWGQ GTLVTVSS    118

SEQ ID NO: 931          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 931
ggatacacct tcaccggcta ctat                                         24

SEQ ID NO: 932          moltype = AA  length = 8
FEATURE                 Location/Qualifiers
REGION                  1..8
                        note = Synthetic
source                  1..8
                        mol_type = protein
                        organism = synthetic construct
SEQUENCE: 932
GYTFTGYY                                                           8

SEQ ID NO: 933          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 933
atcaacccta acagtgatgt caca                                         24

SEQ ID NO: 934          moltype = AA  length = 8
FEATURE                 Location/Qualifiers
REGION                  1..8
                        note = Synthetic
source                  1..8
                        mol_type = protein
                        organism = synthetic construct
SEQUENCE: 934
INPNSDVT                                                           8

SEQ ID NO: 935          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 935
gcgagaatgg gggacggtgc agtgtttgac tac                               33

SEQ ID NO: 936          moltype = AA  length = 11
FEATURE                 Location/Qualifiers
REGION                  1..11
                        note = Synthetic
source                  1..11
                        mol_type = protein
                        organism = synthetic construct
SEQUENCE: 936
ARMGDGAVFD Y                                                       11

SEQ ID NO: 937          moltype = DNA  length = 324
FEATURE                 Location/Qualifiers
misc_feature            1..324
                        note = Synthetic
```

```
source                  1..324
                        mol_type = other DNA
                        organism = synthetic construct
SEQUENCE: 937
gacatccagt tgacccagtc tccatcctcc ctgtctgcat ctgtaggaga cagagtcacc  60
atcacttgcc gggcaagtca acgcattagc agctatttaa attggtatca acagaaacca  120
gggaaagccc ctaaggtgct gatctctgtt gcatccagtt tacaaagtgg ggtcccatca  180
aggttcagtg gcagtggatt tgggacagat ttcactctca ccatcagcag tctgcaacct  240
gaggattctg catcttacta ctgtcaacag agttacaata ccccgctcac tttcggcggc  300
gggaccaagc tggagatcaa acga                                         324

SEQ ID NO: 938          moltype = AA  length = 108
FEATURE                 Location/Qualifiers
REGION                  1..108
                        note = Synthetic
source                  1..108
                        mol_type = protein
                        organism = synthetic construct
SEQUENCE: 938
DIQLTQSPSS LSASVGDRVT ITCRASQRIS SYLNWYQQKP GKAPKVLISV ASSLQSGVPS  60
RFSGSGFGTD FTLTISSLQP EDSASYYCQQ SYNTPLTFGG GTKLEIKR               108

SEQ ID NO: 939          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 939
caacgcatta gcagctat                                                18

SEQ ID NO: 940          moltype = AA  length = 6
FEATURE                 Location/Qualifiers
REGION                  1..6
                        note = Synthetic
source                  1..6
                        mol_type = protein
                        organism = synthetic construct
SEQUENCE: 940
QRISSY                                                             6

SEQ ID NO: 941          moltype =   length =
SEQUENCE: 941
000

SEQ ID NO: 942          moltype =   length =
SEQUENCE: 942
000

SEQ ID NO: 943          moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 943
caacagagtt acaatacccc gctcact                                      27

SEQ ID NO: 944          moltype = AA  length = 9
FEATURE                 Location/Qualifiers
REGION                  1..9
                        note = Synthetic
source                  1..9
                        mol_type = protein
                        organism = synthetic construct
SEQUENCE: 944
QQSYNTPLT                                                          9

SEQ ID NO: 945          moltype = DNA  length = 354
FEATURE                 Location/Qualifiers
misc_feature            1..354
                        note = Synthetic
source                  1..354
                        mol_type = other DNA
                        organism = synthetic construct
SEQUENCE: 945
gaggtgcagc tggtggagtc tggggctgaa gtgaagaagc ctggggcctc agtgaaggtc  60
```

-continued

```
tcctgcaaga cttctggata cagtttcatt ggctattata tacactggat gcgacaggcc  120
cctggacaag ggcttgaatg gatgggatgg atcaacccta agagtggtgt cacaaattat  180
gcacagaggt ttcagggcag ggtcaccatg accagggaca cgtccatcag tactgcctac  240
atggaactga gcaggctgaa atctgacgac acggccgtgt atttctgtgc gagaatgggg  300
gacggtgcag tgtttgactt ctggggccag ggaaccctgg tcaccgtctc ctca        354

SEQ ID NO: 946          moltype = AA  length = 118
FEATURE                 Location/Qualifiers
REGION                  1..118
                        note = Synthetic
source                  1..118
                        mol_type = protein
                        organism = synthetic construct
SEQUENCE: 946
EVQLVESGAE VKKPGASVKV SCKTSGYSFI GYYIHWMRQA PGQGLEWMGW INPKSGVTNY  60
AQRFQGRVTM TRDTSISTAY MELSRLKSDD TAVYFCARMG DGAVFDFWGQ GTLVTVSS    118

SEQ ID NO: 947          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 947
ggatacagtt tcattggcta ttat                                          24

SEQ ID NO: 948          moltype = AA  length = 8
FEATURE                 Location/Qualifiers
REGION                  1..8
                        note = Synthetic
source                  1..8
                        mol_type = protein
                        organism = synthetic construct
SEQUENCE: 948
GYSFIGYY                                                            8

SEQ ID NO: 949          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 949
atcaacccta agagtggtgt caca                                          24

SEQ ID NO: 950          moltype = AA  length = 8
FEATURE                 Location/Qualifiers
REGION                  1..8
                        note = Synthetic
source                  1..8
                        mol_type = protein
                        organism = synthetic construct
SEQUENCE: 950
INPKSGVT                                                            8

SEQ ID NO: 951          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 951
gcgagaatgg gggacggtgc agtgtttgac ttc                                33

SEQ ID NO: 952          moltype = AA  length = 11
FEATURE                 Location/Qualifiers
REGION                  1..11
                        note = Synthetic
source                  1..11
                        mol_type = protein
                        organism = synthetic construct
SEQUENCE: 952
ARMGDGAVFD F                                                        11

SEQ ID NO: 953          moltype = DNA  length = 324
FEATURE                 Location/Qualifiers
```

```
misc_feature           1..324
                       note = Synthetic
source                 1..324
                       mol_type = other DNA
                       organism = synthetic construct
SEQUENCE: 953
gacatccagt tgacccagtc tccatcctcc ctgtctgcat ctgtaggaga cagagtcacc  60
atcacttgcc gggcaagtca gaggattagc agctttttaa attggtatca gcagaaacca  120
gggaaagtcc ctaagctcct gatctatact gcatccaatt tacaaaatgg ggtcccatca  180
aggttcagtg gcactggatc tgggacagat ttcactctca ccatcagcag tctgcaacct  240
gaagattttg caacttacta ctgtcaacag agttacagga ccccgctcac tttcggcgga  300
gggaccaaag tggatatcaa acga                                         324

SEQ ID NO: 954         moltype = AA  length = 108
FEATURE                Location/Qualifiers
REGION                 1..108
                       note = Synthetic
source                 1..108
                       mol_type = protein
                       organism = synthetic construct
SEQUENCE: 954
DIQLTQSPSS LSASVGDRVT ITCRASQRIS SFLNWYQQKP GKVPKLLIYT ASNLQNGVPS  60
RFSGTGSGTD FTLTISSLQP EDFATYYCQQ SYRTPLTFGG GTKVDIKR               108

SEQ ID NO: 955         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 955
cagaggatta gcagcttt                                                18

SEQ ID NO: 956         moltype = AA  length = 6
FEATURE                Location/Qualifiers
REGION                 1..6
                       note = Synthetic
source                 1..6
                       mol_type = protein
                       organism = synthetic construct
SEQUENCE: 956
QRISSF                                                             6

SEQ ID NO: 957         moltype =   length =
SEQUENCE: 957
000

SEQ ID NO: 958         moltype =   length =
SEQUENCE: 958
000

SEQ ID NO: 959         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 959
caacagagtt acaggacccc gctcact                                      27

SEQ ID NO: 960         moltype = AA  length = 9
FEATURE                Location/Qualifiers
REGION                 1..9
                       note = Synthetic
source                 1..9
                       mol_type = protein
                       organism = synthetic construct
SEQUENCE: 960
QQSYRTPLT                                                          9

SEQ ID NO: 961         moltype = DNA  length = 354
FEATURE                Location/Qualifiers
misc_feature           1..354
                       note = Synthetic
source                 1..354
                       mol_type = other DNA
                       organism = synthetic construct
```

```
SEQUENCE: 961
gaggtgcagc tggtggagtc tggggctgaa gtgaagaagc ctggggcctc agtgaaggtc  60
tcctgcaaga cttctggata caccttcacc ggctactata tgcactggat acgacaggcc  120
cctggacaag ggcttgagtg gatgggatgg atcaacccta aaagtggtgg cacaaattat  180
gcacagaagt ttcagggcag ggtcaccatg accagggaca cgtccatcag cacagcctac  240
atggaactga gcaggctgag atccgacgac atggccgtgt attattgtgc gagaatgggg  300
gacggtgcag tgtttgactt ctggggccag ggaaccctgg tcaccgtctc ctca        354

SEQ ID NO: 962          moltype = AA  length = 118
FEATURE                 Location/Qualifiers
REGION                  1..118
                        note = Synthetic
source                  1..118
                        mol_type = protein
                        organism = synthetic construct
SEQUENCE: 962
EVQLVESGAE VKKPGASVKV SCKTSGYTFT GYYMHWIRQA PGQGLEWMGW INPKSGGTNY  60
AQKFQGRVTM TRDTSISTAY MELSRLRSDD MAVYYCARMG DGAVFDFWGQ GTLVTVSS    118

SEQ ID NO: 963          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 963
ggatacacct tcaccggcta ctat                                         24

SEQ ID NO: 964          moltype = AA  length = 8
FEATURE                 Location/Qualifiers
REGION                  1..8
                        note = Synthetic
source                  1..8
                        mol_type = protein
                        organism = synthetic construct
SEQUENCE: 964
GYTFTGYY                                                           8

SEQ ID NO: 965          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 965
atcaacccta aaagtggtgg caca                                         24

SEQ ID NO: 966          moltype = AA  length = 8
FEATURE                 Location/Qualifiers
REGION                  1..8
                        note = Synthetic
source                  1..8
                        mol_type = protein
                        organism = synthetic construct
SEQUENCE: 966
INPKSGGT                                                           8

SEQ ID NO: 967          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 967
gcgagaatgg gggacggtgc agtgtttgac ttc                               33

SEQ ID NO: 968          moltype = AA  length = 11
FEATURE                 Location/Qualifiers
REGION                  1..11
                        note = Synthetic
source                  1..11
                        mol_type = protein
                        organism = synthetic construct
SEQUENCE: 968
ARMGDGAVFD F                                                       11
```

-continued

```
SEQ ID NO: 969          moltype = DNA  length = 327
FEATURE                 Location/Qualifiers
misc_feature            1..327
                        note = Synthetic
source                  1..327
                        mol_type = other DNA
                        organism = synthetic construct
SEQUENCE: 969
gacatcgtga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta cccctccgct cactttcggc  300
ggagggacca aagtggatat caaacga                                      327

SEQ ID NO: 970          moltype = AA  length = 109
FEATURE                 Location/Qualifiers
REGION                  1..109
                        note = Synthetic
source                  1..109
                        mol_type = protein
                        organism = synthetic construct
SEQUENCE: 970
DIVMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPLTFG GGTKVDIKR              109

SEQ ID NO: 971          moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 971
cagagcatta gcagctat                                                18

SEQ ID NO: 972          moltype = AA  length = 6
FEATURE                 Location/Qualifiers
REGION                  1..6
                        note = Synthetic
source                  1..6
                        mol_type = protein
                        organism = synthetic construct
SEQUENCE: 972
QSISSY                                                             6

SEQ ID NO: 973          moltype =   length =
SEQUENCE: 973
000

SEQ ID NO: 974          moltype =   length =
SEQUENCE: 974
000

SEQ ID NO: 975          moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 975
caacagagtt acagtacccc tccgctcact                                   30

SEQ ID NO: 976          moltype = AA  length = 10
FEATURE                 Location/Qualifiers
REGION                  1..10
                        note = Synthetic
source                  1..10
                        mol_type = protein
                        organism = synthetic construct
SEQUENCE: 976
QQSYSTPPLT                                                         10

SEQ ID NO: 977          moltype = DNA  length = 354
FEATURE                 Location/Qualifiers
misc_feature            1..354
                        note = Synthetic
source                  1..354
```

```
                        mol_type = other DNA
                        organism = synthetic construct
SEQUENCE: 977
caggttcagc tggtgcagtc tgggactgag gtgaagaagc ctggggcctc agtgaaggtc  60
tcctgcaagg cttctggata caccttcacc ggctactata tgcactgggt gcgacaggcc  120
cctggacaag ggcttgagtg gatgggatgg atcaacccta acagtgatgt cacaaactat  180
gcacagaagt ttcagggcag ggtcaccttg accagggaca cgtccatcag tacagcctac  240
attgacctga gcaggctgag atctgacgac acggccattt attactgtgc gagaatgggg  300
gacggtgcag tgtttgacta ctggggccag ggaaccctgg tcaccgtctc ctca        354

SEQ ID NO: 978          moltype = AA  length = 118
FEATURE                 Location/Qualifiers
REGION                  1..118
                        note = Synthetic
source                  1..118
                        mol_type = protein
                        organism = synthetic construct
SEQUENCE: 978
QVQLVQSGTE VKKPGASVKV SCKASGYTFT GYYMHWVRQA PGQGLEWMGW INPNSDVTNY  60
AQKFQGRVTL TRDTSISTAY IDLSRLRSDD TAIYYCARMG DGAVFDYWGQ GTLVTVSS    118

SEQ ID NO: 979          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 979
ggatacacct tcaccggcta ctat                                         24

SEQ ID NO: 980          moltype = AA  length = 8
FEATURE                 Location/Qualifiers
REGION                  1..8
                        note = Synthetic
source                  1..8
                        mol_type = protein
                        organism = synthetic construct
SEQUENCE: 980
GYTFTGYY                                                           8

SEQ ID NO: 981          moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 981
atcaacccta acagtgatgt caca                                         24

SEQ ID NO: 982          moltype = AA  length = 8
FEATURE                 Location/Qualifiers
REGION                  1..8
                        note = Synthetic
source                  1..8
                        mol_type = protein
                        organism = synthetic construct
SEQUENCE: 982
INPNSDVT                                                           8

SEQ ID NO: 983          moltype = DNA  length = 33
FEATURE                 Location/Qualifiers
misc_feature            1..33
                        note = Synthetic
source                  1..33
                        mol_type = other DNA
                        organism = synthetic construct
SEQUENCE: 983
gcgagaatgg gggacggtgc agtgtttgac tac                               33

SEQ ID NO: 984          moltype = AA  length = 11
FEATURE                 Location/Qualifiers
REGION                  1..11
                        note = Synthetic
source                  1..11
                        mol_type = protein
                        organism = synthetic construct
SEQUENCE: 984
```

```
ARMGDGAVFD Y                                                    11

SEQ ID NO: 985         moltype = DNA  length = 324
FEATURE                Location/Qualifiers
misc_feature           1..324
                       note = Synthetic
source                 1..324
                       mol_type = other DNA
                       organism = synthetic construct
SEQUENCE: 985
gacatccaga tgacccagtc tccatcctcc ctgtctgcat ctgtaggaga cagagtcacc  60
atcacttgcc gggcaagtca gcgcattagc agctatttaa attggtatca gcagaaacca  120
gggaaagccc ctaaggtgct gatctctgtt gcatccagtt tgcaaagtgg ggtcccatca  180
aggttcagtg gcagtggatc tgggacagat ttcactctca ccattagtag tctgcaacct  240
gaggattttg catcttacta ctgtcaacag agttacaata ccccgctcac tttcggcgga  300
gggaccaagg tggagatcaa acga                                      324

SEQ ID NO: 986         moltype = AA  length = 108
FEATURE                Location/Qualifiers
REGION                 1..108
                       note = Synthetic
source                 1..108
                       mol_type = protein
                       organism = synthetic construct
SEQUENCE: 986
DIQMTQSPSS LSASVGDRVT ITCRASQRIS SYLNWYQQKP GKAPKVLISV ASSLQSGVPS  60
RFSGSGSGTD FTLTISSLQP EDFASYYCQQ SYNTPLTFGG GTKVEIKR             108

SEQ ID NO: 987         moltype = DNA  length = 18
FEATURE                Location/Qualifiers
misc_feature           1..18
                       note = Synthetic
source                 1..18
                       mol_type = other DNA
                       organism = synthetic construct
SEQUENCE: 987
cagcgcatta gcagctat                                             18

SEQ ID NO: 988         moltype = AA  length = 6
FEATURE                Location/Qualifiers
REGION                 1..6
                       note = Synthetic
source                 1..6
                       mol_type = protein
                       organism = synthetic construct
SEQUENCE: 988
QRISSY                                                          6

SEQ ID NO: 989         moltype =   length =
SEQUENCE: 989
000

SEQ ID NO: 990         moltype =   length =
SEQUENCE: 990
000

SEQ ID NO: 991         moltype = DNA  length = 27
FEATURE                Location/Qualifiers
misc_feature           1..27
                       note = Synthetic
source                 1..27
                       mol_type = other DNA
                       organism = synthetic construct
SEQUENCE: 991
caacagagtt acaatacccc gctcact                                   27

SEQ ID NO: 992         moltype = AA  length = 9
FEATURE                Location/Qualifiers
REGION                 1..9
                       note = Synthetic
source                 1..9
                       mol_type = protein
                       organism = synthetic construct
SEQUENCE: 992
QQSYNTPLT                                                       9

SEQ ID NO: 993         moltype = DNA  length = 381
FEATURE                Location/Qualifiers
misc_feature           1..381
```

-continued

```
                              note = Synthetic
source                        1..381
                              mol_type = other DNA
                              organism = synthetic construct
SEQUENCE: 993
caggtgcagc tggtgcagtc tgggggaggc ttggtcaagc ctggggggtc cctgagactc    60
tcctgtgcag cctctggatt caccttcagt agctatgaca tgagctgggt ccgccaggct   120
ccagggaagg ggctggagtg ggtttcatac attagtagta gtggtaatac catacattac   180
gcagactctg tgaagggccg attcaccatc tccagagaca attccaagaa ctcactttat   240
ctgcaaatga acagcctgag agccgaggac acggccgtgt attactgtgc gaaagccggt   300
cccgctacgg tgacacggag gtactactac tactacggtt tggacgtctg gggccaaggg   360
accacggtca ccgtctcctc a                                             381

SEQ ID NO: 994           moltype = AA  length = 127
FEATURE                  Location/Qualifiers
REGION                   1..127
                         note = Synthetic
source                   1..127
                         mol_type = protein
                         organism = synthetic construct
SEQUENCE: 994
QVQLVQSGGG LVKPGGSLRL SCAASGFTFS SYDMSWVRQA PGKGLEWVSY ISSSGNTIHY    60
ADSVKGRFTI SRDNSKNSLY LQMNSLRAED TAVYYCAKAG PATVTRRYYY YYGLDVWGQG   120
TTVTVSS                                                             127

SEQ ID NO: 995           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 995
ggattcacct tcagtagcta tgac                                           24

SEQ ID NO: 996           moltype = AA  length = 8
FEATURE                  Location/Qualifiers
REGION                   1..8
                         note = Synthetic
source                   1..8
                         mol_type = protein
                         organism = synthetic construct
SEQUENCE: 996
GFTFSSYD                                                              8

SEQ ID NO: 997           moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 997
attagtagta gtggtaatac cata                                           24

SEQ ID NO: 998           moltype = AA  length = 8
FEATURE                  Location/Qualifiers
REGION                   1..8
                         note = Synthetic
source                   1..8
                         mol_type = protein
                         organism = synthetic construct
SEQUENCE: 998
ISSSGNTI                                                              8

SEQ ID NO: 999           moltype = DNA  length = 60
FEATURE                  Location/Qualifiers
misc_feature             1..60
                         note = Synthetic
source                   1..60
                         mol_type = other DNA
                         organism = synthetic construct
SEQUENCE: 999
gcgaaagccg gtcccgctac ggtgacacgg aggtactact actactacgg tttggacgtc    60

SEQ ID NO: 1000          moltype = AA  length = 20
FEATURE                  Location/Qualifiers
REGION                   1..20
                         note = Synthetic
```

```
source                  1..20
                        mol_type = protein
                        organism = synthetic construct
SEQUENCE: 1000
AKAGPATVTR RYYYYYGLDV                                              20

SEQ ID NO: 1001         moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 1001
gacatcgtga tgacccagtc tccatcctcc ctgtctgcat ctgtacgaga cagagtcacc  60
atcacttgcc gggcaagtca gagaattagc agctatttaa attggtttca gcagaaacca  120
gggaaagccc ctaaggtcct gatctatact gcatccagtt tgcaaaatgg ggtcccatca  180
aggttcagtg gcagtggatc tgggacagat ttcactctca ccatcagcag tctgcaacct  240
gaagactttg caacttacta ctgtcagcag agttacagga ccccgctcac tttcggcgga  300
gggaccaagg tggagatcaa acga                                         324

SEQ ID NO: 1002         moltype = AA  length = 108
FEATURE                 Location/Qualifiers
REGION                  1..108
                        note = Synthetic
source                  1..108
                        mol_type = protein
                        organism = synthetic construct
SEQUENCE: 1002
DIVMTQSPSS LSASVRDRVT ITCRASQRIS SYLNWFQQKP GKAPKVLIYT ASSLQNGVPS  60
RFSGSGSGTD FTLTISSLQP EDFATYYCQQ SYRTPLTFGG GTKVEIKR               108

SEQ ID NO: 1003         moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 1003
cagagaatta gcagctat                                                18

SEQ ID NO: 1004         moltype = AA  length = 6
FEATURE                 Location/Qualifiers
REGION                  1..6
                        note = Synthetic
source                  1..6
                        mol_type = protein
                        organism = synthetic construct
SEQUENCE: 1004
QRISSY                                                             6

SEQ ID NO: 1005         moltype =   length =
SEQUENCE: 1005
000

SEQ ID NO: 1006         moltype =   length =
SEQUENCE: 1006
000

SEQ ID NO: 1007         moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 1007
cagcagagtt acaggacccc gctcact                                      27

SEQ ID NO: 1008         moltype = AA  length = 9
FEATURE                 Location/Qualifiers
REGION                  1..9
                        note = Synthetic
source                  1..9
                        mol_type = protein
                        organism = synthetic construct
SEQUENCE: 1008
QQSYRTPLT                                                          9
```

```
SEQ ID NO: 1009        moltype = DNA  length = 354
FEATURE                Location/Qualifiers
misc_feature           1..354
                       note = Synthetic
source                 1..354
                       mol_type = other DNA
                       organism = synthetic construct
SEQUENCE: 1009
caggtgcagc tggtacagtc tggggctgag gtgaagaagc ctggggcctc agtgaaggtc  60
tcctgcaagg cttctggata cacattcatc ggctactata tgcactgggt gcgacaggcc  120
cctggacaag ggcttgagtg gatgggatgg atcaacccta aaagtggtgg cacaaactat  180
gcacagaagt ttcagggcag ggtcaccatg accggggaca cgtccatcag cacagcctac  240
atggagctga gcaggctgag atctgacgac acggccgtgt tttactgtgc gagaatgggg  300
gacggtgcaa tgtttgacta ctggggccag ggaaccctgg tcaccgtctc ctca        354

SEQ ID NO: 1010        moltype = AA  length = 118
FEATURE                Location/Qualifiers
REGION                 1..118
                       note = Synthetic
source                 1..118
                       mol_type = protein
                       organism = synthetic construct
SEQUENCE: 1010
QVQLVQSGAE VKKPGASVKV SCKASGYTFI GYYMHWVRQA PGQGLEWMGW INPKSGGTNY  60
AQKFQGRVTM TGDTSISTAY MELSRLRSDD TAVFYCARMG DGAMFDYWGQ GTLVTVSS    118

SEQ ID NO: 1011        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1011
ggatacacat tcatcggcta ctat                                         24

SEQ ID NO: 1012        moltype = AA  length = 8
FEATURE                Location/Qualifiers
REGION                 1..8
                       note = Synthetic
source                 1..8
                       mol_type = protein
                       organism = synthetic construct
SEQUENCE: 1012
GYTFIGYY                                                           8

SEQ ID NO: 1013        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1013
atcaacccta aaagtggtgg caca                                         24

SEQ ID NO: 1014        moltype = AA  length = 8
FEATURE                Location/Qualifiers
REGION                 1..8
                       note = Synthetic
source                 1..8
                       mol_type = protein
                       organism = synthetic construct
SEQUENCE: 1014
INPKSGGT                                                           8

SEQ ID NO: 1015        moltype = DNA  length = 33
FEATURE                Location/Qualifiers
misc_feature           1..33
                       note = Synthetic
source                 1..33
                       mol_type = other DNA
                       organism = synthetic construct
SEQUENCE: 1015
gcgagaatgg gggacggtgc aatgtttgac tac                               33

SEQ ID NO: 1016        moltype = AA  length = 11
FEATURE                Location/Qualifiers
```

```
REGION               1..11
                     note = Synthetic
source               1..11
                     mol_type = protein
                     organism = synthetic construct
SEQUENCE: 1016
ARMGDGAMFD Y                                                      11

SEQ ID NO: 1017      moltype = DNA  length = 321
FEATURE              Location/Qualifiers
misc_feature         1..321
                     note = Synthetic
source               1..321
                     mol_type = other DNA
                     organism = synthetic construct
SEQUENCE: 1017
gacatccaga tgacccagtc tccatcctcc ctgtctgcat ctgtaggaga cagagtcacc  60
atcacttgcc gggcaagtca gagaattagc agctatttaa attggtatca gcagaaagca  120
gggaaagccc ctaaggtcct gatctatact gcatccagtt tgcaaagtgg ggtcccatca  180
cgattcagtg gcagtggatc tgggacagat ttcactctca ccatcagcag tctgcaacct  240
gaagattttg caacttacta ctgtcaacag agttacagta ccccgctcac tttcggcgga  300
gggaccaagg tggagatcaa a                                           321

SEQ ID NO: 1018      moltype = AA  length = 107
FEATURE              Location/Qualifiers
REGION               1..107
                     note = Synthetic
source               1..107
                     mol_type = protein
                     organism = synthetic construct
SEQUENCE: 1018
DIQMTQSPSS LSASVGDRVT ITCRASQRIS SYLNWYQQKA GKAPKVLIYT ASSLQSGVPS  60
RFSGSGSGTD FTLTISSLQP EDFATYYCQQ SYSTPLTFGG GTKVEIK               107

SEQ ID NO: 1019      moltype = DNA  length = 18
FEATURE              Location/Qualifiers
misc_feature         1..18
                     note = Synthetic
source               1..18
                     mol_type = other DNA
                     organism = synthetic construct
SEQUENCE: 1019
cagagaatta gcagctat                                               18

SEQ ID NO: 1020      moltype = AA  length = 6
FEATURE              Location/Qualifiers
REGION               1..6
                     note = Synthetic
source               1..6
                     mol_type = protein
                     organism = synthetic construct
SEQUENCE: 1020
QRISSY                                                            6

SEQ ID NO: 1021      moltype =   length =
SEQUENCE: 1021
000

SEQ ID NO: 1022      moltype =   length =
SEQUENCE: 1022
000

SEQ ID NO: 1023      moltype = DNA  length = 27
FEATURE              Location/Qualifiers
misc_feature         1..27
                     note = Synthetic
source               1..27
                     mol_type = other DNA
                     organism = synthetic construct
SEQUENCE: 1023
caacagagtt acagtacccc gctcact                                     27

SEQ ID NO: 1024      moltype = AA  length = 9
FEATURE              Location/Qualifiers
REGION               1..9
                     note = Synthetic
source               1..9
                     mol_type = protein
                     organism = synthetic construct
```

```
SEQUENCE: 1024
QQSYSTPLT                                                   9

SEQ ID NO: 1025        moltype = DNA  length = 375
FEATURE                Location/Qualifiers
misc_feature           1..375
                       note = Synthetic
source                 1..375
                       mol_type = other DNA
                       organism = synthetic construct
SEQUENCE: 1025
caggtgcagc tggtacagtc tgggggaggc gtggtacagc ctggggggtc cctgagactc  60
tcctgtgcag cctctggatt cacctttgat gattatgcca tgcactgggt ccgtcaagct  120
ccagggaagg gtctggagtg ggtctctctt attagtgggg atggtggtag cacatactat  180
gcagactctg tgaagggccg attcaccatc tccagagaca acagcaaaaa ctccctgtat  240
ctgcaaatga acagtctgag aactgaggac accgccttgt attactgtgc aaaagatgat  300
agcagctcgt cctggtacta ctactactac ggtatggacg tctggggccg agggaccacg  360
gtcaccgtct cctca                                                  375

SEQ ID NO: 1026        moltype = AA  length = 125
FEATURE                Location/Qualifiers
REGION                 1..125
                       note = Synthetic
source                 1..125
                       mol_type = protein
                       organism = synthetic construct
SEQUENCE: 1026
QVQLVQSGGG VVQPGGSLRL SCAASGFTFD DYAMHWVRQA PGKGLEWVSL ISGDGGSTYY  60
ADSVKGRFTI SRDNSKNSLY LQMNSLRTED TALYYCAKDD SSSSWYYYYY GMDVWGRGTT  120
VTVSS                                                             125

SEQ ID NO: 1027        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1027
ggattcacct ttgatgatta tgcc                                  24

SEQ ID NO: 1028        moltype = AA  length = 8
FEATURE                Location/Qualifiers
REGION                 1..8
                       note = Synthetic
source                 1..8
                       mol_type = protein
                       organism = synthetic construct
SEQUENCE: 1028
GFTFDDYA                                                    8

SEQ ID NO: 1029        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1029
attagtgggg atggtggtag caca                                  24

SEQ ID NO: 1030        moltype = AA  length = 8
FEATURE                Location/Qualifiers
REGION                 1..8
                       note = Synthetic
source                 1..8
                       mol_type = protein
                       organism = synthetic construct
SEQUENCE: 1030
ISGDGGST                                                    8

SEQ ID NO: 1031        moltype = DNA  length = 54
FEATURE                Location/Qualifiers
misc_feature           1..54
                       note = Synthetic
source                 1..54
                       mol_type = other DNA
                       organism = synthetic construct
SEQUENCE: 1031
```

```
gcaaaagatg atagcagctc gtcctggtac tactactact acggtatgga cgtc       54

SEQ ID NO: 1032         moltype = AA  length = 18
FEATURE                 Location/Qualifiers
REGION                  1..18
                        note = Synthetic
source                  1..18
                        mol_type = protein
                        organism = synthetic construct
SEQUENCE: 1032
AKDDSSSSWY YYYYGMDV                                               18

SEQ ID NO: 1033         moltype = DNA  length = 324
FEATURE                 Location/Qualifiers
misc_feature            1..324
                        note = Synthetic
source                  1..324
                        mol_type = other DNA
                        organism = synthetic construct
SEQUENCE: 1033
gacatccaga tgacccagtc tccatcctcc ctgtctgcat ctgtaggaga cagagtcacc  60
atcacttgcc gggcaagtca gcgcattagc agctatttaa attggtatca gcagaaacca  120
gggaaagccc ctaaggtgct gatctctgtt gcatccagtt tgcaaagtgg ggtcccatca  180
aggttcagtg gcagtggatc tgggacagat ttcactctca ccatcagcag tctgcaacct  240
gaggattttg catcttacta ctgtcaacag agttacaata ccccgctcac tttcggcgga  300
gggaccaagg tggagatcaa acga                                        324

SEQ ID NO: 1034         moltype = AA  length = 108
FEATURE                 Location/Qualifiers
REGION                  1..108
                        note = Synthetic
source                  1..108
                        mol_type = protein
                        organism = synthetic construct
SEQUENCE: 1034
DIQMTQSPSS LSASVGDRVT ITCRASQRIS SYLNWYQQKP GKAPKVLISV ASSLQSGVPS  60
RFSGSGSGTD FTLTISSLQP EDFASYYCQQ SYNTPLTFGG GTKVEIKR               108

SEQ ID NO: 1035         moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 1035
cagcgcatta gcagctat                                               18

SEQ ID NO: 1036         moltype = AA  length = 6
FEATURE                 Location/Qualifiers
REGION                  1..6
                        note = Synthetic
source                  1..6
                        mol_type = protein
                        organism = synthetic construct
SEQUENCE: 1036
QRISSY                                                            6

SEQ ID NO: 1037         moltype =   length =
SEQUENCE: 1037
000

SEQ ID NO: 1038         moltype =   length =
SEQUENCE: 1038
000

SEQ ID NO: 1039         moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 1039
caacagagtt acaatacccc gctcact                                     27

SEQ ID NO: 1040         moltype = AA  length = 9
FEATURE                 Location/Qualifiers
REGION                  1..9
```

-continued

```
                      note = Synthetic
source                1..9
                      mol_type = protein
                      organism = synthetic construct
SEQUENCE: 1040
QQSYNTPLT                                                         9

SEQ ID NO: 1041       moltype = DNA  length = 372
FEATURE               Location/Qualifiers
misc_feature          1..372
                      note = Synthetic
source                1..372
                      mol_type = other DNA
                      organism = synthetic construct
SEQUENCE: 1041
gaggtgcagc tggtggagtc tgggggaggc ttggtacagc ctggcaggtc cctgagactc  60
tcctgtgcag cctctggatt cacctttggt gattatacca tgcactgggt ccggcaagct  120
ccagggaagg gcctggagtg ggtctccgat attagttgga atagtggtag caaagactat  180
gcggactctg tgaagggccg attcaccatc tccagagaca acgccaagaa ctccctctat  240
cttcaaatga acagtctgag aactgaggat acggcctttt attactgtgc aaaagatagt  300
aggggctacg gtctctacta ccacctcggt ttggacgtct ggggccaagg gaccacggtc  360
accgtctcct ca                                                      372

SEQ ID NO: 1042       moltype = AA  length = 124
FEATURE               Location/Qualifiers
REGION                1..124
                      note = Synthetic
source                1..124
                      mol_type = protein
                      organism = synthetic construct
SEQUENCE: 1042
EVQLVESGGG LVQPGRSLRL SCAASGFTFG DYTMHWVRQA PGKGLEWVSD ISWNSGSKDY  60
ADSVKGRFTI SRDNAKNSLY LQMNSLRTED TAFYYCAKDS RGYGLYYHLG LDVWGQGTTV  120
TVSS                                                               124

SEQ ID NO: 1043       moltype = DNA  length = 24
FEATURE               Location/Qualifiers
misc_feature          1..24
                      note = Synthetic
source                1..24
                      mol_type = other DNA
                      organism = synthetic construct
SEQUENCE: 1043
ggattcacct ttggtgatta tacc                                        24

SEQ ID NO: 1044       moltype = AA  length = 8
FEATURE               Location/Qualifiers
REGION                1..8
                      note = Synthetic
source                1..8
                      mol_type = protein
                      organism = synthetic construct
SEQUENCE: 1044
GFTFGDYT                                                          8

SEQ ID NO: 1045       moltype = DNA  length = 24
FEATURE               Location/Qualifiers
misc_feature          1..24
                      note = Synthetic
source                1..24
                      mol_type = other DNA
                      organism = synthetic construct
SEQUENCE: 1045
attagttgga atagtggtag caaa                                        24

SEQ ID NO: 1046       moltype = AA  length = 8
FEATURE               Location/Qualifiers
REGION                1..8
                      note = Synthetic
source                1..8
                      mol_type = protein
                      organism = synthetic construct
SEQUENCE: 1046
ISWNSGSK                                                          8

SEQ ID NO: 1047       moltype = DNA  length = 51
FEATURE               Location/Qualifiers
misc_feature          1..51
                      note = Synthetic
```

-continued

```
source                  1..51
                        mol_type = other DNA
                        organism = synthetic construct
SEQUENCE: 1047
gcaaaagata gtaggggcta cggtctctac taccacctcg gtttggacgt c          51

SEQ ID NO: 1048         moltype = AA  length = 17
FEATURE                 Location/Qualifiers
REGION                  1..17
                        note = Synthetic
source                  1..17
                        mol_type = protein
                        organism = synthetic construct
SEQUENCE: 1048
AKDSRGYGLY YHLGLDV                                                17

SEQ ID NO: 1049         moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 1049
gaggtgcagc tggtggagtc tgggggaggc ttggtgcagc ctggcaggtc cctgagactc  60
tcctgtgcag cctctggatt cacctttgct gattatacca tgcactgggt ccggcaagct  120
ccagggaagg gcctggagtg ggtctcagat attagttgga atagtggtag tatagcctat  180
gcggactctg tgaagggccg attcaccatc tccagagaca acgccaagaa ctccctctat  240
cttcaaatga acagtctgag aactgaggac acggcctttt attactgtgc aaaagatagt  300
aggggctacg gtcactataa gtacctcggt ttggacgtct ggggccaagg gaccacggtc  360
accgtctcct ca                                                     372

SEQ ID NO: 1050         moltype = AA  length = 124
FEATURE                 Location/Qualifiers
REGION                  1..124
                        note = Synthetic
source                  1..124
                        mol_type = protein
                        organism = synthetic construct
SEQUENCE: 1050
EVQLVESGGG LVQPGRSLRL SCAASGFTFA DYTMHWVRQA PGKGLEWVSD ISWNSGSIAY  60
ADSVKGRFTI SRDNAKNSLY LQMNSLRTED TAFYYCAKDS RGYGHYKYLG LDVWGQGTTV  120
TVSS                                                              124

SEQ ID NO: 1051         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1051
ggattcacct ttgctgatta tacc                                        24

SEQ ID NO: 1052         moltype = AA  length = 8
FEATURE                 Location/Qualifiers
REGION                  1..8
                        note = Synthetic
source                  1..8
                        mol_type = protein
                        organism = synthetic construct
SEQUENCE: 1052
GFTFADYT                                                          8

SEQ ID NO: 1053         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1053
attagttgga atagtggtag tata                                        24

SEQ ID NO: 1054         moltype = AA  length = 8
FEATURE                 Location/Qualifiers
REGION                  1..8
                        note = Synthetic
source                  1..8
```

```
                        mol_type = protein
                        organism = synthetic construct
SEQUENCE: 1054
ISWNSGSI                                                                 8

SEQ ID NO: 1055         moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 1055
gcaaaagata gtaggggcta cggtcactat aagtacctcg gtttggacgt c                 51

SEQ ID NO: 1056         moltype = AA  length = 17
FEATURE                 Location/Qualifiers
REGION                  1..17
                        note = Synthetic
source                  1..17
                        mol_type = protein
                        organism = synthetic construct
SEQUENCE: 1056
AKDSRGYGHY KYLGLDV                                                       17

SEQ ID NO: 1057         moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 1057
gaggtgcagc tggtggagtc tgggggaggc atggtacagc ctggcaggtc cctgagactc  60
tcctgtgcag cctctggatt ccccttcaat gattacacca tgcactgggt ccggcaagtc  120
ccagggaggg gcctggagtg ggtctcagat attagttgga atagcggcag taaaggctat  180
gcggactctg tgaagggtcg attcatcatc tccagagaca acgccaagaa ctccctgtac  240
ctgcaaatga acagtctgag agttgaagac acggccttgt attactgtgt aaaagatgga  300
agtggctacg ggaggttcca ttattacgct atggacgtct ggggccaagg gaccacggtc  360
accgtctcct ca                                                      372

SEQ ID NO: 1058         moltype = AA  length = 124
FEATURE                 Location/Qualifiers
REGION                  1..124
                        note = Synthetic
source                  1..124
                        mol_type = protein
                        organism = synthetic construct
SEQUENCE: 1058
EVQLVESGGG MVQPGRSLRL SCAASGFPFN DYTMHWVRQV PGRGLEWVSD ISWNSGSKGY  60
ADSVKGRFII SRDNAKNSLY LQMNSLRVED TALYYCVKDG SGYGRFHYYA MDVWGQGTTV  120
TVSS                                                               124

SEQ ID NO: 1059         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1059
ggattcccct tcaatgatta cacc                                         24

SEQ ID NO: 1060         moltype = AA  length = 8
FEATURE                 Location/Qualifiers
REGION                  1..8
                        note = Synthetic
source                  1..8
                        mol_type = protein
                        organism = synthetic construct
SEQUENCE: 1060
GFPFNDYT                                                           8

SEQ ID NO: 1061         moltype = DNA  length = 24
FEATURE                 Location/Qualifiers
misc_feature            1..24
                        note = Synthetic
source                  1..24
                        mol_type = other DNA
```

```
                         organism = synthetic construct
SEQUENCE: 1061
attagttgga atagcggcag taaa                                           24

SEQ ID NO: 1062          moltype = AA  length = 8
FEATURE                  Location/Qualifiers
REGION                   1..8
                         note = Synthetic
source                   1..8
                         mol_type = protein
                         organism = synthetic construct
SEQUENCE: 1062
ISWNSGSK                                                             8

SEQ ID NO: 1063          moltype = DNA  length = 51
FEATURE                  Location/Qualifiers
misc_feature             1..51
                         note = Synthetic
source                   1..51
                         mol_type = other DNA
                         organism = synthetic construct
SEQUENCE: 1063
gtaaaagatg gaagtggcta cgggaggttc cattattacg ctatggacgt c             51

SEQ ID NO: 1064          moltype = AA  length = 17
FEATURE                  Location/Qualifiers
REGION                   1..17
                         note = Synthetic
source                   1..17
                         mol_type = protein
                         organism = synthetic construct
SEQUENCE: 1064
VKDGSGYGRF HYYAMDV                                                   17

SEQ ID NO: 1065          moltype = DNA  length = 372
FEATURE                  Location/Qualifiers
misc_feature             1..372
                         note = Synthetic
source                   1..372
                         mol_type = other DNA
                         organism = synthetic construct
SEQUENCE: 1065
gaggtgcagc tggtggagtc tggtggaggc ttggtacagc ctggcaggtc cctgagactc  60
tcctgtgcag cctctggatt cacctttgct gattatacca tgcactgggt ccgccaagtt  120
ccagggaagg gcctggagtg ggtctcagat attagttgga atagtggtag caaagactat  180
gcggactctg tgaagggccg cttcaccatc tccagagaca acgccaagaa tttcctgtat  240
ctgcaaatga acagtctgag agctgaagac acggccttgt attactgtgt aaaatatgga  300
agtggctacg ggaaattcta cttctacgct atggacgtct ggggccaagg gaccacggtc  360
accgtctcct ca                                                        372

SEQ ID NO: 1066          moltype = AA  length = 124
FEATURE                  Location/Qualifiers
REGION                   1..124
                         note = Synthetic
source                   1..124
                         mol_type = protein
                         organism = synthetic construct
SEQUENCE: 1066
EVQLVESGGG LVQPGRSLRL SCAASGFTFA DYTMHWVRQV PGKGLEWVSD ISWNSGSKDY  60
ADSVKGRFTI SRDNAKNFLY LQMNSLRAED TALYYCVKYG SGYGKFYFYA MDVWGQGTTV  120
TVSS                                                                 124

SEQ ID NO: 1067          moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 1067
ggattcacct ttgctgatta tacc                                           24

SEQ ID NO: 1068          moltype = AA  length = 8
FEATURE                  Location/Qualifiers
REGION                   1..8
                         note = Synthetic
source                   1..8
                         mol_type = protein
                         organism = synthetic construct
```

```
SEQUENCE: 1068
GFTFADYT                                                        8

SEQ ID NO: 1069        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1069
attagttgga atagtggtag caaa                                      24

SEQ ID NO: 1070        moltype = AA  length = 8
FEATURE                Location/Qualifiers
REGION                 1..8
                       note = Synthetic
source                 1..8
                       mol_type = protein
                       organism = synthetic construct
SEQUENCE: 1070
ISWNSGSK                                                        8

SEQ ID NO: 1071        moltype = DNA  length = 51
FEATURE                Location/Qualifiers
misc_feature           1..51
                       note = Synthetic
source                 1..51
                       mol_type = other DNA
                       organism = synthetic construct
SEQUENCE: 1071
gtaaaatatg gaagtggcta cgggaaattc tacttctacg ctatggacgt c        51

SEQ ID NO: 1072        moltype = AA  length = 17
FEATURE                Location/Qualifiers
REGION                 1..17
                       note = Synthetic
source                 1..17
                       mol_type = protein
                       organism = synthetic construct
SEQUENCE: 1072
VKYGSGYGKF YFYAMDV                                              17

SEQ ID NO: 1073        moltype = DNA  length = 372
FEATURE                Location/Qualifiers
misc_feature           1..372
                       note = Synthetic
source                 1..372
                       mol_type = other DNA
                       organism = synthetic construct
SEQUENCE: 1073
gaggtgcagc tggtgcagtc tgggggaggc ttggtacagc ctggcaggtc cctgagactc  60
tcctgtgcag cctctggatt cacctttgct gattatacca tgcactgggt ccggcaaact  120
ccagggaagg gcctggagtg ggtctcaggt attagttgga atagtggtag caaagactat  180
gcggactctg tgaagggccg attcaccatc tccagagaca acgccaagaa ctccctgtat  240
ctgcaaatga acagtctgag aactgaggac acggccttgt attactgtgc aaaatatgga  300
agtggctacg ggagatattt cttctacgct atggacgtct ggggccaagg gaccacggtc  360
accgtctcct ca                                                   372

SEQ ID NO: 1074        moltype = AA  length = 124
FEATURE                Location/Qualifiers
REGION                 1..124
                       note = Synthetic
source                 1..124
                       mol_type = protein
                       organism = synthetic construct
SEQUENCE: 1074
EVQLVQSGGG LVQPGRSLRL SCAASGFTFA DYTMHWVRQT PGKGLEWVSG ISWNSGSKDY  60
ADSVKGRFTI SRDNAKNSLY LQMNSLRTED TALYYCAKYG SGYGRYFFYA MDVWGQGTTV  120
TVSS                                                            124

SEQ ID NO: 1075        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1075
```

```
ggattcacct ttgctgatta tacc                                        24

SEQ ID NO: 1076        moltype = AA  length = 8
FEATURE                Location/Qualifiers
REGION                 1..8
                       note = Synthetic
source                 1..8
                       mol_type = protein
                       organism = synthetic construct
SEQUENCE: 1076
GFTFADYT                                                          8

SEQ ID NO: 1077        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1077
attagttgga atagtggtag caaa                                        24

SEQ ID NO: 1078        moltype = AA  length = 8
FEATURE                Location/Qualifiers
REGION                 1..8
                       note = Synthetic
source                 1..8
                       mol_type = protein
                       organism = synthetic construct
SEQUENCE: 1078
ISWNSGSK                                                          8

SEQ ID NO: 1079        moltype = DNA  length = 51
FEATURE                Location/Qualifiers
misc_feature           1..51
                       note = Synthetic
source                 1..51
                       mol_type = other DNA
                       organism = synthetic construct
SEQUENCE: 1079
gcaaaatatg gaagtggcta cgggagatat ttcttctacg ctatggacgt c          51

SEQ ID NO: 1080        moltype = AA  length = 17
FEATURE                Location/Qualifiers
REGION                 1..17
                       note = Synthetic
source                 1..17
                       mol_type = protein
                       organism = synthetic construct
SEQUENCE: 1080
AKYGSGYGRY FFYAMDV                                                17

SEQ ID NO: 1081        moltype = DNA  length = 372
FEATURE                Location/Qualifiers
misc_feature           1..372
                       note = Synthetic
source                 1..372
                       mol_type = other DNA
                       organism = synthetic construct
SEQUENCE: 1081
gaggtgcagc tggtggagtc aaggggagcc ttggtacagc ctggcaggtc cctgagactc  60
tcctgtgcag cctctggatt cgcctttaat gattatacca tgcactgggt ccggcaagct  120
ccagggaagg gcctggagtg ggtctcagat attagttgga atagtaatag taaagactat  180
gcggactctg tgaagggccg attcaccatc tccagagaca atgccaagaa ctccctctat  240
ctacaaatga acagtctgag agctgaggac acggccttgt attactgtgt aaaagatgga  300
agtggctacg ggaaattttc cctctacgct ttggacgtct ggggccaagg gaccacggtc  360
accgtctcct ca                                                     372

SEQ ID NO: 1082        moltype = AA  length = 124
FEATURE                Location/Qualifiers
REGION                 1..124
                       note = Synthetic
source                 1..124
                       mol_type = protein
                       organism = synthetic construct
SEQUENCE: 1082
EVQLVESRGA LVQPGRSLRL SCAASGFAFN DYTMHWVRQA PGKGLEWVSD ISWNSNSKDY  60
ADSVKGRFTI SRDNAKNSLY LQMNSLRAED TALYYCVKDG SGYGKFSLYA LDVWGQGTTV  120
TVSS                                                              124
```

```
SEQ ID NO: 1083        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1083
ggattcgcct ttaatgatta tacc                                        24

SEQ ID NO: 1084        moltype = AA  length = 8
FEATURE                Location/Qualifiers
REGION                 1..8
                       note = Synthetic
source                 1..8
                       mol_type = protein
                       organism = synthetic construct
SEQUENCE: 1084
GFAFNDYT                                                          8

SEQ ID NO: 1085        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1085
attagttgga atagtaatag taaa                                        24

SEQ ID NO: 1086        moltype = AA  length = 8
FEATURE                Location/Qualifiers
REGION                 1..8
                       note = Synthetic
source                 1..8
                       mol_type = protein
                       organism = synthetic construct
SEQUENCE: 1086
ISWNSNSK                                                          8

SEQ ID NO: 1087        moltype = DNA  length = 51
FEATURE                Location/Qualifiers
misc_feature           1..51
                       note = Synthetic
source                 1..51
                       mol_type = other DNA
                       organism = synthetic construct
SEQUENCE: 1087
gtaaaagatg gaagtggcta cgggaaattt tccctctacg ctttggacgt c          51

SEQ ID NO: 1088        moltype = AA  length = 17
FEATURE                Location/Qualifiers
REGION                 1..17
                       note = Synthetic
source                 1..17
                       mol_type = protein
                       organism = synthetic construct
SEQUENCE: 1088
VKDGSGYGKF SLYALDV                                                17

SEQ ID NO: 1089        moltype = DNA  length = 372
FEATURE                Location/Qualifiers
misc_feature           1..372
                       note = Synthetic
source                 1..372
                       mol_type = other DNA
                       organism = synthetic construct
SEQUENCE: 1089
caggtgcagc tggtggagtc tgggggaggc ttggttcacc ctggcaggtc cctgagactc  60
tcctgtgcag cctctggatt caaatttgat gattatacca tgcactgggt ccggcaagct  120
ccagggaagg gcctagagtg ggtctcagat attagttgga atagtggtag taaaggctat  180
gcggactctg tgaagggccg attcaccatc tccagagaca acgccaagga ttccctatat  240
ctgcagatgg acagtctgag agctgcagac acggccttct attactgtgc aaaagataaa  300
agtggctacg gccacttcta ctactacgct atggacgtct ggggccaagg gaccacggtc  360
accgtctcct ca                                                      372

SEQ ID NO: 1090        moltype = AA  length = 124
FEATURE                Location/Qualifiers
```

```
REGION                  1..124
                        note = Synthetic
source                  1..124
                        mol_type = protein
                        organism = synthetic construct
SEQUENCE: 1090
QVQLVESGGG LVHPGRSLRL SCAASGFKFD DYTMHWVRQA PGKGLEWVSD ISWNSGSKGY  60
ADSVKGRFTI SRDNAKDSLY LQMDSLRAAD TAFYYCAKDK SGYGHFYYYA MDVWGQGTTV  120
TVSS                                                              124

SEQ ID NO: 1091         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1091
ggattcaaat ttgatgatta tacc                                        24

SEQ ID NO: 1092         moltype = AA  length = 8
FEATURE                 Location/Qualifiers
REGION                  1..8
                        note = Synthetic
source                  1..8
                        mol_type = protein
                        organism = synthetic construct
SEQUENCE: 1092
GFKFDDYT                                                          8

SEQ ID NO: 1093         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1093
attagttgga atagtggtag taaa                                        24

SEQ ID NO: 1094         moltype = AA  length = 8
FEATURE                 Location/Qualifiers
REGION                  1..8
                        note = Synthetic
source                  1..8
                        mol_type = protein
                        organism = synthetic construct
SEQUENCE: 1094
ISWNSGSK                                                          8

SEQ ID NO: 1095         moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 1095
gcaaaagata aaagtggcta cggccacttc tactactacg ctatggacgt c          51

SEQ ID NO: 1096         moltype = AA  length = 17
FEATURE                 Location/Qualifiers
REGION                  1..17
                        note = Synthetic
source                  1..17
                        mol_type = protein
                        organism = synthetic construct
SEQUENCE: 1096
AKDKSGYGHF YYYAMDV                                                17

SEQ ID NO: 1097         moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 1097
gaggtgcagc tggtggagtc tgggggaggc ttggtacacc ctggcaggtc cctaagactc  60
```

```
tcctgtacag cctctggatt caagtttgct gattatacca tgcactgggt ccggcaagct  120
ccagggaagg gcctggagtg ggtctcagat attagttgga atagtggtag taaaggctat  180
gcggactctg taaagggccg attcaccatc tccagagaca atgacaagaa ctccctgtat  240
ctgcaaatga acagtctgag aggtgaggac acggccttgt attactgtgc aaaagatgga  300
agtggctacg ggaggttcca cttctacgct atcgacgtct ggggccaagg gaccacggtc  360
accgtctcct ca                                                      372

SEQ ID NO: 1098        moltype = AA  length = 124
FEATURE                Location/Qualifiers
REGION                 1..124
                       note = Synthetic
source                 1..124
                       mol_type = protein
                       organism = synthetic construct
SEQUENCE: 1098
EVQLVESGGG LVHPGRSLRL SCTASGFKFA DYTMHWVRQA PGKGLEWVSD ISWNSGSKGY  60
ADSVKGRFTI SRDNDKNSLY LQMNSLRGED TALYYCAKDG SGYGRFHFYA IDVWGQGTTV  120
TVSS                                                               124

SEQ ID NO: 1099        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1099
ggattcaagt ttgctgatta tacc                                         24

SEQ ID NO: 1100        moltype = AA  length = 8
FEATURE                Location/Qualifiers
REGION                 1..8
                       note = Synthetic
source                 1..8
                       mol_type = protein
                       organism = synthetic construct
SEQUENCE: 1100
GFKFADYT                                                           8

SEQ ID NO: 1101        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1101
attagttgga atagtggtag taaa                                         24

SEQ ID NO: 1102        moltype = AA  length = 8
FEATURE                Location/Qualifiers
REGION                 1..8
                       note = Synthetic
source                 1..8
                       mol_type = protein
                       organism = synthetic construct
SEQUENCE: 1102
ISWNSGSK                                                           8

SEQ ID NO: 1103        moltype = DNA  length = 51
FEATURE                Location/Qualifiers
misc_feature           1..51
                       note = Synthetic
source                 1..51
                       mol_type = other DNA
                       organism = synthetic construct
SEQUENCE: 1103
gcaaaagatg gaagtggcta cgggaggttc cacttctacg ctatcgacgt c           51

SEQ ID NO: 1104        moltype = AA  length = 17
FEATURE                Location/Qualifiers
REGION                 1..17
                       note = Synthetic
source                 1..17
                       mol_type = protein
                       organism = synthetic construct
SEQUENCE: 1104
AKDGSGYGRF HFYAIDV                                                 17
```

```
SEQ ID NO: 1105        moltype = DNA  length = 372
FEATURE                Location/Qualifiers
misc_feature           1..372
                       note = Synthetic
source                 1..372
                       mol_type = other DNA
                       organism = synthetic construct
SEQUENCE: 1105
gaggtgcagc tggtggagtc tgggggaggc ttggtacagc ctggcaggtc cctgagactc  60
tcctgtgtag cctctggatt cacctttgat gattattcca tgcactgggt ccggcaagct  120
ccagggaagg gcctggagtg ggtctcaggt attagttgga atagtggtag caaagactat  180
gcggactctg tgaagggccg attcaccatc tccagagaca acgccaagaa ctccctgtat  240
ctgcaaatga acagtctgag agctgaagac acggccttgt attactgtgc aaaatatgga  300
agtggctacg ggaagttcta ccactacggt ttggacgtct ggggccaagg gaccacggtc  360
accgtctcct ca                                                      372

SEQ ID NO: 1106        moltype = AA  length = 124
FEATURE                Location/Qualifiers
REGION                 1..124
                       note = Synthetic
source                 1..124
                       mol_type = protein
                       organism = synthetic construct
SEQUENCE: 1106
EVQLVESGGG LVQPGRSLRL SCVASGFTFD DYSMHWVRQA PGKGLEWVSG ISWNSGSKDY  60
ADSVKGRFTI SRDNAKNSLY LQMNSLRAED TALYYCAKYG SGYGKFYHYG LDVWGQGTTV  120
TVSS                                                               124

SEQ ID NO: 1107        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1107
ggattcacct ttgatgatta ttcc                                         24

SEQ ID NO: 1108        moltype = AA  length = 8
FEATURE                Location/Qualifiers
REGION                 1..8
                       note = Synthetic
source                 1..8
                       mol_type = protein
                       organism = synthetic construct
SEQUENCE: 1108
GFTFDDYS                                                           8

SEQ ID NO: 1109        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1109
attagttgga atagtggtag caaa                                         24

SEQ ID NO: 1110        moltype = AA  length = 8
FEATURE                Location/Qualifiers
REGION                 1..8
                       note = Synthetic
source                 1..8
                       mol_type = protein
                       organism = synthetic construct
SEQUENCE: 1110
ISWNSGSK                                                           8

SEQ ID NO: 1111        moltype = DNA  length = 51
FEATURE                Location/Qualifiers
misc_feature           1..51
                       note = Synthetic
source                 1..51
                       mol_type = other DNA
                       organism = synthetic construct
SEQUENCE: 1111
gcaaaatatg gaagtggcta cgggaagttc taccactacg gtttggacgt c           51

SEQ ID NO: 1112        moltype = AA  length = 17
```

```
FEATURE                Location/Qualifiers
REGION                 1..17
                       note = Synthetic
source                 1..17
                       mol_type = protein
                       organism = synthetic construct
SEQUENCE: 1112
AKYGSGYGKF YHYGLDV                                                17

SEQ ID NO: 1113        moltype = DNA  length = 372
FEATURE                Location/Qualifiers
misc_feature           1..372
                       note = Synthetic
source                 1..372
                       mol_type = other DNA
                       organism = synthetic construct
SEQUENCE: 1113
caggtgcagt tggtggagtc tgggggaggc ttggtacagc ctggcaggtc cctgagactc  60
tcctgtgcag cctctggatt cacctttgct gattatacca tgcactgggt ccggcaggct  120
ccagggaagg gcctggagtg ggtctcagat attagttgga atagtggtag catgggctat  180
gcggactctg tgaagggccg attcaccatc tccagagaca acgccaagaa atccctgtat  240
ctgcaaatga acagtctgag aactgaggac acggccttgt attactgtgc aaaagatgga  300
agtggctacg ggaaatactt cttctacgct atggacgtct ggggccaagg gaccacggtc  360
accgtctcct ca                                                     372

SEQ ID NO: 1114        moltype = AA  length = 124
FEATURE                Location/Qualifiers
REGION                 1..124
                       note = Synthetic
source                 1..124
                       mol_type = protein
                       organism = synthetic construct
SEQUENCE: 1114
QVQLVESGGG LVQPGRSLRL SCAASGFTFA DYTMHWVRQA PGKGLEWVSD ISWNSGSMGY  60
ADSVKGRFTI SRDNAKKSLY LQMNSLRTED TALYYCAKDG SGYGKYFFYA MDVWGQGTTV  120
TVSS                                                              124

SEQ ID NO: 1115        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1115
ggattcacct ttgctgatta tacc                                        24

SEQ ID NO: 1116        moltype = AA  length = 8
FEATURE                Location/Qualifiers
REGION                 1..8
                       note = Synthetic
source                 1..8
                       mol_type = protein
                       organism = synthetic construct
SEQUENCE: 1116
GFTFADYT                                                          8

SEQ ID NO: 1117        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1117
attagttgga atagtggtag catg                                        24

SEQ ID NO: 1118        moltype = AA  length = 8
FEATURE                Location/Qualifiers
REGION                 1..8
                       note = Synthetic
source                 1..8
                       mol_type = protein
                       organism = synthetic construct
SEQUENCE: 1118
ISWNSGSM                                                          8

SEQ ID NO: 1119        moltype = DNA  length = 51
FEATURE                Location/Qualifiers
```

```
misc_feature            1..51
                        note = Synthetic
source                  1..51
                        mol_type = other DNA
                        organism = synthetic construct
SEQUENCE: 1119
gcaaaagatg gaagtggcta cgggaaatac ttcttctacg ctatggacgt c           51

SEQ ID NO: 1120         moltype = AA  length = 17
FEATURE                 Location/Qualifiers
REGION                  1..17
                        note = Synthetic
source                  1..17
                        mol_type = protein
                        organism = synthetic construct
SEQUENCE: 1120
AKDGSGYGKY FFYAMDV                                                 17

SEQ ID NO: 1121         moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 1121
gaggtgcagc tggtgcagtc tgggggaggc ttggtacagc ctggcaggtc cctgagactc  60
tcctgtgcag cctctggatt caccttttct gattatacta tgcattgggt ccggcaaggt  120
ccagggaagg gcctggagtg ggtctcagat attagttgga atagtggtag taaaggctat  180
acggactctg tgaagggccg attcaccatt tccagagaca acgccaagaa gtccctgtat  240
ctacaaatga acagtctgag agctgaggac acggccttgt actactgtgt aaaagatgga  300
agtggctacg ggaaatacca cttctacgct atggacgtct ggggccaagg gaccctggtc  360
accgtctcct ca                                                      372

SEQ ID NO: 1122         moltype = AA  length = 124
FEATURE                 Location/Qualifiers
REGION                  1..124
                        note = Synthetic
source                  1..124
                        mol_type = protein
                        organism = synthetic construct
SEQUENCE: 1122
EVQLVQSGGG LVQPGRSLRL SCAASGFTFS DYTMHWVRQG PGKGLEWVSD ISWNSGSKGY  60
TDSVKGRFTI SRDNAKKSLY LQMNSLRAED TALYYCVKDG SGYGKYHFYA MDVWGQGTLV  120
TVSS                                                               124

SEQ ID NO: 1123         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1123
ggattcacct tttctgatta tact                                         24

SEQ ID NO: 1124         moltype = AA  length = 8
FEATURE                 Location/Qualifiers
REGION                  1..8
                        note = Synthetic
source                  1..8
                        mol_type = protein
                        organism = synthetic construct
SEQUENCE: 1124
GFTFSDYT                                                           8

SEQ ID NO: 1125         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1125
attagttgga atagtggtag taaa                                         24

SEQ ID NO: 1126         moltype = AA  length = 8
FEATURE                 Location/Qualifiers
REGION                  1..8
```

```
                        note = Synthetic
source                  1..8
                        mol_type = protein
                        organism = synthetic construct
SEQUENCE: 1126
ISWNSGSK                                                         8

SEQ ID NO: 1127         moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 1127
gtaaaagatg gaagtggcta cgggaaatac cacttctacg ctatggacgt c          51

SEQ ID NO: 1128         moltype = AA  length = 17
FEATURE                 Location/Qualifiers
REGION                  1..17
                        note = Synthetic
source                  1..17
                        mol_type = protein
                        organism = synthetic construct
SEQUENCE: 1128
VKDGSGYGKY HFYAMDV                                               17

SEQ ID NO: 1129         moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 1129
gaggtgcagc tggtggagtc gggggaggc ttggttcacc ctggcaggtc cctgagactc  60
tcctgtgcag cctctggatt cacctttgat gattatacca tgcactgggt ccggcaagct  120
ccagggaagg gcctggaatg ggtctcagat attagttgga atagtggtag cagaggctat  180
gcggactctg tgaagggccg attcaccatc tccagagata atgccgagaa ctccctgtac  240
ctgcaaatga acagtctgag agctgaggac acggccttgt attactgtgc aaaagataaa  300
agtggctacg gccactacta ctactacgct atggacgtct ggggccaagg gaccacggtc  360
accgtctcct ca                                                    372

SEQ ID NO: 1130         moltype = AA  length = 124
FEATURE                 Location/Qualifiers
REGION                  1..124
                        note = Synthetic
source                  1..124
                        mol_type = protein
                        organism = synthetic construct
SEQUENCE: 1130
EVQLVESGGG LVHPGRSLRL SCAASGFTFD DYTMHWVRQA PGKGLEWVSD ISWNSGSRGY  60
ADSVKGRFTI SRDNAENSLY LQMNSLRAED TALYYCAKDK SGYGHYYYYA MDVWGQGTTV  120
TVSS                                                             124

SEQ ID NO: 1131         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1131
ggattcacct ttgatgatta tacc                                       24

SEQ ID NO: 1132         moltype = AA  length = 8
FEATURE                 Location/Qualifiers
REGION                  1..8
                        note = Synthetic
source                  1..8
                        mol_type = protein
                        organism = synthetic construct
SEQUENCE: 1132
GFTFDDYT                                                         8

SEQ ID NO: 1133         moltype = DNA  length = 24
FEATURE                 Location/Qualifiers
misc_feature            1..24
                        note = Synthetic
```

```
source                  1..24
                        mol_type = other DNA
                        organism = synthetic construct
SEQUENCE: 1133
attagttgga atagtggtag caga                                        24

SEQ ID NO: 1134         moltype = AA  length = 8
FEATURE                 Location/Qualifiers
REGION                  1..8
                        note = Synthetic
source                  1..8
                        mol_type = protein
                        organism = synthetic construct
SEQUENCE: 1134
ISWNSGSR                                                          8

SEQ ID NO: 1135         moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 1135
gcaaaagata aaagtggcta cggccactac tactactacg ctatggacgt c          51

SEQ ID NO: 1136         moltype = AA  length = 17
FEATURE                 Location/Qualifiers
REGION                  1..17
                        note = Synthetic
source                  1..17
                        mol_type = protein
                        organism = synthetic construct
SEQUENCE: 1136
AKDKSGYGHY YYYAMDV                                                17

SEQ ID NO: 1137         moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 1137
gaggtgcagc tggtggagtc tgggggaggc ttggtacagc ctggcgggtc cctgagactc  60
tcctgtgaag cctctggatt cacctttgct gattatacct tgcactgggt ccggcaagct  120
ccagggaagg gcctggaatg ggtctcagat attagttgga atagtggcac cagaggctat  180
gcggactctg tgaggggccg attcaccatc tccagagaca acgccaagaa gtccctgtat  240
ctgcaaatga acagtctgag atctgaggac acggccttgt attactgtgt gaaagatgga  300
agtggctacg ggagatataa tttctacgct atggacgtct ggggccaagg gaccacggtc  360
accgtctcct ca                                                     372

SEQ ID NO: 1138         moltype = AA  length = 124
FEATURE                 Location/Qualifiers
REGION                  1..124
                        note = Synthetic
source                  1..124
                        mol_type = protein
                        organism = synthetic construct
SEQUENCE: 1138
EVQLVESGGG LVQPGGSLRL SCEASGFTFA DYTLHWVRQA PGKGLEWVSD ISWNSGTRGY  60
ADSVRGRFTI SRDNAKKSLY LQMNSLRSED TALYYCVKDG SGYGRYNFYA MDVWGQGTTV  120
TVSS                                                              124

SEQ ID NO: 1139         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1139
ggattcacct ttgctgatta tacc                                        24

SEQ ID NO: 1140         moltype = AA  length = 8
FEATURE                 Location/Qualifiers
REGION                  1..8
                        note = Synthetic
source                  1..8
```

```
                        mol_type = protein
                        organism = synthetic construct
SEQUENCE: 1140
GFTFADYT                                                    8

SEQ ID NO: 1141         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1141
attagttgga atagtggcac caga                                  24

SEQ ID NO: 1142         moltype = AA  length = 8
FEATURE                 Location/Qualifiers
REGION                  1..8
                        note = Synthetic
source                  1..8
                        mol_type = protein
                        organism = synthetic construct
SEQUENCE: 1142
ISWNSGTR                                                    8

SEQ ID NO: 1143         moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 1143
gtgaaagatg gaagtggcta cgggagatat aatttctacg ctatggacgt c    51

SEQ ID NO: 1144         moltype = AA  length = 17
FEATURE                 Location/Qualifiers
REGION                  1..17
                        note = Synthetic
source                  1..17
                        mol_type = protein
                        organism = synthetic construct
SEQUENCE: 1144
VKDGSGYGRY NFYAMDV                                          17

SEQ ID NO: 1145         moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 1145
gaggtgcagc tggtggagtc tgggggaggc ttggttcagc ctggcaggtc cctgagactc  60
tcctgtgcag cctctggatt tacctttgct gactatacca tgcactgggt ccggcaaggt  120
ccagggaagg gcctggagtg ggtctcagat attggttgga atagtaatac tataggctat  180
gcggactctg tgaagggccg attcgccatc tccagagaca acgccaagaa ctccctgtat  240
cttcaaatga acagtctgcg acctgaggac acggccttat attactgtgt aaaggataaa  300
agtggctacg ggaaattcca atacggtttg gacgtctggg gccaagggac cacggtcacc  360
gtctcctca                                                   369

SEQ ID NO: 1146         moltype = AA  length = 123
FEATURE                 Location/Qualifiers
REGION                  1..123
                        note = Synthetic
source                  1..123
                        mol_type = protein
                        organism = synthetic construct
SEQUENCE: 1146
EVQLVESGGG LVQPGRSLRL SCAASGFTFA DYTMHWVRQG PGKGLEWVSD IGWNSNTIGY  60
ADSVKGRFAI SRDNAKNSLY LQMNSLRPED TALYYCVKDK SGYGKFQYGL DVWGQGTTVT  120
VSS                                                         123

SEQ ID NO: 1147         moltype = DNA  length = 24
FEATURE                 Location/Qualifiers
misc_feature            1..24
                        note = Synthetic
source                  1..24
                        mol_type = other DNA
```

```
                        organism = synthetic construct
SEQUENCE: 1147
ggatttacct ttgctgacta tacc                                   24

SEQ ID NO: 1148         moltype = AA  length = 8
FEATURE                 Location/Qualifiers
REGION                  1..8
                        note = Synthetic
source                  1..8
                        mol_type = protein
                        organism = synthetic construct
SEQUENCE: 1148
GFTFADYT                                                     8

SEQ ID NO: 1149         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1149
attggttgga atagtaatac tata                                   24

SEQ ID NO: 1150         moltype = AA  length = 8
FEATURE                 Location/Qualifiers
REGION                  1..8
                        note = Synthetic
source                  1..8
                        mol_type = protein
                        organism = synthetic construct
SEQUENCE: 1150
IGWNSNTI                                                     8

SEQ ID NO: 1151         moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 1151
gtaaaggata aaagtggcta cgggaaattc caatacggtt tggacgtc         48

SEQ ID NO: 1152         moltype = AA  length = 16
FEATURE                 Location/Qualifiers
REGION                  1..16
                        note = Synthetic
source                  1..16
                        mol_type = protein
                        organism = synthetic construct
SEQUENCE: 1152
VKDKSGYGKF QYGLDV                                            16

SEQ ID NO: 1153         moltype = DNA  length = 369
FEATURE                 Location/Qualifiers
misc_feature            1..369
                        note = Synthetic
source                  1..369
                        mol_type = other DNA
                        organism = synthetic construct
SEQUENCE: 1153
gaggtgcagc tggtggagtc tgggggaggc ttggtacagc ctggcaggtc cctgagactc  60
tcctgtgcag cctctggatt tacatttgac gattatacca tgcactgggt ccggcaaggt  120
ccagggaagg gcctggagtg ggtctcagat attggttgga atagtaacag tataggctat  180
gcggactctg tgaagggccg attcaccatc tccagagaca acgccaagaa ctccctgtat  240
ctccaaatga acagtctgag acctgaggac acggccttgt atttctgtgt aaaggataaa  300
agtggctacg ggaaattttt catcggtttg gacgtctggg gccaagggac aatggtcacc  360
gtctcttca                                                    369

SEQ ID NO: 1154         moltype = AA  length = 123
FEATURE                 Location/Qualifiers
REGION                  1..123
                        note = Synthetic
source                  1..123
                        mol_type = protein
                        organism = synthetic construct
SEQUENCE: 1154
EVQLVESGGG LVQPGRSLRL SCAASGFTFD DYTMHWVRQG PGKGLEWVSD IGWNSNSIGY  60
```

```
ADSVKGRFTI SRDNAKNSLY LQMNSLRPED TALYFCVKDK SGYGKFFIGL DVWGQGTMVT  120
VSS                                                               123

SEQ ID NO: 1155        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1155
ggatttacat ttgacgatta tacc                                        24

SEQ ID NO: 1156        moltype = AA  length = 8
FEATURE                Location/Qualifiers
REGION                 1..8
                       note = Synthetic
source                 1..8
                       mol_type = protein
                       organism = synthetic construct
SEQUENCE: 1156
GFTFDDYT                                                          8

SEQ ID NO: 1157        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1157
attggttgga atagtaacag tata                                        24

SEQ ID NO: 1158        moltype = AA  length = 8
FEATURE                Location/Qualifiers
REGION                 1..8
                       note = Synthetic
source                 1..8
                       mol_type = protein
                       organism = synthetic construct
SEQUENCE: 1158
IGWNSNSI                                                          8

SEQ ID NO: 1159        moltype = DNA  length = 48
FEATURE                Location/Qualifiers
misc_feature           1..48
                       note = Synthetic
source                 1..48
                       mol_type = other DNA
                       organism = synthetic construct
SEQUENCE: 1159
gtaaaggata aaagtggcta cgggaaattt ttcatcggtt tggacgtc              48

SEQ ID NO: 1160        moltype = AA  length = 16
FEATURE                Location/Qualifiers
REGION                 1..16
                       note = Synthetic
source                 1..16
                       mol_type = protein
                       organism = synthetic construct
SEQUENCE: 1160
VKDKSGYGKF FIGLDV                                                 16

SEQ ID NO: 1161        moltype = DNA  length = 369
FEATURE                Location/Qualifiers
misc_feature           1..369
                       note = Synthetic
source                 1..369
                       mol_type = other DNA
                       organism = synthetic construct
SEQUENCE: 1161
caggtgcagt tggtggagtc tgggggaggc ttggtacagc ctggcaggtc cctgagactc  60
tcctgtgcag cctctggatt tacatttgac gattatacca tgcactgggt ccggcaaggt  120
ccagggaagg gcctggagtg ggtctcagat attggttgga atagtaatac taaaggctat  180
gcggactctg tgaagggccg attcaccatc tccagagaca acgccaagaa ttccctgtat  240
ctccaaatga acagtctgag acctgaggac acggccttgt atttctgtgt gaaggataaa  300
agtggctacg ggaaattttt catcggtttg gacgtctggg gccaagggac aatggtcacc  360
gtctcttca                                                         369
```

-continued

```
SEQ ID NO: 1162        moltype = AA  length = 123
FEATURE                Location/Qualifiers
REGION                 1..123
                       note = Synthetic
source                 1..123
                       mol_type = protein
                       organism = synthetic construct
SEQUENCE: 1162
QVQLVESGGG LVQPGRSLRL SCAASGFTFD DYTMHWVRQG PGKGLEWVSD IGWNSNTKGY  60
ADSVKGRFTI SRDNAKNSLY LQMNSLRPED TALYFCVKDK SGYGKFFIGL DVWGQGTMVT  120
VSS                                                               123

SEQ ID NO: 1163        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1163
ggatttacat ttgacgatta tacc                                        24

SEQ ID NO: 1164        moltype = AA  length = 8
FEATURE                Location/Qualifiers
REGION                 1..8
                       note = Synthetic
source                 1..8
                       mol_type = protein
                       organism = synthetic construct
SEQUENCE: 1164
GFTFDDYT                                                          8

SEQ ID NO: 1165        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1165
attggttgga atagtaatac taaa                                        24

SEQ ID NO: 1166        moltype = AA  length = 8
FEATURE                Location/Qualifiers
REGION                 1..8
                       note = Synthetic
source                 1..8
                       mol_type = protein
                       organism = synthetic construct
SEQUENCE: 1166
IGWNSNTK                                                          8

SEQ ID NO: 1167        moltype = DNA  length = 48
FEATURE                Location/Qualifiers
misc_feature           1..48
                       note = Synthetic
source                 1..48
                       mol_type = other DNA
                       organism = synthetic construct
SEQUENCE: 1167
gtgaaggata aaagtggcta cgggaaattt ttcatcggtt tggacgtc              48

SEQ ID NO: 1168        moltype = AA  length = 16
FEATURE                Location/Qualifiers
REGION                 1..16
                       note = Synthetic
source                 1..16
                       mol_type = protein
                       organism = synthetic construct
SEQUENCE: 1168
VKDKSGYGKF FIGLDV                                                 16

SEQ ID NO: 1169        moltype = DNA  length = 369
FEATURE                Location/Qualifiers
misc_feature           1..369
                       note = Synthetic
source                 1..369
                       mol_type = other DNA
                       organism = synthetic construct
```

```
SEQUENCE: 1169
gaggtgcagc tggtggagtc tgggggaggc ttggtccagc ctgggcggtc cctgagactc  60
tcctgtgcag cctccggatt cacctttgct gattatacca tgcactgggt ccggcaaggt  120
ccagggacgg gcctggagtg ggtctcagat attggttgga gtggtggtag tttaggctat  180
gcggactctg tgaagggccg attcaccatc tccagagaca acgccaagaa ctccctgtat  240
ttggaaatga acaatctgcg acctgaagac acggccttgt attattgtgt aaaggataaa  300
agtggctacg ggaaattcca gtacggtttg gacgtctggg gccaagggac cacggtcacc  360
gtctcctca                                                          369

SEQ ID NO: 1170        moltype = AA  length = 123
FEATURE                Location/Qualifiers
REGION                 1..123
                       note = Synthetic
source                 1..123
                       mol_type = protein
                       organism = synthetic construct
SEQUENCE: 1170
EVQLVESGGG LVQPGRSLRL SCAASGFTFA DYTMHWVRQG PGTGLEWVSD IGWSGGSLGY  60
ADSVKGRFTI SRDNAKNSLY LEMNNLRPED TALYYCVKDK SGYGKFQYGL DVWGQGTTVT  120
VSS                                                                123

SEQ ID NO: 1171        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1171
ggattcacct ttgctgatta tacc                                         24

SEQ ID NO: 1172        moltype = AA  length = 8
FEATURE                Location/Qualifiers
REGION                 1..8
                       note = Synthetic
source                 1..8
                       mol_type = protein
                       organism = synthetic construct
SEQUENCE: 1172
GFTFADYT                                                           8

SEQ ID NO: 1173        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1173
attggttgga gtggtggtag ttta                                         24

SEQ ID NO: 1174        moltype = AA  length = 8
FEATURE                Location/Qualifiers
REGION                 1..8
                       note = Synthetic
source                 1..8
                       mol_type = protein
                       organism = synthetic construct
SEQUENCE: 1174
IGWSGGSL                                                           8

SEQ ID NO: 1175        moltype = DNA  length = 48
FEATURE                Location/Qualifiers
misc_feature           1..48
                       note = Synthetic
source                 1..48
                       mol_type = other DNA
                       organism = synthetic construct
SEQUENCE: 1175
gtaaaggata aaagtggcta cgggaaattc cagtacggtt tggacgtc               48

SEQ ID NO: 1176        moltype = AA  length = 16
FEATURE                Location/Qualifiers
REGION                 1..16
                       note = Synthetic
source                 1..16
                       mol_type = protein
                       organism = synthetic construct
SEQUENCE: 1176
```

```
VKDKSGYGKF QYGLDV                                               16

SEQ ID NO: 1177        moltype = DNA  length = 369
FEATURE                Location/Qualifiers
misc_feature           1..369
                       note = Synthetic
source                 1..369
                       mol_type = other DNA
                       organism = synthetic construct
SEQUENCE: 1177
gaggtgcagc tggtggagtc tgggggaggc gtggtacagc ctggcaggtc cctgagactc  60
tcctgtgcag cctctgggtt taaatttgat ggttatacca tgcactgggt ccggcaaggt  120
ccagggaagg gcctggagtg ggtctcagat attggttgga atagtaacac tataggctat  180
gcggactctg tgaagggccg attcaccatc tccagagaca acgccaagaa ctccctgtat  240
ctccaaatga acagtctgag accagaggac acggccttgt atttctgtgt aaaggataaa  300
agtggctacg ggaaattttt catcggtttg gacgtctggg gccaagggac aatggtcacc  360
gtctcttca                                                       369

SEQ ID NO: 1178        moltype = AA  length = 123
FEATURE                Location/Qualifiers
REGION                 1..123
                       note = Synthetic
source                 1..123
                       mol_type = protein
                       organism = synthetic construct
SEQUENCE: 1178
EVQLVESGGG VVQPGRSLRL SCAASGFKFD GYTMHWVRQG PGKGLEWVSD IGWNSNTIGY  60
ADSVKGRFTI SRDNAKNSLY LQMNSLRPED TALYFCVKDK SGYGKFFIGL DVWGQGTMVT  120
VSS                                                             123

SEQ ID NO: 1179        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1179
gggtttaaat ttgatggtta tacc                                      24

SEQ ID NO: 1180        moltype = AA  length = 8
FEATURE                Location/Qualifiers
REGION                 1..8
                       note = Synthetic
source                 1..8
                       mol_type = protein
                       organism = synthetic construct
SEQUENCE: 1180
GFKFDGYT                                                        8

SEQ ID NO: 1181        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1181
attggttgga atagtaacac tata                                      24

SEQ ID NO: 1182        moltype = AA  length = 8
FEATURE                Location/Qualifiers
REGION                 1..8
                       note = Synthetic
source                 1..8
                       mol_type = protein
                       organism = synthetic construct
SEQUENCE: 1182
IGWNSNTI                                                        8

SEQ ID NO: 1183        moltype = DNA  length = 48
FEATURE                Location/Qualifiers
misc_feature           1..48
                       note = Synthetic
source                 1..48
                       mol_type = other DNA
                       organism = synthetic construct
SEQUENCE: 1183
gtaaaggata aaagtggcta cgggaaattt ttcatcggtt tggacgtc            48
```

```
SEQ ID NO: 1184        moltype = AA  length = 16
FEATURE                Location/Qualifiers
REGION                 1..16
                       note = Synthetic
source                 1..16
                       mol_type = protein
                       organism = synthetic construct
SEQUENCE: 1184
VKDKSGYGKF FIGLDV                                                  16

SEQ ID NO: 1185        moltype = DNA  length = 369
FEATURE                Location/Qualifiers
misc_feature           1..369
                       note = Synthetic
source                 1..369
                       mol_type = other DNA
                       organism = synthetic construct
SEQUENCE: 1185
caggtgcagc tggtggagtc tgggggaggc ttggtacagc ctggcaggtc cctgagactc  60
tcctgtgcag cctctggatt cacctttgat gattatacca tgcactgggt ccggcaaggt  120
ccagggaagg gcctggagtg ggtctcagat attggttgga atagtaatac tataggctat  180
gcggactctg tgaagggccg attcaccatc tccagagaca acgccaggaa ctccctgtat  240
ctgcaaatga acagtctgcg acctgaagac acggccttat attactgtgt aaaggataaa  300
agtggctacg ggaaattcca atacggtttg gacgtctggg gccaagggac cacggtcacc  360
gtctcctca                                                          369

SEQ ID NO: 1186        moltype = AA  length = 123
FEATURE                Location/Qualifiers
REGION                 1..123
                       note = Synthetic
source                 1..123
                       mol_type = protein
                       organism = synthetic construct
SEQUENCE: 1186
QVQLVESGGG LVQPGRSLRL SCAASGFTFD DYTMHWVRQG PGKGLEWVSD IGWNSNTIGY  60
ADSVKGRFTI SRDNARNSLY LQMNSLRPED TALYYCVKDK SGYGKFQYGL DVWGQGTTVT  120
VSS                                                                123

SEQ ID NO: 1187        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1187
ggattcacct ttgatgatta tacc                                         24

SEQ ID NO: 1188        moltype = AA  length = 8
FEATURE                Location/Qualifiers
REGION                 1..8
                       note = Synthetic
source                 1..8
                       mol_type = protein
                       organism = synthetic construct
SEQUENCE: 1188
GFTFDDYT                                                           8

SEQ ID NO: 1189        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1189
attggttgga atagtaatac tata                                         24

SEQ ID NO: 1190        moltype = AA  length = 8
FEATURE                Location/Qualifiers
REGION                 1..8
                       note = Synthetic
source                 1..8
                       mol_type = protein
                       organism = synthetic construct
SEQUENCE: 1190
IGWNSNTI                                                           8
```

```
SEQ ID NO: 1191        moltype = DNA  length = 48
FEATURE                Location/Qualifiers
misc_feature           1..48
                       note = Synthetic
source                 1..48
                       mol_type = other DNA
                       organism = synthetic construct
SEQUENCE: 1191
gtaaaggata aaagtggcta cgggaaattc caatacggtt tggacgtc              48

SEQ ID NO: 1192        moltype = AA  length = 16
FEATURE                Location/Qualifiers
REGION                 1..16
                       note = Synthetic
source                 1..16
                       mol_type = protein
                       organism = synthetic construct
SEQUENCE: 1192
VKDKSGYGKF QYGLDV                                                 16

SEQ ID NO: 1193        moltype = DNA  length = 369
FEATURE                Location/Qualifiers
misc_feature           1..369
                       note = Synthetic
source                 1..369
                       mol_type = other DNA
                       organism = synthetic construct
SEQUENCE: 1193
caggtgcaac tggtggagtc tgggggaggc ttggtacagc ctggcaggtc cctgagactc  60
tcctgtgcag cctctggatt caagtttgat gattatacca tgcactgggt ccggcaaggt  120
ccagggaagg gcctggagtg ggtctcagac attagttgga gtggtggtag catagactat  180
acggactctg tgaagggccg attctccatc tccagagaca acgccaagaa ctccctgtat  240
ctgcaaatga acagtctgag agttgaagac acggccttgt attattgtgt aaaagataaa  300
agtggctacg ggaagtactc ttacggtttg gacgtctggg gccaagggac cacggtcacc  360
gtctcctca                                                         369

SEQ ID NO: 1194        moltype = AA  length = 123
FEATURE                Location/Qualifiers
REGION                 1..123
                       note = Synthetic
source                 1..123
                       mol_type = protein
                       organism = synthetic construct
SEQUENCE: 1194
QVQLVESGGG LVQPGRSLRL SCAASGFKFD DYTMHWVRQG PGKGLEWVSD ISWSGGSIDY  60
TDSVKGRFSI SRDNAKNSLY LQMNSLRVED TALYYCVKDK SGYGKYSYGL DVWGQGTTVT  120
VSS                                                               123

SEQ ID NO: 1195        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1195
ggattcaagt ttgatgatta tacc                                        24

SEQ ID NO: 1196        moltype = AA  length = 8
FEATURE                Location/Qualifiers
REGION                 1..8
                       note = Synthetic
source                 1..8
                       mol_type = protein
                       organism = synthetic construct
SEQUENCE: 1196
GFKFDDYT                                                          8

SEQ ID NO: 1197        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1197
attagttgga gtggtggtag cata                                        24

SEQ ID NO: 1198        moltype = AA  length = 8
```

```
FEATURE                Location/Qualifiers
REGION                 1..8
                       note = Synthetic
source                 1..8
                       mol_type = protein
                       organism = synthetic construct
SEQUENCE: 1198
ISWSGGSI                                                                   8

SEQ ID NO: 1199        moltype = DNA  length = 48
FEATURE                Location/Qualifiers
misc_feature           1..48
                       note = Synthetic
source                 1..48
                       mol_type = other DNA
                       organism = synthetic construct
SEQUENCE: 1199
gtaaaagata aaagtggcta cgggaagtac tcttacggtt tggacgtc                      48

SEQ ID NO: 1200        moltype = AA  length = 16
FEATURE                Location/Qualifiers
REGION                 1..16
                       note = Synthetic
source                 1..16
                       mol_type = protein
                       organism = synthetic construct
SEQUENCE: 1200
VKDKSGYGKY SYGLDV                                                          16

SEQ ID NO: 1201        moltype = DNA  length = 357
FEATURE                Location/Qualifiers
misc_feature           1..357
                       note = Synthetic
source                 1..357
                       mol_type = other DNA
                       organism = synthetic construct
SEQUENCE: 1201
gaggtgcagc tggtggagtc tgggggaggc ttggtaaagc cggggggggtc ccttagaatc  60
tcctgtgcag cctctggatt ctctttcatt aacgcctgga tgaactgggt ccgccaggct  120
ccagggaagg ggctggagtg ggttggccgt attaaaagca taagtgatgg tgggacaaca  180
gactacgctg catccgtgaa aggcagattc accatctcaa gagaagattc aaaaaatatg  240
ctgtttctgg aaatgaatag tctgaaaacc gaggacacag ccgtgtttta ctgtaccaca  300
gaggtcgcta gaactccgaa ctactggggc cggggaaccc tggtcaccgt ctcctca     357

SEQ ID NO: 1202        moltype = AA  length = 119
FEATURE                Location/Qualifiers
REGION                 1..119
                       note = Synthetic
source                 1..119
                       mol_type = protein
                       organism = synthetic construct
SEQUENCE: 1202
EVQLVESGGG LVKPGGSLRI SCAASGFSFI NAWMNWVRQA PGKGLEWVGR IKSISDGGTT  60
DYAASVKGRF TISREDSKNM LFLEMNSLKT EDTAVFYCTT EVARTPNYWG RGTLVTVSS   119

SEQ ID NO: 1203        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1203
ggattctctt tcattaacgc ctgg                                                 24

SEQ ID NO: 1204        moltype = AA  length = 8
FEATURE                Location/Qualifiers
REGION                 1..8
                       note = Synthetic
source                 1..8
                       mol_type = protein
                       organism = synthetic construct
SEQUENCE: 1204
GFSFINAW                                                                   8

SEQ ID NO: 1205        moltype = DNA  length = 30
FEATURE                Location/Qualifiers
misc_feature           1..30
                       note = Synthetic
```

```
source                  1..30
                        mol_type = other DNA
                        organism = synthetic construct
SEQUENCE: 1205
attaaaagca taagtgatgg tgggacaaca                                   30

SEQ ID NO: 1206         moltype = AA  length = 10
FEATURE                 Location/Qualifiers
REGION                  1..10
                        note = Synthetic
source                  1..10
                        mol_type = protein
                        organism = synthetic construct
SEQUENCE: 1206
IKSISDGGTT                                                         10

SEQ ID NO: 1207         moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 1207
accacagagg tcgctagaac tccgaactac                                   30

SEQ ID NO: 1208         moltype = AA  length = 10
FEATURE                 Location/Qualifiers
REGION                  1..10
                        note = Synthetic
source                  1..10
                        mol_type = protein
                        organism = synthetic construct
SEQUENCE: 1208
TTEVARTPNY                                                         10

SEQ ID NO: 1209         moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 1209
gaagtacagc ttgtagaatc cggcggagga ctggtacaac ctggaagaag tcttagactg  60
agttgcgcag ctagtgggtt tacattcgac gattacagca tgcattgggt gaggcaagct  120
cctggtaaag gattggaatg ggttagcggg atatcatgga actcaggaag caagggatac  180
gccgacagcg tgaaaggccg atttacaata tctagggaca acgcaaaaaa ctctctctac  240
cttcaaatga actctcttag ggcagaagac acagcattgt attattgcgc aaaatacggc  300
agtggttatg gcaagtttta tcattatgga ctggacgtgt ggggacaagg gacaacagtg  360
acagtgagta gc                                                      372

SEQ ID NO: 1210         moltype = AA  length = 124
FEATURE                 Location/Qualifiers
REGION                  1..124
                        note = Synthetic
source                  1..124
                        mol_type = protein
                        organism = synthetic construct
SEQUENCE: 1210
EVQLVESGGG LVQPGRSLRL SCAASGFTFD DYSMHWVRQA PGKGLEWVSG ISWNSGSKGY  60
ADSVKGRFTI SRDNAKNSLY LQMNSLRAED TALYYCAKYG SGYGKFYHYG LDVWGQGTTV  120
TVSS                                                               124

SEQ ID NO: 1211         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1211
gggtttacat tcgacgatta cagc                                         24

SEQ ID NO: 1212         moltype = AA  length = 8
FEATURE                 Location/Qualifiers
REGION                  1..8
                        note = Synthetic
source                  1..8
```

```
                        mol_type = protein
                        organism = synthetic construct
SEQUENCE: 1212
GFTFDDYS                                                     8

SEQ ID NO: 1213         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1213
atatcatgga actcaggaag caag                                   24

SEQ ID NO: 1214         moltype = AA  length = 8
FEATURE                 Location/Qualifiers
REGION                  1..8
                        note = Synthetic
source                  1..8
                        mol_type = protein
                        organism = synthetic construct
SEQUENCE: 1214
ISWNSGSK                                                     8

SEQ ID NO: 1215         moltype = DNA  length = 51
FEATURE                 Location/Qualifiers
misc_feature            1..51
                        note = Synthetic
source                  1..51
                        mol_type = other DNA
                        organism = synthetic construct
SEQUENCE: 1215
gcaaaatacg gcagtggtta tggcaagttt tatcattatg gactggacgt g     51

SEQ ID NO: 1216         moltype = AA  length = 17
FEATURE                 Location/Qualifiers
REGION                  1..17
                        note = Synthetic
source                  1..17
                        mol_type = protein
                        organism = synthetic construct
SEQUENCE: 1216
AKYGSGYGKF YHYGLDV                                           17

SEQ ID NO: 1217         moltype = DNA  length = 372
FEATURE                 Location/Qualifiers
misc_feature            1..372
                        note = Synthetic
source                  1..372
                        mol_type = other DNA
                        organism = synthetic construct
SEQUENCE: 1217
gaagtacaac tggtcgaatc tggaggaggt cttgttcaac ctggtcgatc acttcgcctt  60
tcttgtgccg cttctggttt cactttcgac gattatagca tgcattgggt acgacaggct  120
cccggaaaag ggctggaatg ggtgtcagga attagttgga actcaggaag tattggatac  180
gctgattcag tcaaaggacg cttcacaatc tcaagggaca acgctaaaaa ctcactttat  240
ttgcaaatga actctctccg cgctgaagat accgctctct attattgcgc caaagatggg  300
tctggttacg gttattttta ctactatgga atggacgttt ggggccaagg aacaactgtc  360
acagtatcat cc                                                372

SEQ ID NO: 1218         moltype = AA  length = 124
FEATURE                 Location/Qualifiers
REGION                  1..124
                        note = Synthetic
source                  1..124
                        mol_type = protein
                        organism = synthetic construct
SEQUENCE: 1218
EVQLVESGGG LVQPGRSLRL SCAASGFTFD DYSMHWVRQA PGKGLEWVSG ISWNSGSIGY  60
ADSVKGRFTI SRDNAKNSLY LQMNSLRAED TALYYCAKDG SGYGYFYYYG MDVWGQGTTV  120
TVSS                                                         124

SEQ ID NO: 1219         moltype = DNA  length = 24
FEATURE                 Location/Qualifiers
misc_feature            1..24
                        note = Synthetic
source                  1..24
                        mol_type = other DNA
```

```
                         organism = synthetic construct
SEQUENCE: 1219
ggtttcactt tcgacgatta tagc                                          24

SEQ ID NO: 1220          moltype = AA  length = 8
FEATURE                  Location/Qualifiers
REGION                   1..8
                         note = Synthetic
source                   1..8
                         mol_type = protein
                         organism = synthetic construct
SEQUENCE: 1220
GFTFDDYS                                                            8

SEQ ID NO: 1221          moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 1221
attagttgga actcaggaag tatt                                          24

SEQ ID NO: 1222          moltype = AA  length = 8
FEATURE                  Location/Qualifiers
REGION                   1..8
                         note = Synthetic
source                   1..8
                         mol_type = protein
                         organism = synthetic construct
SEQUENCE: 1222
ISWNSGSI                                                            8

SEQ ID NO: 1223          moltype = DNA  length = 51
FEATURE                  Location/Qualifiers
misc_feature             1..51
                         note = Synthetic
source                   1..51
                         mol_type = other DNA
                         organism = synthetic construct
SEQUENCE: 1223
gccaaagatg ggtctggtta cggttatttt tactactatg gaatggacgt t            51

SEQ ID NO: 1224          moltype = AA  length = 17
FEATURE                  Location/Qualifiers
REGION                   1..17
                         note = Synthetic
source                   1..17
                         mol_type = protein
                         organism = synthetic construct
SEQUENCE: 1224
AKDGSGYGYF YYYGMDV                                                  17

SEQ ID NO: 1225          moltype = DNA  length = 372
FEATURE                  Location/Qualifiers
misc_feature             1..372
                         note = Synthetic
source                   1..372
                         mol_type = other DNA
                         organism = synthetic construct
SEQUENCE: 1225
gaagtgcaac tcgttgaaag cggaggagga ctggtccagc ccggcagatc tctcagattg  60
tcttgcgctg catccggatt tacatttgac gactattcaa tgcactgggt acggcaagcc  120
ccaggtaaag gactcgaatg ggtaagcggc atatcttgga actcaggcag tattggctac  180
gcagattcag taaaaggaag attcactatt tcaagggata atgctaagaa cagtctctac  240
ttgcaaatga atagcttgcg cgcagaagat acagcacttt attattgtgc aaaagatgga  300
agcggttatg ggaaatttta ttattatggt atggatgtat ggggtcaagg tacaacagtt  360
actgtgtcaa gt                                                       372

SEQ ID NO: 1226          moltype = AA  length = 124
FEATURE                  Location/Qualifiers
REGION                   1..124
                         note = Synthetic
source                   1..124
                         mol_type = protein
                         organism = synthetic construct
SEQUENCE: 1226
EVQLVESGGG LVQPGRSLRL SCAASGFTFD DYSMHWVRQA PGKGLEWVSG ISWNSGSIGY  60
```

```
ADSVKGRFTI SRDNAKNSLY LQMNSLRAED TALYYCAKDG SGYGKFYYYG MDVWGQGTTV  120
TVSS                                                              124

SEQ ID NO: 1227        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1227
ggatttacat ttgacgacta ttca                                        24

SEQ ID NO: 1228        moltype = AA  length = 8
FEATURE                Location/Qualifiers
REGION                 1..8
                       note = Synthetic
source                 1..8
                       mol_type = protein
                       organism = synthetic construct
SEQUENCE: 1228
GFTFDDYS                                                          8

SEQ ID NO: 1229        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1229
atatcttgga actcaggcag tatt                                        24

SEQ ID NO: 1230        moltype = AA  length = 8
FEATURE                Location/Qualifiers
REGION                 1..8
                       note = Synthetic
source                 1..8
                       mol_type = protein
                       organism = synthetic construct
SEQUENCE: 1230
ISWNSGSI                                                          8

SEQ ID NO: 1231        moltype = DNA  length = 51
FEATURE                Location/Qualifiers
misc_feature           1..51
                       note = Synthetic
source                 1..51
                       mol_type = other DNA
                       organism = synthetic construct
SEQUENCE: 1231
gcaaaagatg gaagcggtta tgggaaattt tattattatg gtatggatgt a          51

SEQ ID NO: 1232        moltype = AA  length = 17
FEATURE                Location/Qualifiers
REGION                 1..17
                       note = Synthetic
source                 1..17
                       mol_type = protein
                       organism = synthetic construct
SEQUENCE: 1232
AKDGSGYGKF YYYGMDV                                                17

SEQ ID NO: 1233        moltype = DNA  length = 324
FEATURE                Location/Qualifiers
misc_feature           1..324
                       note = Synthetic
source                 1..324
                       mol_type = other DNA
                       organism = synthetic construct
SEQUENCE: 1233
gacatccaga tgacccagtc tccatcctcc ctgtctgcat ctgtaggaga cagagtcacc  60
atcacttgcc gggcaagtca gagcattagc agctatttaa attggtatca gcagaaacca  120
gggaaagccc ctaagctcct gatctatgct gcatccagtt tgcaaagtgg ggtcccgtca  180
aggttcagtg gcagtggatc tgggacagat ttcactctca ccatcagcag tctgcaacct  240
gaagattttg caacttacta ctgtcaacag agttacagta cccctccgat caccttcggc  300
caagggacac gactggagat taaa                                        324

SEQ ID NO: 1234        moltype = AA  length = 108
```

```
FEATURE                 Location/Qualifiers
REGION                  1..108
                        note = Synthetic
source                  1..108
                        mol_type = protein
                        organism = synthetic construct
SEQUENCE: 1234
DIQMTQSPSS LSASVGDRVT ITCRASQSIS SYLNWYQQKP GKAPKLLIYA ASSLQSGVPS  60
RFSGSGSGTD FTLTISSLQP EDFATYYCQQ SYSTPPITFG QGTRLEIK               108

SEQ ID NO: 1235         moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 1235
cagagcatta gcagctat                                                18

SEQ ID NO: 1236         moltype = AA  length = 6
FEATURE                 Location/Qualifiers
REGION                  1..6
                        note = Synthetic
source                  1..6
                        mol_type = protein
                        organism = synthetic construct
SEQUENCE: 1236
QSISSY                                                             6

SEQ ID NO: 1237         moltype =   length =
SEQUENCE: 1237
000

SEQ ID NO: 1238         moltype =   length =
SEQUENCE: 1238
000

SEQ ID NO: 1239         moltype = DNA  length = 30
FEATURE                 Location/Qualifiers
misc_feature            1..30
                        note = Synthetic
source                  1..30
                        mol_type = other DNA
                        organism = synthetic construct
SEQUENCE: 1239
caacagagtt acagtacccc tccgatcacc                                   30

SEQ ID NO: 1240         moltype = AA  length = 10
FEATURE                 Location/Qualifiers
REGION                  1..10
                        note = Synthetic
source                  1..10
                        mol_type = protein
                        organism = synthetic construct
SEQUENCE: 1240
QQSYSTPPIT                                                         10

SEQ ID NO: 1241         moltype = DNA  length = 382
FEATURE                 Location/Qualifiers
misc_feature            1..382
                        note = Synthetic
source                  1..382
                        mol_type = other DNA
                        organism = synthetic construct
SEQUENCE: 1241
gaagtacagc tggtggagtc tgggggaggc ttggtacagc ctggcaggtc cctgagactc  60
tcctgtgtag cctctggatt cacctttaat gattatgcca tgcactgggt ccggcaagct  120
ccagggaagg gcctggaatg ggtctcagtt attagttgga atagtgatag cataggctat  180
gcggactctg tgaagggccg attcaccatc tccagagaca acgccaagaa ctccctgtat  240
ctgcaaatgc acagtctgag agctgaggac acggccttgt attactgtgc aaaagataat  300
cactatggtt cggggagtta ttactactac caatacggta tggacgtctg gggccaaggg  360
accacggtca ccgtctcctc ag                                           382

SEQ ID NO: 1242         moltype = AA  length = 127
FEATURE                 Location/Qualifiers
REGION                  1..127
                        note = Synthetic
source                  1..127
```

```
                         mol_type = protein
                         organism = synthetic construct
SEQUENCE: 1242
EVQLVESGGG LVQPGRSLRL SCVASGFTFN DYAMHWVRQA PGKGLEWVSV ISWNSDSIGY  60
ADSVKGRFTI SRDNAKNSLY LQMHSLRAED TALYYCAKDN HYGSGSYYYY QYGMDVWGQG  120
TTVTVSS                                                            127

SEQ ID NO: 1243          moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 1243
ggattcacct ttaatgatta tgcc                                         24

SEQ ID NO: 1244          moltype = AA  length = 8
FEATURE                  Location/Qualifiers
REGION                   1..8
                         note = Synthetic
source                   1..8
                         mol_type = protein
                         organism = synthetic construct
SEQUENCE: 1244
GFTFNDYA                                                           8

SEQ ID NO: 1245          moltype = DNA  length = 24
FEATURE                  Location/Qualifiers
misc_feature             1..24
                         note = Synthetic
source                   1..24
                         mol_type = other DNA
                         organism = synthetic construct
SEQUENCE: 1245
attagttgga atagtgatag cata                                         24

SEQ ID NO: 1246          moltype = AA  length = 8
FEATURE                  Location/Qualifiers
REGION                   1..8
                         note = Synthetic
source                   1..8
                         mol_type = protein
                         organism = synthetic construct
SEQUENCE: 1246
ISWNSDSI                                                           8

SEQ ID NO: 1247          moltype = DNA  length = 60
FEATURE                  Location/Qualifiers
misc_feature             1..60
                         note = Synthetic
source                   1..60
                         mol_type = other DNA
                         organism = synthetic construct
SEQUENCE: 1247
gcaaaagata atcactatgg ttcggggagt tattactact accaatacgg tatggacgtc  60

SEQ ID NO: 1248          moltype = AA  length = 20
FEATURE                  Location/Qualifiers
REGION                   1..20
                         note = Synthetic
source                   1..20
                         mol_type = protein
                         organism = synthetic construct
SEQUENCE: 1248
AKDNHYGSGS YYYYQYGMDV                                              20

SEQ ID NO: 1249          moltype = DNA  length = 369
FEATURE                  Location/Qualifiers
misc_feature             1..369
                         note = Synthetic
source                   1..369
                         mol_type = other DNA
                         organism = synthetic construct
SEQUENCE: 1249
gaagtgcagc tggtggagtc tgggggaggc ttggtacagc ctggcaggtc cctgagactc  60
tcctgtgcag cctctggatt cacctttgat gattatacca tgcactgggt ccggcaagct  120
ccagggaagg gcctggagtg ggtctcaggt attagttgga atagtggtag tataggctat  180
gcggactctg tgaagggccg attcaccatc tccagagaca acgccaagaa gtccctgtat  240
```

```
ctgcaaatga acagtctgag agctgaggac acggccttgt attactgtgc aaaagataat  300
agtggctacg gtcactacta ctacggaatg gacgtctggg gccaagggac cacggtcacc  360
gtcgcctca                                                          369

SEQ ID NO: 1250        moltype = AA  length = 123
FEATURE                Location/Qualifiers
REGION                 1..123
                       note = Synthetic
source                 1..123
                       mol_type = protein
                       organism = synthetic construct
SEQUENCE: 1250
EVQLVESGGG LVQPGRSLRL SCAASGFTFD DYTMHWVRQA PGKGLEWVSG ISWNSGSIGY  60
ADSVKGRFTI SRDNAKKSLY LQMNSLRAED TALYYCAKDN SGYGHYYYGM DVWGQGTTVT  120
VAS                                                                123

SEQ ID NO: 1251        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1251
ggattcacct ttgatgatta tacc                                         24

SEQ ID NO: 1252        moltype = AA  length = 8
FEATURE                Location/Qualifiers
REGION                 1..8
                       note = Synthetic
source                 1..8
                       mol_type = protein
                       organism = synthetic construct
SEQUENCE: 1252
GFTFDDYT                                                           8

SEQ ID NO: 1253        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1253
attagttgga atagtggtag tata                                         24

SEQ ID NO: 1254        moltype = AA  length = 8
FEATURE                Location/Qualifiers
REGION                 1..8
                       note = Synthetic
source                 1..8
                       mol_type = protein
                       organism = synthetic construct
SEQUENCE: 1254
ISWNSGSI                                                           8

SEQ ID NO: 1255        moltype = DNA  length = 48
FEATURE                Location/Qualifiers
misc_feature           1..48
                       note = Synthetic
source                 1..48
                       mol_type = other DNA
                       organism = synthetic construct
SEQUENCE: 1255
gcaaaagata atagtggcta cggtcactac tactacggaa tggacgtc               48

SEQ ID NO: 1256        moltype = AA  length = 16
FEATURE                Location/Qualifiers
REGION                 1..16
                       note = Synthetic
source                 1..16
                       mol_type = protein
                       organism = synthetic construct
SEQUENCE: 1256
AKDNSGYGHY YYGMDV                                                  16

SEQ ID NO: 1257        moltype = DNA  length = 320
FEATURE                Location/Qualifiers
misc_feature           1..320
```

```
                         note = Synthetic
source                   1..320
                         mol_type = other DNA
                         organism = synthetic construct
SEQUENCE: 1257
gaaatagtga tgacgcagtc tccagccacc ctgtctgtgt ctccagggga aagagccacc  60
ctctcctgca gggccagtca gagtgttagc agcaacttag cctggtacca gcaaaaacct  120
ggccaggctc ccaggctcct catctatggt gcatccacca gggccactgg tatcccagcc  180
aggttcagtg gcagtgggtc tgggacagag ttcactctca ccatcagcag cctgcagtct  240
gaagattttg cagtttatta ctgtcagcac tatattaact ggcctctcac tttcggcgga  300
gggaccaagg tggagatcaa                                              320

SEQ ID NO: 1258          moltype = AA  length = 108
FEATURE                  Location/Qualifiers
REGION                   1..108
                         note = Synthetic
source                   1..108
                         mol_type = protein
                         organism = synthetic construct
SEQUENCE: 1258
AEIVMTQSPA TLSVSPGERA TLSCRASQSV SSNLAWYQQK PGQAPRLLIY GASTRATGIP  60
ARFSGSGSGT EFTLTISSLQ SEDFAVYYCQ HYINWPLTFG GGTKVEIK               108

SEQ ID NO: 1259          moltype = DNA  length = 18
FEATURE                  Location/Qualifiers
misc_feature             1..18
                         note = Synthetic
source                   1..18
                         mol_type = other DNA
                         organism = synthetic construct
SEQUENCE: 1259
cagagtgtta gcagcaac                                                18

SEQ ID NO: 1260          moltype = AA  length = 6
FEATURE                  Location/Qualifiers
REGION                   1..6
                         note = Synthetic
source                   1..6
                         mol_type = protein
                         organism = synthetic construct
SEQUENCE: 1260
QSVSSN                                                             6

SEQ ID NO: 1261          moltype =   length =
SEQUENCE: 1261
000

SEQ ID NO: 1262          moltype =   length =
SEQUENCE: 1262
000

SEQ ID NO: 1263          moltype = DNA  length = 27
FEATURE                  Location/Qualifiers
misc_feature             1..27
                         note = Synthetic
source                   1..27
                         mol_type = other DNA
                         organism = synthetic construct
SEQUENCE: 1263
cagcactata ttaactggcc tctcact                                      27

SEQ ID NO: 1264          moltype = AA  length = 9
FEATURE                  Location/Qualifiers
REGION                   1..9
                         note = Synthetic
source                   1..9
                         mol_type = protein
                         organism = synthetic construct
SEQUENCE: 1264
QHYINWPLT                                                          9

SEQ ID NO: 1265          moltype = DNA  length = 369
FEATURE                  Location/Qualifiers
misc_feature             1..369
                         note = Synthetic
source                   1..369
                         mol_type = other DNA
                         organism = synthetic construct
SEQUENCE: 1265
```

```
gaagtgcaac tggtggagtc tgggggaggc ttagtacagc ctggcgggtc cctgagactc  60
tcctgtgcag ccactggatt cacctttgat gattttacca tgcactgggt ccggcaagct  120
ccagggaagg gcctggagtg ggtctcaggt atcagttgga atagtggtag cataggctat  180
gtggactctg tgaagggccg attcaccatc tccagagaca acgccaagaa ctccctgtat  240
ctgcaaatga acagtctgag agctgaggac acggccttgt actactgtgc aaaagataat  300
agtggctacg gctattatta ctacggtatg gacgtctggg gccaagggac cacggtcacc  360
gtctcctca                                                         369

SEQ ID NO: 1266        moltype = AA  length = 123
FEATURE                Location/Qualifiers
REGION                 1..123
                       note = Synthetic
source                 1..123
                       mol_type = protein
                       organism = synthetic construct
SEQUENCE: 1266
EVQLVESGGG LVQPGGSLRL SCAATGFTFD DFTMHWVRQA PGKGLEWVSG ISWNSGSIGY  60
VDSVKGRFTI SRDNAKNSLY LQMNSLRAED TALYYCAKDN SGYGYYYYGM DVWGQGTTVT  120
VSS                                                               123

SEQ ID NO: 1267        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1267
ggattcacct ttgatgattt tacc                                        24

SEQ ID NO: 1268        moltype = AA  length = 8
FEATURE                Location/Qualifiers
REGION                 1..8
                       note = Synthetic
source                 1..8
                       mol_type = protein
                       organism = synthetic construct
SEQUENCE: 1268
GFTFDDFT                                                          8

SEQ ID NO: 1269        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1269
atcagttgga atagtggtag cata                                        24

SEQ ID NO: 1270        moltype = AA  length = 8
FEATURE                Location/Qualifiers
REGION                 1..8
                       note = Synthetic
source                 1..8
                       mol_type = protein
                       organism = synthetic construct
SEQUENCE: 1270
ISWNSGSI                                                          8

SEQ ID NO: 1271        moltype = DNA  length = 48
FEATURE                Location/Qualifiers
misc_feature           1..48
                       note = Synthetic
source                 1..48
                       mol_type = other DNA
                       organism = synthetic construct
SEQUENCE: 1271
gcaaaagata atagtggcta cggctattat tactacggta tggacgtc              48

SEQ ID NO: 1272        moltype = AA  length = 16
FEATURE                Location/Qualifiers
REGION                 1..16
                       note = Synthetic
source                 1..16
                       mol_type = protein
                       organism = synthetic construct
SEQUENCE: 1272
AKDNSGYGYY YYGMDV                                                 16
```

```
SEQ ID NO: 1273        moltype = DNA  length = 321
FEATURE                Location/Qualifiers
misc_feature           1..321
                       note = Synthetic
source                 1..321
                       mol_type = other DNA
                       organism = synthetic construct
SEQUENCE: 1273
gaaatagtga tgacgcagtc tccagccacc ctgtctgtgt ctccagggga aagagccacc  60
ctctcctgca gggccagtca cagtgttagc aggaactcag cctggtacca gcagaaacct  120
ggccaggctc ccaggctcct catctatggt gcatccacca gggccactgg tatcccagcc  180
aggttcagtg gcagtgggtc tgggacagaa ttcactctca ccatcagcag cctgcagtct  240
gaagattttg caatttatta ctgtcagcag tataataatt ggcctctcac tttcggcgga  300
gggaccaagg tggagatcaa a                                            321

SEQ ID NO: 1274        moltype = AA  length = 107
FEATURE                Location/Qualifiers
REGION                 1..107
                       note = Synthetic
source                 1..107
                       mol_type = protein
                       organism = synthetic construct
SEQUENCE: 1274
EIVMTQSPAT LSVSPGERAT LSCRASHSVS RNSAWYQQKP GQAPRLLIYG ASTRATGIPA  60
RFSGSGSGTE FTLTISSLQS EDFAIYYCQQ YNNWPLTFGG GTKVEIK                107

SEQ ID NO: 1275        moltype = DNA  length = 18
FEATURE                Location/Qualifiers
misc_feature           1..18
                       note = Synthetic
source                 1..18
                       mol_type = other DNA
                       organism = synthetic construct
SEQUENCE: 1275
cacagtgtta gcaggaac                                                18

SEQ ID NO: 1276        moltype = AA  length = 6
FEATURE                Location/Qualifiers
REGION                 1..6
                       note = Synthetic
source                 1..6
                       mol_type = protein
                       organism = synthetic construct
SEQUENCE: 1276
HSVSRN                                                             6

SEQ ID NO: 1277        moltype =   length =
SEQUENCE: 1277
000

SEQ ID NO: 1278        moltype =   length =
SEQUENCE: 1278
000

SEQ ID NO: 1279        moltype = DNA  length = 27
FEATURE                Location/Qualifiers
misc_feature           1..27
                       note = Synthetic
source                 1..27
                       mol_type = other DNA
                       organism = synthetic construct
SEQUENCE: 1279
cagcagtata ataattggcc tctcact                                      27

SEQ ID NO: 1280        moltype = AA  length = 9
FEATURE                Location/Qualifiers
REGION                 1..9
                       note = Synthetic
source                 1..9
                       mol_type = protein
                       organism = synthetic construct
SEQUENCE: 1280
QQYNNWPLT                                                          9

SEQ ID NO: 1281        moltype = DNA  length = 369
FEATURE                Location/Qualifiers
misc_feature           1..369
                       note = Synthetic
```

```
source                  1..369
                        mol_type = other DNA
                        organism = synthetic construct
SEQUENCE: 1281
gaagtgcagc tggtggagtc tgggggaggc ttggtacagc ctggcaggtc cctgagactc  60
tcctgtgcag cctctggatt cacctttgat gattatacca tgcactgggt ccggcaagct  120
ccagggaagg gcctggagtg ggtctcaggt attagttgga atagtggtag tataggctat  180
gcggactctg tgaagggccg attcaccatc tccagagaca acgccaagaa gtccctgtat  240
ctgcaaatga acagtctgag agctgaggac acggccttgt attactgtgc aaaagataat  300
agtggctacg gtcactacta ctacggaatg gacgtctggg gccaagggac cacggtcacc  360
gtcgcctca                                                          369

SEQ ID NO: 1282         moltype = AA  length = 123
FEATURE                 Location/Qualifiers
REGION                  1..123
                        note = Synthetic
source                  1..123
                        mol_type = protein
                        organism = synthetic construct
SEQUENCE: 1282
EVQLVESGGG LVQPGRSLRL SCAASGFTFD DYTMHWVRQA PGKGLEWVSG ISWNSGSIGY  60
ADSVKGRFTI SRDNAKKSLY LQMNSLRAED TALYYCAKDN SGYGHYYYGM DVWGQGTTVT  120
VAS                                                                123

SEQ ID NO: 1283         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1283
ggattcacct ttgatgatta tacc                                         24

SEQ ID NO: 1284         moltype = AA  length = 8
FEATURE                 Location/Qualifiers
REGION                  1..8
                        note = Synthetic
source                  1..8
                        mol_type = protein
                        organism = synthetic construct
SEQUENCE: 1284
GFTFDDYT                                                           8

SEQ ID NO: 1285         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1285
attagttgga atagtggtag tata                                         24

SEQ ID NO: 1286         moltype = AA  length = 8
FEATURE                 Location/Qualifiers
REGION                  1..8
                        note = Synthetic
source                  1..8
                        mol_type = protein
                        organism = synthetic construct
SEQUENCE: 1286
ISWNSGSI                                                           8

SEQ ID NO: 1287         moltype = DNA  length = 48
FEATURE                 Location/Qualifiers
misc_feature            1..48
                        note = Synthetic
source                  1..48
                        mol_type = other DNA
                        organism = synthetic construct
SEQUENCE: 1287
gcaaaagata atagtggcta cggtcactac tactacggaa tggacgtc               48

SEQ ID NO: 1288         moltype = AA  length = 16
FEATURE                 Location/Qualifiers
REGION                  1..16
                        note = Synthetic
source                  1..16
```

```
                        mol_type = protein
                        organism = synthetic construct
SEQUENCE: 1288
AKDNSGYGHY YYGMDV                                                   16

SEQ ID NO: 1289         moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 1289
gaaatagtga tgacgcagtc tccagccacc ctgtctgtgt ctccagggga aagagccacc  60
ctctcctgca gggccagtca gagtgttagc agcaacttag cctggtacca gcaaaaacct  120
ggccaggctc ccaggctcct catctatggt gcatccacca gggccactgg tatcccagcc  180
aggttcagtg gcagtgggtc tgggacagag ttcactctca ccatcagcag cctgcagtct  240
gaagattttg cagtttatta ctgtcagcac tatattaact ggcctctcac tttcggcgga  300
gggaccaagg tggagatcaa a                                             321

SEQ ID NO: 1290         moltype = AA  length = 107
FEATURE                 Location/Qualifiers
REGION                  1..107
                        note = Synthetic
source                  1..107
                        mol_type = protein
                        organism = synthetic construct
SEQUENCE: 1290
EIVMTQSPAT LSVSPGERAT LSCRASQSVS SNLAWYQQKP GQAPRLLIYG ASTRATGIPA  60
RFSGSGSGTE FTLTISSLQS EDFAVYYCQH YINWPLTFGG GTKVEIK                107

SEQ ID NO: 1291         moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 1291
cagagtgtta gcagcaac                                                 18

SEQ ID NO: 1292         moltype = AA  length = 6
FEATURE                 Location/Qualifiers
REGION                  1..6
                        note = Synthetic
source                  1..6
                        mol_type = protein
                        organism = synthetic construct
SEQUENCE: 1292
QSVSSN                                                              6

SEQ ID NO: 1293         moltype =   length =
SEQUENCE: 1293
000

SEQ ID NO: 1294         moltype =   length =
SEQUENCE: 1294
000

SEQ ID NO: 1295         moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 1295
cagcactata ttaactggcc tctcact                                       27

SEQ ID NO: 1296         moltype = AA  length = 9
FEATURE                 Location/Qualifiers
REGION                  1..9
                        note = Synthetic
source                  1..9
                        mol_type = protein
                        organism = synthetic construct
SEQUENCE: 1296
QHYINWPLT                                                           9
```

```
SEQ ID NO: 1297        moltype = DNA  length = 354
FEATURE                Location/Qualifiers
misc_feature           1..354
                       note = Synthetic
source                 1..354
                       mol_type = other DNA
                       organism = synthetic construct
SEQUENCE: 1297
caggtgcagc tggtggagtc tgggggaggc gtggtccagc ctgggaggtc cctgagactc  60
tcctgtgctg cgtctggatt taccttcaga agttatgcca tgcactgggt ccgccaggct  120
ccaggcaagg ggctggagtg ggtggcaatg gtatactatg atggaaataa tcaatactat  180
gcagactccg tgaggggccg attcaccatc tccagagaca attccaagaa cacgctgtat  240
ctgcaaatga acagcctgag agccgatgac acggctgtgt atttctgtgc gcgagggcct  300
gggtacaact ggctcgaccc ctggggccag ggaaccctgg tcaccgtctc ctca        354

SEQ ID NO: 1298        moltype = AA  length = 118
FEATURE                Location/Qualifiers
REGION                 1..118
                       note = Synthetic
source                 1..118
                       mol_type = protein
                       organism = synthetic construct
SEQUENCE: 1298
QVQLVESGGG VVQPGRSLRL SCAASGFTFR SYAMHWVRQA PGKGLEWVAM VYYDGNNQYY  60
ADSVRGRFTI SRDNSKNTLY LQMNSLRADD TAVYFCARGP GYNWLDPWGQ GTLVTVSS    118

SEQ ID NO: 1299        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1299
ggatttacct tcagaagtta tgcc                                         24

SEQ ID NO: 1300        moltype = AA  length = 8
FEATURE                Location/Qualifiers
REGION                 1..8
                       note = Synthetic
source                 1..8
                       mol_type = protein
                       organism = synthetic construct
SEQUENCE: 1300
GFTFRSYA                                                           8

SEQ ID NO: 1301        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1301
gtatactatg atggaaataa tcaa                                         24

SEQ ID NO: 1302        moltype = AA  length = 8
FEATURE                Location/Qualifiers
REGION                 1..8
                       note = Synthetic
source                 1..8
                       mol_type = protein
                       organism = synthetic construct
SEQUENCE: 1302
VYYDGNNQ                                                           8

SEQ ID NO: 1303        moltype = DNA  length = 33
FEATURE                Location/Qualifiers
misc_feature           1..33
                       note = Synthetic
source                 1..33
                       mol_type = other DNA
                       organism = synthetic construct
SEQUENCE: 1303
gcgcgagggc ctgggtacaa ctggctcgac ccc                               33

SEQ ID NO: 1304        moltype = AA  length = 11
FEATURE                Location/Qualifiers
REGION                 1..11
```

```
                        note = Synthetic
source                  1..11
                        mol_type = protein
                        organism = synthetic construct
SEQUENCE: 1304
ARGPGYNWLD P                                                        11

SEQ ID NO: 1305         moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 1305
gaaatagtga tgacgcagtc tccagccacc ctgtctgtgt ctccagggga aagagccacc  60
ctctcctgca gggccagtca gagtgttagc aggaacttgg cctggtacca gcaaaaacct  120
ggccaggctc ccaggctcct catctatggt gcatccacca gggccactgg tatcccggcc  180
aggttcagtg gcagtgggtc tgggacagac ttcactctca ccatcagcag cctgcagtct  240
gaagattttg cagtttatta ctgtcagcag tataataact ggcctctcac tttcggcgga  300
gggaccaagg tggtgatcaa a                                             321

SEQ ID NO: 1306         moltype = AA  length = 107
FEATURE                 Location/Qualifiers
REGION                  1..107
                        note = Synthetic
source                  1..107
                        mol_type = protein
                        organism = synthetic construct
SEQUENCE: 1306
EIVMTQSPAT LSVSPGERAT LSCRASQSVS RNLAWYQQKP GQAPRLLIYG ASTRATGIPA  60
RFSGSGSGTD FTLTISSLQS EDFAVYYCQQ YNNWPLTFGG GTKVVIK                 107

SEQ ID NO: 1307         moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 1307
cagagtgtta gcaggaac                                                 18

SEQ ID NO: 1308         moltype = AA  length = 6
FEATURE                 Location/Qualifiers
REGION                  1..6
                        note = Synthetic
source                  1..6
                        mol_type = protein
                        organism = synthetic construct
SEQUENCE: 1308
QSVSRN                                                              6

SEQ ID NO: 1309         moltype =   length =
SEQUENCE: 1309
000

SEQ ID NO: 1310         moltype =   length =
SEQUENCE: 1310
000

SEQ ID NO: 1311         moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 1311
cagcagtata ataactggcc tctcact                                       27

SEQ ID NO: 1312         moltype = AA  length = 9
FEATURE                 Location/Qualifiers
REGION                  1..9
                        note = Synthetic
source                  1..9
                        mol_type = protein
                        organism = synthetic construct
SEQUENCE: 1312
```

-continued

```
QQYNNWPLT                                                          9

SEQ ID NO: 1313        moltype = DNA  length = 354
FEATURE                Location/Qualifiers
misc_feature           1..354
                       note = Synthetic
source                 1..354
                       mol_type = other DNA
                       organism = synthetic construct
SEQUENCE: 1313
caggtgcagt tggtggagtc tgggggaggc gtggtccagc ctgggaggtc cctgagactc  60
gcctgtgttg cgtctggatt caccttcaga agttatggca tgcactgggt ccgccaggct  120
ccaggcaagg gactgcagtg ggtggcaatg atttactatg atggtaagaa taaatattat  180
gcagactccg tgaggggccg attcaccatc tccagagaca attccaagaa cacactgtat  240
ctgcaaatga acaatctgag agtcgaggac acggctatgt atttctgtgc gcgagggcct  300
gggtacaatt ggctcgaccc ctggggccag ggaaccctgg tcactgtttc ctca        354

SEQ ID NO: 1314        moltype = AA  length = 118
FEATURE                Location/Qualifiers
REGION                 1..118
                       note = Synthetic
source                 1..118
                       mol_type = protein
                       organism = synthetic construct
SEQUENCE: 1314
QVQLVESGGG VVQPGRSLRL ACVASGFTFR SYGMHWVRQA PGKGLQWVAM IYYDGKNKYY  60
ADSVRGRFTI SRDNSKNTLY LQMNNLRVED TAMYFCARGP GYNWLDPWGQ GTLVTVSS    118

SEQ ID NO: 1315        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1315
ggattcacct tcagaagtta tggc                                         24

SEQ ID NO: 1316        moltype = AA  length = 8
FEATURE                Location/Qualifiers
REGION                 1..8
                       note = Synthetic
source                 1..8
                       mol_type = protein
                       organism = synthetic construct
SEQUENCE: 1316
GFTFRSYG                                                           8

SEQ ID NO: 1317        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1317
atttactatg atggtaagaa taaa                                         24

SEQ ID NO: 1318        moltype = AA  length = 8
FEATURE                Location/Qualifiers
REGION                 1..8
                       note = Synthetic
source                 1..8
                       mol_type = protein
                       organism = synthetic construct
SEQUENCE: 1318
IYYDGKNK                                                           8

SEQ ID NO: 1319        moltype = DNA  length = 33
FEATURE                Location/Qualifiers
misc_feature           1..33
                       note = Synthetic
source                 1..33
                       mol_type = other DNA
                       organism = synthetic construct
SEQUENCE: 1319
gcgcgagggc ctgggtacaa ttggctcgac ccc                               33

SEQ ID NO: 1320        moltype = AA  length = 11
```

```
FEATURE                 Location/Qualifiers
REGION                  1..11
                        note = Synthetic
source                  1..11
                        mol_type = protein
                        organism = synthetic construct
SEQUENCE: 1320
ARGPGYNWLD P                                                11

SEQ ID NO: 1321         moltype = DNA  length = 321
FEATURE                 Location/Qualifiers
misc_feature            1..321
                        note = Synthetic
source                  1..321
                        mol_type = other DNA
                        organism = synthetic construct
SEQUENCE: 1321
gaaatagtga tgacgcagtc tccagccacc ctgtctgtgt ctccagggga aagagccacc  60
ctctcctgca gggccagtca gagaattagc agcaacttgg cctggtacca gcaaaaacct  120
ggccaggctc ccaggctcct catctatggt gcatccacca gggccactgg tagcccagcc  180
aggttcagtg gcagtgggtc tgggacagac ttcactctca ccatcagcag cctgcagtct  240
gaggatgttg cagtttatta ctgtcagcaa catcataact ggcctctcac tttcggcgga  300
gggaccaagg tggagatcaa a                                     321

SEQ ID NO: 1322         moltype = AA  length = 107
FEATURE                 Location/Qualifiers
REGION                  1..107
                        note = Synthetic
source                  1..107
                        mol_type = protein
                        organism = synthetic construct
SEQUENCE: 1322
EIVMTQSPAT LSVSPGERAT LSCRASQRIS SNLAWYQQKP GQAPRLLIYG ASTRATGSPA  60
RFSGSGSGTD FTLTISSLQS EDVAVYYCQQ HHNWPLTFGG GTKVEIK           107

SEQ ID NO: 1323         moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 1323
cagagaatta gcagcaac                                         18

SEQ ID NO: 1324         moltype = AA  length = 6
FEATURE                 Location/Qualifiers
REGION                  1..6
                        note = Synthetic
source                  1..6
                        mol_type = protein
                        organism = synthetic construct
SEQUENCE: 1324
QRISSN                                                      6

SEQ ID NO: 1325         moltype =   length =
SEQUENCE: 1325
000

SEQ ID NO: 1326         moltype =   length =
SEQUENCE: 1326
000

SEQ ID NO: 1327         moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 1327
cagcaacatc ataactggcc tctcact                               27

SEQ ID NO: 1328         moltype = AA  length = 9
FEATURE                 Location/Qualifiers
REGION                  1..9
                        note = Synthetic
source                  1..9
                        mol_type = protein
```

```
                        organism = synthetic construct
SEQUENCE: 1328
QQHHNWPLT                                                        9

SEQ ID NO: 1329         moltype = AA  length = 119
FEATURE                 Location/Qualifiers
REGION                  1..119
                        note = Synthetic
source                  1..119
                        mol_type = protein
                        organism = synthetic construct
SEQUENCE: 1329
DVQLVQSGAE VKKPGASVKV SCKASGYTFT RYTMHWVRQA PGQGLEWIGY INPSRGYTNY  60
ADSVKGRFTI TTDKSTSTAY MELSSLRSED TATYYCARYY DDHYCLDYWG QGTTVTVSS   119

SEQ ID NO: 1330         moltype = AA  length = 8
FEATURE                 Location/Qualifiers
REGION                  1..8
                        note = Synthetic
source                  1..8
                        mol_type = protein
                        organism = synthetic construct
SEQUENCE: 1330
GYTFTRYT                                                         8

SEQ ID NO: 1331         moltype = AA  length = 8
FEATURE                 Location/Qualifiers
REGION                  1..8
                        note = Synthetic
source                  1..8
                        mol_type = protein
                        organism = synthetic construct
SEQUENCE: 1331
INPSRGYT                                                         8

SEQ ID NO: 1332         moltype = AA  length = 12
FEATURE                 Location/Qualifiers
REGION                  1..12
                        note = Synthetic
source                  1..12
                        mol_type = protein
                        organism = synthetic construct
SEQUENCE: 1332
ARYYDDHYCL DY                                                    12

SEQ ID NO: 1333         moltype = AA  length = 106
FEATURE                 Location/Qualifiers
REGION                  1..106
                        note = Synthetic
source                  1..106
                        mol_type = protein
                        organism = synthetic construct
SEQUENCE: 1333
DIVLTQSPAT LSLSPGERAT LSCRASQSVS YMNWYQQKPG KAPKRWIYDT SKVASGVPAR  60
FSGSGSGTDY SLTINSLEAE DAATYYCQQW SSNPLTFGGG TKVEIK               106

SEQ ID NO: 1334         moltype = AA  length = 11
FEATURE                 Location/Qualifiers
REGION                  1..11
                        note = Synthetic
source                  1..11
                        mol_type = protein
                        organism = synthetic construct
SEQUENCE: 1334
LSCRASQSVS Y                                                     11

SEQ ID NO: 1335         moltype =   length =
SEQUENCE: 1335
000

SEQ ID NO: 1336         moltype = AA  length = 9
FEATURE                 Location/Qualifiers
REGION                  1..9
                        note = Synthetic
source                  1..9
                        mol_type = protein
                        organism = synthetic construct
SEQUENCE: 1336
QQWSSNPLT                                                        9
```

```
SEQ ID NO: 1337        moltype = DNA  length = 367
FEATURE                Location/Qualifiers
misc_feature           1..367
                       note = Synthetic
source                 1..367
                       mol_type = other DNA
                       organism = synthetic construct
SEQUENCE: 1337
gaagtgcagc tggtggagtc tgggggaggc ttggtacagc ctggcaggtc cctgagactc  60
tcctgtgcag cctctggatt caccttttat gattatgcca tgcactgggt ccggcaagct  120
ccagggaagg gcctggagtg ggtctcaggt attagctgga atagtgatac cataggctat  180
gcggactctg tgaagggccg attcaccatc tccagagaca acgccaagaa ctccctgtat  240
ctgcaaatga acagtctgag agctgaggac acggccttat attactgtac aaaagatggc  300
agctatggtc acttctactc cggtttggac gtctggggcc aagggaccac ggtcaccgtc  360
tcctcag                                                            367

SEQ ID NO: 1338        moltype = AA  length = 122
FEATURE                Location/Qualifiers
REGION                 1..122
                       note = Synthetic
source                 1..122
                       mol_type = protein
                       organism = synthetic construct
SEQUENCE: 1338
EVQLVESGGG LVQPGRSLRL SCAASGFTFY DYAMHWVRQA PGKGLEWVSG ISWNSDTIGY  60
ADSVKGRFTI SRDNAKNSLY LQMNSLRAED TALYYCTKDG SYGHFYSGLD VWGQGTTVTV  120
SS                                                                 122

SEQ ID NO: 1339        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1339
ggattcacct tttatgatta tgcc                                         24

SEQ ID NO: 1340        moltype = AA  length = 8
FEATURE                Location/Qualifiers
REGION                 1..8
                       note = Synthetic
source                 1..8
                       mol_type = protein
                       organism = synthetic construct
SEQUENCE: 1340
GFTFYDYA                                                           8

SEQ ID NO: 1341        moltype = DNA  length = 24
FEATURE                Location/Qualifiers
misc_feature           1..24
                       note = Synthetic
source                 1..24
                       mol_type = other DNA
                       organism = synthetic construct
SEQUENCE: 1341
attagctgga atagtgatac cata                                         24

SEQ ID NO: 1342        moltype = AA  length = 8
FEATURE                Location/Qualifiers
REGION                 1..8
                       note = Synthetic
source                 1..8
                       mol_type = protein
                       organism = synthetic construct
SEQUENCE: 1342
ISWNSDTI                                                           8

SEQ ID NO: 1343        moltype = DNA  length = 45
FEATURE                Location/Qualifiers
misc_feature           1..45
                       note = Synthetic
source                 1..45
                       mol_type = other DNA
                       organism = synthetic construct
SEQUENCE: 1343
acaaaagatg gcagctatgg tcacttctac tccggtttgg acgtc                  45
```

-continued

```
SEQ ID NO: 1344          moltype = AA   length = 15
FEATURE                  Location/Qualifiers
REGION                   1..15
                         note = Synthetic
source                   1..15
                         mol_type = protein
                         organism = synthetic construct
SEQUENCE: 1344
TKDGSYGHFY SGLDV                                                  15

SEQ ID NO: 1345          moltype = DNA   length = 322
FEATURE                  Location/Qualifiers
misc_feature             1..322
                         note = Synthetic
source                   1..322
                         mol_type = other DNA
                         organism = synthetic construct
SEQUENCE: 1345
gaaatagtga tgacgcagtc tccagccacc ctgtctgtgt ctccagggga aagagccacc   60
ctctcctgca gggccagtca gagtgttagc agcaacttag cctggtacca gcagaaacct  120
ggccaggctc cccgactcct catctatggt acatccacca gggccactgg tatcccagcc  180
aggttcagtg gcagtgggtc tgggacagag ttcactctca ccatcagcag cctgcagtct  240
gaagattttg cagtttatta ctgtcaacaa tataataact ggccgctcac tttcggcgga  300
gggaccaagg tggagatcaa ac                                           322

SEQ ID NO: 1346          moltype = AA   length = 107
FEATURE                  Location/Qualifiers
REGION                   1..107
                         note = Synthetic
source                   1..107
                         mol_type = protein
                         organism = synthetic construct
SEQUENCE: 1346
EIVMTQSPAT LSVSPGERAT LSCRASQSVS SNLAWYQQKP GQAPRLLIYG TSTRATGIPA   60
RFSGSGSGTE FTLTISSLQS EDFAVYYCQQ YNNWPLTFGG GTKVEIK               107

SEQ ID NO: 1347          moltype = DNA   length = 18
FEATURE                  Location/Qualifiers
misc_feature             1..18
                         note = Synthetic
source                   1..18
                         mol_type = other DNA
                         organism = synthetic construct
SEQUENCE: 1347
cagagtgtta gcagcaac                                                18

SEQ ID NO: 1348          moltype = AA   length = 6
FEATURE                  Location/Qualifiers
REGION                   1..6
                         note = Synthetic
source                   1..6
                         mol_type = protein
                         organism = synthetic construct
SEQUENCE: 1348
QSVSSN                                                              6

SEQ ID NO: 1349          moltype =    length =
SEQUENCE: 1349
000

SEQ ID NO: 1350          moltype =    length =
SEQUENCE: 1350
000

SEQ ID NO: 1351          moltype = DNA   length = 27
FEATURE                  Location/Qualifiers
misc_feature             1..27
                         note = Synthetic
source                   1..27
                         mol_type = other DNA
                         organism = synthetic construct
SEQUENCE: 1351
caacaatata ataactggcc gctcact                                      27

SEQ ID NO: 1352          moltype = AA   length = 9
FEATURE                  Location/Qualifiers
REGION                   1..9
                         note = Synthetic
source                   1..9
```

```
                        mol_type = protein
                        organism = synthetic construct
SEQUENCE: 1352
QQYNNWPLT                                                                 9

SEQ ID NO: 1353         moltype = DNA  length = 379
FEATURE                 Location/Qualifiers
misc_feature            1..379
                        note = Synthetic
source                  1..379
                        mol_type = other DNA
                        organism = synthetic construct
SEQUENCE: 1353
gaagagcaac tggtggagtc tgggggagac ttggtacagc ctggcaggtc cctgaggctc  60
tcctgtgcag cctctggatt cacctttcat gattacacca tgcactgggt ccggcaagct  120
ccagggaagg gcctggagtg ggtctcaggt attagttgga atagtggaag tctaggctat  180
gcggactctg tgaagggccg attcaccatc tccagagaca acgccaagaa gtccctgtat  240
ctgcaaatga acagtctgag agctgaggac acggccttat attactgtgc aaaagatccc  300
tcttatggtt cggggtcgta tcactcctac tacggaatgg acgtctgggg ccaagggacc  360
acggtcactg tctcctcag                                                      379

SEQ ID NO: 1354         moltype = AA  length = 126
FEATURE                 Location/Qualifiers
REGION                  1..126
                        note = Synthetic
source                  1..126
                        mol_type = protein
                        organism = synthetic construct
SEQUENCE: 1354
EEQLVESGGD LVQPGRSLRL SCAASGFTFH DYTMHWVRQA PGKGLEWVSG ISWNSGSLGY  60
ADSVKGRFTI SRDNAKKSLY LQMNSLRAED TALYYCAKDP SYGSGSYHSY YGMDVWGQGT  120
TVTVSS                                                                    126

SEQ ID NO: 1355         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1355
ggattcacct ttcatgatta cacc                                                24

SEQ ID NO: 1356         moltype = AA  length = 8
FEATURE                 Location/Qualifiers
REGION                  1..8
                        note = Synthetic
source                  1..8
                        mol_type = protein
                        organism = synthetic construct
SEQUENCE: 1356
GFTFHDYT                                                                  8

SEQ ID NO: 1357         moltype = DNA  length = 24
FEATURE                 Location/Qualifiers
misc_feature            1..24
                        note = Synthetic
source                  1..24
                        mol_type = other DNA
                        organism = synthetic construct
SEQUENCE: 1357
attagttgga atagtggaag tcta                                                24

SEQ ID NO: 1358         moltype = AA  length = 8
FEATURE                 Location/Qualifiers
REGION                  1..8
                        note = Synthetic
source                  1..8
                        mol_type = protein
                        organism = synthetic construct
SEQUENCE: 1358
ISWNSGSL                                                                  8

SEQ ID NO: 1359         moltype = DNA  length = 57
FEATURE                 Location/Qualifiers
misc_feature            1..57
                        note = Synthetic
source                  1..57
                        mol_type = other DNA
```

```
                        organism = synthetic construct
SEQUENCE: 1359
gcaaaagatc cctcttatgg ttcggggtcg tatcactcct actacggaat ggacgtc     57

SEQ ID NO: 1360         moltype = AA  length = 19
FEATURE                 Location/Qualifiers
REGION                  1..19
                        note = Synthetic
source                  1..19
                        mol_type = protein
                        organism = synthetic construct
SEQUENCE: 1360
AKDPSYGSGS YHSYYGMDV                                               19

SEQ ID NO: 1361         moltype = DNA  length = 322
FEATURE                 Location/Qualifiers
misc_feature            1..322
                        note = Synthetic
source                  1..322
                        mol_type = other DNA
                        organism = synthetic construct
SEQUENCE: 1361
gaaattgtgt tgacacagtc tccagccacc ctgtctttgt ctccagggga aagagccacc  60
ctctcctgct gggccagtca gagtattagc aggtacttag tctggtacca acagaaatgt  120
ggccaggcac ccagactcct catctatgaa gcatctaaga gggccaccgg catcccagtc  180
aggttcagtg gcagtgggtc tgggacagac ttcactctca ccatcagcag cctagagtct  240
gaagattttg cagtttatta ttgtcagcag cgtttcaatt ggcctctcac tttcggcgga  300
gggaccaagg tggagatcaa ac                                           322

SEQ ID NO: 1362         moltype = AA  length = 107
FEATURE                 Location/Qualifiers
REGION                  1..107
                        note = Synthetic
source                  1..107
                        mol_type = protein
                        organism = synthetic construct
SEQUENCE: 1362
EIVLTQSPAT LSLSPGERAT LSCWASQSIS RYLVWYQQKC GQAPRLLIYE ASKRATGIPV  60
RFSGSGSGTD FTLTISSLES EDFAVYYCQQ RFNWPLTFGG GTKVEIK                107

SEQ ID NO: 1363         moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 1363
cagagtatta gcaggtac                                                18

SEQ ID NO: 1364         moltype = AA  length = 6
FEATURE                 Location/Qualifiers
REGION                  1..6
                        note = Synthetic
source                  1..6
                        mol_type = protein
                        organism = synthetic construct
SEQUENCE: 1364
QSISRY                                                             6

SEQ ID NO: 1365         moltype =   length =
SEQUENCE: 1365
000

SEQ ID NO: 1366         moltype =   length =
SEQUENCE: 1366
000

SEQ ID NO: 1367         moltype = DNA  length = 27
FEATURE                 Location/Qualifiers
misc_feature            1..27
                        note = Synthetic
source                  1..27
                        mol_type = other DNA
                        organism = synthetic construct
SEQUENCE: 1367
cagcagcgtt tcaattggcc tctcact                                      27

SEQ ID NO: 1368         moltype = AA  length = 9
```

```
FEATURE                 Location/Qualifiers
REGION                  1..9
                        note = Synthetic
source                  1..9
                        mol_type = protein
                        organism = synthetic construct
SEQUENCE: 1368
QQRFNWPLT                                                           9

SEQ ID NO: 1369         moltype = AA  length = 297
FEATURE                 Location/Qualifiers
REGION                  1..297
                        note = hCD20
source                  1..297
                        mol_type = protein
                        organism = synthetic construct
SEQUENCE: 1369
MTTPRNSVNG TFPAEPMKGP IAMQSGPKPL FRRMSSLVGP TQSFFMRESK TLGAVQIMNG  60
LFHIALGGLL MIPAGIYAPI CVTVWYPLWG GIMYIISGSL LAATEKNSRK CLVKGKMIMN  120
SLSLFAAISG MILSIMDILN IKISHFLKME SLNFIRAHTP YINIYNCEPA NPSEKNSPST  180
QYCYSIQSLF LGILSVMLIF AFFQELVIAG IVENEWKRTC SRPKSNIVLL SAEEKKEQTI  240
EIKEEVVGLT ETSSQPKNEE DIEIIPIQEE EEEETETNFP EPPQDQESSP IENDSSP     297

SEQ ID NO: 1370         moltype = AA  length = 104
FEATURE                 Location/Qualifiers
REGION                  1..104
                        note = hCD3 epsilon
source                  1..104
                        mol_type = protein
                        organism = synthetic construct
SEQUENCE: 1370
DGNEEMGGIT QTPYKVSISG TTVILTCPQY PGSEILWQHN DKNIGGDEDD KNIGSDEDHL  60
SLKEFSELEQ SGYYVCYPRG SKPEDANFYL YLRARVSENS MEMD                   104

SEQ ID NO: 1371         moltype = AA  length = 79
FEATURE                 Location/Qualifiers
REGION                  1..79
                        note = hCD3 delta
source                  1..79
                        mol_type = protein
                        organism = synthetic construct
SEQUENCE: 1371
FKIPIEELED RVFVNCNTSI TWVEGTVGTL LSDITRLDLG KRILDPRGIY RCNGTDIYKD  60
KESTVQVHYR MSQSSVELD                                                79

SEQ ID NO: 1372         moltype = AA  length = 227
FEATURE                 Location/Qualifiers
REGION                  1..227
                        note = hFc-delta-Adp
source                  1..227
                        mol_type = protein
                        organism = synthetic construct
SEQUENCE: 1372
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNRFTQKS LSLSPGK                227

SEQ ID NO: 1373         moltype = AA  length = 227
FEATURE                 Location/Qualifiers
REGION                  1..227
                        note = hFc
source                  1..227
                        mol_type = protein
                        organism = synthetic construct
SEQUENCE: 1373
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSRDELTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 1374         moltype = AA  length = 233
FEATURE                 Location/Qualifiers
REGION                  1..233
                        note = mFc-delta-Adp
source                  1..233
                        mol_type = protein
                        organism = synthetic construct
SEQUENCE: 1374
```

-continued

```
EPRGPTIKPC PPCKCPAPNL LGGPSVFIFP PKIKDVLMIS LSPIVTCVVV DVSEDDPDVQ  60
ISWFVNNVEV HTAQTQTHRE DYNSTLRVVS ALPIQHQDWM SGKEFKCKVN NKDLPAPIER  120
TISKPKGSVR APQVYVLPPP EEEMTKKQVT LTCMVTDFMP EDIYVEWTNN GKTELNYKNT  180
EPVLDSDGSY FMYSKLRVEK KNWVERNSYS CSVVHEGLHN RFTTKSFSRT PGK         233

SEQ ID NO: 1375         moltype = AA  length = 233
FEATURE                 Location/Qualifiers
REGION                  1..233
                        note = mFc
source                  1..233
                        mol_type = protein
                        organism = synthetic construct
SEQUENCE: 1375
EPRGPTIKPC PPCKCPAPNL LGGPSVFIFP PKIKDVLMIS LSPIVTCVVV DVSEDDPDVQ  60
ISWFVNNVEV HTAQTQTHRE DYNSTLRVVS ALPIQHQDWM SGKEFKCKVN NKDLPAPIER  120
TISKPKGSVR APQVYVLPPP EEEMTKKQVT LTCMVTDFMP EDIYVEWTNN GKTELNYKNT  180
EPVLDSDGSY FMYSKLRVEK KNWVERNSYS CSVVHEGLHN HHTTKSFSRT PGK         233
```